US011155505B2

(12) United States Patent
Wampler et al.

(10) Patent No.: US 11,155,505 B2
(45) Date of Patent: Oct. 26, 2021

(54) SYNTHESIS OF PHEROMONES AND RELATED MATERIALS VIA OLEFIN METATHESIS

(71) Applicant: Provivi, Inc., Santa Monica, CA (US)

(72) Inventors: Keith M. Wampler, Santa Monica, CA (US); Vu Bui, Santa Monica, CA (US); David Rozzell, Burbank, CA (US); Pedro Coelho, Santa Monica, CA (US); Arthur Floruti, Santa Monica, CA (US); Levente Ondi, Veresegyház (HU); Hasan Mehdi, Budapest (HU); Gabor Eros, Tard (HU)

(73) Assignee: PROVIVI, INC., Santa Monica, CA (US)

( * ) Notice: Subject to any disclaimer, the term of this patent is extended or adjusted under 35 U.S.C. 154(b) by 0 days.

(21) Appl. No.: 16/543,384

(22) Filed: Aug. 16, 2019

(65) Prior Publication Data

US 2020/0039900 A1 Feb. 6, 2020

Related U.S. Application Data

(63) Continuation of application No. PCT/IB2018/050980, filed on Feb. 17, 2018.

(60) Provisional application No. 62/460,661, filed on Feb. 17, 2017, provisional application No. 62/460,667, filed on Feb. 17, 2017, provisional application No. 62/511,903, filed on May 26, 2017.

(51) Int. Cl.
*C07C 6/04* (2006.01)
*B01J 31/22* (2006.01)

(52) U.S. Cl.
CPC .............. *C07C 6/04* (2013.01); *B01J 31/22* (2013.01); *B01J 2231/543* (2013.01); *B01J 2531/64* (2013.01); *B01J 2531/66* (2013.01); *B01J 2531/821* (2013.01)

(58) Field of Classification Search
CPC ....... C07C 6/04; B01J 31/22; B01J 2231/543; B01J 2531/64; B01J 2531/821
USPC ......................................................... 554/127
See application file for complete search history.

(56) References Cited

U.S. PATENT DOCUMENTS

| | | | |
|---|---|---|---|
| 4,057,593 A | 11/1977 | Bestmann et al. | |
| 4,639,429 A | 1/1987 | Basset et al. | |
| 4,792,620 A | 12/1988 | Paulik et al. | |
| 4,837,358 A | 6/1989 | Byers et al. | |
| 5,292,973 A | 3/1994 | Fukumoto et al. | |
| 5,831,105 A | 11/1998 | Aulbach | |
| 5,916,983 A | 6/1999 | Pederson et al. | |
| 5,981,812 A | 11/1999 | Eufinger et al. | |
| 5,994,590 A | 11/1999 | Tsuda et al. | |
| 6,215,019 B1 * | 4/2001 | Pederson ............. C07C 67/293 560/234 |
| 6,533,960 B2 | 3/2003 | Mimoun | |
| 6,696,597 B2 * | 2/2004 | Pederson ................. C07C 6/04 560/231 |
| 8,598,400 B2 | 12/2013 | Hoveyda et al. | |
| 8,987,531 B2 | 3/2015 | Grubbs et al. | |
| 9,079,173 B2 | 7/2015 | Schrock et al. | |
| 9,487,471 B1 | 11/2016 | Coelho et al. | |
| 2002/0022741 A1 | 2/2002 | Pederson et al. | |
| 2013/0204022 A1 | 8/2013 | Snead et al. | |
| 2013/0231499 A1 | 9/2013 | Grubbs et al. | |
| 2013/0274482 A1 | 10/2013 | Schrock et al. | |
| 2014/0031592 A1 | 1/2014 | Shinde | |
| 2014/0275595 A1 | 9/2014 | Wampler et al. | |
| 2014/0288319 A1 | 9/2014 | Grubbs et al. | |
| 2014/0371454 A1 | 12/2014 | Hoveyda et al. | |
| 2014/0378637 A1 | 12/2014 | Schrock et al. | |
| 2015/0240008 A1 | 8/2015 | Schrock et al. | |
| 2015/0307438 A1 | 10/2015 | Abraham et al. | |
| 2016/0039737 A1 | 2/2016 | Champagne et al. | |
| 2017/0137365 A1 | 5/2017 | Wampler et al. | |

FOREIGN PATENT DOCUMENTS

| | | |
|---|---|---|
| CN | 103319704 A | 9/2013 |
| EP | 0241335 A1 | 10/1987 |
| GB | 2085881 A | 5/1982 |
| JP | 5115368 B2 | 1/2013 |
| WO | 2008/066754 A1 | 6/2008 |
| WO | 2009/094201 A2 | 7/2009 |
| WO | 2011/040963 A1 | 4/2011 |
| WO | 2011/095991 A2 | 8/2011 |
| WO | 2011/097642 A1 | 8/2011 |
| WO | 2013/070725 A1 | 5/2013 |
| WO | 2013/163071 A1 | 10/2013 |

(Continued)

OTHER PUBLICATIONS

Higman, C.M. et al; "Olefin Metathesis at the Dawn of Implementation in Pharmaceutical and Specialty-Chemicals Manufacturing"; *Angew. Chem. Int. Ed.* (2016) 55, 3552-3565.

Abe, K et al. "Vapor-phase catalytic dehydration of terminal diols." Catalysis Today 164(2011) 419-424.

Akermark, B et al. "Eutectic potassium-sodium-aluminum chloride as a mild catalyst for ene reactions: simple synthesis of the sex pheromone from Douglas fir tussock moth." Oct. 1, 1978, J. Org. Chem. 43, 22, pp. 4387-4388.

Banasiak, D., "Insect Pheromones From Olefin Metathesis," Journal of Molecular Catalysis, Jan. 1, 1985, vol. 28, No. 1-2, pp. 107-115.

Brewitz, L et al. "Formal Total Synthesis of the Algal Toxin (−)-Polycavernoside A." Feb. 18, 2013. Chemistry A European Journal, 19, 14, pp. 4532-4537.

(Continued)

*Primary Examiner* — Deborah D Carr
(74) *Attorney, Agent, or Firm* — Kilpatrick Townsend & Stockton LLP

(57) ABSTRACT

Methods for preparation of olefins, including 8- and 11-unsaturated monoenes and polyenes, via transition metathesis-based synthetic routes are described. Metathesis reactions in the methods are catalyzed by transition metal catalysts including tungsten-, molybdenum-, and ruthenium-based catalysts. The olefins include insect pheromones useful in a number of agricultural applications.

17 Claims, No Drawings

(56) References Cited

FOREIGN PATENT DOCUMENTS

| WO | 2013/171302 A1 | 11/2013 |
|---|---|---|
| WO | 2014/085393 A1 | 6/2014 |
| WO | 2014/139030 A1 | 9/2014 |
| WO | 2014/139679 A2 | 9/2014 |
| WO | 2014/152309 A1 | 9/2014 |
| WO | 2014/160417 A1 | 10/2014 |
| WO | 2014/201300 A1 | 12/2014 |
| WO | 2015/127192 A1 | 8/2015 |
| WO | 2015/136093 A1 | 9/2015 |
| WO | 2015/155593 A1 | 10/2015 |
| WO | 2018/150379 A2 | 8/2018 |

OTHER PUBLICATIONS

Brown et al., "A New Convenient Approach to the Preparation of Z-1 Alkenylboranates by the cis-Hydrogenation of 1-Alkynyldiisoporpoxyborabes," Tetrahedron Ltrs, 1988, vol. 29, No. 22, pp. 2635-2638.
Brown et al., "A Simple, General Synthesis of 1-Alkynyldiisopropoxyboranes," Tetrahedron Ltrs, 1988, vol. 29, No. 22, pp. 2631-2634.
Cannon et al. "Alkene Chemoselectivity in Ruthenium-Catalyzed Z-Selective Olefin Metathesis," Angew. Chem. Int. Ed., 2013. vol. 52, pp. 9001-9004.
Chandrasekhar et al., "One Pot Conversion of Carboxylic Acids to Aldehydes with DIBAL-H," Tetrahedron Letters 39, 1998, pp. 909-910.
Davini, E et al. "A large scale preparation of 1-ethynylcyclopentene and 1-hexene-4-yne." 1995, *Organic Preparations and Procedures Intl.* 27, 5, pp. 586-590.
Dewi et al., "Cross-metathesis of 1,3-dienes with electron-deficient olefins," Tetrahedron Ltrs, 2005, vol. 46, pp. 577-580.
Eisenhuth et al. "Alkine and Cumulene, XV: Über die Photodimerisierung konjugierter Enine." Dec. 1981. *Chemische Berichte*, 114, 12, pp. 3772-3788.
Ferrie et al., "Chemoselective cross-metathesis reaction between electron-deficient 1,3-dienes and olefins," Journal of Organometallic Chemistry, 2006, vol. 691, pp. 5456-5465.
Funk et al., "Chemoselective Construction of Substituted Conjugated Dienes using an Olefin Cross-Metathesis Protocol," Organic Letters, 2005, vol. 7, No. 2, pp. 187-190.
Herbert, M. et al., "Concise Syntheses of Insect Pheromones Using Z-Selective Cross Metathesis," Angew. Chem. Int. Ed. 2013, vol. 52, pp. 310-314.
Herbert, M., "Chapter 2: Synthetic Applications of Highly Z-Selective Ruthenium Metathesis Catalysts." Z-Selective Olefin Metathesis Using Chelating Ruthenium Alkylidene Catalysts. California Institute of Technology. Copyright 2014. Deposited on: May 19, 2015, 58 pages.
Hou, J. et al. "Preparation and Characterization of Cross-Linked Composite Polymer Electrolytes." Oct. 10, 1998; Chem. Mater. 1998, 10, pp. 3311-3318.
Ibrahem, I. et al. "Highly Z- and Enantioselective Ring-Opening/Cross-Metathesis Reactions Catalyzed by Stereogenic-at-Mo Adamantylimido Complexes." J. Am. Chem. Soc. 2009, 131, pp. 3844-3845.
International Application No. PCT/162018/050980, International Search Report dated Aug. 13, 2018, 3 pages.
Kaufmann et al., Science of Synthesis, Houben-Weyl Methods of Molecular Transformation, vol. 6, Thieme: Stuttgart, 2004, pp. 635-658.
Krasovskiy, Al et al. "Stereoretentive Pd-Catalyzed Kumada-Corriu Couplings of Alkenyl Halides at Room Temperature." Aug. 7, 2014. *Org Lett.* 16, 16, pp. 4066-4069.
Kupper, F., et al., "Synthese von Insektenpheromonen an Metathesekatalysatoren," Chemiker-Zeitung, 1975, 99, pp. 464 (4 pages).
Levisalles et al., "Metathese D'Acetates D'Alcools ω-Insatures," Tetrahedron, vol. 36, No. 22, Jan. 1, 1980, pp. 3181-3185.

Liu, P. et al. "Z-Selectivity in Olefin Metathesis with Chelated Ru Catalysts: Computational Studies of Mechanism and Selectivity." J. Am. Chem. Soc. 2012, 134, pp. 1454-1467.
Luo et al., "Z-Selective Cross-Metathesis and Homodimerization of 3E-1,3-Diens: Reaction Optimization, Computational Analysis, and Sythetic Applications," Sep. 30, 2016, J. Am. Chem. Soc., vol. 138, pp. 14039-14046.
Marinescu, S., et al., "Isolation of Pure Disubstituted E Olefins through Mo-Catalyzed Z-Selective Ethenolysis of Stereoisomeric Mixtures," J. Am Chem Soc. 2011, 133(30), pp. 11512-11514.
Marx, V., et al., "Stereoselective Access to Z and E Macrocycles by Ruthenium-Catalyzed Z-Selective Ring-Closing Metathesis and Ethenolysis," J. Am. Chem. Soc. 2013, 135: pp. 94-47.
Micalizio et al., "An Alkynylboronic Ester Annulation: Development of Synthetic Methods for Application to Diversity-Oriented Organic Synthesis," Angew. Chem. Int. Ed., 2002, vol. 41, No. 17, pp. 3272-3276.
Mimoun, H., "Selective Reduction of Carbonyl Compounds by Polymethylhydrosiloxane in the Presence of Metal Hydride Catalysts," J. Org. Chem. 1999, 64: pp. 2582-2589.
Miyaura, N et al. "Novel and convenient method for the stereo- and regiospecific synthesis of conjugated alkadienes and alkenynes via the palladium-catalyzed cross-coupling reaction of 1-alkenylboranes with bromoalkenes and bromoalkynes." Feb. 1, 1985, *J. Am. Chem. Soc.* 1985, 107, 4, pp. 972-980.
Miyazaki, H., et al., "Z-Selective Ethenolysis with a Ruthenium Metathesis Catalyst: Experiment and Theory," J. Am. Chem. Soc. 2013, 135: pp. 5848-5858.
Nguyen, TT et al. "Kinetically controlled E-selective catalytic olefin metathesis" Apr. 29, 2016; Science, 352 (6285): pp. 569-575.
Pederson et al., "Applications of Olefin Cross Metathesis to Commercial Products," Advanced Synthesis and Catalysis, 2002, vol. 344, No. 6-7; pp. 728-735.
Ranganathan et al "The synthesis of PGF1α by re-structuring of castor oil," 1980, Tetrahedron, 36(12), pp. 1869-1875.
Rizzo et al., "Microsomal fatty aldehyde dehydrogenase catalyzes the oxidation of aliphatic aldehyde derived from ether glycerolipid catabolism: implications for Sjogren-Larsson syndrome," Biochimica et Biophysica Acta, vol. 1535, 2000, pp. 1-9.
Rizzo et al., "Sjogren-Larsson Syndrome Deficient Activity of the Fatty Aldehyde Dehydrogenase Component of Fatty Alcohoi:NAD+ Oxidoreductase in Cultured Fibroblasts," Journal of Clinical Investigations, vol. 88, 1991, pp. 1643-1648.
Sato et al. "Selective Dehydration of Alkanediols into Unsaturated Alcohols over Rare Earth Oxide Catalysts." ACS Catalysis, vol. 3, 2013, pp. 721-734.
Sarkar et al. "Cyclopentanoid Allylsilanes in Synthesis of Di- and Triquinanes. A Stereoselective Synthesis of (±)-Hirsutene." 1992, Tetrahedron, 48(33), pp. 6897-6908.
Shin et al., "Partial Reduction of Esters to Aldehydes Using a Novel Modified Red-AI Reducing Agent," Bulletin of Korean Chemical Society, 2014, vol. 35, No. 7, pp. 2169-2171.
Snider et al. Stereoselective and Regioselective Ene Reactions of Methyl Alpha-Chloroacrylate. Aug. 1, 1980, *J. Am. Chem. Soc.* 102, 18, pp. 5926-5928.
Snider, B.B. "Lewis-Acid catalyzed ene reactions." Nov. 1, 1980, Accounts of Chemical Research, 13, 11, pp. 426-432.
Spasyuk et al., "Chemoselective Hydrogenation of Carbonyl Compounds and Acceptorless Dehydrogenative Coupling of Alcohols," J. Am. Chem. Soc., 2015, 137: pp. 3743-3746.
Speed et al., "Catalytic Z-Selective Cross-Metathesis in complex Molecule Sythesis: A Convergent Stereoselective Route to Disorazole C1," J. Am. Chem. Society, 2014, vol. 136, pp. 16136-16139.
Tan et al., "Highly Efficient Tetradentate Ruthenium Catalyst for Ester Reduction: Especially for Hydrogenation of Fatty Acid Esters," Org. Lett., 2015, 17: pp. 454-457.
Torrente-Murciano et al. "Tandem isomerization/telmerization of long chain dienes." Jun. 13, 2014, *Frontiers in Chemistry*, vol. 2, Article 37, pp. 1-5.
Townsend et al., "Z-Selective Metathesis Homocoupling of 1,3-Dienes by Molybdenum and Tungsten Monoariloxide Pyrrolide (MAP) Complexes," J. Am. Chem. Soc., 2012, vol. 134, pp. 11334-11337.

(56) References Cited

OTHER PUBLICATIONS

Zhang et al., "Preparation of Macrocyclic Z-Enoates and (E,Z)- or (Z,E)-Dienoates through Catalytic Stereoselective Ring-Closing Metathesis," J. Am. Chem. Soc., 2014, 136, pp. 16493-16496.

* cited by examiner

SYNTHESIS OF PHEROMONES AND RELATED MATERIALS VIA OLEFIN METATHESIS

CROSS-REFERENCES TO RELATED APPLICATIONS

The present application is a continuation of International Pat. Appl. No. PCT/IB/2018/050980, filed on Feb. 17, 2018, which claims priority to U.S. Provisional Pat. Appl. No. 62/460,661, filed on Feb. 17, 2017; U.S. Provisional Pat. Appl. No. 62/460,667, filed on Feb. 17, 2017; and U.S. Provisional Pat. Appl. No. 62/511,903, filed on May 26, 2017; which applications are incorporated herein by reference in their entirety.

BACKGROUND OF THE INVENTION

Insect infestation is a primary cause of crop loss throughout the United States. A wide variety of chemical pesticides has been relied upon in the past to control insect pests. However, environmental concerns as well as consumer safety concerns have led to the de-registration of many pesticides and a reluctance to use others on agricultural products which are ultimately consumed as food. As a consequence, there is a desire for the development of alternative biological control agents.

Pheromones are chemicals which are secreted outside the body of insects and can be classified according to the type of behavioral reaction they induce. Pheromone classes include aggregation pheromones, sexual pheromones, trail pheromones, and alarm pheromones. Sex pheromones, for example, are typically secreted by insects to attract partners for mating.

When pheromones are dispersed on leaves of a crop plant, or in an orchard environment in small quantities over a continuous period of time, pheromone levels reach thresholds that can modify insect behavior. Maintenance of pheromone levels at or above such thresholds can impact insect reproductive processes and reduce mating. Use of pheromones in conjunction with conventional insecticides can therefore reduce the quantity of insecticide required for effective control and can specifically target pest insects while preserving beneficial insect populations. These advantages can reduce risks to humans and the environment and lower overall insect control costs.

Despite these advantages, pheromones are not widely used today because of the high cost of active ingredient (AI). Even though thousands of insect pheromones have been identified, less than about twenty insect pests worldwide are currently controlled using pheromone strategies, and only 0.05% of global agricultural land employs pheromones. Lepidopteran pheromones, which are naturally occurring compounds, or identical or substantially similar synthetic compounds, are typically characterized by an unbranched aliphatic chain (between 9 and 18 carbon atoms) ending in an alcohol, aldehyde, or acetate functional group and containing up to 3 double bonds in the aliphatic backbone. Improved methods for preparing lepidopteran insect pheromones, particularly polyene pheromones and pheromones containing 8-unsaturated fatty olefins and 11-unsaturated fatty olefins, and structurally related compounds are needed. The present invention meets this and other needs.

BRIEF SUMMARY OF THE INVENTION

Provided herein are methods for synthesizing fatty olefin derivatives. The methods include:

a) contacting an olefin according to Formula I

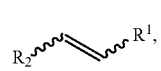
(I)

with a metathesis reaction partner according to Formula II

(II)

in the presence of a metathesis catalyst under conditions sufficient to form a metathesis product according to Formula III

(III)

and b) converting the metathesis product to the fatty olefin derivative;

wherein:

$R^1$ and $R^3$ are independently selected from the group consisting of hydrogen and $C_{1-18}$ alkyl;

$R^2$ is $C_{1-18}$ alkyl;

$R^4$ is selected from the group consisting of $-C(O)OR^{4a}$ and $-CH_2OR^{4b}$;

$R^{4a}$ is selected from the group consisting of hydrogen and $C_{1-8}$ alkyl;

$R^{4b}$ is an alcohol protecting group; and subscript y is 6 or 9.

Also provided herein are methods for synthesizing fatty polyene derivatives comprising:

a) contacting an olefin according to Formula XI

(XI)

with a metathesis reaction partner according to Formula XII

(XII)

in the presence of a metathesis catalyst under conditions sufficient to form a metathesis product according to Formula XIII:

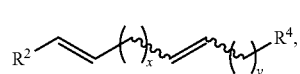
(XIII)

and
b) optionally converting the metathesis product to the fatty olefin derivative;
wherein:
$R^1$ and $R^3$ are independently selected from the group consisting of hydrogen, $C_{1-18}$ alkyl, and $C_{2-18}$ alkenyl;
$R^2$ is selected from the group consisting of $C_{1-18}$ alkyl and $C_{2-18}$ alkenyl;
$R^4$ is selected from the group consisting of —$CH_2X$, —$CH_2OR^{4a}$, —$C(O)OR^{4b}$, and —$COC(O)R^{4c}$;
X is halogen;
$R^{4a}$ is selected from the group consisting of an alcohol protecting group and hydrogen;
$R^{4b}$ is selected from the group consisting of hydrogen and $C_{1-8}$ alkyl;
$R^{4c}$ is selected from the group consisting of hydrogen, $C_{1-5}$ alkyl, and $C_{1-5}$ haloalkyl;
subscript x is 0 or 1; and
subscript y is an integer ranging from 0 to 15.
Also provided are methods for synthesizing fatty olefin derivatives comprising:
a) contacting an olefin according to Formula XXI

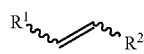
(XXI)

with a polyene reaction partner according to Formula XXII

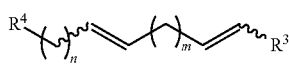
(XXII)

in the presence of a metathesis catalyst under conditions sufficient to form a metathesis product according to Formula XXIII

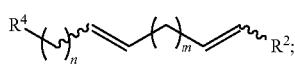
(XXIII)

and
b) optionally converting the metathesis product to the fatty olefin derivative;
wherein:
$R^1$ and $R^3$ are independently selected from the group consisting of hydrogen, $C_{1-18}$ alkyl, and $C_{2-18}$ alkenyl;
$R^2$ is selected from the group consisting of $C_{1-18}$ alkyl and $C_{2-18}$ alkenyl;
$R^4$ is selected from the group consisting of —$COC(O)R^{4a}$, —$CH_2OR^{4b}$, —$C(O)OR^{4c}$, and —$CH_2X$;
$R^{4a}$ is selected from the group consisting of hydrogen, $C_{1-5}$ alkyl, and $C_{1-5}$ haloalkyl;
$R^{4b}$ is an alcohol protecting group;
$R^{4c}$ is selected from the group consisting of hydrogen and $C_{1-8}$ alkyl;
X is halogen;
subscript m is 0 or 1; and
subscript n is an integer ranging from 0 to 15.
Also provided herein are methods for synthesizing fatty olefin derivatives comprising:

a) contacting an olefin according to Formula XXXI

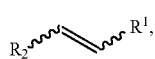
(XXXI)

with a metathesis reaction partner according to Formula XXXII

(XXXII)

in the presence of a metathesis catalyst under conditions sufficient to form a metathesis product according to Formula XXXIII:

(XXXIII)

and
b) optionally converting the metathesis product to the fatty olefin derivative;
wherein:
$R^1$ and $R^3$ are independently selected from the group consisting of hydrogen and $C_{1-18}$ alkyl;
$R^2$ is selected from the group consisting of $C_{1-18}$ alkyl and $C_{2-18}$ alkenyl;
$R^4$ is selected from the group consisting of —$CH_2OR^{4a}$, —$C(O)OR^{4b}$, —$CH_2OC(O)R^{4c}$, and halogen;
$R^{4a}$ is selected from the group consisting of hydrogen and an alcohol protecting group;
$R^{4b}$ is selected from the group consisting of hydrogen and $C_{1-8}$ alkyl;
$R^{4c}$ is selected from the group consisting of hydrogen, $C_{1-8}$ alkyl, and $C_{1-8}$ haloalkyl; and
subscript x is an integer ranging from 3 to 15.
In some embodiments, the metathesis catalyst is a tungsten metathesis catalyst, a molybdenum metathesis catalyst, or a ruthenium metathesis catalyst. In certain embodiments, the metathesis catalyst is a tungsten catalyst or a molybdenum catalyst.
In some embodiments, metathesis reaction partners, e.g., those according to Formula II, are derived from natural oils (e.g., seed oils and the like) or prepared from commercially available diols or halogenated alcohols. In some embodiments, conversion of metathesis products to the desired fatty olefin derivatives includes one or more reduction, esterification, and/or oxidation steps.
A number of pheromones and pheromone precursors, including unsaturated fatty alcohols, unsaturated fatty alcohol acetates, unsaturated fatty aldehydes, unsaturated fatty acid esters, and polyenes, can be synthesized using the methods of the invention.

DETAILED DESCRIPTION OF THE INVENTION

I. Introduction

The present invention provides methods for the synthesis of fatty olefin derivatives (such as straight-chain lepidopteran pheromones; "SCLPs") through the cross-metathesis of fatty alcohols or fatty acid esters with olefins (e.g., α-olefins). Through the use of a variety of fatty alcohols, fatty acid alkyl esters, and α-olefin feedstocks in concert with olefin metathesis catalysts (including Group VI Z-selective catalysts), a wide variety of protected unsaturated fatty alcohol precursors with high Z-olefin content can be obtained. These precursor compounds can be converted to pheromones (e.g., long chain Z-alcohols, Z-aldehydes, Z-acetates, and Z-nitrates) and other useful fatty olefin derivatives as described in detail below. Alternatively, non-selective olefin metathesis catalysts (including Group VI non-selective catalysts) can be used to generate cis/trans mixtures of protected long chain fatty alcohols. Such mixtures can be refined to provide pure E-pheromone precursors and other fatty E-olefin derivatives via Z-selective ethenolysis. E-selective catalysts can also be employed without an ethenolysis step. The methods provide access to valuable products, including SCLPs containing 8- and 11-monounsaturation as well as polyunsaturation.

II. Definitions

The following definitions and abbreviations are to be used for the interpretation of the invention. The term "invention" or "present invention" as used herein is a non-limiting term and is not intended to refer to any single embodiment but encompasses all possible embodiments.

As used herein, the terms "comprises," "comprising," "includes," "including," "has," "having, "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, and in certain instances, a value from 0.95X to 1.05X or from 0.98X to 1.02X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.99X."

As used herein, the term "pheromone" refers to a substance, or characteristic mixture of substances, that is secreted and released by an organism and detected by a second organism of the same species or a closely related species. Typically, detection of the pheromone by the second organism promotes a specific reaction, such as a definite behavioral reaction or a developmental process. Insect pheromones, for example, can influence behaviors such as mating and aggregation. Examples of pheromones include, but are not limited to, compounds produced by Lepidoptera (i.e., moths and butterflies belonging to the Geometridae, Noctuidae, Arctiidae, and Lymantriidae families) such as $C_{10}$-$C_{18}$ acetates, $C_{10}$-$C_{18}$ alcohols, $C_{10}$-$C_{18}$ aldehydes, and $C_{17}$-$C_{23}$ polyenes. An "unsaturated pheromone" refers to any pheromone having at least one carbon-carbon double bond.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents that can be produced in the reaction mixture.

As used herein, the term "olefin" refers to a straight-chain or branched hydrocarbon compound containing at least one carbon-carbon double bond and derivatives thereof. The olefin can be unsubstituted or substituted with one or more functional groups including alcohol groups, protected alcohol groups, carboxylate groups, and carboxylic acid ester groups. As used herein, the term "olefin" encompasses hydrocarbons having more than one carbon-carbon double bond (e.g., di-olefins, tri-olefins, etc.). Hydrocarbons having more than one carbon-carbon double bond and derivatives thereof are also referred to as "polyenes." The term "fatty olefin" refers to an olefin having at least four carbon atoms; fatty olefins can have, for example, 4, 6, 8, 10, 12, 14, 16, 18, 20, 22, 24, or 28 carbon atoms. A "fatty olefin derivative" refers to a compound obtained from an olefin starting material or a fatty olefin starting material. Examples of fatty olefin derivatives include, but are not limited to, unsaturated fatty alcohols, unsaturated fatty alcohol acetates, unsaturated fatty aldehydes, unsaturated fatty acid esters, and polyenes. In certain embodiments, fatty olefins derivatives synthesized according to the methods of the invention have from 8 to 28 carbon atoms.

As used herein, the term "metathesis reaction" refers to a catalytic reaction which involves the interchange of alkylidene units (i.e., $R_2C=$ units) among compounds containing one or more carbon-carbon double bonds (e.g., olefinic compounds) via the formation and cleavage of the carbon-carbon double bonds. Metathesis can occur between two molecules having the same structure (often referred to as self-metathesis) and/or between two molecules having different structures (often referred to as cross-metathesis). The term "metathesis reaction partner" refers to a compound having a carbon-carbon double bond that can react with an olefin in a metathesis reaction to form a new carbon-carbon double bond.

As used herein, the term "metathesis catalyst" refers to any catalyst or catalyst system that catalyzes a metathesis reaction. One of skill in the art will appreciate that a metathesis catalyst can participate in a metathesis reaction so as to increase the rate of the reaction, but is itself not consumed in the reaction. A "tungsten catalyst" refers to a metathesis catalyst having one or more tungsten atoms. A "molybdenum catalyst" refers to a metathesis catalyst having one or more molybdenum atoms. A "ruthenium catalyst" refers to a metathesis catalyst having one or more ruthenium atoms.

As used herein, the term "metathesis product" refers to an olefin containing at least one double bond, the bond being formed via a metathesis reaction.

As used herein, the term "converting" refers to reacting a starting material with at least one reagent to form an intermediate species or a product. The converting can also include reacting an intermediate with at least one reagent to form a further intermediate species or a product.

As used herein, the term "oxidizing" refers to the transfer of electron density from a substrate compound to an oxidizing agent. The electron density transfer typically occurs via a process including addition of oxygen to the substrate compound or removal of hydrogen from the substrate compound. The term "oxidizing agent" refers to a reagent which can accept electron density from the substrate compound. Examples of oxidizing agents include, but are not limited to, pyridinium chlorochromate, o-iodoxybenzoic acid, and 2,2, 6,6-tetramethylpiperidine 1-oxyl.

As used herein, the term "reducing" refers to the transfer of electron density from a reducing agent to a substrate compound. The electron density transfer typically occurs via a process including addition of hydrogen to the substrate compound. The term "reducing agent" refers to a reagent which can donate electron density to the substrate compound. Examples of reducing agents include, but are not limited to, sodium borohydride and sodium triacetoxyborohydride.

As used herein, the term "acylating" refers to converting a alcohol group (—OH), to and ester group (—OC(O)R, where R is an alkyl group as described below).

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. In some embodiments, "cycloaliphatic" (or "carbocycle") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl, or (cycloalkyl)alkenyl. The term "heteroaliphatic" refers to an aliphatic group wherein at least one carbon atom of the aliphatic group is replaced with a heteroatom (i.e., nitrogen, oxygen, or sulfur, including any oxidized form of nitrogen or sulfur, and any quaternized form of a basic nitrogen).

As used herein, the term "alkyl" is given its ordinary meaning in the art and includes straight-chain alkyl groups and branched-chain alkyl groups. In certain embodiments, a straight chain or branched chain alkyl has about 1-30 carbon atoms in its backbone (e.g., $C_1$-$C_{30}$ for straight chain, $C_3$-$C_{30}$ for branched chain), and alternatively, about 1-20. In some embodiments, an alkyl group may be a lower alkyl group, wherein a lower alkyl group comprises 1-4 carbon atoms (e.g., $C_1$-$C_4$ for straight chain lower alkyls).

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, and the like.

As used herein, the term "alkoxy" refers to a moiety —OR wherein R is an alkyl group as defined above. The term "silylalkyl" refers to an alkyl group as defined herein wherein as least one carbon atom is replaced with a silicon atom. The term "silyloxy" refers to a moiety —$OSiR_3$, wherein each R is independently selected from the group consisting of hydrogen, alkyl, substituted alkyl, aryl, and substituted aryl as described herein.

As used herein, the term "cycloalkyl" refers to a saturated, monocyclic hydrocarbon, bicyclic hydrocarbon, or tricyclic hydrocarbon group that has a single point of attachment to the rest of the molecule. Cycloalkyl groups include alkyl substituted cycloalkyl groups and cycloalkyl substituted alkyl groups. In some embodiments, cycloalkyl rings have from about 3-10 carbon atoms in their ring structure where such rings are monocyclic or bicyclic, and alternatively about 5, 6 or 7 carbons in the ring structure.

As used herein, the term "alkenyl" refers to an alkyl group, as defined herein, having one or more double bonds. The term "heteroalkenyl" refers to an alkenyl group wherein one or more carbon atoms is replaced with a heteroatom (i.e., nitrogen, oxygen, or sulfur, including any oxidized form of nitrogen or sulfur, and any quaternized form of a basic nitrogen).

As used herein, the term "alkenol" refers to a compound having a formula R—OR' wherein R is an alkenyl group and R' is hydrogen or an alcohol protecting group.

As used herein, the term "alkynyl" refers to an alkyl group, as defined herein, having one or more triple bonds.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "aryloxy" refers to a moiety —OR, wherein R is an aryl group as defined above.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 pi electrons shared in a cyclic arrangement; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least one functional group that has sufficient ionic character to coordinate the metal center, such as a biphenolate group, for example.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more heteroatoms (e.g., one to four heteroatoms), as defined above. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl-ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

The terms "halogen" and "halo" are used interchangeably to refer to F, $C_1$, Br, or I.

As used herein, the term "protecting group" refers to a chemical moiety that renders a functional group unreactive, but is also removable so as to restore the functional group. Examples of "alcohol protecting groups" include, but are not limited to, benzyl; tert-butyl; trityl; tert-butyldimethylsilyl (TBDMS; TBS); 4,5-dimethoxy-2-nitrobenzyloxycarbonyl (Dmnb); propargyloxycarbonyl (Poc); and the like. Examples of "amine protecting groups" include, but are not limited to, benzyloxycarbonyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other alcohol protecting groups and amine protecting groups are known to those of skill in the art including, for example, those described by Green and Wuts (*Protective Groups in Organic Synthesis*, $4^{th}$ Ed. 2007, Wiley-Interscience, New York).

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are generally those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^{\alpha}$; —$(CH_2)_{0-4}OR^{\alpha}$; —O$(CH_2)_{0-4}R^{\alpha}$, —O—$(CH_2)_{0-4}C(O)OR^{\alpha}$; —$(CH_2)_{0-4}CH(OR^{\alpha})_2$; —$(CH_2)_{0-4}SR^{\alpha}$; —$(CH_2)_{0-4}Ph$, which may be substituted with $R^{\alpha}$; —$(CH_2)_{0-4}O(CH_2)_{0-1}Ph$ which may be substituted with $R^{\alpha}$; —CH=CHPh, which may be substituted with $R^{\alpha}$; —$(CH_2)_{0-4}O(CH_2)_{0-1}$-pyridyl which may be substituted with $R^{\alpha}$; —$NO_2$; —CN; —$N_3$; —$(CH_2)_{0-4}N(R^{\alpha})_2$; —$(CH_2)_{0-4}N(R^{\alpha})C(O)R^{\alpha}$; —$N(R^{\circ})C(S)R^{\alpha}$; —$(CH_2)_{0-4}N(R^{\alpha})C(O)NR^{\alpha}_2$; —$N(R^{\alpha})C(S)NR^{\alpha}_2$; —$(CH_2)_{0-4}N(R^{\alpha})C(O)OR^{\alpha}$; —$N(R^{\alpha})N(R^{\alpha})C(O)R^{\alpha}$; —$N(R^{\alpha})N(R^{\alpha})C(O)NR^{\alpha}_2$; —$N(R^{\alpha})N(R^{\alpha})C(O)OR^{\alpha}$; —$(CH_2)_{0-4}C(O)R^{\alpha}$; —$C(S)R^{\alpha}$; —$(CH_2)_{0-4}C(O)OR^{\alpha}$; —$(CH_2)_{0-4}C(O)SR^{\alpha}$; —$(CH_2)_{0-4}C(O)OSiR^{\alpha}_3$; —$(CH_2)_{0-4}OC(O)R^{\alpha}$; —OC(O)$(CH_2)_{0-4}SR$—SC(S)$SR^{\alpha}$; —$(CH_2)_{0-4}SC(O)R^{\alpha}$; —$(CH_2)_{0-4}C(O)NR^{\alpha}_2$; —$C(S)NR^{\alpha}_2$, —$C(S)SR^{\alpha}$; —SC(S)$SR^{\alpha}$, —$(CH_2)_{0-4}OC(O)NR^{\alpha}_2$; —C(O)N$(OR^{\alpha})R^{\alpha}$; —C(O)C(O)$R^{\alpha}$; —C(O)$CH_2C(O)R^{\alpha}$; —C(NOR^{\alpha})$R^{\alpha}$; —$(CH_2)_{0-4}SSR^{\alpha}$; —$(CH_2)_{0-4}S(O)_2R^{\alpha}$; —$(CH_2)_{0-4}S(O)_2OR^{\alpha}$; —$(CH_2)_{0-4}OS(O)_2R^{\alpha}$; —$S(O)_2NR^{\alpha}_2$; —$(CH_2)_{0-4}S(O)R^{\alpha}$; —$N(R^{\alpha})S(O)_2NR^{\alpha}_2$; —$N(R^{\alpha})S(O)_2R^{\alpha}$; —$N(OR^{\alpha})R^{\alpha}$; —C(NH)$NR^{\alpha}_2$; —$P(O)_2R^{\alpha}$; —P(O)$R^{\alpha}_2$; —OP(O)$R^{\alpha}_2$; —OP(O)$(OR^{\alpha})_2$; $SiR^{\alpha}_3$; —$(C_{1-4}$ straight or branched)alkylene)O—$N(R^{\alpha})_2$; or —$(C_{1-4}$ straight or branched)alkylene)C(O)O—$N(R^{\alpha})_2$, wherein each $R^{\alpha}$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aromatic ring having 0-4 heteroatoms independently selected from nitrogen, oxygen, and sulfur, or, notwithstanding the definition above, two independent occurrences of $R^{\alpha}$, taken together with their intervening atom(s), form a 3-12-membered saturated, partially unsaturated, or aromatic mono- or bi-cyclic ring having 0-4 heteroatoms independently selected from nitrogen, oxygen, and sulfur, which may be substituted as defined below.

Suitable monovalent substituents on $R^{\alpha}$ (or the ring formed by taking two independent occurrences of $R^{\alpha}$ together with their intervening atoms), are independently halogen, —$(CH_2)_{0-2}R^{\beta}$; -(halo$R^{\beta}$); —$(CH_2)_{0-2}OH$; —$(CH_2)_{0-2}OR^{\beta}$; —$(CH_2)_{0-2}CH(OR^{\beta})_2$; —O(halo$R^{\beta}$);

—CN; —N$_3$; —(CH$_2$)$_{0-2}$C(O)R$^\beta$; —(CH$_2$)$_{0-2}$C(O)OH; —(CH$_2$)$_{0-2}$C(O)OR$^\beta$; —(CH$_2$)$_{0-2}$SR$^\beta$; —(CH$_2$)$_{0-2}$SH; —(CH$_2$)$_{0-2}$NH$_2$; —(CH$_2$)$_{0-2}$NHR$^\beta$; —(CH$_2$)$_{0-2}$NR$^\beta{}_2$; —NO$_2$; SiR$^\beta{}_3$; —OSiR$^\beta{}_3$; —C(O)SR$^\beta$; —(C$_{1-4}$ straight or branched alkylene)C(O)OR$^\beta$; or —SSR$^\beta$; wherein each RR is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aromatic ring having 0-4 heteroatoms independently selected from nitrogen, oxygen, and sulfur. Suitable divalent substituents on a saturated carbon atom of R$^\alpha$ include =O and =S.

Suitable divalent substituents on a saturated carbon atom of an "optionally substituted" group include the following: =O; =S; =NNR$^\gamma{}_2$; =NNHC(O)R$^\gamma$; =NNHC(O)OR$^\gamma$; =NNHS(O)$_2$R$^\gamma$; =NR$^\gamma$; =NOR$^\gamma$; —O(C(R$^\gamma{}_2$))$_{2-3}$O—; or —S(C(R$^\gamma{}_2$))$_{2-3}$S—; wherein each independent occurrence of R$^\gamma$ is selected from hydrogen, C$_{1-6}$ aliphatic which may be substituted as defined below, or an unsubstituted 5-6-membered saturated, partially unsaturated, or aromatic ring having 0-4 heteroatoms independently selected from nitrogen, oxygen, and sulfur. Suitable divalent substituents that are bound to vicinal substitutable carbons of an "optionally substituted" group include: —O(CR$^\beta{}_2$)$_{2-3}$O—, wherein each independent occurrence of RR is selected from hydrogen, C$_{1-6}$ aliphatic which may be substituted as defined below, or an unsubstituted 5-6-membered saturated, partially unsaturated, or aromatic ring having 0-4 heteroatoms independently selected from nitrogen, oxygen, and sulfur.

Suitable substituents on the aliphatic group of R$^\gamma$ include halogen, —R$^\delta$, -(haloR$^\delta$), —OH, —OR$^\delta$, —O(haloR$^\delta$), —CN, —C(O)OH, —C(O)OR$^\delta$, —NH$_2$, —NHR$^\delta$, —NR$^\delta{}_2$, or —NO$_2$, wherein each R$^\delta$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aromatic ring having 0-4 heteroatoms independently selected from nitrogen, oxygen, and sulfur.

Suitable substituents on a substitutable nitrogen of an "optionally substituted" group include —R$^\epsilon$, —NR$^\epsilon{}_2$, —C(O)R$^\epsilon$, —C(O)OR$^\epsilon$, —C(O)C(O)R$^\epsilon$, —C(O)CH$_2$C(O) R$^\epsilon$, —S(O)$_2$R$^\epsilon$, —S(O)$_2$NR$^\epsilon{}_2$, —C(S)NR$^\epsilon{}_2$, —C(NH)NR$^\epsilon{}_2$, or —N(R$^\epsilon$)S(O)$_2$R$^\epsilon$; wherein each R$^\epsilon$ is independently hydrogen, C$_{1-6}$ aliphatic which may be substituted as defined below, unsubstituted —OPh, or an unsubstituted 5-6-membered saturated, partially unsaturated, or aromatic ring having 0-4 heteroatoms independently selected from nitrogen, oxygen, and sulfur, or, notwithstanding the definition above, two independent occurrences of RE, taken together with their intervening atom(s) form an unsubstituted 3-12-membered saturated, partially unsaturated, or aromatic mono- or bicyclic ring having 0-4 heteroatoms independently selected from nitrogen, oxygen, and sulfur.

Suitable substituents on the aliphatic group of R$^\epsilon$ are independently halogen, —R$^\delta$, -(haloR$^\delta$), —OH, —OR$^\delta$, —CN, —C(O)OH, —C(O)OR$^\delta$, —NH$_2$, —NHR$^\delta$, —NR$^\delta{}_2$, or —NO$_2$, wherein each R$^\delta$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aromatic ring having 0-4 heteroatoms independently selected from nitrogen, oxygen, and sulfur.

In some embodiments, the term "substituted" is contemplated to include all permissible substituents of organic compounds, "permissible" being in the context of the chemical rules of valence known to those of ordinary skill in the art. In some cases, "substituted" may generally refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group. In a broad aspect, permissible substituents include acyclic and cyclic, branched and unbranched, carbocyclic and heterocyclic, aromatic and nonaromatic substituents of organic compounds. Illustrative substituents include, for example, those described herein. Permissible substituents can be one or more and the same or different for appropriate organic compounds. For example, a substituted alkyl group may be CF$_3$. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, carboxamido, nitro, acyloxy, aminoalkyl, alkylaminoaryl, alkylaryl, alkylaminoalkyl, alkoxyaryl, arylamino, arylalkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like.

As used herein, the term "natural oil" refers to an oil derived from a plant, yeast, or animal source. The term "natural oil" includes natural oil derivatives, unless otherwise indicated. The sources can be modified plant, yeast, or animal sources (e.g., genetically modified plant, yeast, or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

"Natural oil derivatives" refer to compounds (or mixtures of compounds) derived from natural oils using any one or combination of methods known in the art. Such methods include but are not limited to saponification, fat splitting, transesterification, esterification, hydrogenation (partial or full), isomerization, oxidation, reduction, and metathesis. Representative non-limiting examples of natural oil derivatives include gums, phospholipids, soapstock, acidulated soapstock, distillate or distillate sludge, fatty acids, and fatty acid alkyl esters (e.g., non-limiting examples such as 2-ethylhexyl ester), and hydroxy substituted variations thereof. For example, the natural oil derivative may be a fatty acid methyl ester ("FAME") derived from the glyceride of the natural oil.

The term "contaminant" refers broadly and without limitation to any impurity, regardless of the amount in which it is present, admixed with a substrate to be used in olefin metathesis. A "catalyst poisoning contaminant" refers to a contaminant having the potential to adversely affect the performance of a metathesis catalyst. Examples of catalyst poisoning contaminants include, but are not limited to, water, peroxides, and hydroperoxides.

As used herein, the term "metal alkyl compound" refers to a compound having the formula $MR_m$ wherein, M is a metal (e.g., a Group II metal or a Group IIIA metal), each R is independently an alkyl radical of 1 to about 20 carbon atoms, and subscript m corresponds to the valence of M. Examples of metal alkyl compounds include $Mg(CH_3)_2$, $Zn(CH_3)_2$, $Al(CH_3)_3$, and the like. Metal alkyl compounds also include substances having one or more halogen or hydride groups, such as Grignard reagents, diisobutylaluminum hydride, and the like.

III. DESCRIPTION OF THE EMBODIMENTS

A. Preparation of 8- and 11-Unsaturated Alkenols and Related Materials

In one aspect, the invention provides a method for synthesizing a fatty olefin derivative. The method includes:

a) contacting an olefin according to Formula I

(I)

with a metathesis reaction partner according to Formula II

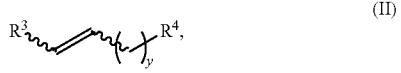
(II)

in the presence of a metathesis catalyst under conditions sufficient to form a metathesis product according to Formula III

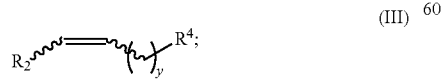
(III)

and b) optionally converting the metathesis product to the fatty olefin derivative;

wherein:

$R^1$ and $R^3$ are independently selected from the group consisting of hydrogen and $C_{1-18}$ alkyl;

$R^2$ is $C_{1-18}$ alkyl;

$R^4$ is selected from the group consisting of $-C(O)OR^{4a}$ and $-CH_2OR^{4b}$;

$R^{4a}$ is selected from the group consisting of hydrogen and $C_{1-8}$ alkyl;

$R^{4b}$ is an alcohol protecting group; and subscript y is 6 or 9.

In the methods of the invention, olefins can be reacted with a variety of metathesis reaction partners to obtain pheromones, pheromone precursors, and other useful fatty olefin derivatives.

Certain embodiments of the method are summarized in Scheme 1. A protected fatty alcohol, a fatty acid, or an alkyl ester of a fatty acid can be reacted with an α-olefin in the presence of a group VI olefin metathesis catalyst (e.g., a Z-selective Group VI metathesis catalyst) to produce a statistical mixture of the desired cross-metathesis product and the self-metathesis co-products. The ratio of the feedstocks can be adjusted to vary the ratio of products. For example, feeding the reactants in a 1.5:1 molar ratio of α-olefin to fatty alcohol/ester can result in a 3:2.25:1 ratio of the internal olefin, metathesis product, and diol/diester products. This process condition results in the efficient utilization of the more costly protected fatty alcohol/ester.

Scheme 1

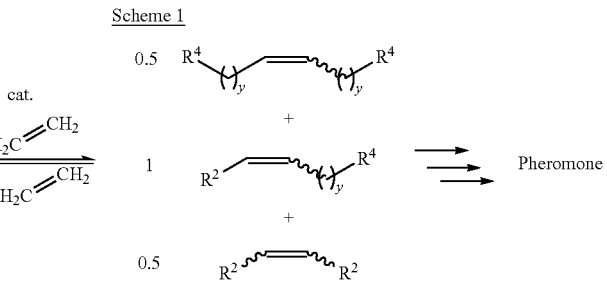

Products obtained from the metathesis of various olefins with 8- or 11-unsaturated fatty alcohols and fatty acid esters can be used for the synthesis of a number of pheromones including, but not limited to, those set forth in Table 1.

TABLE 1

| Olefin | Fatty Olefin Derivative |
| --- | --- |
| But-1-ene | (E)-8-Undecenyl acetate |
| But-1-ene | (Z)-8-Undecenyl acetate |
| Pent-1-ene | (E)-8-Dodecen-1-ol |
| Pent-1-ene | (E)-8-Dodecenyl acetate |
| Pent-1-ene | (Z)-8-Dodecen-1-ol |
| Pent-1-ene | (Z)-8-Dodecenyl acetate |
| Hex-1-ene | (E)-8-Tridecenyl acetate |
| Hex-1-ene | (Z)-8-Tridecenyl acetate |
| Hept-1-ene | (E)-8-Tetradecenyl acetate |
| Hept-1-ene | (E)-8-Tetradecenyl formate |
| Hept-1-ene | (Z)-8-Tetradecen-1-ol |
| Hept-1-ene | (Z)-8-Tetradecenyl acetate |
| Hept-1-ene | (Z)-8-Tetradecenyl formate |
| Oct-1-ene | (Z)-8-Pentadecenyl acetate |

TABLE 1-continued

| Olefin | Fatty Olefin Derivative |
| --- | --- |
| 7-Methyl-1-nonene | (E)-14-Methyl-8-hexadecen-1-ol |
| 7-Methyl-1-nonene | (E)-14-Methyl-8-hexadecenal |
| 7-Methyl-1-nonene | (Z)-14-Methyl-8-hexadecen-1-ol |
| 7-Methyl-1-nonene | (Z)-14-Methyl-8-hexadecenal |
| 7-Methyl-1-nonene | Methyl (E)-14-methyl-8-hexadecenoate |
| 7-Methyl-1-nonene | Methyl (Z)-14-methyl-8-hexadecenoate |
| But-1-ene | (E)-8-Undecenyl acetate |
| But-1-ene | (Z)-8-Undecenyl acetate |
| Pent-1-ene | (E)-8-Dodecen-1-ol |
| Pent-1-ene | (E)-8-Dodecenyl acetate |
| Pent-1-ene | (Z)-8-Dodecen-1-ol |
| Pent-1-ene | (Z)-8-Dodecenyl acetate |
| Hex-1-ene | (E)-8-Tridecenyl acetate |
| Hex-1-ene | (Z)-8-Tridecenyl acetate |
| Hept-1-ene | (E)-8-Tetradecenyl acetate |
| Hept-1-ene | (E)-8-Tetradecenyl formate |
| Hept-1-ene | (Z)-8-Tetradecen-1-ol |
| Hept-1-ene | (Z)-8-Tetradecenyl acetate |
| Hept-1-ene | (Z)-8-Tetradecenyl formate |
| Oct-1-ene | (Z)-8-Pentadecenyl acetate |
| 7-Methyl-1-nonene | (E)-14-Methyl-8-hexadecen-1-ol |
| 7-Methyl-1-nonene | (E)-14-Methyl-8-hexadecenal |
| 7-Methyl-1-nonene | (Z)-14-Methyl-8-hexadecen-1-ol |
| 7-Methyl-1-nonene | (Z)-14-Methyl-8-hexadecenal |
| 7-Methyl-1-nonene | Methyl (E)-14-methyl-8-hexadecenoate |
| 7-Methyl-1-nonene | Methyl (Z)-14-methyl-8-hexadecenoate |
| Hex-1-ene | (Z)-11-hexadecenal |
| Hex-1-ene | (Z)-11-hexadecenyl acetate |
| But-1-ene | (Z)-11-tetradecenyl acetate |

As described herein, diols and related intermediates can be prepared according to the methods of the invention and used for the synthesis of a number of pheromones including, but not limited to, those set forth in Table 2.

TABLE 2

| Semiochemical | Abbreviation | α,ω-Diol | α-Olefin |
| --- | --- | --- | --- |
| (Z)-dodec-7-en-1-yl acetate | Z7-12Ac | octane-1,8-diol | hex-1-ene |
| (Z)-tetradec-9-en-1-yl acetate | Z9-14Ac | decane-1,10-diol | hex-1-ene |
| (Z)-hexadec-9-enal | Z9-16Ald | decane-1,10-diol | oct-1-ene |
| (Z)-hexadec-11-enal | Z11-16Ald | dodecane-1,12-diol | hex-1-ene |
| (Z)-hexadec-11-en-1-yl acetate | Z11-16Ac | dodecane-1,12-diol | hex-1-ene |
| (Z)-octadec-13-enal | Z13-18Ald | tetraecane-1,14-diol | hex-1-ene |
| (Z)-dodec-8-en-1-yl acetate | Z8-12Ac | nonane-1,9-diol | pent-1-ene |
| (Z)-dodec-9-en-1-yl acetate | Z9-12Ac | octane-1,8-diol | but-1-ene |
| (Z)-tetradec-11-en-1-yl acetate | Z11-14Ac | octane-1,8-diol | but-1-ene |

Accordingly, some embodiments of the invention provide a method wherein $R^4$ is —$CH_2OR^{4a}$, i.e., the metathesis reaction partner is a compound according to Formula IIa:

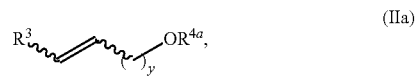

and the metathesis reaction product is a compound according to Formula IIIa:

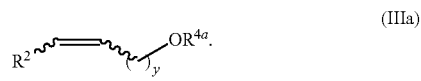

In some embodiments, $R^4$ is —$C(O)OR^{4b}$, i.e., the metathesis reaction partner is a compound according to Formula IIb:

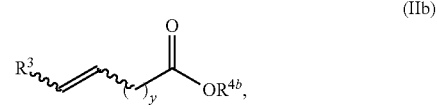

and the metathesis reaction product is a compound according to Formula IIIb:

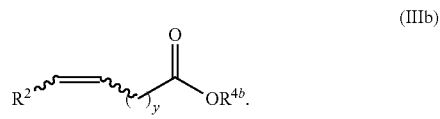

Metathesis products according to Formula IIIa or Formula IIIb wherein the olefin is a Z olefin can be prepared using a number of Z-selective catalysts as described below.

In some embodiments $R^2$ is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, or octadecyl. In some embodiments $R^2$ is pentyl, hexyl, heptyl, octyl, or nonyl. In some embodiments $R^2$ is ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, or octadecenyl. In some embodiments $R^2$ is pentenyl, hexenyl, heptenyl, octenyl, or nonenyl.

The invention also provides advantageous routes to 8- and 11-unsaturated intermediates for use in metathesis reactions. As shown in Schemes 2 and 3, for example, 8- and 11-unsaturated intermediates can be prepared from commercially available diols and halogenated alcohols.

Scheme 2

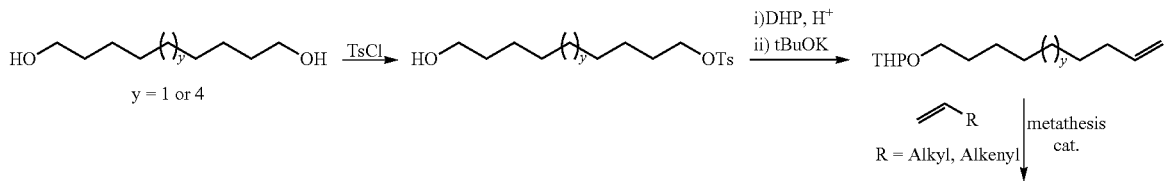

-continued

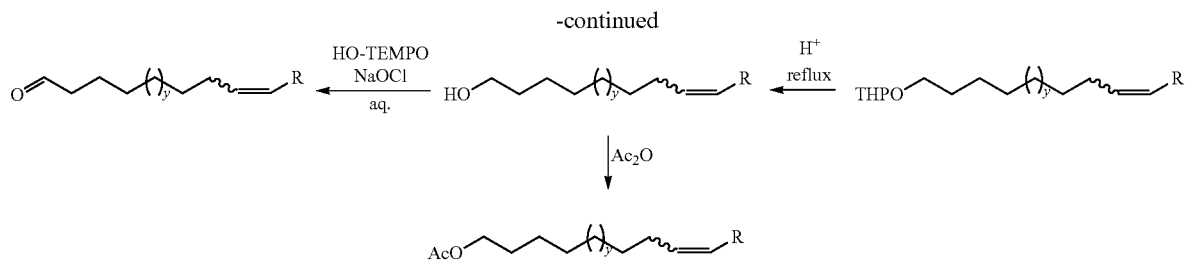

Scheme 3

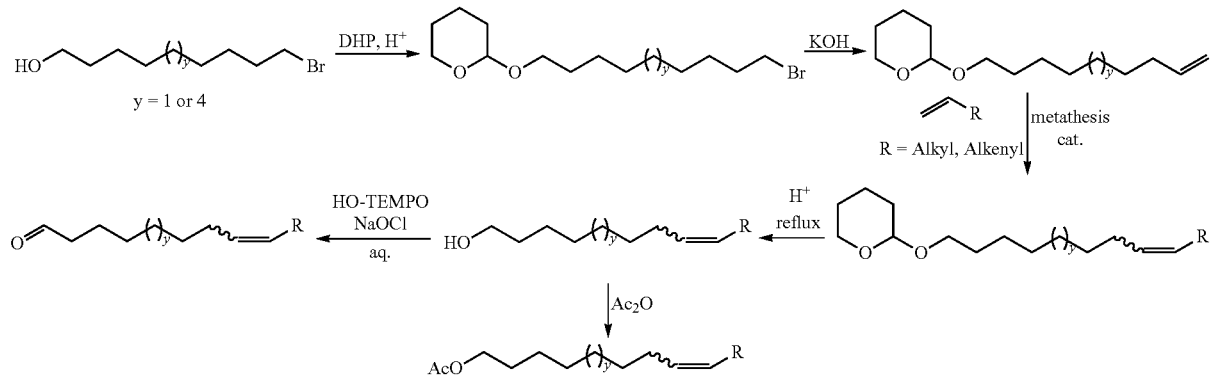

Accordingly, some embodiments of the invention provide methods wherein metathesis reaction partners according to Formula II are prepared by a method comprising:

i) converting a diol according to Formula VII:

 (VII)

to an alcohol according to Formula VIII:

 (VIII)

wherein $R^5$ is a leaving group;

ii) protecting the alcohol to form a protected alcohol according to Formula IX

 (IX)

and iii) eliminating leaving group $R^5$ to form the metathesis reaction partner according to Formula II.

Diol VII can be converted to an alcohol VIII with any suitable leaving group $R^5$. In some embodiments, $R^5$ is a halogen. For example, $R^5$ can be chloro, bromo, or iodo. In some embodiments, $R^5$ is bromo. In some embodiments, $R^5$ is a sulfonate (i.e., —OS(O)$_2$R, wherein R is alkyl, haloalkyl, aryl, or substituted aryl). Suitable sulfonates include, but are not limited to, mesylate (methanesulfonate), triflate (trifluoromethanesulfonate), besylate (benzenesulfonate), tosylate (p-toluenesulfonate), and brosylate (4-bromobenzenesulfonate). In some embodiments, $R^5$ is mesylate (abbreviated —OMs) or tosylate (abbreviated —OTs).

Protected alcohol IX can contain any suitable protecting group $R^{4a}$. Examples of protecting groups include, but are not limited to, methyl ethers, a substituted methyl ethers, an ethyl ethers, a substituted ethyl ethers, a benzyl ethers, a substituted benzyl ether, and a silyl ethers. In some embodiments, protecting group $R^{4a}$ is a substituted methyl ether. For example, $R^{4a}$ can be methoxymethyl; methylthiomethyl; (phenyldimethylsilyl)-methoxymethyl; benzyloxymethyl; p-methoxybenzytoxymethyl; [(3,4-dimethoxybenzyl)oxy]methyl; p-nitrobenzyloxymethyl; o-nitrobenzyloxymethyl; [(R)-1-(2-nitrophenyl)ethoxy]methyl; (4-methoxyphenoxy)methyl; guaiacolmethyl; {(p-phenylphenyl)oxy}methyl; t-butoxymethyl; siloxymethyl; 2-methoxyethoxymethyl; 2-cyanoethoxymethyl; bis(2-chloroethoxy)methyl; 2,2,2-trichloroethoxymethyl; 2-(trimethylsilyl)ethoxymethyl; menthoxymethyl; O-bis(2-acetoxyethoxy)methyl; tetrahydropyranyl; fluorine-substituted tetrahydropyranyl; 3-bromotetrahydro-pyranyl; tetrahydrothiopyranyl; 1-methoxycyclohexyl; 4-methoxytetrahydropyranyl; 4-methoxytetrahydrothiopyranyl; 4-methoxytetrahydrothiopyranyl S,S-dioxide; 1-[(2-chloro-4-methyl)phenyl]-4-methoxypiperidin-4-yl; 1-(2-fluorophenyl)-4-methoxypiperidin-4-yl; 1-(4-chlorophenyl)-4-methoxypiperidin-4-yl; 1,4-dioxan-2-yl; tetrahydrofuranyl; tetrahydrothiofuranyl; or 2.3.3a,4,5,6,7,7a-octahydro-7,8,8-trimethyl-4,7-methanobenzofuran-2-yl. In some embodiments, $R^{4a}$ is selected from the group consisting of tetrahydropyranyl, fluorine-substituted tetrahydropyranyl; 3-bromotetrahydropyranyl; tetrahydrothiopyranyl; 1-methoxycyclohexyl; 4-methoxytetrahydro-pyranyl; 4-methoxytetrahydrothiopyranyl; and 4-methoxytetrahydrothiopyranyl S,S-dioxide. In some embodiments, $R^{4a}$ is tetrahydropyranyl. The protecting groups can be introduced via a number of known methods, including those described by Green and Wuts, supra.

In some embodiments, the metathesis reaction partner according to Formula II is prepared by a method comprising:
i) protecting an alcohol according to Formula VIIIa:

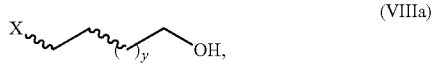

wherein X is a halogen;
to form a protected alcohol according to Formula IXa

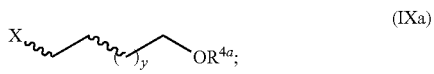

and
ii) eliminating the halogen X to form the metathesis reaction partner according to Formula II.

A number of useful intermediates for metathesis reactions can be derived from natural oils, i.e., oils produced by plants, animals, or other organisms (including genetically engineered organisms such as engineered bacteria, yeast, or algae). Representative examples of natural oils include but are not limited to vegetable oils, algal oils, animal fats, tall oils (e.g., by-products of wood pulp manufacture), derivatives of these oils, and the like, and combinations thereof. Representative examples of vegetable oils include but are not limited to canola oil, rapeseed oil, coconut oil, corn oil, cottonseed oil, olive oil, palm oil, peanut oil, safflower oil, sesame oil, soybean oil, sunflower oil, high oleic sunflower oil, linseed oil, palm kernel oil, tung oil, jatropha oil, jojoba oil, mustard oil, pennycress oil, camelina oil, hemp oil, castor oil, and the like, and combinations thereof. Representative examples of animal fats include but are not limited to lard, tallow, poultry fat, yellow grease, brown grease, fish oil, and the like, and combinations thereof. The natural oil can be refined, bleached, and/or deodorized. In some embodiments, the natural oil is selected from the group consisting of canola oil, soybean oil, palm oil, olive oil, peanut oil, sesame oil, sunflower oil, high oleic sunflower oil, and combinations thereof.

Representative examples of natural oil derivatives for use in accordance with the method of the invention include, but are not limited to, gums, phospholipids, soapstock, acidulated soapstock, distillate or distillate sludge, fatty acids, fatty acid esters (e.g., non-limiting examples such as 2-ethylhexyl ester, etc.), hydroxy-substituted variations thereof, and the like, and combinations thereof. In some embodiments, the natural oil derivative comprises an ester. In some embodiments, the derivative is selected from the group consisting of a monoacylglyceride (MAG), a diacylglyceride (DAG), a triacylglyceride (TAG), and combinations thereof. In some embodiments, the natural oil derivative comprises a fatty acid methyl ester (FAME) derived from the glyceride of the natural oil.

In some embodiments, a feedstock includes canola or soybean oil, e.g., refined, bleached, and/or deodorized soybean oil (i.e., RBD soybean oil). Soybean oil typically contains about 95% weight or greater (e.g., 99% weight or greater) triglycerides of fatty acids. Major fatty acids in the polyol esters of soybean oil include saturated fatty acids, including palmitic acid (hexadecanoic acid) and stearic acid (octadecanoic acid), and unsaturated fatty acids, including oleic acid (9-octadecenoic acid), linoleic acid (9, 12-octadecadienoic acid), and linolenic acid (9, 12, 15-octadecatrienoic acid).

In some embodiments, materials to be reacted in a metathesis reaction-including those derived from natural oils-will contain one or more contaminants with the potential to adversely affect the performance of a metathesis catalyst. Such contaminants can be referred to as "catalyst poisons" or "catalyst poisoning contaminants." Contaminant levels in natural oil feedstocks can be reduced using known methods including those described, for example, in U.S. patent application Ser. No. 15/354,916, issued as U.S. Pat. No. 9,776,179, and International Pat. Appl. No. PCT/US2016/062595, published as WO 2017/087710, which applications are incorporated herein by reference in their entirety.

Representative contaminants include but are not limited to water, peroxides, peroxide decomposition products, hydroperoxides, protic materials, polar materials, Lewis basic catalyst poisons, and the like, and combinations thereof. It is to be understood that some contaminants may properly be classified in multiple categories (e.g., an alcohol can be considered both a protic material and a polar material). It is to be further understood that different catalysts may have different susceptibilities to a particular contaminant, and that a contaminant that adversely affects the performance of one catalyst (e.g., a ruthenium-based catalyst) may or may not affect (to a similar extent or to any extent whatsoever) a different catalyst (e.g., a molybdenum-based catalyst).

Representative protic materials that may be found as contaminants in a substrate that is to be reacted in a metathesis reaction include but are not limited to materials having a hydrogen atom bonded to oxygen (e.g., carboxylic acids, alcohols, and the like) and/or a hydrogen atom bonded to nitrogen (e.g., primary amines, secondary amines, and the like). In some embodiments, particularly though not exclusively in natural oil substrates, a protic material contaminant may comprise a carboxylic acid functional group, a hydroxyl functional group, or a combination thereof. In some embodiments, the protic material is selected from the group consisting of free fatty acids, hydroxyl-containing materials, MAGs, DAGs, and the like, and combinations thereof.

Representative polar materials that may be found as contaminants in a substrate that is to be reacted in a metathesis reaction include but are not limited to heteroatom-containing materials such as oxygenates. In some embodiments, the polar material is selected from the group consisting of alcohols, aldehydes, ethers, and the like, and combinations thereof.

Representative Lewis basic catalyst poisons that may be found as contaminants in a substrate that is to be reacted in a metathesis reaction include but are not limited to heteroatom-containing materials. In some embodiments, the Lewis basic catalyst poisons are selected from the group consisting of N-containing materials, P-containing materials, S-containing materials, and the like, and combinations thereof.

Reaction materials containing contaminants can be treated with one or more conditioning agents that mitigate potentially adverse effects of one or more of the contaminants. Conditioning agents that can be used in the methods of the invention (individually, or in combination sequentially or simultaneously) include heat, molecular sieves, alumina (aluminum oxide), silica gel, montmorillonite clay, fuller's earth, bleaching clay, diatomaceous earth, zeolites, kaolin, activated metals (e.g., Cu, Mg, and the like), acid anhydrides (e.g., acetic anhydride and the like), activated carbon (i.e., activated charcoal), soda ash, metal hydrides (e.g., alkaline earth metal hydrides such as $CaH_2$ and the like), metal sulfates (e.g., alkaline earth metal sulfates such as calcium sulfate, magnesium sulfate, and the like; alkali metal sulfates such as potassium sulfate, sodium sulfate, and the like; and other metal sulfates such as aluminum sulfate, potassium magnesium sulfate, and the like), metal halides (e.g., alkali earth metal halides such as potassium chloride and the like), metal carbonates (e.g., calcium carbonate, sodium carbonate, and the like), metal silicates (e.g., magnesium silicate and the like), phosphorous pentoxide, metal aluminum hydrides (e.g., alkali metal aluminum hydrides such as $LiAlH_4$, $NaAlH_4$, and the like), alkyl aluminum hydrides (e.g., DIBALH), metal borohydrides (e.g., alkali metal borohydrides such as $LiBH_4$, $NaBH_4$, and the like), organometallic reagents (e.g., Grignard reagents; organolithium reagents such as n-butyl lithium, t-butyl lithium, sec-butyl lithium; trialkyl aluminums such as triethyl aluminum, tributyl aluminum, triisobutyl aluminum, triisopropyl aluminum, trioctyl aluminum, and the like, metal amides (e.g., lithium diisopropyl amide, metal bis(trimethylsilyl) amides such as KHMDS, and the like), palladium on carbon (Pd/C) catalysts, and combinations thereof.

In some embodiments, the conditioning agent is a metal alkyl compound. In some embodiments, the metal, M, can be lithium, sodium, potassium, magnesium, calcium, zinc, cadmium, aluminum, or gallium. Examples of suitable alkyl radicals, R, include, but are not limited to, methyl, ethyl, butyl, hexyl, decyl, tetradecyl, and eicosyl. Examples of metal alkyl compounds include, but are not limited to, $Mg(CH_3)_2$, $Mg(C_2H_5)_2$, $Mg(C_2H_5)(C_4H_9)$, $Mg(C_4H_9)_2$, $Mg(C_6H_{13})_2$, $Mg(C_{12}H_{25})_2$, $Zn(CH_3)_2$, $Zn(C_2H_5)_2$, $Zn(C_4H_9)_2$, $Zn(C_4H_9)(C_8H_{17})$, $Zn(C_6H_{13})_2$, $Zn(C_6H_3)_2$, $Al(C_2H_5)_3$, $Al(CH_3)_3$, $Al(n-C_4H_9)_3$, $Al(C_8H_{17})_3$, $Al(iso-C_4H_9)_3$, $Al(C_{12}H_{25})_3$, and combinations thereof. Metal alkyl compounds also include substances having one or more halogen or hydride groups, such as ethylaluminum dichloride, diethylaluminum chloride, diethylaluminum hydride, Grignard reagents, diisobutylaluminum hydride, and the like. In some embodiments, the metal alkyl compound is triethylaluminum.

In some embodiments, the treating of the metathesis reaction material (e.g., a natural oil or a natural oil derivative) can include contacting the reaction material with a metal alkyl compound and, either simultaneously or separately, contacting the reaction material with a hydride-containing compound. In some embodiments, where the reaction material is contacted simultaneously with the metal alkyl compound and the hydride-containing compound, the hydride-containing compounds can be included in the metal alkyl compound. For example, in some instances, processes used to make certain metal alkyl compounds, such as trialkyl aluminum compounds, can lead to the formation of a certain concentration of hydride-containing compounds. In other embodiments, however, the metal alkyl compounds can be combined with one or more hydride-containing compounds. Or, in some embodiments, the metathesis reaction material can be treated by the hydride-containing compounds in a separate treatment step, which can be performed before, after, or both before and after, treatment of the reaction material with the metal alkyl compounds.

Any suitable hydride-containing compounds can be used. In some embodiments, the hydride-containing compounds are selected from the group consisting of metal aluminum hydrides (e.g., alkali metal aluminum hydrides such as $LiAlH_4$, $NaAlH_4$, and the like), alkyl aluminum hydrides (e.g., DIBALH), and combinations thereof. In some embodiments, the hydride-containing compound is an alkyl aluminum hydride, such as DIBALH.

In some embodiments, contacting the metathesis reaction material with the hydride-containing compound occurs in the same step as contacting the reaction material with the metal alkyl compound. In some embodiments, the weight-to-weight ratio of the metal alkyl compound to the hydride-containing compound in the treatment composition is from 2:1, or from 5:1, or from 10:1, or from 15:1, or from 20:1 to 1000:1. In some embodiments, the weight-to-weight ratio of the metal alkyl compound to the hydride-containing compound in the treatment composition is at least 2:1, or at least 5:1, or at least 10:1, or at least 15:1, or at least 20:1.

After any optional pre-treatment, the natural oil feedstock can be refined in any suitable manner to form an internal unsaturated ester and/or a terminal unsaturated ester. In some embodiments, a feedstock comprising a natural oil is reacted in the presence of a metathesis catalyst to form a metathesized product comprising one or more unsaturated glycerides and one or more olefins. The unsaturated glycerides in the metathesized product are separated from the olefins in the metathesized product, and the separated unsaturated glycerides are transesterified in the presence of an alcohol (e.g., methanol or ethanol) to form a transesterified product which can be converted to metathesis reaction partners (e.g., metathesis reaction partners according to Formula II or Formula XII). Refinement of natural feedstocks can include the use of known methods and apparatuses such as those described in WO 2014/058867, which is incorporated herein by reference in its entirety.

A non-limiting synthetic route for the synthesis of 8-unsaturated fatty olefin derivatives starting with methyl dec-9-enoate, derived from natural oils, is shown in Scheme 4. Methyl dec-9-enoate (9-DAME) can be converted to methyl dec-8-enoate (8-NAME) which is either reacted directly or first ethenolyized then reacted with a second olefin in a cross-metathesis reaction.

Scheme 4

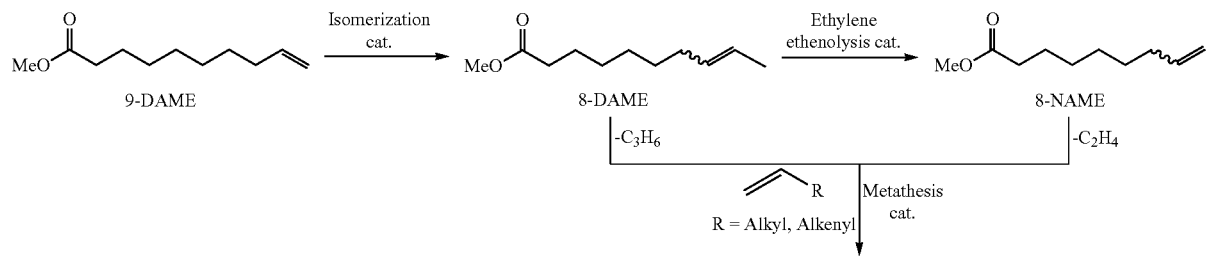

-continued

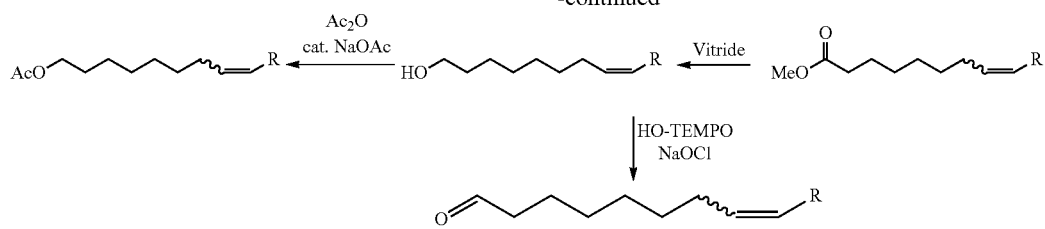

Accordingly, some embodiments of the invention provide methods that further include contacting an alkyl ester of 9-decenoate with an isomerization catalyst under conditions sufficient to form an alkyl ester 8-decenoate. In some embodiments, the alkyl ester of 8-decenoate is the metathesis reaction partner according to Formula II (or Formula XII as described below). In some embodiments, the alkyl ester of 9-decenoate is methyl 9-decenoate and the alkyl ester of 8-decenoate is methyl 8-decenoate.

Any suitable isomerization catalyst can be used for forming 8-DAME including, but not limited to, ruthenium-based catalysts such as Ru(H)Cl(PPh$_3$)$_3$, and iridium-based catalysts such as:

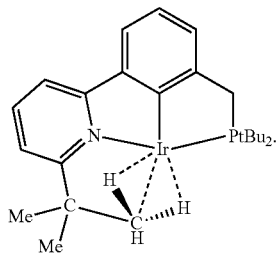

Any suitable ethenolysis catalyst can be used for forming 8-NAME including, but not limited to, a ruthenium-based catalyst selected from the group consisting of:

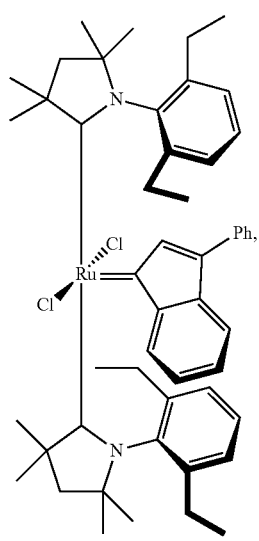

-continued

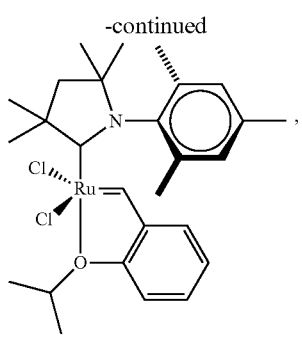

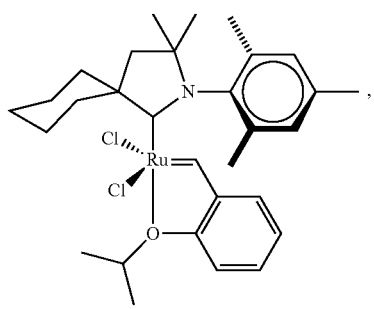

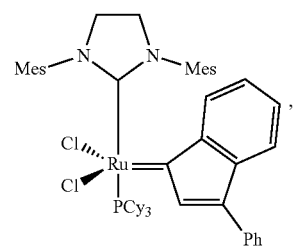

25
-continued

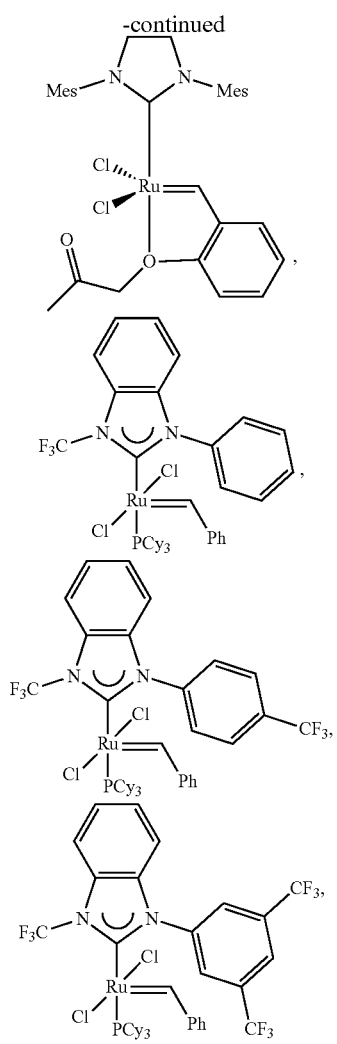

26
-continued

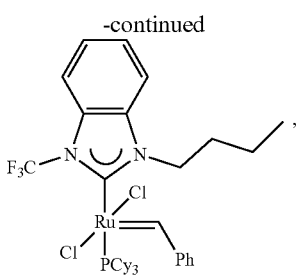

and other catalysts described in WO/2015/157736 and WO 2015/114323.

Isomerization of 9-DAME (or another alkyl ester of 9-decenoate) may not provide complete conversion to 8-DAME (or other alkyl ester of 8-decenoate) under certain conditions, in which case a portion of the 9-DAME will remain after the formation of the 8-DAME. The remaining 9-unsaturated ester can used for the preparation of 9-unsaturated fatty olefin derivatives (e.g., methyl (Z)-9-tetradecenoate). In certain embodiments, two molecules of the remaining 9-decenoate ester can be reacted in the presence of a self-metathesis catalyst to provide a dialkyl ester of 9-octadecenedioate. Advantageously, the 9-octadecenedioate ester is more readily separable under certain conditions (e.g., under reduced pressure) than the 9-decenoate ester from the 8-deconate ester. As shown in Scheme 5, the self-metathesis route provides a useful means for recovering and recycling unreacted 9-decenoate esters by way of the 9-octadecenedioate ester; once the 9-octadecendioate is recovered, it can be converted back to 9-decenoate via ethenolysis and resubjected to isomerization conditions for forming the 8-decenoate ester and downstream 8-unsaturated fatty olefin derivatives.

Scheme 5

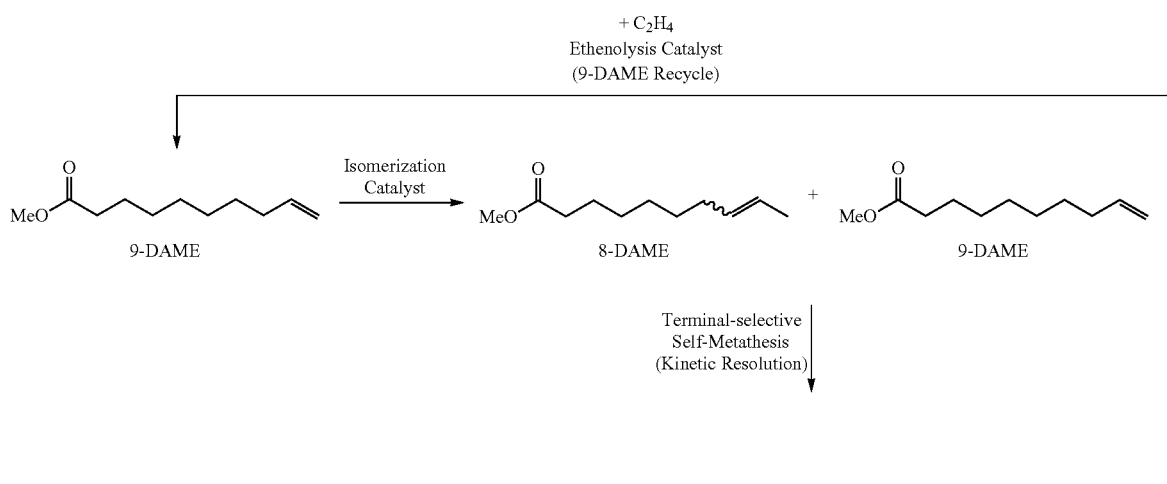

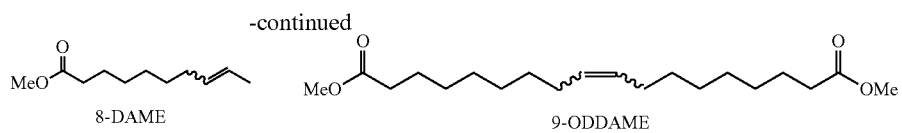

8-DAME

9-ODDAME

A number of terminally selective metathesis catalysts can be used for forming the dialkyl ester of 9-octadecenedioate. Examples of terminally selective metathesis catalysts include, but are not limited to those described in U.S. Pat. No. 9,518,002, which patent is incorporated herein by reference in its entirety.

Accordingly, some embodiments of the invention provide methods for synthesizing fatty olefin derivatives as described above, wherein a portion of the alkyl ester of 9-decenoate remains after the formation of the alkyl ester of 8-decenoate. In some embodiments, the method further comprises contacting the remaining alkyl ester of 9-decenoate with a terminal olefin in the presence of a cross-metathesis catalyst under conditions sufficient to form a 9-unsaturated cross-metathesis product. In some embodiments, the method further comprises contacting the remaining alkyl ester of 9-decenoate with a self-metathesis catalyst under conditions sufficient to form a dialkyl ester of 9-octadecenedioate. In some embodiments, the method further comprises separating at least a portion of the dialkyl ester of octadec-9-enedioate from the alkyl ester of 8-decenoate, the alkyl ester of 9-decenoate, or a combination thereof. In some embodiments, the method further includes contacting the separated dialkyl ester of octadec-9-enedioate with ethylene in the presence of an ethenolysis catalyst to form an alkyl ester of 9-decenoate.

Diol feedstocks, arising from either existing commercial supply, hydrogenation of commercially available α,ω-diacids, or synthetic routes such as alkyl-alkyl cross-coupling, can be selectively dehydrated to yield α,ω-alkenols as shown in Scheme 6. These metathesis feedstocks are further converted into pheromones and other olefin products via cross-metathesis with inexpensive linear α-olefins or other olefinic starting materials.

In some embodiments, the metathesis reaction partner is an alkenol wherein $R^3$ is hydrogen, $R^4$ is —$CH_2OR^{4a}$, and $R^{4a}$ is hydrogen, i.e., the metathesis reaction partner is a compound according to Formula XXXIId:

(XXXIId)

In some embodiments, the alkenol according to Formula XXXIId is formed by dehydrating a diol according to Formula XXXVII:

(XXXVII)

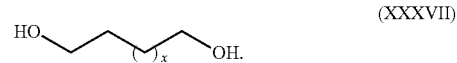

Alkenol formation via diol dehydration can be promoted through the use of catalysts including, but not limited to, acid catalysts. Examples of useful acid catalysts include, but are not limited to, hydrochloric acid, sulfuric acid, nitric acid, acetic acid, trifluoroacetic acid, and sulfamic acid (also referred to as amidosulfonic acid and sulfamidic acid). The acid can also be a sulfonic acid such as methanesulfonic acid, trifluoromethanesulfonic acid, p-toluenesulfonic acid, and the like. Heterogenous acid catalysts can be particularly useful in the methods of the invention. A number of heterogenous acid catalysts can be used in the methods of the invention including, but not limited to: sulfated zirconia; tungstated zirconia; cation exchange resins (known to those of skill in the art by names including NKC-9, D002, and the like); gelular and microporous type ion-exchange resins Scheme 6

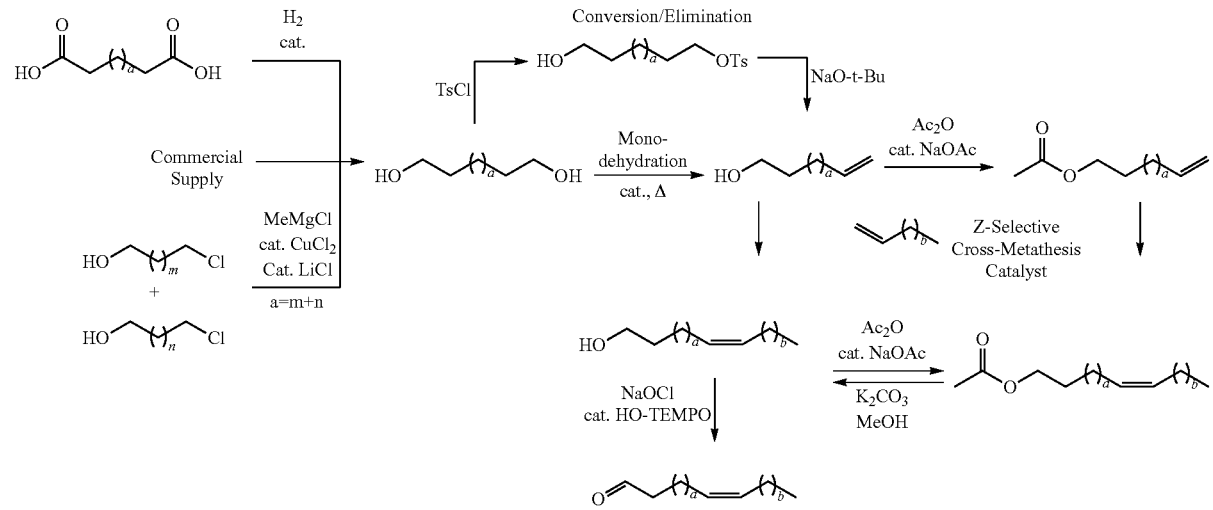

(known to those of skill in the art by names including EBD 100, EBD 200, and the like); polyvinyl alcohol (PVA) cross-linked with sulfosuccinic acid and the like; heteropolyacids (e.g., $H_3PW_{12}O_{40}$, $Cs_{2.5}H_{0.5}PW_{12}O_{40}$, and the like); zeolites (e.g., H-ZSM5, mordenite zeolite, and the like); polyaniline sulfate on solid supports such as activated carbon; sulfonic acid ion exchange resins (e.g., Dowex-50, Amberlyst-15, Amberlyst XN-1010, and the like); and mineral clays (e.g., montmorillonite, beidellite, nontronite, hectorite, saponite, sauconite, volkhonskoite, medmontite, pimelite, and the like). Rare earth oxides (e.g., $CeO_2$, $La_2O_3$, $Gd_2O_3$, $Sc_2O_3$, and the like), alkali metal pyrophosphates and alkaline earth metal pyrophosphates (e.g., $Li_4P_2O_7$, $Na_4P_2O_7$, $Ba_2P_2O_7$, $Sr_2P_2O_7$, and the like), and alkaline earth metal phosphates (e.g., $Ca(H_2PO_4)_2$, $CaHPO_4$, $Ba_3(PO4)_2$, and the like) can also be used as dehydration catalysts in the methods of the invention.

Any suitable about of catalyst can be used in the methods of the invention. Typically, reaction mixtures for diol dehydration will contain from about 1 mol % to about 10 mol % catalyst. The reaction mixture can contain, for example, from about 1 mol % to about 3 mol % catalyst, or from about 3 mol % to about 5 mol % catalyst, or from about 5 mol % to about 7 mol % catalyst, or from about 7 mol % to about 9 mol % catalyst, or from about 2 mol % to about 8 mol % catalyst, or from about 4 mol % to about 6 mol % catalyst.

In some embodiments, the alkenol intermediates (e.g., alkenols according to Formula XXXIId) are formed by:
i) converting a diol according to Formula XXXVII:

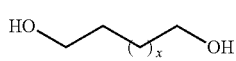
(XXXVI)

to an alcohol according to Formula XXXVIII:

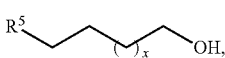
(XXXVIII)

and
ii) eliminating leaving group $R^5$ to form the metathesis reaction partner according to form the corresponding alkenol (e.g., a metathesis reaction partner according to Formula XXXIId).

The conversion step (e.g., a mono-sulfonationation step) and elimination step can be conducted as described with respect to compounds of Formula XVII, Formula XVIII, and Formula XIX.

In some embodiments, the alkenol according to Formula XXXIId is the metathesis reaction partner and the metathesis product is an alkenol according to Formula XXXIV:

(XXXIV)

In some embodiments, the method further comprises protecting the alkenol to form the metathesis reaction partner according to Formula XXXIIa

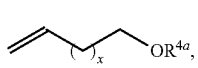
(XXXIIa)

wherein $R^{4a}$ is an alcohol protecting group.

In some embodiments, the method further comprises acylating the alkenol to form the metathesis reaction partner according to Formula XXXIIc:

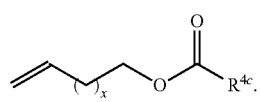
(XXXIIc)

In some embodiments, the method further comprises
i) converting a diol according to Formula XXXVII:

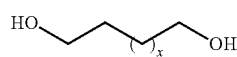
(XXXVII)

to an alcohol according to Formula XXXVIII:

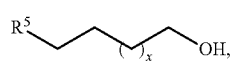
(XXXVIII)

wherein $R^5$ is a leaving group;
ii) acylating the alcohol to form an ester according to Formula XXXIXb

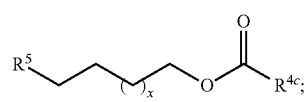
(XXXIXc)

and
iii) eliminating leaving group $R^5$ to form the metathesis reaction partner according to Formula IIc:

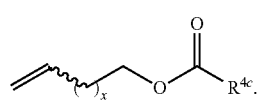
(XXXIIc)

In some embodiments, $R^{4a}$ in the metathesis reaction product is an alcohol protecting group (e.g., a substituted methyl ether as described above), and converting the metathesis product to the fatty olefin derivative comprises deprotecting the metathesis product to form an alkenol according to Formula XXXIV:

(XXXIV)

In some embodiments, the alkenol according to Formula XXXIV is the fatty olefin derivative. In some embodiments, converting the metathesis product to the fatty olefin derivative comprises contacting the alkenol according to Formula XXXIV with an acylating agent (e.g., acetic anhydride) under conditions sufficient to form an alkenol ester according to Formula XXXV:

(XXXV)

wherein $R^{4c}$ is selected from the group consisting of hydrogen, $C_{1-5}$ alkyl, and $C_{1-5}$ haloalkyl, and
wherein the alkenol ester is the fatty olefin derivative.

In some embodiments, the olefin according to Formula XXXI is selected from the group consisting of but-1-ene, pent-1-ene, hex-1-ene, hept-1-ene, oct-1-ene, 7-methyl-1-nonene, and trans-1,3-pentadiene. In some embodiments, the olefin according to Formula XXXI is selected from the group consisting of but-1-ene, pent-1-ene, hex-1-ene, oct-1-ene, and trans-1,3-pentadiene.

In some embodiments, the fatty olefin derivative prepared from the olefin according to Formula XXXI and the metathesis reaction partner according to Formula XXXII is selected from the group consisting of (E)-dec-5-en-1-ol and (8E,10E)-dodeca-8,10-dien-1-ol.

In some embodiments, the fatty olefin derivative prepared from the olefin according to Formula XXXI and the metathesis reaction partner according to Formula XXXII is selected from the group consisting of (E)-dec-5-en-1-yl acetate, (Z)-dodec-7-en-1-yl acetate; (Z)-dodec-8-en-1-yl acetate; (Z)-dodec-9-en-1-yl acetate; (Z)-tetradec-9-en-1-yl acetate; (Z)-tetradec-11-en-1-yl acetate; (Z)-hexadec-11-en-1-yl acetate; and (7E,9Z) dodeca-7,9-dien-1-yl acetate.

In some embodiments, the fatty olefin derivative prepared from the olefin according to Formula XXXI and the metathesis reaction partner according to Formula XXXII is selected from the group consisting of (Z)-hexadec-9-enal, (Z)-hexadec-11-enal, and (Z)-octadec-13-enal.

B. Preparation of Polyenes and Related Materials

In some embodiments, the invention provides a method for synthesizing a fatty olefin derivative including:
a) contacting an olefin according to Formula XI

(XI)

with a metathesis reaction partner according to Formula XII

(XII)

in the presence of a metathesis catalyst under conditions sufficient to form a metathesis product according to Formula XIII

(XIII)

and
b) optionally converting the metathesis product to the fatty olefin derivative;
wherein:
$R^1$ and $R^3$ are independently selected from the group consisting of hydrogen, $C_{1-18}$ alkyl, and $C_{2-18}$ alkenyl;
$R^2$ is selected from the group consisting of $C_{1-18}$ alkyl and $C_{2-18}$ alkenyl;
$R^4$ is selected from the group consisting of —$CH_2X$, —$CH_2OR^{4a}$, —$C(O)OR^{4b}$, and —$COC(O)R^{4c}$;
X is halogen;
$R^{4a}$ is an alcohol protecting group;
$R^{4b}$ is selected from the group consisting of hydrogen and $C_{1-8}$ alkyl;
$R^{4c}$ is selected from the group consisting of hydrogen, $C_{1-5}$ alkyl, and $C_{1-5}$ haloalkyl;
subscript x is 0 or 1; and
subscript y is an integer ranging from 0 to 15.

Certain embodiments of the method are summarized in Scheme 7. A protected fatty alcohol, a fatty acid, or an alkyl ester of a fatty acid can be reacted with an α-olefin in the presence of a group VI olefin metathesis catalyst (e.g., a Z-selective Group VI metathesis catalyst) to produce a statistical mixture of the desired cross-metathesis product and the self-metathesis co-products. The ratio of the feedstocks can be adjusted to vary the ratio of products. For example, feeding the reactants in a 1.5:1 molar ratio of α-olefin to fatty alcohol/ester can result in a 3:2.25:1 ratio of the internal olefin, metathesis product, and diol/diester products. This process condition results in the efficient utilization of the more costly protected fatty alcohol/ester.

Scheme 7

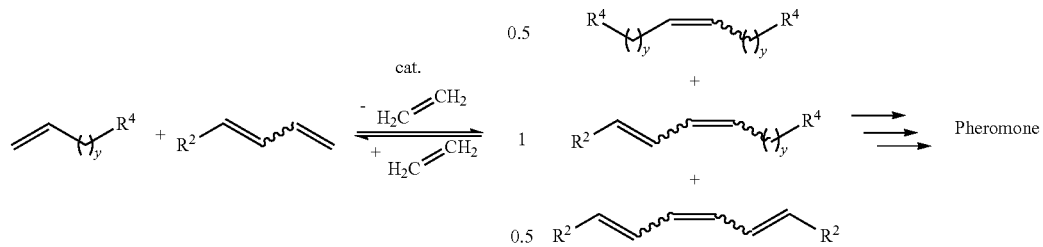

Products obtained from the metathesis of various olefins with unsaturated fatty alcohols and fatty acid esters can be used for the synthesis of a number of pheromones including, but not limited to, those set forth in Table 3.

TABLE 3

| Olefin | Fatty Olefin Derivative |
| --- | --- |
| (E)-Pent-1,3-diene | (E,E)-8,10-Dodecadien-1-ol |
| (E)-Pent-1,3-diene | (E,E)-8,10-Dodecadienal |
| (E)-Pent-1,3-diene | (E,E)-8,10-Dodecadienyl acetate |
| (Z)-Pent-1,3-diene | (E,Z)-8,10-Dodecadien-1-ol |
| (Z)-Pent-1,3-diene | (E,Z)-8,10-Dodecadienal |
| (Z)-Pent-1,3-diene | (E,Z)-8,10-Dodecadienyl acetate |
| (E)-Pent-1,3-diene | (Z,E)-8,10-Dodecadien-1-ol |
| (E)-Pent-1,3-diene | (Z,E)-8,10-Dodecadienal |
| (E)-Pent-1,3-diene | (Z,E)-8,10-Dodecadienyl acetate |
| (Z)-Pent-1,3-diene | (Z,Z)-8,10-Dodecadien-1-ol |
| (Z)-Pent-1,3-diene | (Z,Z)-8,10-Dodecadienyl acetate |
| (E)-Hepta-1,3-diene | (E,E)-8,10-Tetradecadien-1-ol |
| (E)-Hepta-1,3-diene | (E,E)-8,10-Tetradecadienal |
| (E)-Hepta-1,3-diene | (E,E)-8,10-Tetradecadienyl acetate |
| (Z)-Hepta-1,3-diene | (E,Z)-8,10-Tetradecadienal |
| (E)-Octa-1,3-diene | (E,E)-8,10-Pentadecadienyl acetate |
| (Z)-Octa-1,3-diene | (E,Z)-8,10-Pentadecadienyl acetate |
| (E)-Octa-1,3-diene | (Z,E)-8,10-Pentadecadienyl acetate |
| (Z)-Octa-1,3-diene | (Z,Z)-8,10-Pentadecadienyl acetate |

TABLE 3-continued

| Olefin | Fatty Olefin Derivative |
| --- | --- |
| (E)-Pent-1,3-diene | (E,E)-8,10-Dodecadien-1-ol |
| (E)-Pent-1,3-diene | (E,E)-8,10-Dodecadienal |
| (E)-Pent-1,3-diene | (E,E)-8,10-Dodecadienyl acetate |
| (Z)-Pent-1,3-diene | (E,Z)-8,10-Dodecadien-1-ol |
| (Z)-Pent-1,3-diene | (E,Z)-8,10-Dodecadienal |
| (Z)-Pent-1,3-diene | (E,Z)-8,10-Dodecadienyl acetate |
| (E)-Pent-1,3-diene | (Z,E)-8,10-Dodecadien-1-ol |
| (E)-Pent-1,3-diene | (Z,E)-8,10-Dodecadienal |
| (E)-Pent-1,3-diene | (Z,E)-8,10-Dodecadienyl acetate |
| (Z)-Pent-1,3-diene | (Z,Z)-8,10-Dodecadien-1-ol |
| (Z)-Pent-1,3-diene | (Z,Z)-8,10-Dodecadienyl acetate |
| (E)-Hepta-1,3-diene | (E,E)-8,10-Tetradecadien-1-ol |
| (E)-Hepta-1,3-diene | (E,E)-8,10-Tetradecadienal |
| (E)-Hepta-1,3-diene | (E,E)-8,10-Tetradecadienyl acetate |
| (Z)-Hepta-1,3-diene | (E,Z)-8,10-Tetradecadienal |
| (E)-Octa-1,3-diene | (E,E)-8,10-Pentadecadienyl acetate |
| (Z)-Octa-1,3-diene | (E,Z)-8,10-Pentadecadienyl acetate |
| (E)-Octa-1,3-diene | (Z,E)-8,10-Pentadecadienyl acetate |
| (Z)-Octa-1,3-diene | (Z,Z)-8,10-Pentadecadienyl acetate |

The invention also provides advantageous routes to diene intermediates, 8-unsaturated intermediates, and 11-unsaturated intermediates for use in metathesis reactions as shown, for example, in Schemes 8-16.

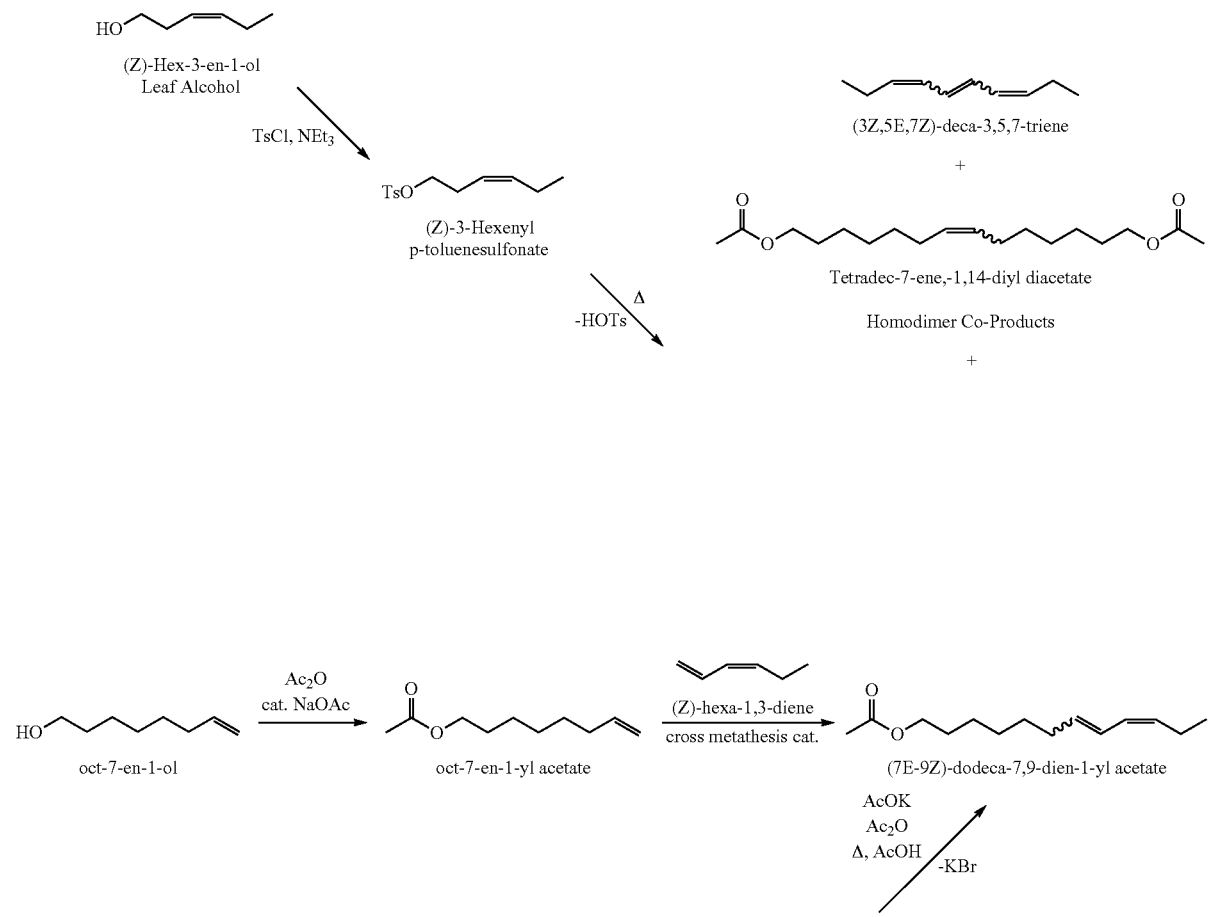

Scheme 8

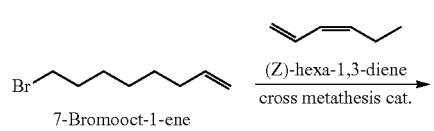
-continued
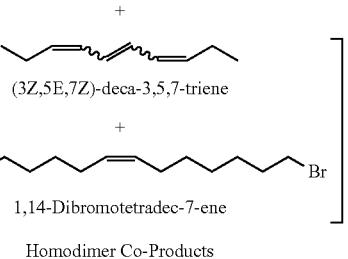
Homodimer Co-Products
Scheme 9
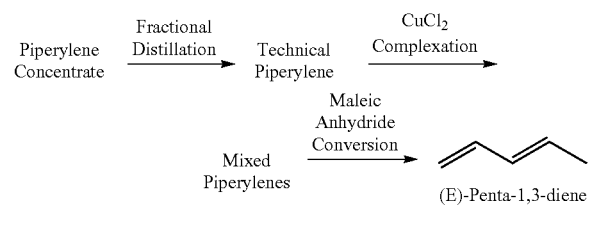
-continued
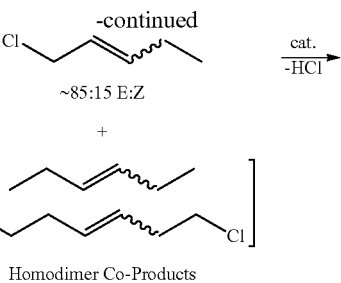
Homodimer Co-Products
Scheme 10
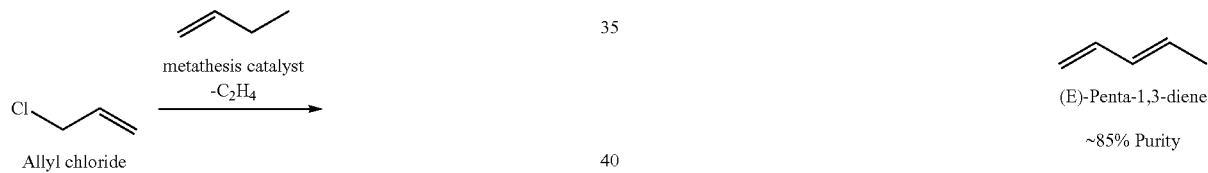
Scheme 11
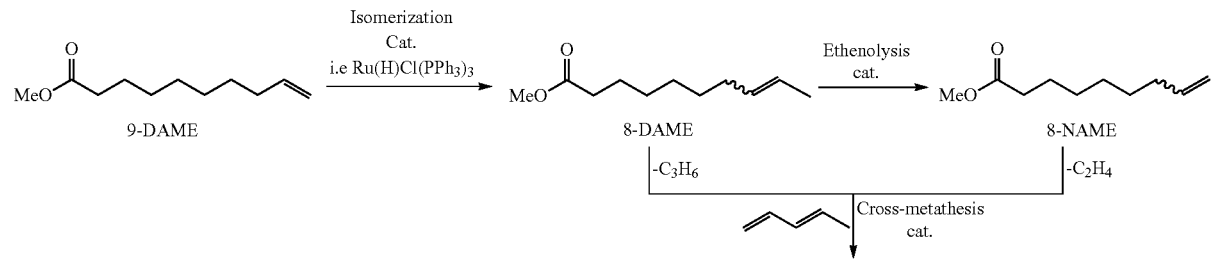
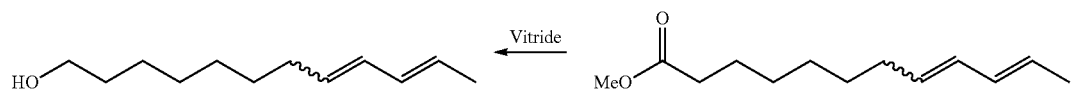

Scheme 12
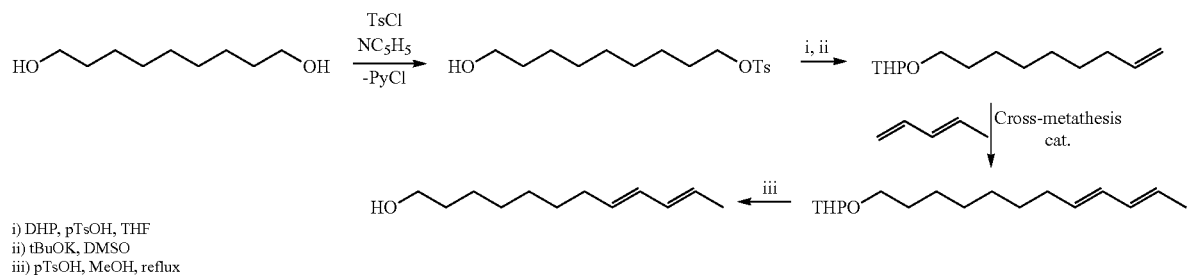
i) DHP, pTsOH, THF
ii) tBuOK, DMSO
iii) pTsOH, MeOH, reflux
Scheme 13
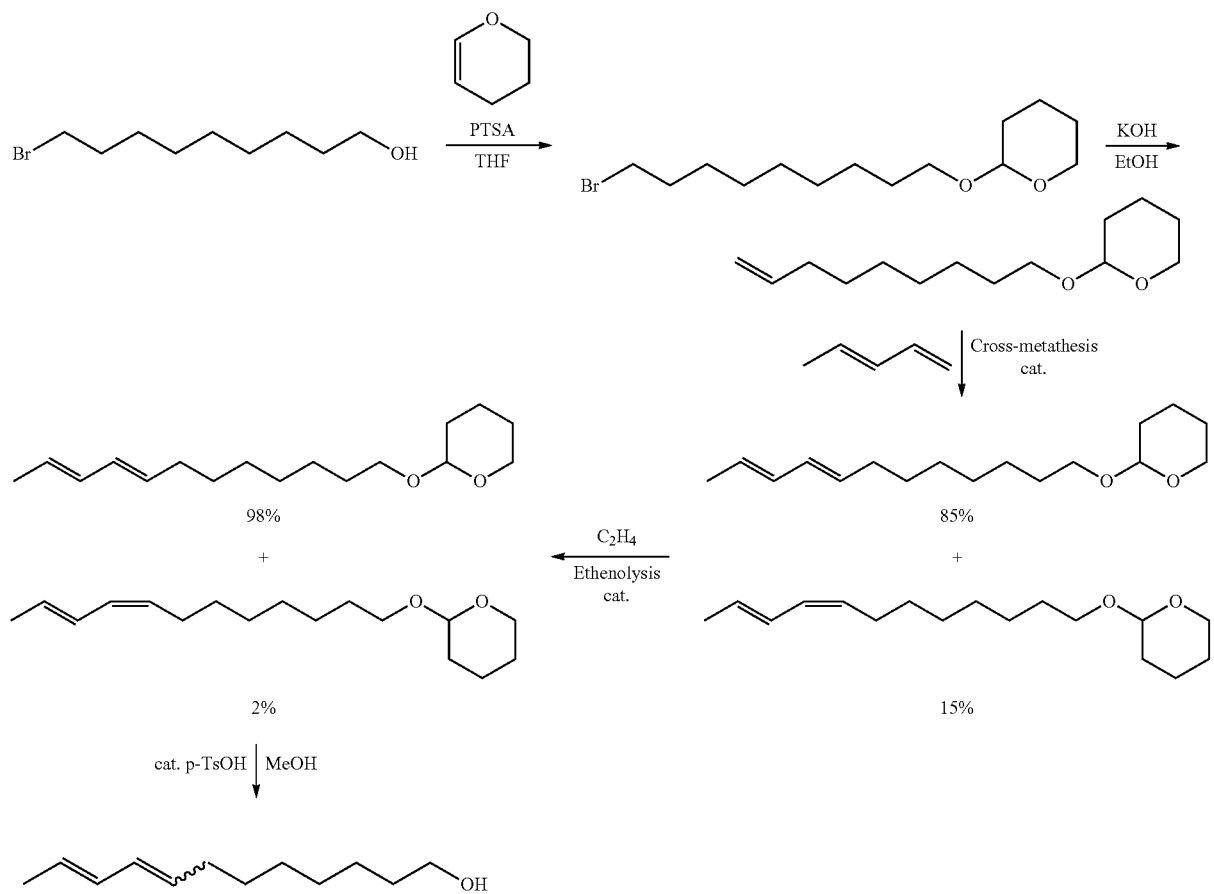
Scheme 14
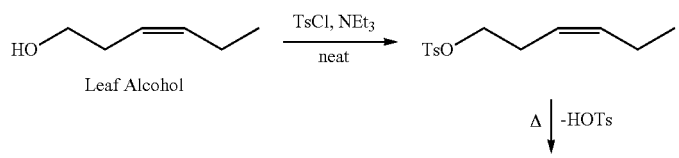

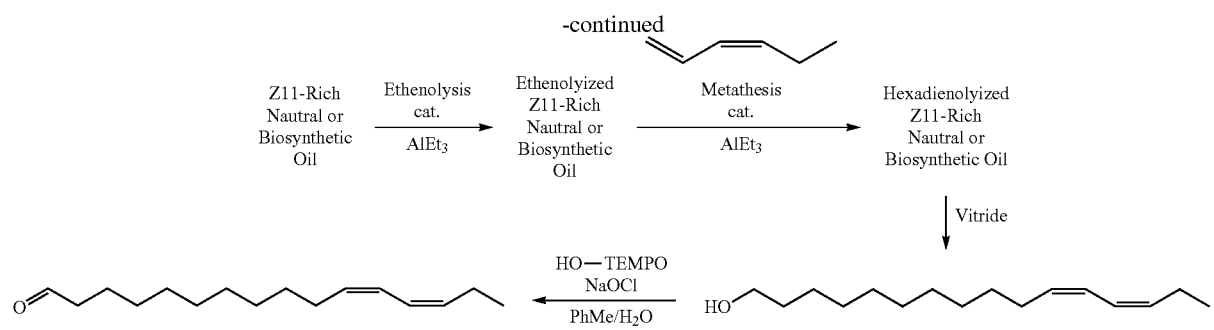
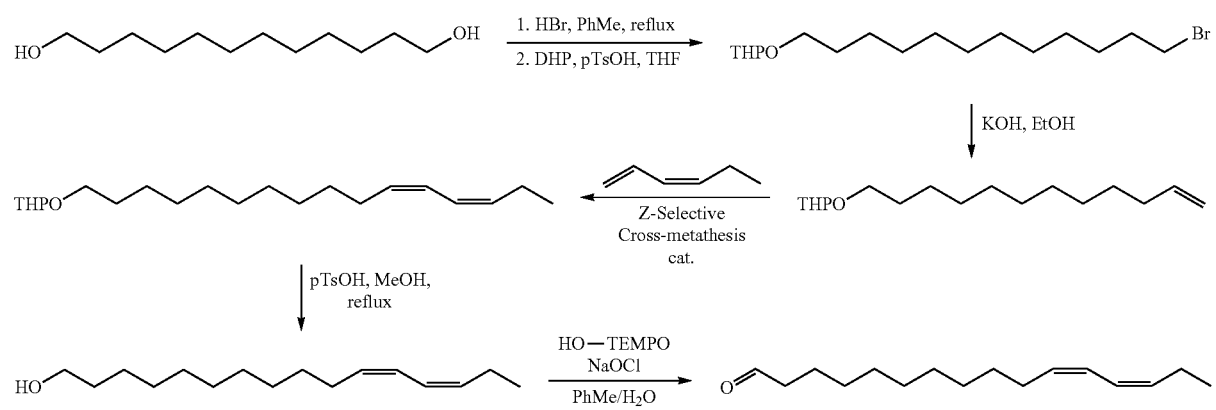
Scheme 15
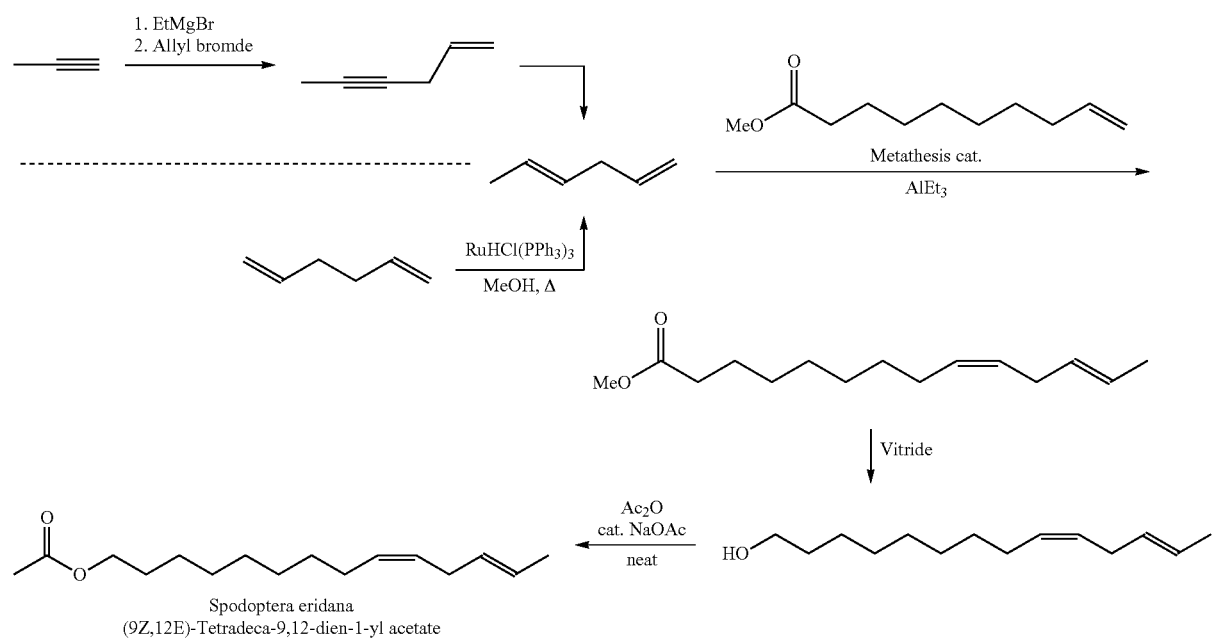
Scheme 16

In some embodiments wherein subscript x is 0, the method further comprises converting an alcohol according to Formula XVII:

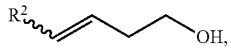
(XVII)

to a compound according to Formula XVIII:

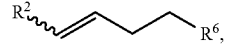
(XVII)

wherein $R^6$ is a leaving group; and
eliminating the leaving group to form an olefin according to Formula XIa:

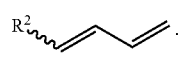
(XIa)

In some embodiments where subscript x is 0, the olefin according to Formula XIa is (Z)-hexa-1,3-diene.

In some embodiments where subscript x is 0, the olefin according to Formula XI is (E)-penta-1,3-diene. In some embodiments, the (E)-penta-1,3-diene is prepared by contacting allyl halide with but-1-ene under conditions sufficient to form 1-halo-pent-2-ene, and eliminating the halogen from the 1-halo-pent-2-ene via dehydrohalogenation to form the (E)-penta-1,3-diene. In some embodiments, the dehydrohalogenation is catalyzed by [Cp*Ru(MeCN)$_3$][PF$_6$]. In some embodiments, the (E)-penta-1,3-diene is obtained by a process comprising fractional distillation of $C_5$ raffinate.

In some embodiments subscript x is 1. In some such embodiments, the olefin according to Formula XI is hexa-1,4-diene. In some embodiments, the hexa-1,4-diene is prepared from hex-1-en-4-yne. In some embodiments, the hexa-1,4-diene is prepared by contacting hexa-1,5-diene with an isomerization catalyst under conditions sufficient to form the hexa-1,4-diene.

In some embodiments where subscript x is 0 or 1, the metathesis reaction is partner is an ester according to Formula XIIc

(XIIc)

and wherein the fatty olefin derivative is obtained as metathesis product according to Formula XV:

(XV)

without converting step (b).

In some embodiments wherein subscript x is 0 or 1, the metathesis reaction is partner is a compound according to Formula XIId

(XIId)

the metathesis product is a halide according to Formula XIIId

(XIIId)

and
converting the metathesis product to the fatty olefin derivative comprises contacting the halide according to Formula XIIId with a $C_{1-8}$ alkanoate under conditions sufficient to form an alkenol ester according to Formula XV:

(XV)

wherein the alkenol ester is the fatty olefin derivative.

In some embodiments, metathesis reaction partners according to Formula XII are prepared by a method comprising:
i) converting a diol according to Formula XVII:

(XVII)

to an alcohol according to Formula XVIII:

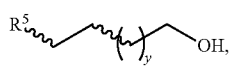
(XVIII)

wherein $R^5$ is a leaving group;
ii) protecting the alcohol to form a protected alcohol according to Formula XIX

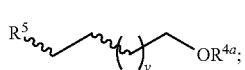
(XIX)

and
iii) eliminating leaving group $R^5$ to form the metathesis reaction partner according to Formula XII.

Diol XVII can be converted to an alcohol XVIII with any suitable leaving group $R^5$. In some embodiments, $R^5$ is a halogen. For example, $R^5$ can be chloro, bromo, or iodo. In some embodiments, $R^5$ is bromo. In some embodiments, $R^5$ is a sulfonate (i.e., —OS(O)$_2$R, wherein R is alkyl, haloalkyl, aryl, or substituted aryl). Suitable sulfonates include, but are not limited to, mesylate (methanesulfonate), triflate (trifluoromethanesulfonate), besylate (benzenesulfonate), tosylate (p-toluenesulfonate), and brosylate (4-bromobenzenesulfonate). In some embodiments, $R^5$ is mesylate (abbreviated —OMs). In some embodiments, $R^5$ is tosylate (abbreviated —OTs). Tosylates and other sulfonates can be formed by contacting the diol with a sulfonyl halide reagent (e.g., a sulfonyl chloride such as p-toluenesulfonyl chloride or methanesulfonyl chloride, or a sulfonyl bromide such as p-toluenesulfonyl bromide or methanesulfonyl bromide) or a sulfonic acid anhydride (e.g., p-toluenesulfonic anhydride, methanesulfonic anhydride) and the like.

In certain instances, selective mono-sulfonylation of a diol can be conducted by slowly adding small portions of the sulfonyl halide or the sulfonic acid anhydride to the diol (e.g., by dropwise or metered addition). Selective mono-sulfonylation can also be promoted by catalytic organotin reagents (e.g., $Bu_2SnO$ or $Me_2SnCl_2$), catalytic borinic acids, silver oxide, montmorillonite, and/or Lewis acid catalysts such as copper (II) triflate (see, e.g., Martinelli et al. *J. Am. Chem. Soc.* 2002, 124, 3578; Voight et al. *J. Org. Chem.* 2002, 67, 8489; Bucher et al. *Tetrahedron Lett.* 2000, 41, 9617; Lee et al. *J. Am. Chem Soc.* 2012, 134, 8260; Bouzide et al. *Org. Lett.* 2002, 4, 2329; Choudary et al. *Tetrahedron* 2000, 56, 7291; Demizu et al. *Tetrahedron Lett.* 2007, 48, 7605-7609; Fiori et al. *Nature Chem.* 2009, 1, 630). Typically, the amount of sulfonyl halide or sulfonic acid anhydride in a sulfonylation reaction mixture will range from about 0.75 molar equivalents to about 1.5 molar equivalents with respect to the diol in the sulfonylation reaction mixture. The sulfonylation reaction mixture can further contain a base such as trimethylamine, diisopropylamine, pyridine, and the like.

Protected alcohol XIX can contain any suitable protecting group $R^{4a}$. Examples of protecting groups include, but are not limited to, methyl ethers, a substituted methyl ethers, an ethyl ethers, a substituted ethyl ethers, a benzyl ethers, a substituted benzyl ether, and a silyl ethers. In some embodiments, protecting group $R^{4a}$ is a substituted methyl ether. For example, $R^{4a}$ can be methoxymethyl; methylthiomethyl; (phenyldimethylsilyl)-methoxymethyl; benzyloxymethyl; p-methoxybenzytoxymethyl; [(3,4-dimethoxybenzyl)oxy]methyl; p-nitrobenzyloxymethyl; o-nitrobenzyloxymethyl; [(R)-1-(2-nitrophenyl)ethoxy]methyl; (4-methoxyphenoxy)methyl; guaiacolmethyl; {(p-phenylphenyl)oxy}methyl; t-butoxymethyl; siloxymethyl; 2-methoxyethoxymethyl; 2-cyanoethoxymethyl; bis(2-chloroethoxy)methyl; 2,2,2-trichloroethoxymethyl; 2-(trimethylsilyl)ethoxymethyl; menthoxymethyl; O-bis(2-acetoxyethoxy)methyl; tetrahydropyranyl; fluorine-substituted tetrahydropyranyl; 3-bromotetrahydro-pyranyl; tetrahydrothiopyranyl; 1-methoxycyclohexyl; 4-methoxytetrahydropyranyl; 4-methoxytetrahydrothiopyranyl; 4-methoxytetrahydrothiopyranyl S,S-dioxide; 1-[(2-chloro-4-methyl)phenyl]-4-methoxypiperidin-4-yl; 1-(2-fluorophenyl)-4-methoxypiperidin-4-yl; 1-(4-chlorophenyl)-4-methoxypiperidin-4-yl; 1,4-dioxan-2-yl; tetrahydrofuranyl; tetrahydrothiofuranyl; or 2.3.3a,4,5,6,7,7a-octahydro-7,8,8-trimethyl-4,7-methanobenzo-furan-2-yl. In some embodiments, $R^{4a}$ is selected from the group consisting of tetrahydropyranyl, fluorine-substituted tetrahydropyranyl; 3-bromotetrahydropyranyl; tetrahydrothiopyranyl; 1-methoxycyclohexyl; 4-methoxytetrahydro-pyranyl; 4-methoxytetrahydrothiopyranyl; and 4-methoxytetrahydrothiopyranyl S,S-dioxide. In some embodiments, $R^{4a}$ is tetrahydropyranyl.

In some embodiments, the metathesis reaction partner according to Formula XII is prepared by a method comprising:

i) protecting an alcohol according to Formula XVIIIa:

(XVIIIa)

wherein X is a halogen;
to form a protected alcohol according to Formula XIXa (XIXa)

and ii) eliminating the halogen X to form the metathesis reaction partner according to Formula XII.

The present invention provides a convenient methods for the preparation of E7Z9-12Ac and other dienes, as summarized in Scheme 17. The methods employ easily-prepared raw materials including, but not limited to, acetoxy-functionalized terminal olefins (e.g., oct-7-en-1-yl acetate) and activated alkenols (e.g., but-3-en-1-yl tosylate). Activated alkenols can be prepared from a number of diols (e.g., 1,4-butanediol and the like). Given the reduction in synthetic steps, the methods of the invention provide for the preparation of the *L. botrana* sex pheromone and other compounds at lower cost and larger scale than conventional methods.

Scheme 17. Exemplary process for preparation of (7E,9Z)-dodeca-7,9-dien-1-yl acetate.

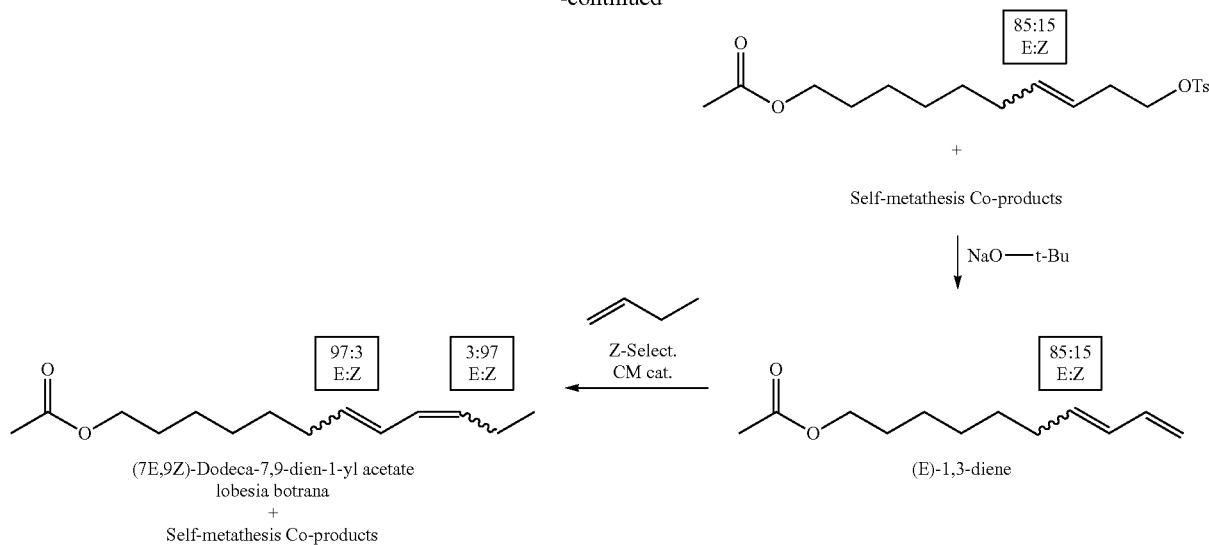

Moreover, the methods of the invention can provide high purity products. In contrast, conventional commercial processes for E7Z9-12Ac yield a product with only ~75% isomeric purity, the minor component (~25%) being (7E, 9E)-dodeca-7,9-dien-1-yl acetate (E7E9-12Ac). In the present invention, the final metathesis step is catalyzed by Z-selective cross metathesis catalysts, which have a much higher rate of reaction with Z-olefins as compared to E-olefins. Accordingly, products and/or intermediates having a Z-olefinic bond (e.g., at carbon 7 of dodeca-7,9-dien-1-yl acetate) can be effectively removed via kinetic resolution during the Z-selective cross metathesis reaction. The methods of the invention advantageously employ E-1,3-dienes, thereby avoiding the use of Z-1,3-dienes which are frequently less tolerated by olefin metathesis catalysts.

Accordingly, some embodiments provide a method of synthesizing a fatty olefin derivative comprising:
a) contacting an olefin according to Formula XXI

(XXI)

with a polyene reaction partner according to Formula XXII

(XXII)

in the presence of a metathesis catalyst under conditions sufficient to form a metathesis product according to Formula XXIII

(XXIII)

and
b) optionally converting the metathesis product to the fatty olefin derivative;

wherein:
$R^1$ and $R^3$ are independently selected from the group consisting of hydrogen, $C_{1-18}$ alkyl, and $C_{2-18}$ alkenyl;
$R^2$ is selected from the group consisting of $C_{1-18}$ alkyl and $C_{2-18}$ alkenyl;
$R^4$ is selected from the group consisting of —COC(O)$R^{4a}$, —CH$_2$OR$^{4b}$, —C(O)OR$^{4c}$, and —CH$_2$X;
$R^{4a}$ is selected from the group consisting of hydrogen, $C_{1-5}$ alkyl, and $C_{1-5}$ haloalkyl;
$R^{4b}$ is an alcohol protecting group;
$R^{4c}$ is selected from the group consisting of hydrogen and $C_{1-8}$ alkyl;
X is halogen;
subscript m is 0 or 1; and
subscript n is an integer ranging from 0 to 15.

In some embodiments, the polyene reaction partner is an ester according to Formula XXIIa

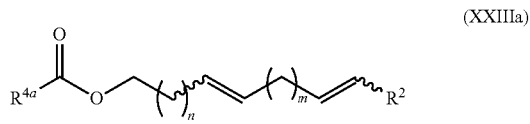
(XXIIa)

and
the fatty olefin derivative is obtained as a metathesis product according to Formula XXIIIa (XXIIIa)

without converting step (b).
In some embodiments, the ester according to Formula XXIIa is obtained by a process comprising:
converting an internal olefin according to Formula XXIIa-i

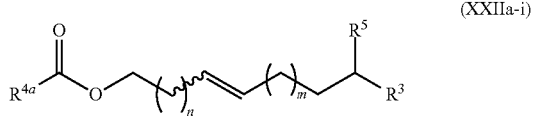

(XXIIa-i)

to the ester according to Formula XXIIa,
wherein $R^5$ is a leaving group.

In some embodiments, the leaving group is selected from the group consisting of a sulfonate and a halide.

In some embodiments, the internal olefin according to Formula XXIIa-i is obtained by a process comprising contacting a compound according to Formula XXIIa-iii

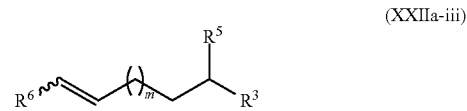

(XXIIa-iii)

with a reaction partner according to formula IIa-ii

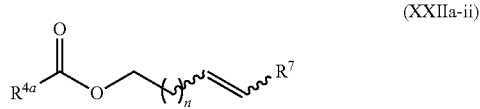

(XXIIa-ii)

in the presence of an intermediate catalyst under conditions sufficient to form the
internal olefin according Formula XXIIa-i;
wherein $R^6$ and $R^7$ are independently selected from the group consisting of hydrogen, $C_{1-18}$ alkyl, and $C_{2-18}$ alkenyl.

In some embodiments, the method comprises:
a-i) contacting a compound according to Formula XXIIa-iii

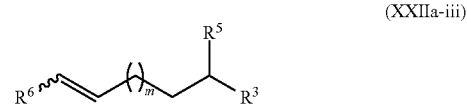

(XXIIa-iii)

with a reaction partner according to formula IIa-ii

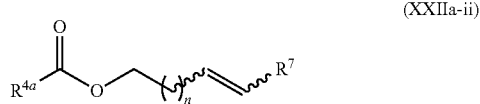

(XXIIa-ii)

in the presence of an intermediate catalyst under conditions sufficient to form an internal olefin according Formula XXIIa-i

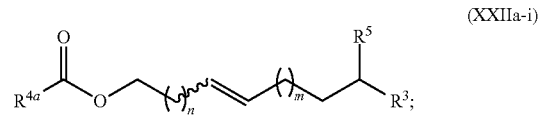

(XXIIa-i)

a-ii) converting the internal olefin according to Formula XXIIa-i to polyene reaction partner to Formula XXIIa

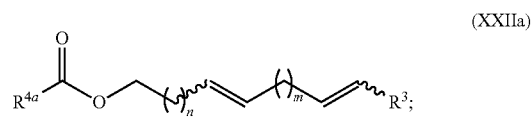

(XXIIa)

and a-iii) contacting the olefin according to Formula XXI with the polyene reaction partner according for Formula XXIIa in the presence of the metathesis catalyst under conditions sufficient to form a metathesis product according to Formula XXIIIa

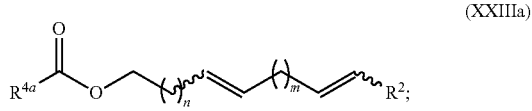

(XXIIIa)

wherein:
the fatty olefin derivative is obtained as the metathesis product according to Formula XXIIIa without converting step (b),
$R^5$ is a leaving group, and
$R^6$ and $R^7$ are independently selected from the group consisting of hydrogen, $C_{1-18}$ alkyl, and $C_{2-18}$ alkenyl.

In some embodiments, leaving group $R^5$ of Formula XXIIa-i or Formula XXIIa-iii is a halogen. For example, $R^5$ can be chloro, bromo, or iodo. In some embodiments, $R^5$ is bromo. In some embodiments, $R^5$ is a sulfonate (i.e., —OS$(O)_2$R, wherein R is alkyl, haloalkyl, aryl, or substituted aryl). Suitable sulfonates include, but are not limited to, mesylate (methanesulfonate), triflate (trifluoromethanesulfonate), besylate (benzenesulfonate), tosylate (p-toluenesulfonate), and brosylate (4-bromobenzenesulfonate). In some embodiments, $R^5$ is mesylate (abbreviated —OMs). In some embodiments, $R^5$ is tosylate (abbreviated —OTs). Tosylates and other sulfonates can be formed by contacting the diol with a sulfonyl halide reagent (e.g., a sulfonyl chloride such as p-toluenesulfonyl chloride or methanesulfonyl chloride, or a sulfonyl bromide such as p-toluenesulfonyl bromide or methanesulfonyl bromide) or a sulfonic acid anhydride (e.g., p-toluenesulfonic anhydride, methanesulfonic anhydride) and the like.

Any suitable conditions for eliminating a leaving group to form a metathesis reaction partner (e.g., converting an internal olefin according to Formula XXIIa-i to a polyene reaction partner according to Formula XXIIa) can be used in conjunction with the methods of the invention. In some embodiments, the elimination conditions (i.e., conditions suitable for eliminating a leaving group) include the use of a non-nucleophilic base such as, for example, potassium tert-butoxide, sodium tert-butoxide, potassium hydride, sodium hydride, potassium bis(trimethylsilyl)amide, sodium bis(trimethylsilyl)amide, lithium diisopropylamide, 1,8-diazabicyclo[5.4.0]undec-7-ene (DBU), 1,5-diazabicyclo[4.3.0]non-5-ene (DBN), or N,N-diisopropylethylamine (DIPEA).

In some embodiments, 1-10 molar equivalents of the non-nucleophilic base with respect to the leaving group-containing compound (e.g., an internal olefin according to Formula XXIIa-i) can be used. For example, 1-5 molar equivalents of the non-nucleophilic base or 1-2 molar equivalents of the non-nucleophilic base can be used. In some embodiments, around 1.0, 1.1, 1.2, 1.3, 1.4, 1.5, 1.6, 1.7, 1.8, 1.9, or 2.0 molar equivalents of the non-nucleophilic base (e.g., potassium tert-butoxide or DBU) with respect to the leaving group-containing compound (e.g., an internal olefin according to Formula XXIIa-i) is used to form the metathesis reaction partner (e.g., the polyene reaction partner according to Formula XXIIa). In some embodiments, the elimination reaction can be conducted at temperatures ranging from around 0° C. to about 100° C. for a period of time sufficient to form the metathesis reaction partner. In general, the elimination reaction is conducted for a period of time ranging from a few minutes to several hours or longer, depending on the particular leaving group-containing compound and non-nucleophilic base used in the reaction. For example, the reaction can be conducted for around 10 minutes, or around 30 minutes, or around 1 hour, or around 2 hours, or around 4 hours, or around 8 hours, or around 12 hours, or around 16 hours, or around 20 hours at around 0° C., or around 5° C., or around 40° C., or around 50° C., or around 60° C., or around 70° C., or around 80° C. In some embodiments, the reaction can be cooled to 0° C.-5° C. during the addition of the non-nucleophilic base, followed by an increase in reaction temperature to no more than 40° C. for 16 hours.

C. Metathesis Catalysts

The catalysts employed in the present invention generally employ metals which can mediate a metathesis reaction. In general, any transition metal can be used to form the catalyst, e.g., a metal selected from one of Groups 3-12 of the periodic table or from the lanthanide series. In some embodiments, the metal is selected from Groups 3-8, or, in some cases, from Groups 4-7. In some embodiments, the metal is selected from Group 6. The term "Group 6" refers to the transition metal group comprising chromium, molybdenum, and tungsten. Additionally, the present invention may also include the formation of heterogeneous catalysts containing forms of these elements (e.g., by immobilizing a metal complex on an insoluble substrate, for example, silica).

The methods of the invention can be assessed in terms of the selectivity of the metathesis reaction—that is, the extent to which the reaction produces a particular olefin isomer, whether a Z olefin (i.e., a cis olefin) or an E olefin (i.e., a trans olefin).

In general, Z-selective catalysts provide metathesis products wherein greater than 15% of the olefin is a Z olefin. For example, the metathesis product can contain the Z olefin in an amount ranging from about 20% to about 100%. The metathesis product can contain the Z olefin in an amount ranging from about 25% to about 95%, or from about 30% to about 90%, or from about 35% to about 85%, or from about 40% to about 80%, or from about 45% to about 75%, or from about 50% to about 70%, or from about 55% to about 65%. The metathesis product can contain the Z olefin in an amount ranging from about 15% to about 20%, or from about 20% to about 25%, or from about 25% to about 30%, or from about 30% to about 35%, or from about 35% to about 40%, or from about 40% to about 45%, or from about 45% to about 50%, or from about 50% to about 60%, or from about 60% to about 65%, or from about 65% to about 70%, or from about 70% to about 75%, or from about 75% to about 80%, or from about 80% to about 85%, or from about 85% to about 90%, or from about 90% to about 95%, or from about 95% to about 99%. The metathesis product can contain the Z olefin in an amount of about 55%, 60%, 65%, 70%, 75%, 80%, 85%, 86%, 87%, 88%, 89%, 90%, 91%, 92%, 93%, 94%, 95%, 96%, 97%, 98%, 99%, or 100%. Certain metathesis reactions involving diene starting materials will provide diene metathesis products with mixed olefin stereochemistry. If metathesis product (7E,9Z) dodeca-7,9-dien-1-yl acetate is said to contain Z olefin in an amount of about 97%, for example, it will be understood that the percentage refers to the olefinic bond formed between $C_9$ and $C_{10}$ of the dodecadiene moiety. The same product may also contain a specified amount of E olefin (e.g., 85%), where the percentage refers to the olefinic bond between $C_7$ and $C_8$ of the dodecadiene moiety.

In certain instances, Z-selectivity is afforded by catalysts containing a Group 6 metal, such as tungsten or molybdenum, bonded to a large, freely rotating aryloxide (e.g., substituted or unsubstituted [1,1'-binaphthalen]-2-ol, substituted or unsubstituted octahydro-[1,1'-binaphthalen]-2-ol, or the like) as well as a smaller imido substituent (e.g., a substituted or unsubstituted phenyl imido group, a substituted or unsubstituted adamantylimido group, or the like). It is believed that a catalyst of this type can provide a Z olefin product via formation of a syn alkylidene adduct and an all-cis metallocyclobutane intermediate. In other instances, Z-selectivity is afforded by catalysts containing a Group 8 metal, such as ruthenium or osmium, bonded to a chelating group (e.g., an adamantyl group) bearing an N-heterocyclic carbene ligand (e.g., a substituted or unsubstituted dihydroimidazole). In such cases, a Z olefin product can result from attack of a metal-alkylidene complex by an olefin via a pathway that is cis to the N-heterocyclic carbene ligand and trans to the chelating group.

In general, E-selective catalysts provide metathesis products wherein greater than 50% of the olefin is an E olefin. Preferably, E-selective catalysts provide metathesis products wherein greater than 85% of the olefin is an E olefin. For example, the metathesis product can contain the E olefin in an amount ranging from about 86% to about 100%. The metathesis product can contain the E olefin in an amount ranging from about 86% to about 99%, or from about 88% to about 98%, or from about 90% to about 96%, or from about 92% to about 94%. The metathesis product can contain the E olefin in an amount ranging from about 86% to about 89%, or from about 89% to about 92%, or from about 92% to about 95%, or from about 95% to about 98%. The metathesis product can contain the E olefin in an amount of about 86%, 87%, 88%, 89%, 90%, 91%, 92%, 93%, 94%, 95%, 96%, 97%, 98%, 99%, or 100%. E-selectivity can be afforded by controlling intermediate stereochemistry in the manner described above. In addition, formation of E olefin products will be favored in many cases due to the greater thermodynamic stability of the E olefin as compared to the corresponding Z olefin.

In some embodiments, the metathesis catalyst has a structure according to Formula XLI:

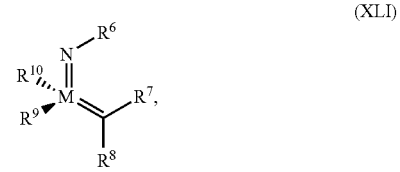

(XLI)

wherein:

M is Mo or W;

$R^6$ is selected from optionally substituted aryl, optionally substituted heteroaryl, optionally substituted aliphatic, and optionally substituted heteroaliphatic;

each of $R^7$ and $R^8$ is independently selected from hydrogen, optionally substituted aliphatic, optionally substituted heteroaliphatic, optionally substituted aryl, and optionally substituted heteroaryl;

$R^9$ is selected from —O-alkyl, —O-heteroalkyl, —O-aryl, —O-heteroaryl, —N(R″)-alkyl, —N(R″)-heteroalkyl, —N(R″)-aryl, and —N(R″)-heteroaryl, wherein each R″ is independently selected from hydrogen, an amino protecting group, and optionally substituted alkyl, and wherein $R^9$ is optionally substituted; and $R^{10}$ is selected from aryl, heteroaryl, alkyl, heteroalkyl, cycloalkyl, heterocycloalkyl, —O-alkyl, —O-heteroalkyl, —O-aryl, and —O-heteroaryl, each of which is optionally substituted, or $R^{10}$ is halogen.

In some embodiments, the metathesis catalyst has a structure according to Formula XLI and the metathesis product comprises a Z olefin.

In some embodiments, $R^9$ is an optionally substituted asymmetric —O-aryl group and $R^{10}$ is an optionally substituted heteroaryl group.

In some cases, the metal complex includes one or more oxygen-containing ligands lacking a plane of symmetry or nitrogen-containing ligands lacking a plane of symmetry (i.e., asymmetric ligands). In some embodiments, such ligands can coordinate the metal atom via an oxygen atom (e.g., via a hydroxyl group), or other atom of the ligand. The oxygen-containing ligand can coordinate the metal atom via one site of the ligand, i.e., the ligand may be a monodentate ligand.

In some embodiments, a ligand can comprise two sites capable of binding the metal center, wherein a first site is bonded to a protecting group, or other group, that may reduce the ability of the first site to coordinate the metal, and the second site coordinates the metal center. For example, the ligand can be a [1,1'-binaphthalene]-2,2'-diol (BINOL) derivative having two hydroxyl groups, wherein one hydroxyl group is bonded to a protecting group (e.g., a silyl protecting group) and another hydroxyl group coordinates the metal center.

In some embodiments, an asymmetric oxygen-containing ligand is of the following structure:

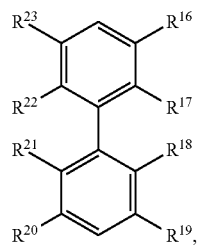

wherein:

$R^{16}$ is an optionally substituted group selected from aryl, heteroaryl, alkyl, or heteroalkyl;

$R^{17}$ is hydrogen, —OH, halogen, —OPG, or an optionally substituted group selected from aliphatic, heteroaliphatic, aryl, aryloxy, heteroaryl, heteroaryloxy, acyl, and acyloxy;

or, together $R^{16}$ and $R^{17}$ are joined to form an optionally substituted partially unsaturated or aryl ring;

$R^{18}$ is —OH, —OPG, or an optionally substituted amino group;

$R^{19}$ is hydrogen, halogen, an optionally substituted group selected from aliphatic, heteroaliphatic, aryl, heteroaryl, or acyl;

each of $R^{20}$, $R^{21}$, $R^{22}$, and $R^{23}$ is independently aryl, heteroaryl, aliphatic, heteroaliphatic, or acyl, optionally substituted;

or, together $R^{20}$ and $R^{21}$ are joined to form an optionally substituted partially unsaturated or aryl ring;

or, together $R^{22}$ and $R^{23}$ are joined to form an optionally substituted partially unsaturated or aryl ring; and each PG is independently a hydroxyl protecting group.

In some embodiments, $R^6$ is an optionally substituted group selected from aryl and aliphatic.

In some embodiments, $R^6$ is selected from

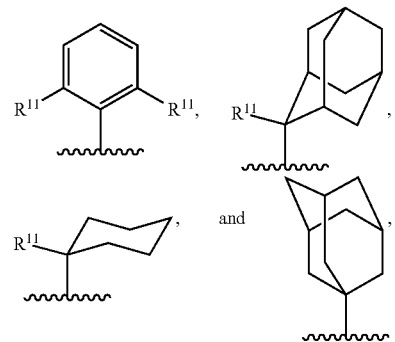

wherein each $R^{11}$ is independently hydrogen or a monovalent substituent.

In some embodiments, $R^{10}$ is an optionally substituted group selected from

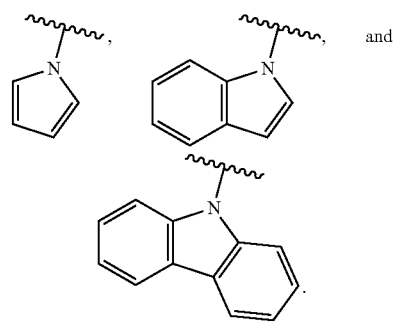

In some embodiments, $R^9$ is an optionally substituted group selected from:

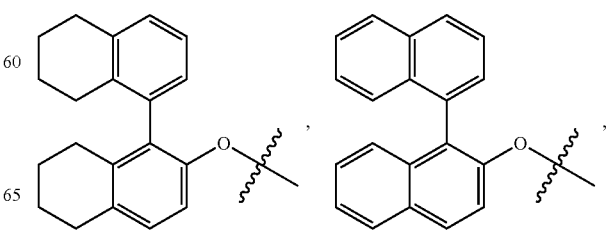

53

-continued

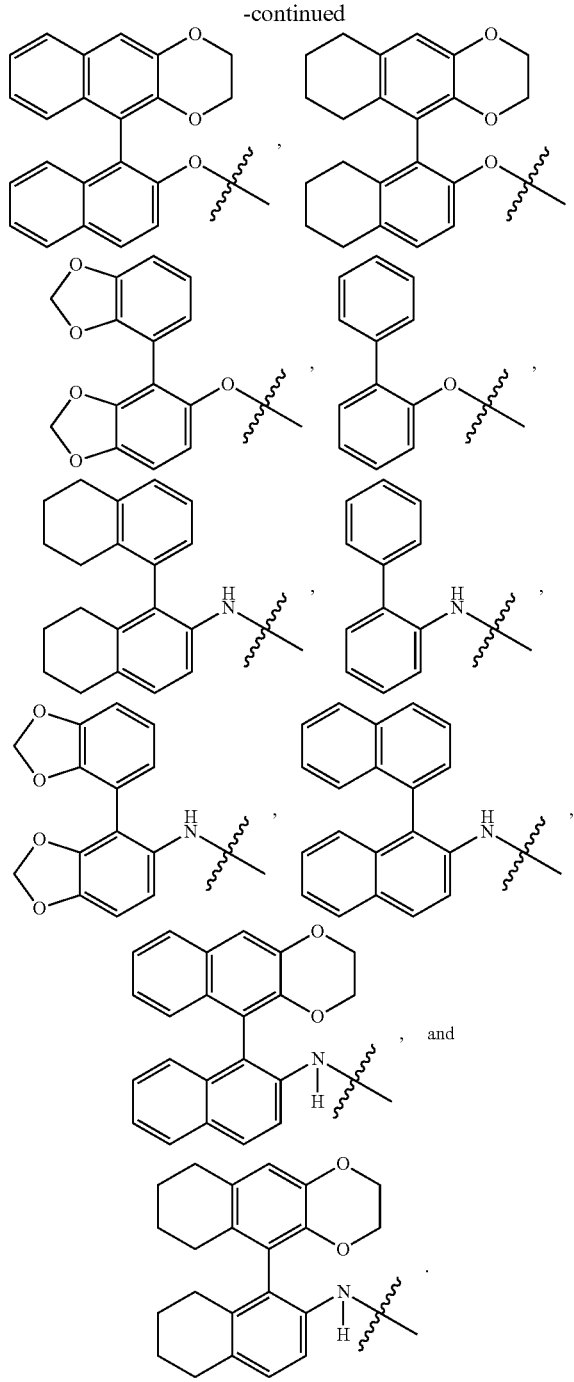

In some embodiments, $R^9$ is

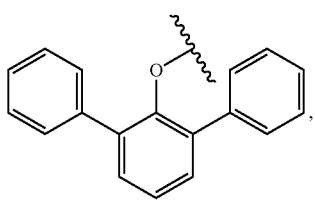 [SMILES: *Oc1c(-c2ccccc2)cccc1-c1ccccc1]

which is optionally substituted.

54

In some embodiments, the metathesis catalyst is selected from

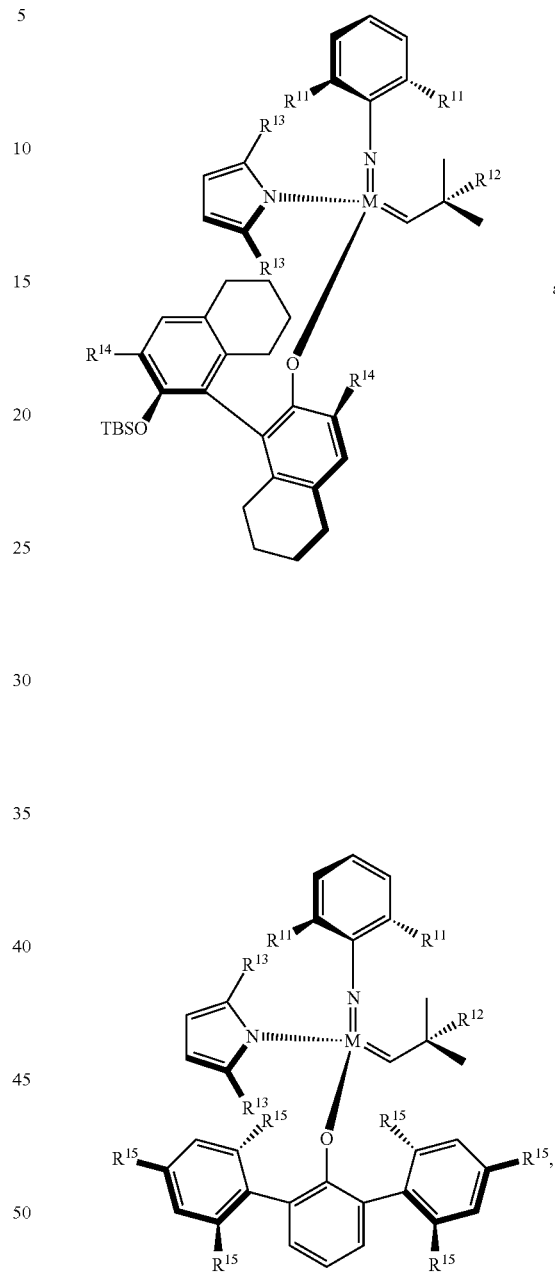

wherein M is Mo or W;
each $R^{11}$ is independently selected from halo and alkyl;
$R^{12}$ is selected from the group of consisting of alkyl, aryl, alkenyl, and heteroaryl;
each $R^{13}$ is independently selected from hydrogen, halo, alkyl, aryl, and heteroaryl;
each $R^{14}$ is independently selected from halo, alkyl, aryl, and heteroaryl; and
each $R^{15}$ is independently an optionally substituted alkyl.

In some embodiments, the metathesis catalyst is selected from:

55
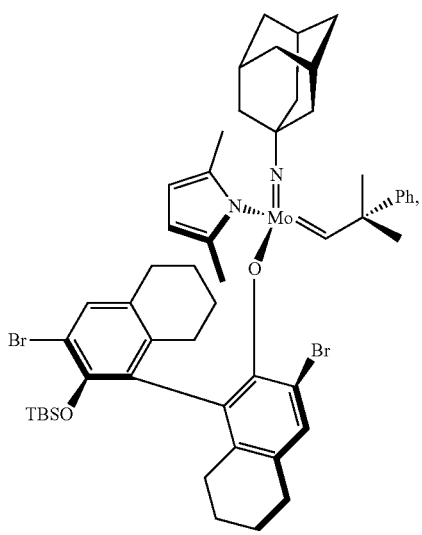
56
-continued
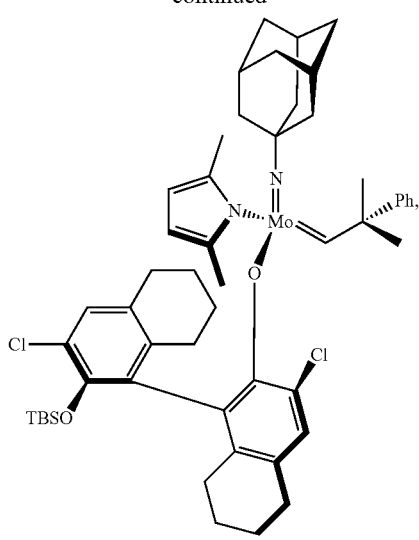
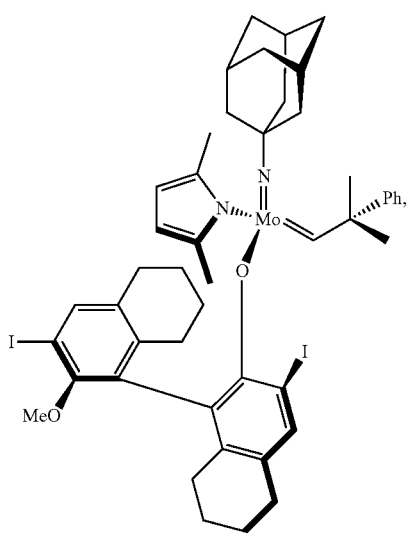
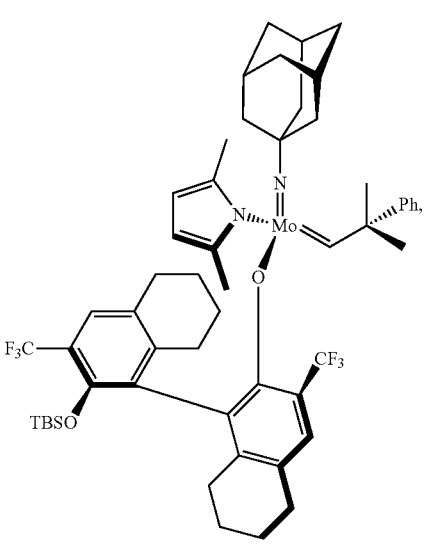
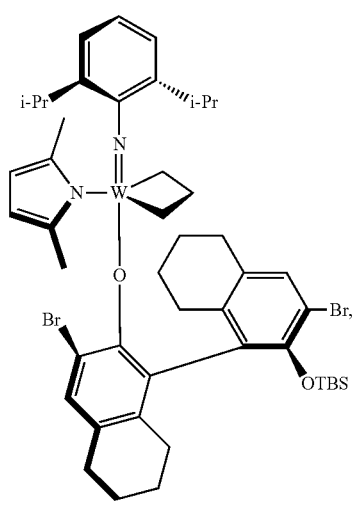
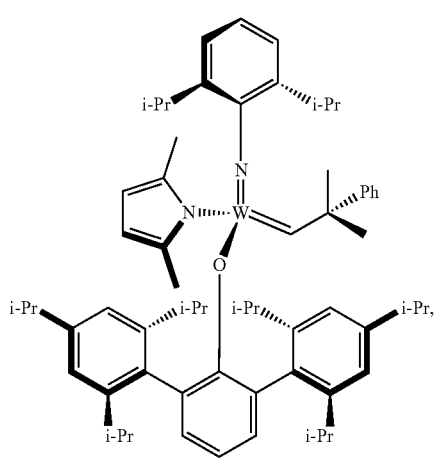

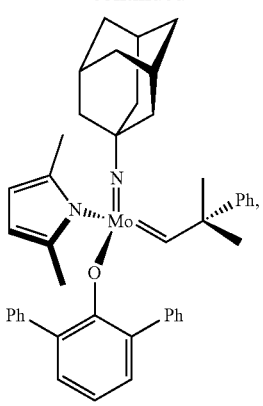

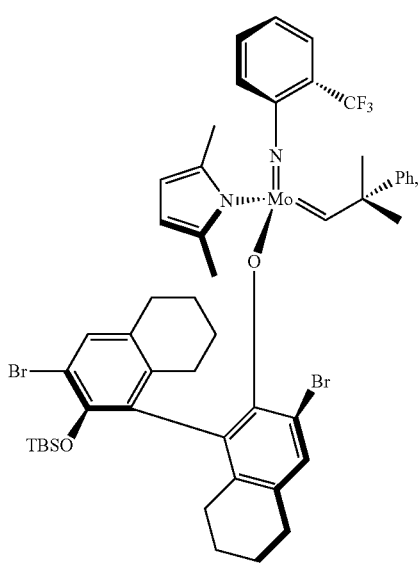

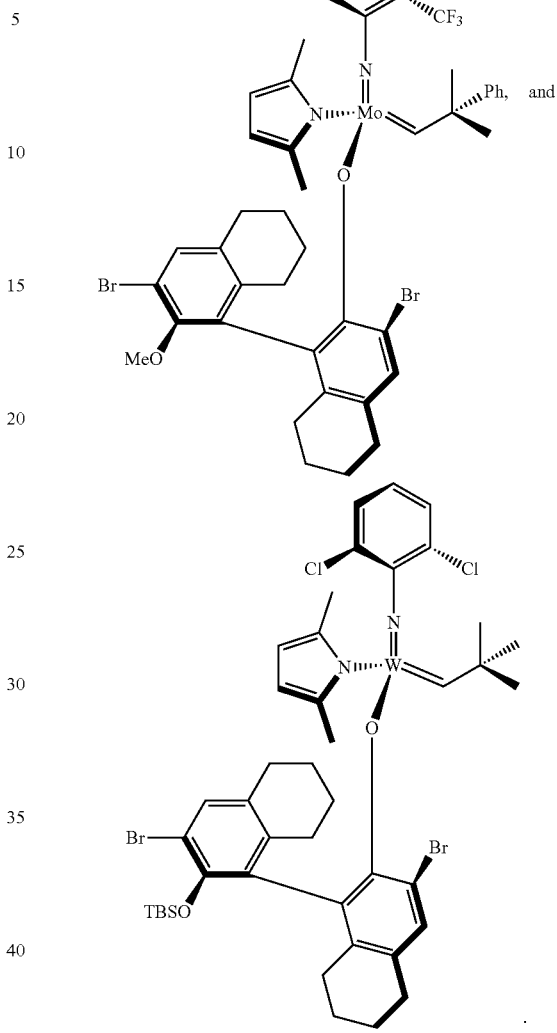

In some embodiments, the metathesis catalyst has a structure according to Formula XLII:

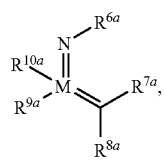

(XLII)

wherein:

M is Mo or W;

$R^{6a}$ is selected from optionally substituted aryl, optionally substituted heteroaryl, optionally substituted alkyl, optionally substituted heteroalkyl, optionally substituted cycloalkyl, and optionally substituted heterocycloalkyl, and $R^{7a}$ and $R^{8a}$ are independently selected from hydrogen, optionally substituted alkyl, optionally substituted alkenyl, optionally substituted heteroalkyl, optionally substituted heteroalkenyl, optionally substituted aryl, and optionally substituted heteroaryl;

$R^{10a}$ is selected from optionally substituted alkyl, optionally substituted alkoxy, optionally substituted heteroalkyl, optionally substituted aryl, optionally substituted aryloxy, optionally substituted heteroaryl, optionally substituted silylalkyl, and optionally substituted silyloxy; and $R^{9a}$ is $R^{11a}$—X—, wherein X is O or S and $R^{11a}$ is optionally substituted aryl; or X is O and $R^{11a}$ is $SiR^{12a}R^{13a}R^{14a}$ or $CR^{15a}R^{16a}R^{17a}$, wherein $R^{12a}$, $R^{13a}$, $R^{14a}R^{15a}$, $R^{16a}$, and $R^{17a}$ are independently selected from optionally substituted alkyl and optionally substituted phenyl; or $R^{9a}$ and $R^{10a}$ are linked together and are bonded to M via oxygen.

In some embodiments, the metathesis catalyst has a structure according to Formula XLII and the metathesis product comprises a Z olefin.

In some embodiments, the catalyst is a compound of Formula XLII wherein:

$R^{10a}$ is selected from the group consisting of alkyl, alkoxy, heteroalkyl, aryl, aryloxy, and heteroaryl, each of which is optionally substituted; and X is O or S and $R^{11a}$ is optionally substituted aryl; or X is O and $R^{11a}$ is $CR^{15a}R^{16a}R^{17a}$.

In some embodiments, the catalyst is a compound of Formula XLII wherein:

$R^{6a}$ is selected from the group consisting of 2,6-dimethylphenyl; 2,6-diisopropylphenyl; 2,6-dichlorophenyl; and adamant-1-yl;

$R^{7a}$ is selected from the group consisting of —C(CH$_3$)$_2$C$_6$H$_5$ and —C(CH$_3$)$_3$;

$R^{8a}$ is H;

$R^{10a}$ is selected from the group consisting of pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenyl-phenoxy; and t-butyloxy; and $R^{9a}$ is $R^{11a}$—X—, wherein X=O and $R^{11a}$ is phenyl which bears two substituents in the ortho positions with respect to O, or which bears at least three substituents, from which two substituents are in the ortho positions with respect to 0 and one substituent is in the para position with respect to 0; or $R^{11a}$ is selected from the group consisting of optionally substituted 8-(naphthalene-1-yl)-naphthalene-1-yl; optionally substituted 8-phenylnaphthalene-1-yl; optionally substituted quinoline-8-yl; triphenylsilyl; triisopropylsilyl; triphenylmethyl; tri(4-methylphenyl)methyl; 9-phenyl-fluorene-9-yl; 2-phenyl-1,1,1,3,3,3-hexafluoro-prop-2-yl; 2-methyl-1,1,1,3,3,3-hexafluoro-prop-2-yl; and t-butyl.

In some embodiments, the catalyst is a compound of Formula XLII: wherein:

$R^{10a}$ is selected from the group consisting of pyrrol-1-yl; 2,5-dimethyl-pyrrol-1-yl; and $R^{11a}$ is phenyl which bears two substituents in the ortho positions with respect to O, or which bears at least three substituents, from which two substituents are in the ortho positions with respect to 0 and one substituent is in the para position with respect to 0; or $R^{11a}$ is selected from the group consisting of optionally substituted 8-(naphthalene-1-yl)-naphthalene-1-yl and optionally substituted 8-phenylnaphthalene-1-yl.

In some embodiments, the catalyst is a compound of Formula XLII wherein $R^7$ is selected from 4-bromo-2,6-diphenylphenoxy; 4-fluoro-2,6-diphenylphenoxy; 4-methyl-2,6-diphenylphenoxy; 4-methoxy-2,6-diphenylphenoxy; 4-dimethylamino-2,6-diphenylphenoxy; 2,4,6-triphenylphenoxy; 4-fluoro-2,6-dimesitylphenoxy; 4-bromo-2,6-di-tert-butylphenoxy; 4-methoxy-2,6-di-tert-butylphenoxy; 4-methyl-2,6-di-tert-butylphenoxy; 2,4,6-tri-tert-butylphenoxy; 4-bromo-2,3,5,6-tetraphenylphenoxy; 4-bromo-2,6-di(4-bromophenyl)-3,5-diphenylphenoxy; 2,6-diphenylphenoxy; 2,3,5,6-tetraphenylphenoxy; 2,6-di(tert-butyl)phenoxy; 2,6-di(2,4,6-triisopropylphenyl)phenoxy; triphenylsilyloxy; triisopropylsilyloxy; triphenylmethyloxy; tri(4-methyphenyl)methyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; t-butyloxy;

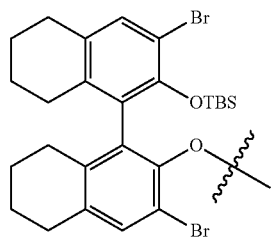

wherein TBS is t-butyldimethylsilyl; or

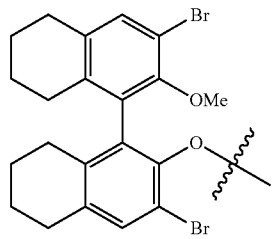

wherein Me=methyl.

In some embodiments, the metathesis catalyst has a structure according to Formula XLIIa:

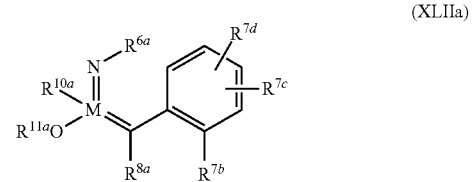

(XLIIa)

$R^{6a}$ is aryl, heteroaryl, alkyl, or cycloalkyl, each of which is optionally substituted;

$R^{10a}$ is pyrrolyl, imidazolyl, indolyl, pyrazolyl, azaindolyl, or indazolyl, each of which is optionally substituted;

$R^{11a}$ is optionally substituted aryl;

$R^{sa}$ is a hydrogen atom, alkyl, or alkoxy;

$R^{7b}$ is a hydrogen atom, —O—(C$_{1-6}$ alkyl), —CH$_2$—O—(C$_{1-6}$ alkyl), heteroalkoxy, or —N(C$_{1-6}$ alkyl)$_2$;

$R^{7c}$ and $R^{7d}$ are independently a hydrogen atom, C$_{1-6}$ alkyl, C$_{1-6}$ alkoxy, a halogen atom, —NO$_2$, an amide, or a sulfonamide.

In some embodiments, the metathesis catalyst has a structure according to Formula XLIIa and the metathesis product comprises a Z olefin.

In some embodiments, $R^{6a}$ in the metathesis catalyst according to Formula XLIIa is phenyl, 2,6-dichlorophenyl, 2,6-dimethylphenyl, 2,6-diisopropylphenyl, 2-trifluoromethylphenyl, pentafluorophenyl, tert-butyl, or 1-adamantyl.

In some embodiments, $R^{11a}$ is

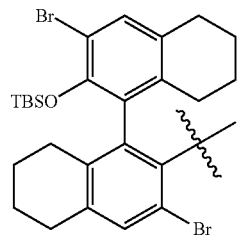

In some embodiments, $R^{7b}$ is methoxy, $R^{7c}$ is hydrogen, and $R^{7d}$ is hydrogen.

In some embodiments, the metathesis catalyst is selected from the group consisting of

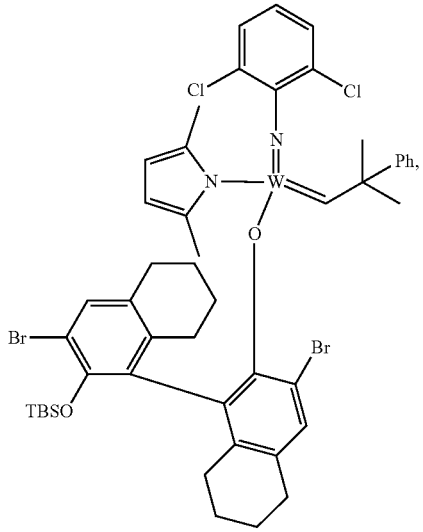

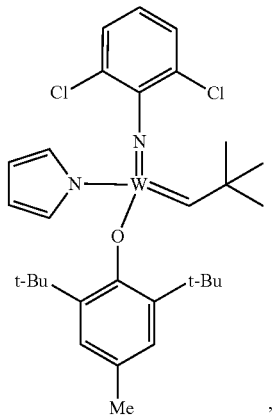

-continued

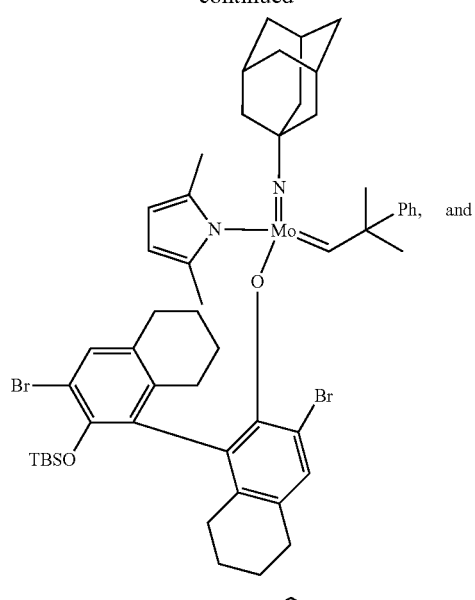

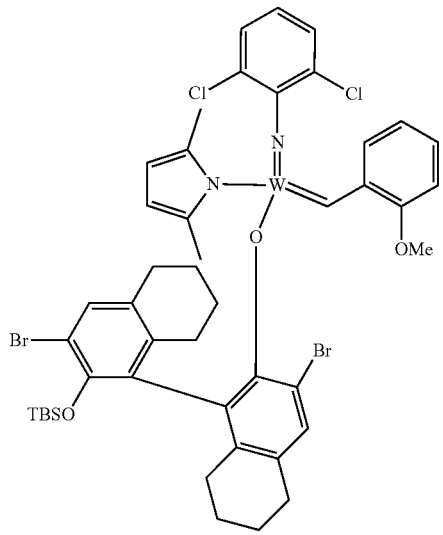

In some embodiments, the metathesis catalyst is

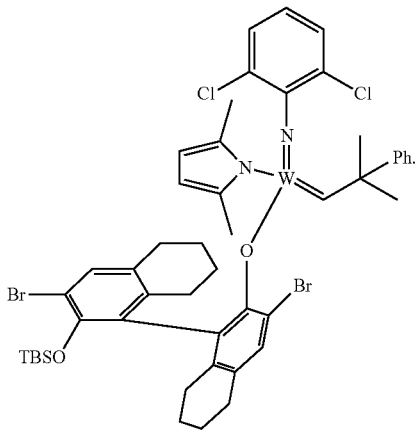

In some embodiments, the metathesis catalyst is
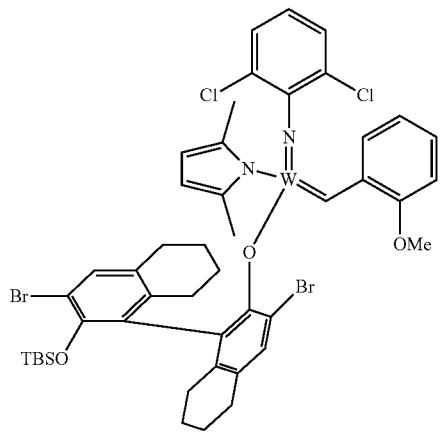
In some embodiments, the metathesis catalyst is selected from:
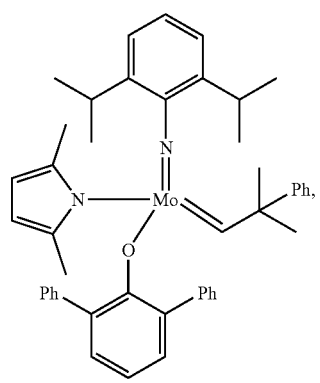
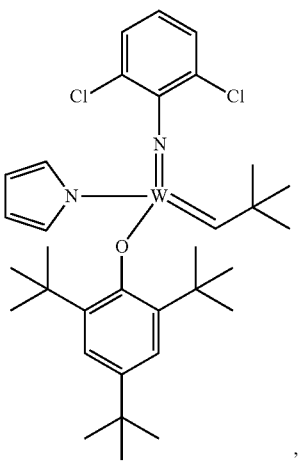
-continued
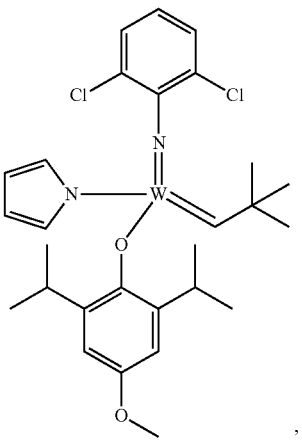
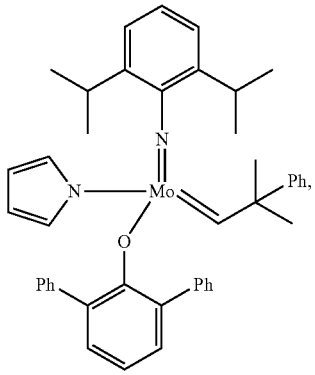
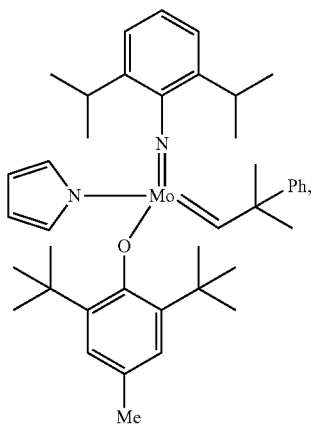

-continued
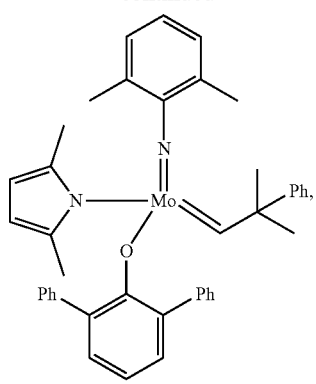
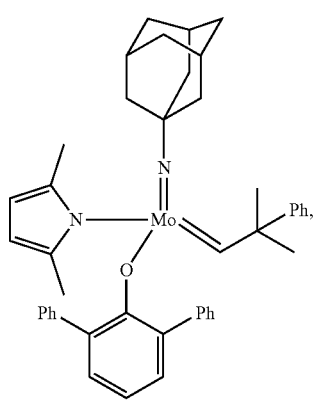
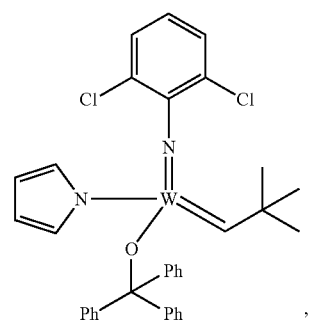
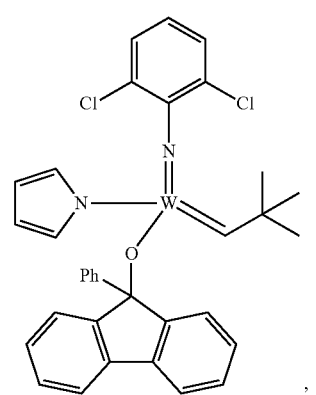
-continued
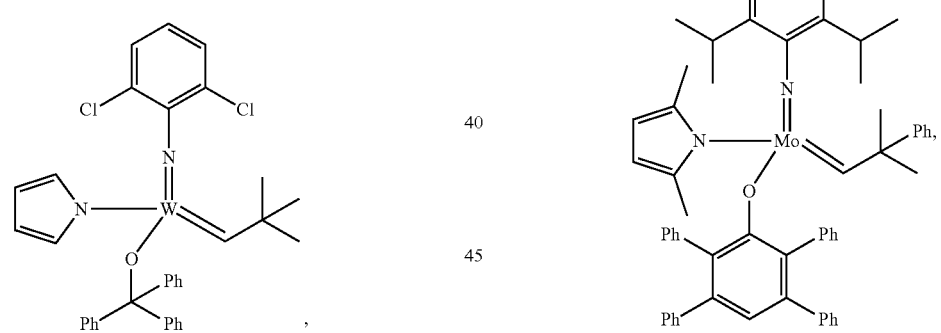
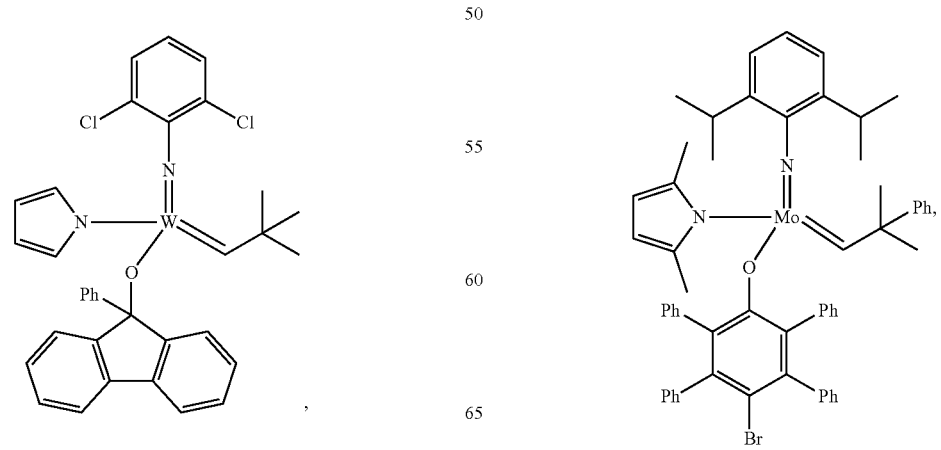

-continued
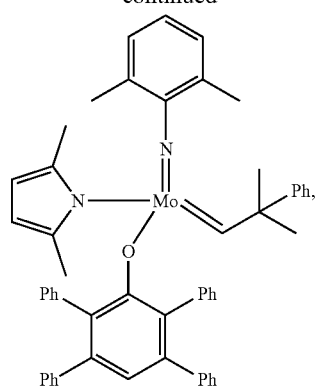
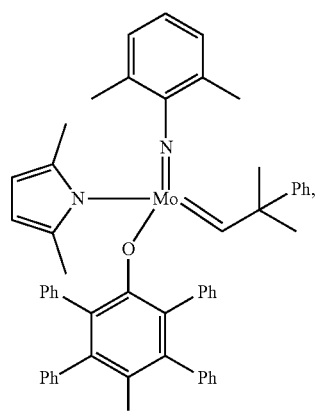
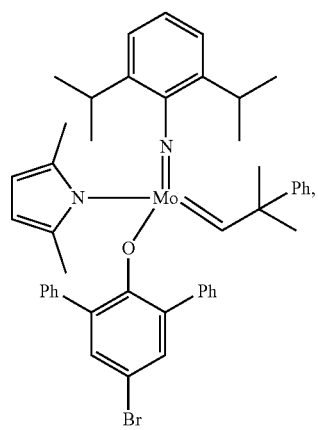
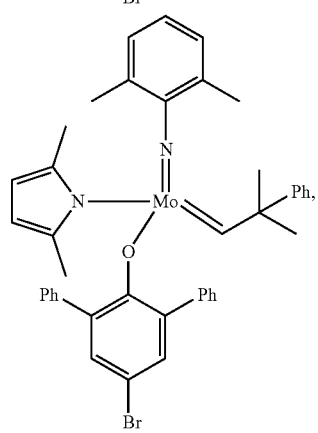
-continued
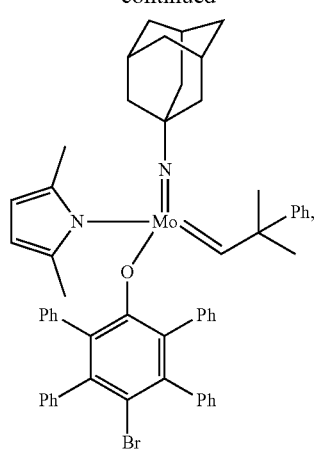
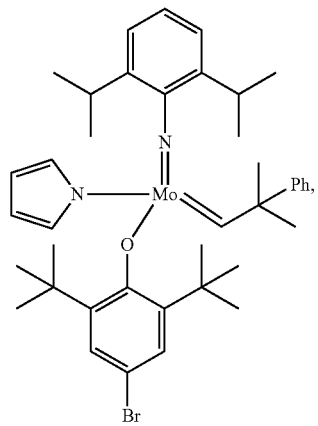
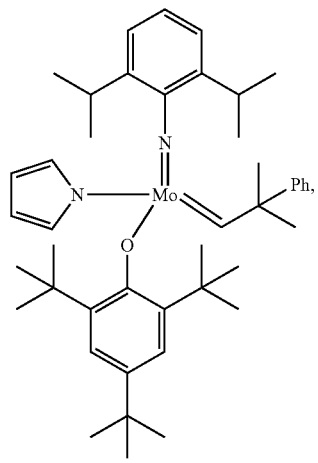

-continued
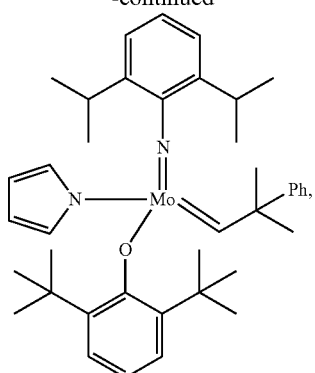
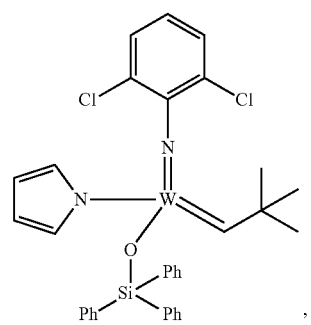
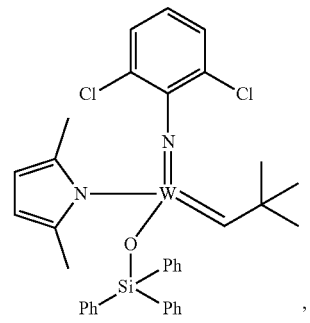
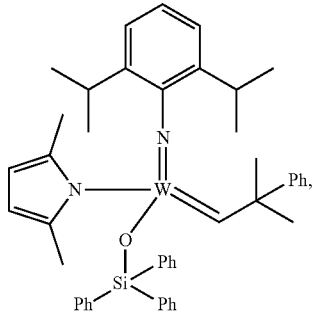
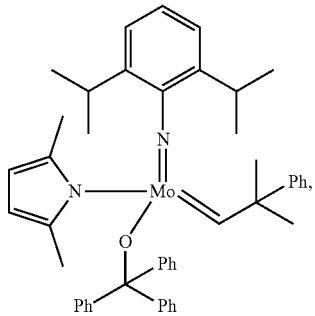
-continued
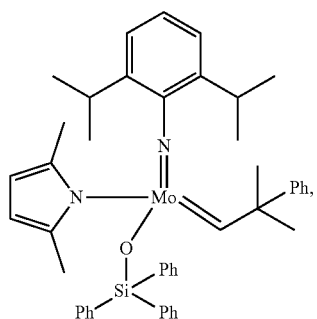
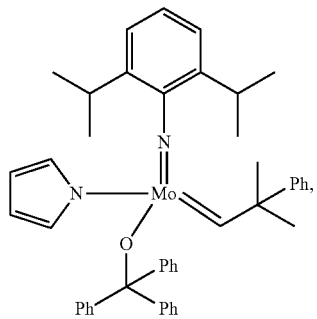
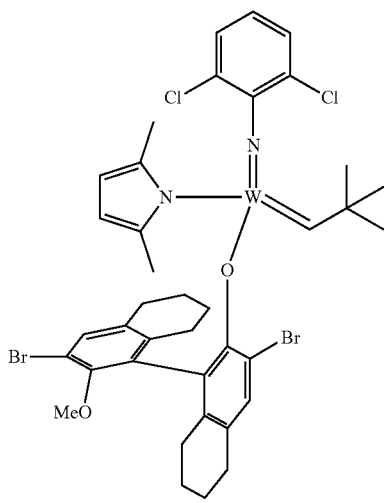
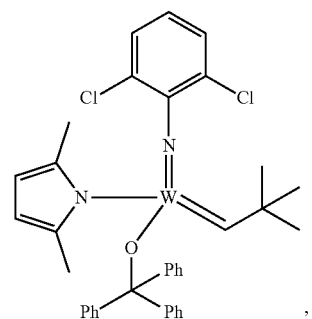

-continued
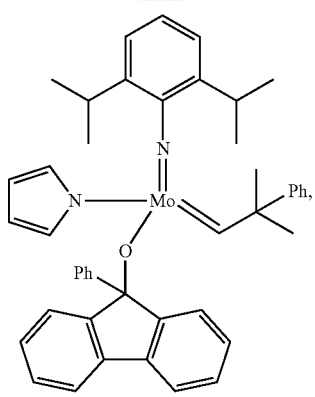
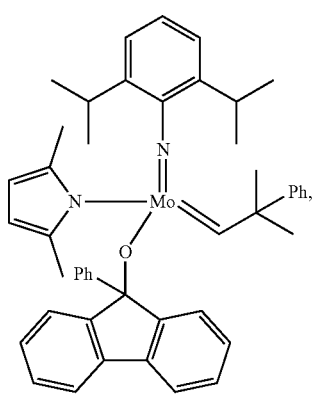
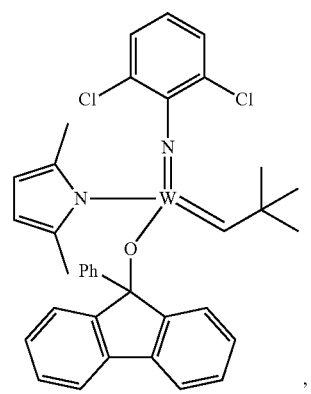
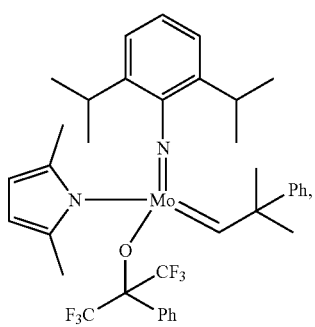
-continued
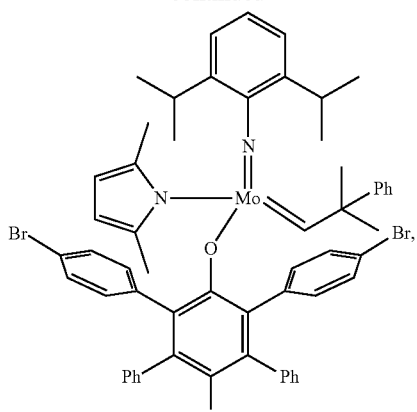
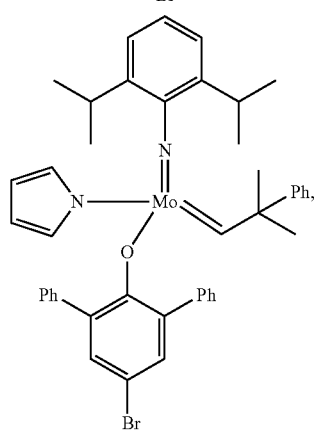
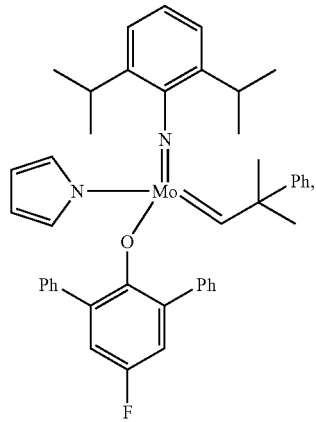
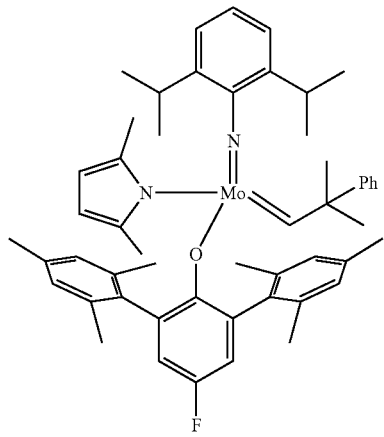

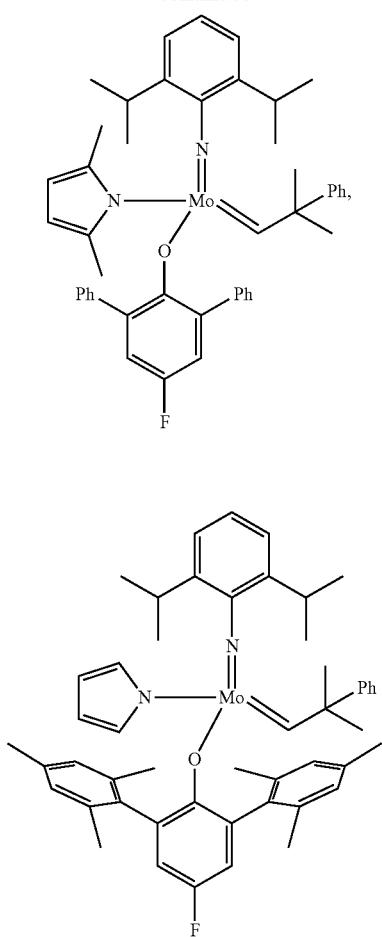
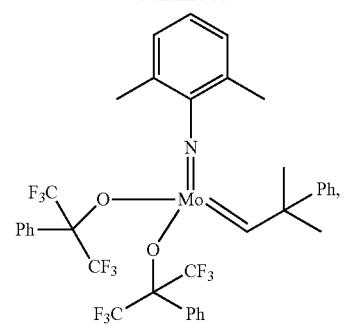
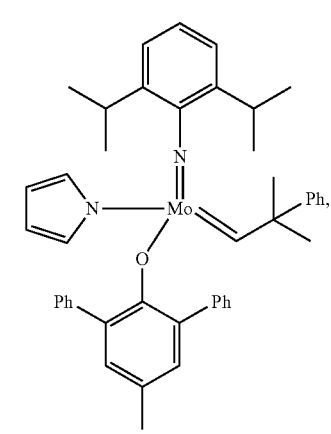
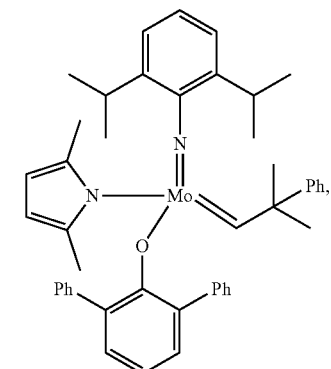
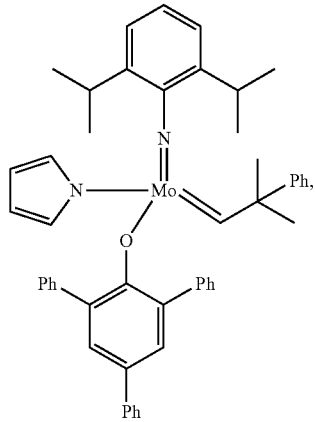

75
-continued
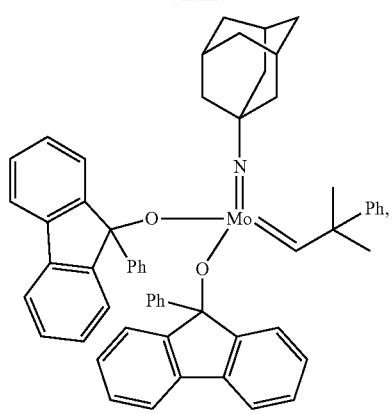
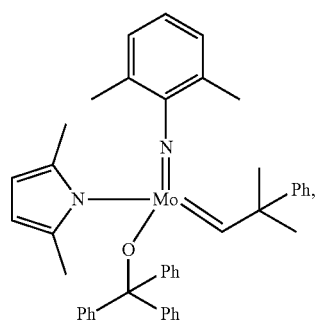
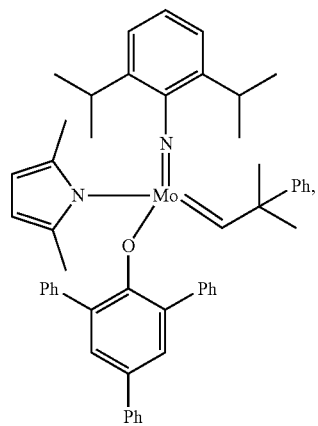
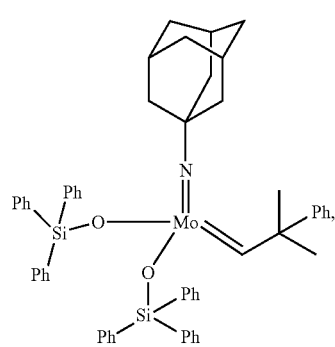
76
-continued
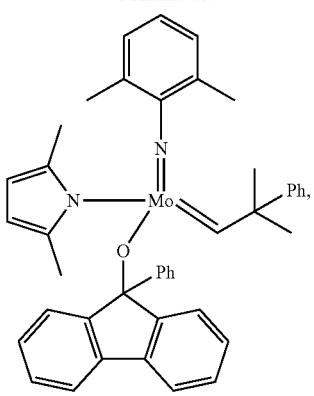
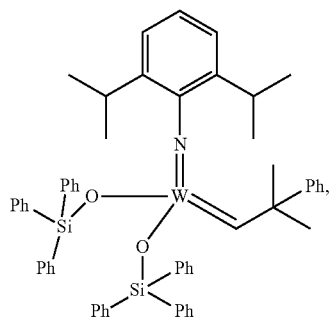
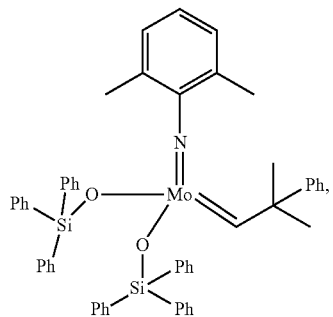
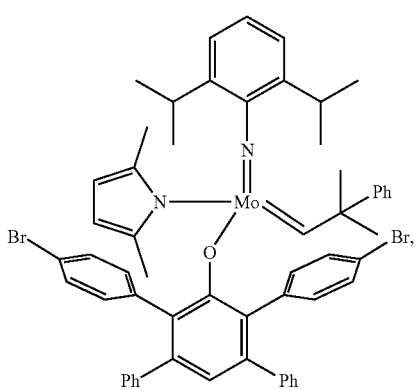

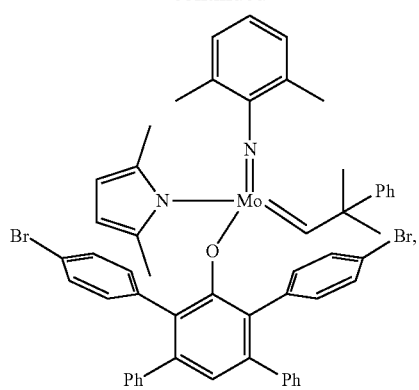
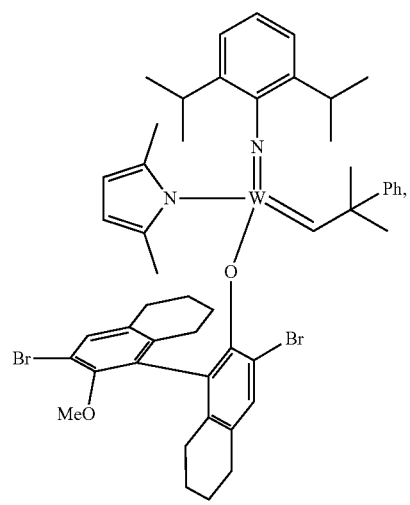
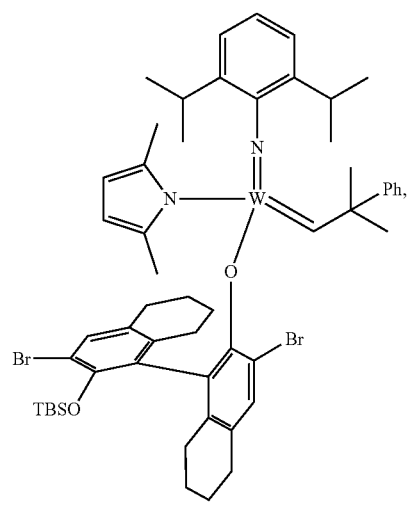
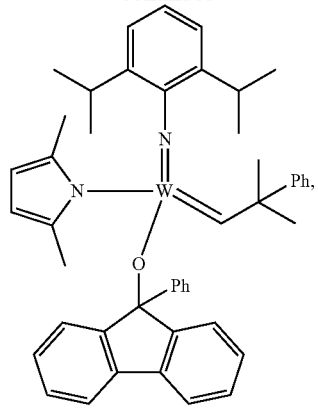
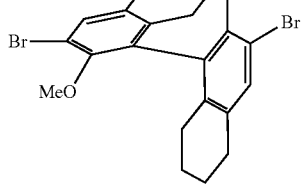
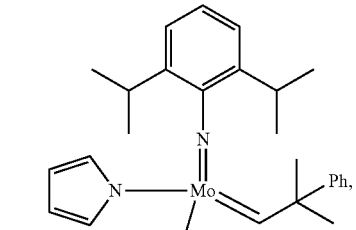
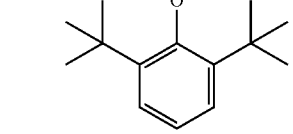
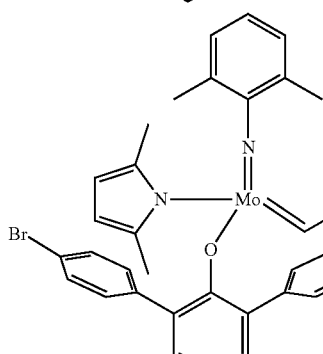

79
-continued
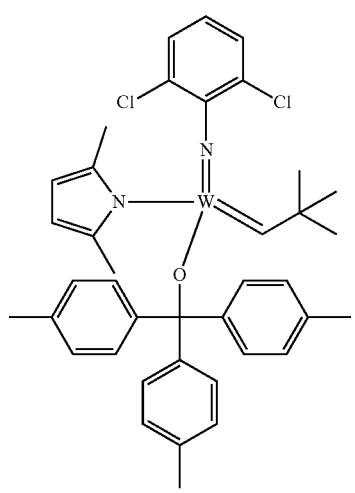
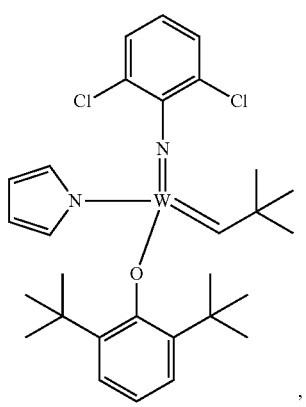
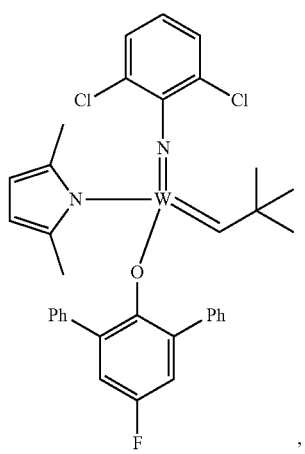
80
-continued
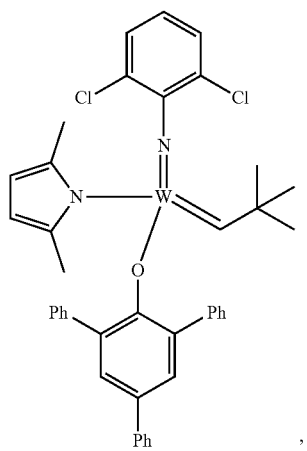
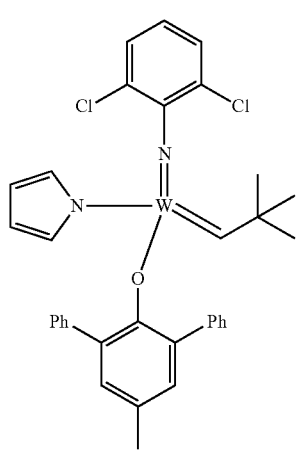
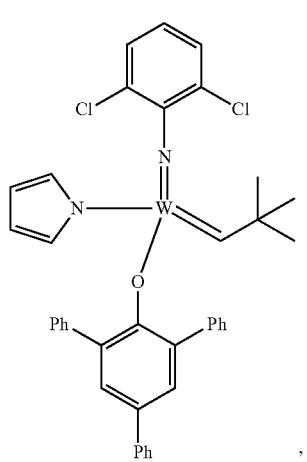

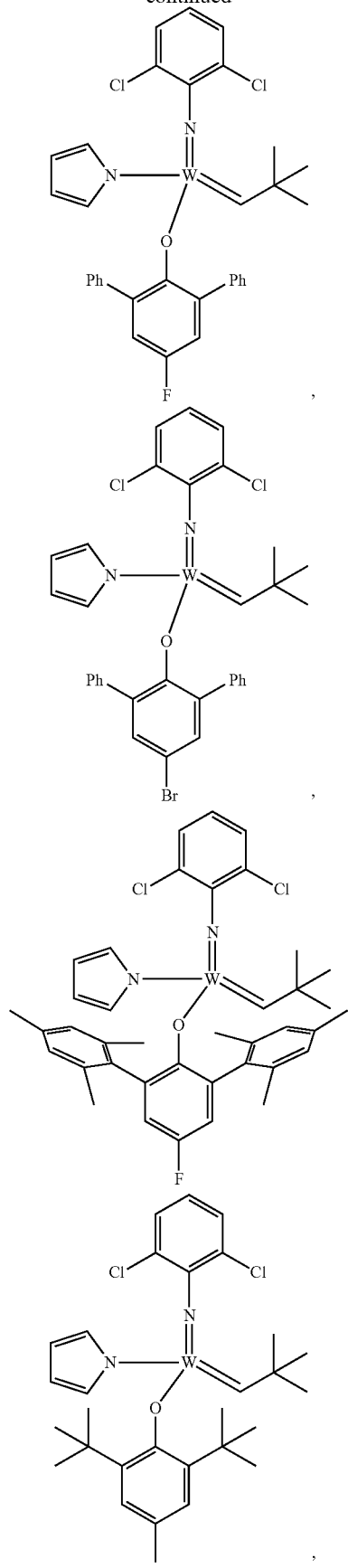
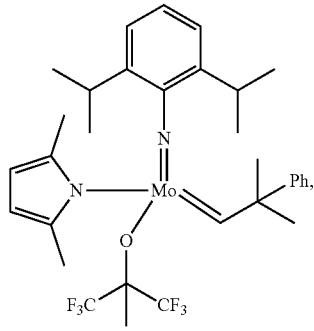
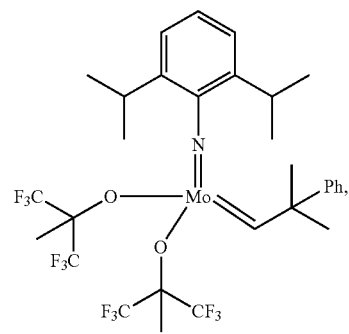
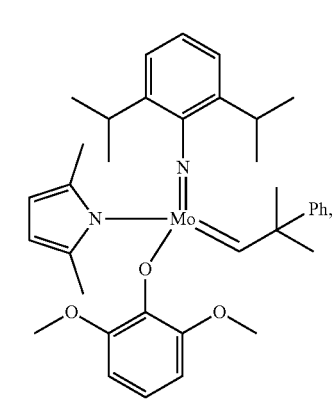
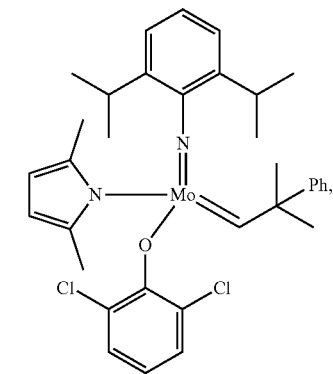

-continued

85
-continued
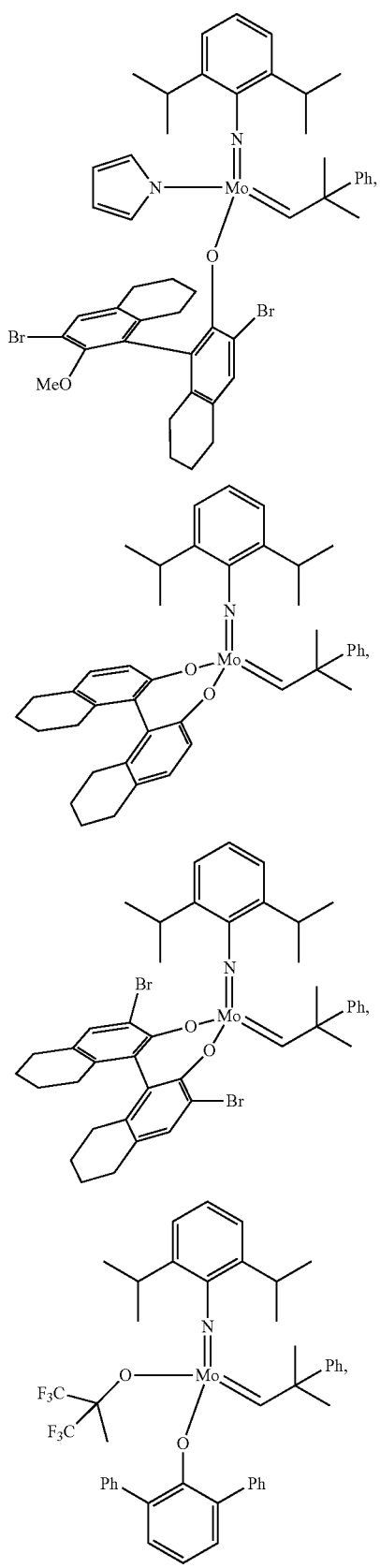
86
-continued
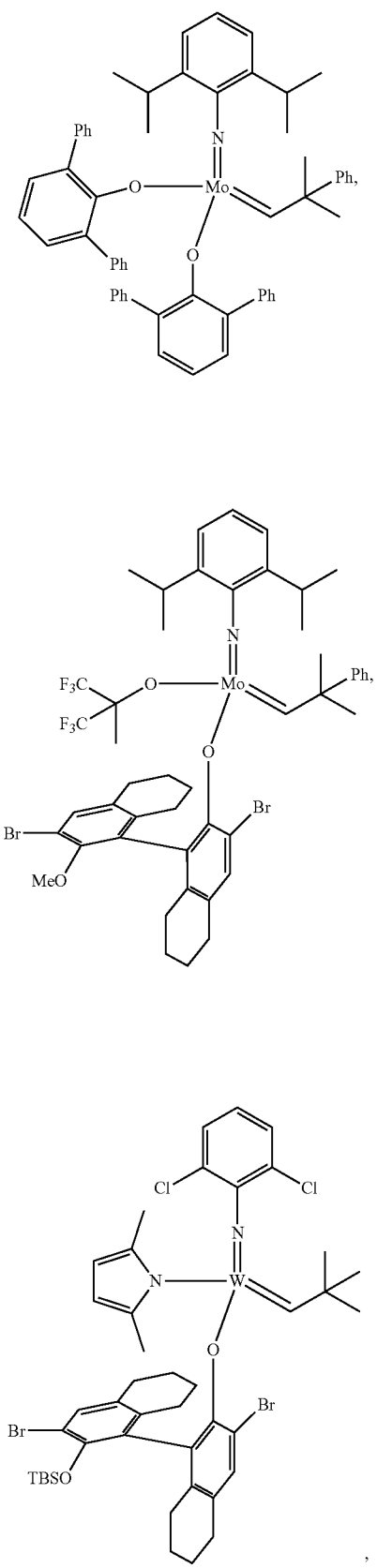

-continued
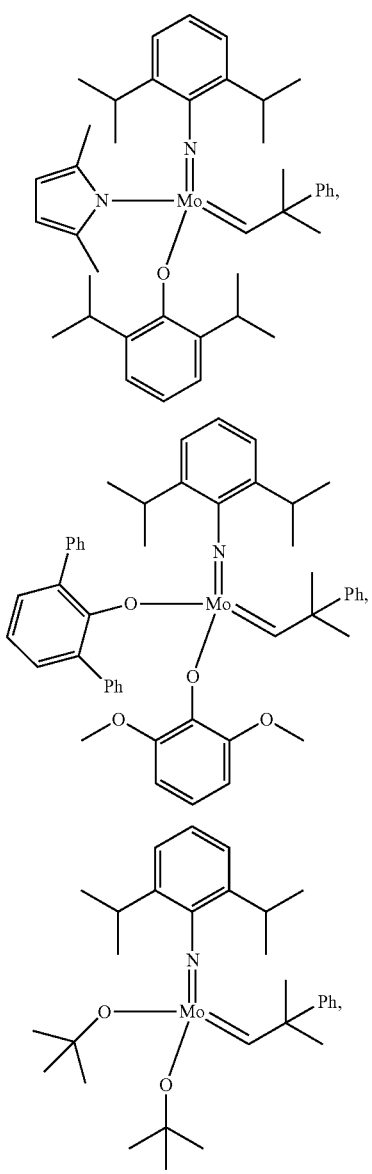
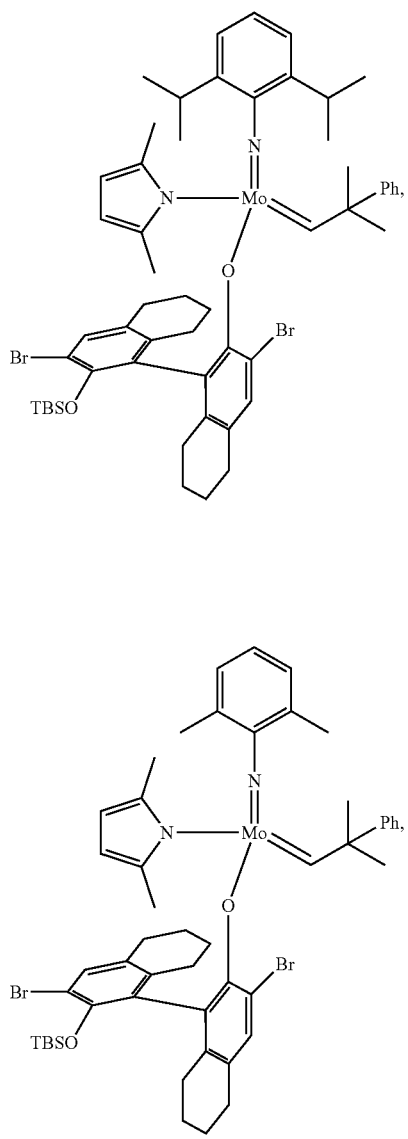
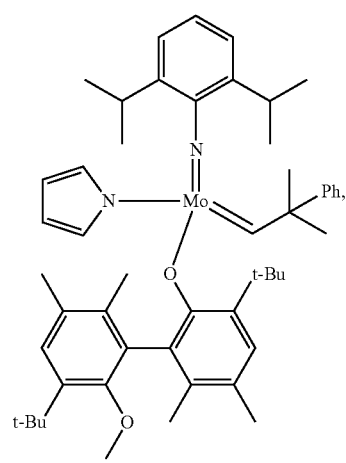
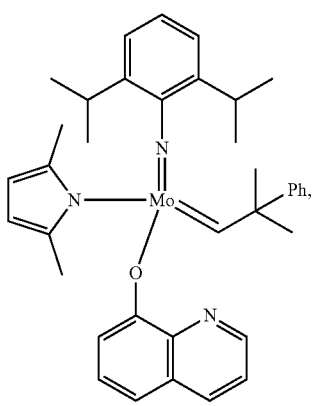

89
-continued
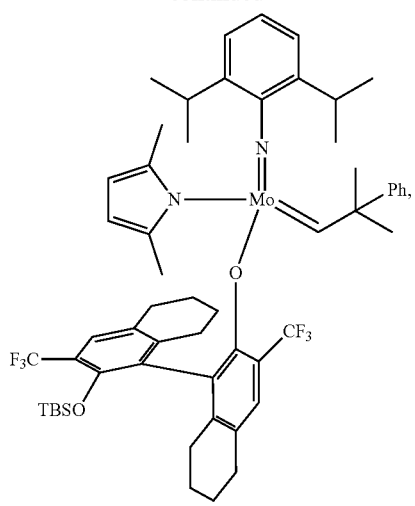
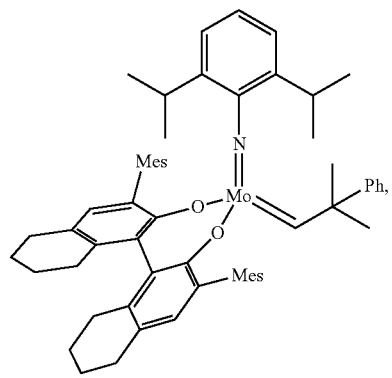
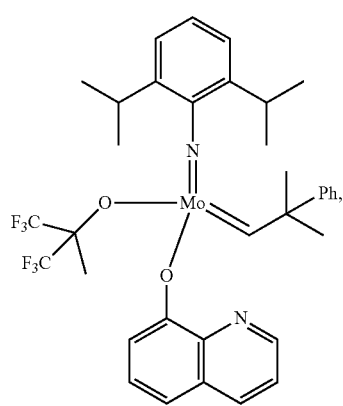
90
-continued
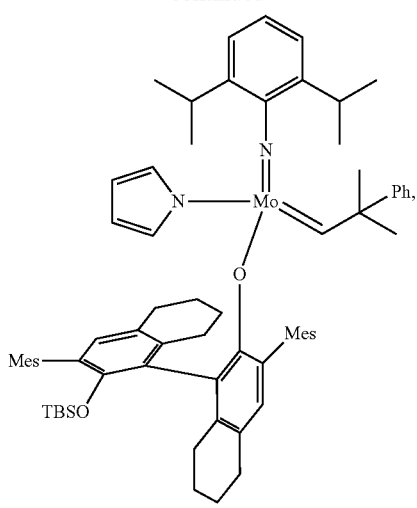
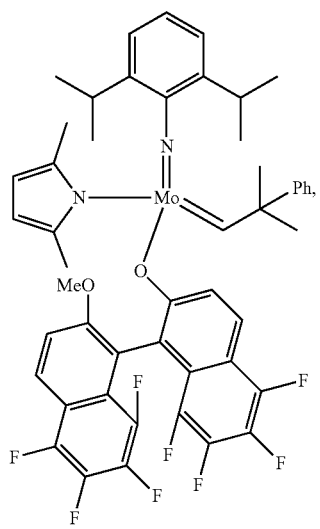

91
-continued
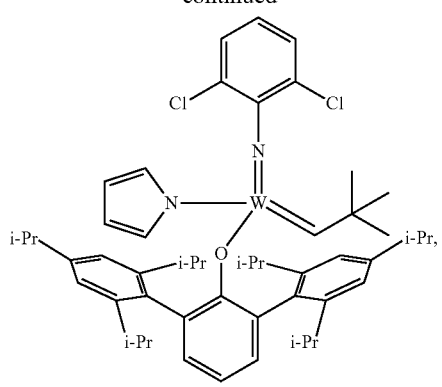
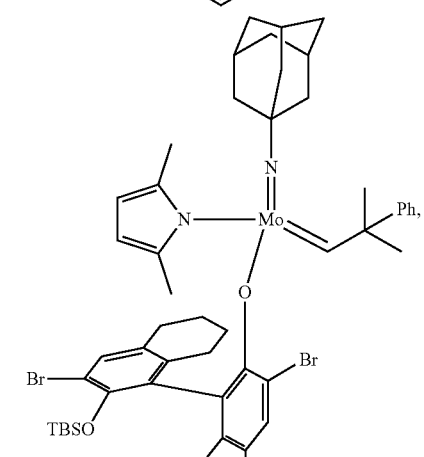
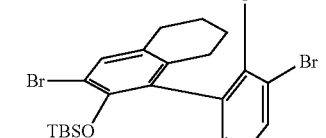
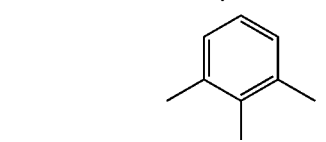
92
-continued
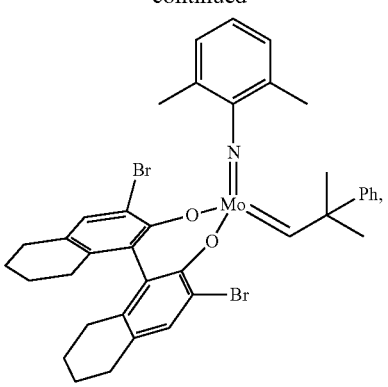
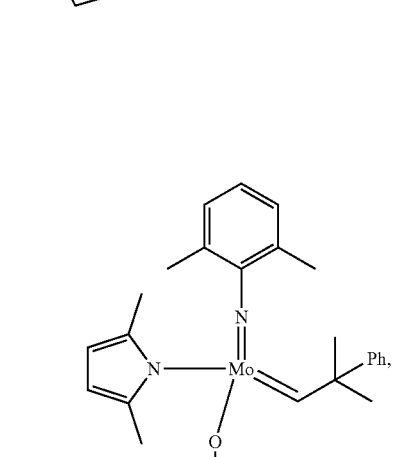
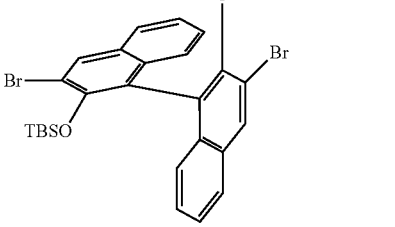
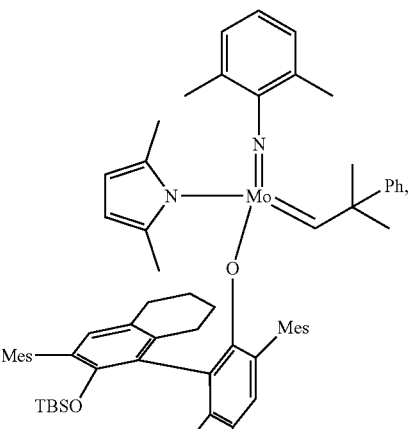

93
-continued
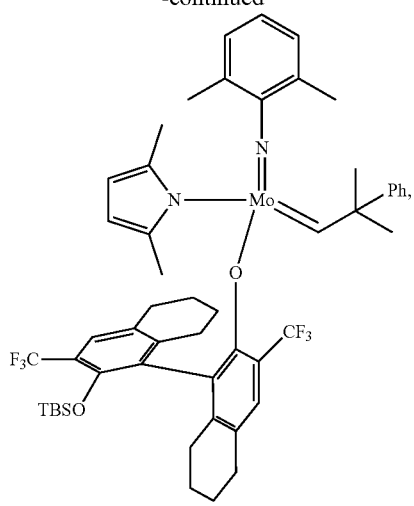
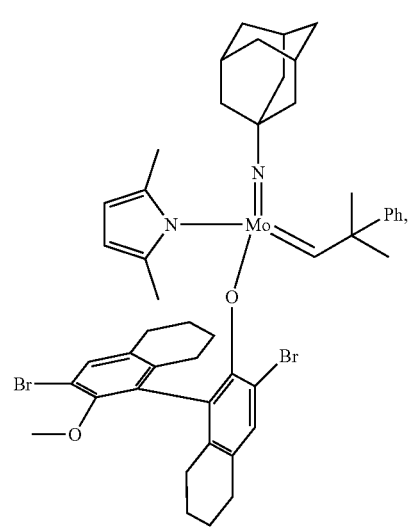
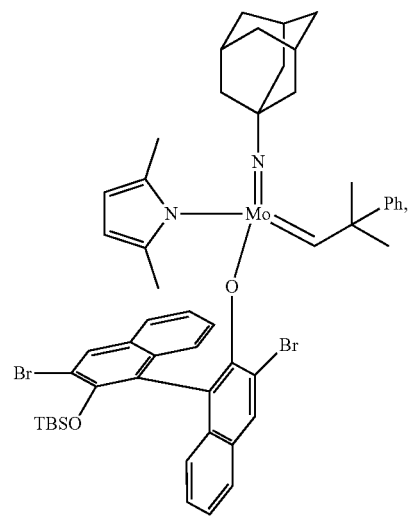
94
-continued
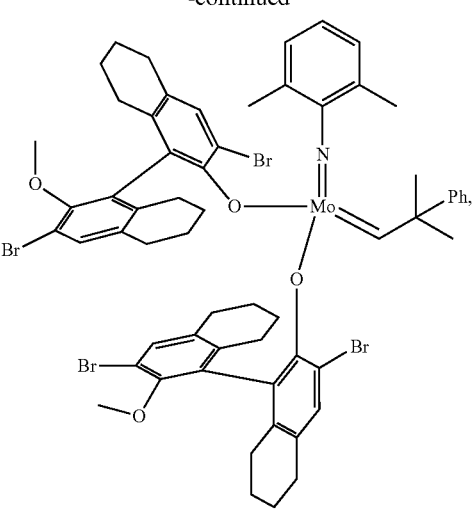
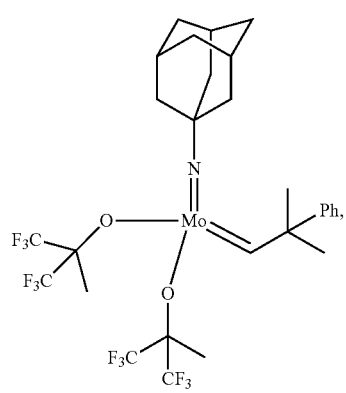
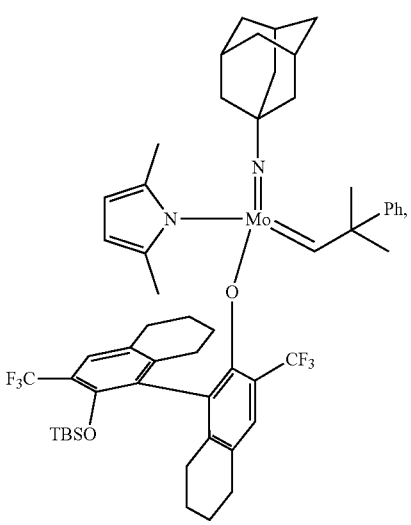

95
-continued
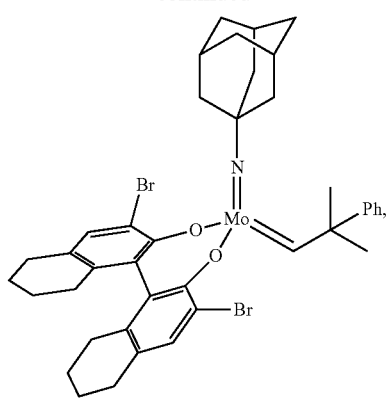
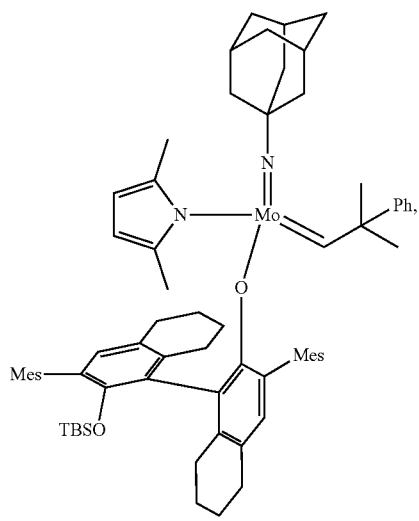
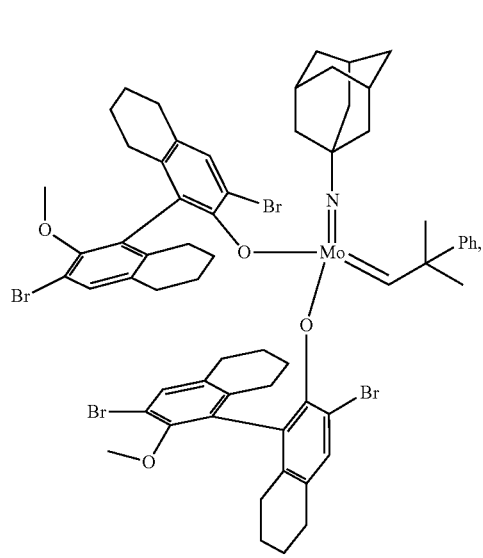
96
-continued
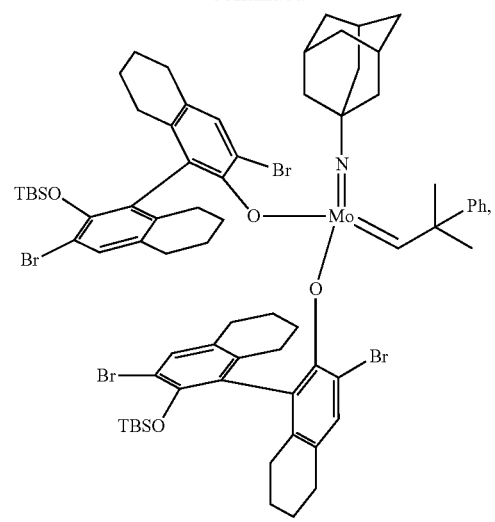
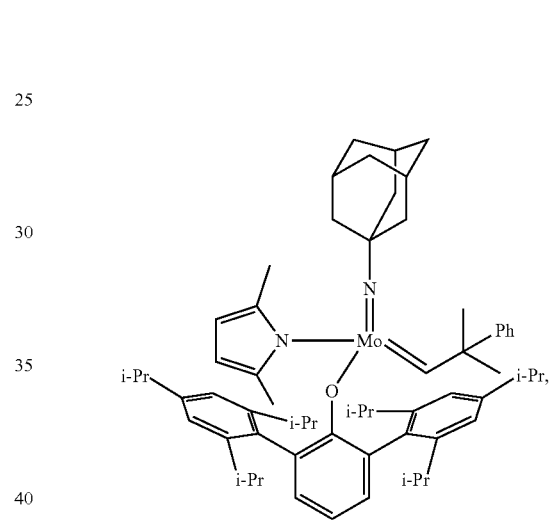
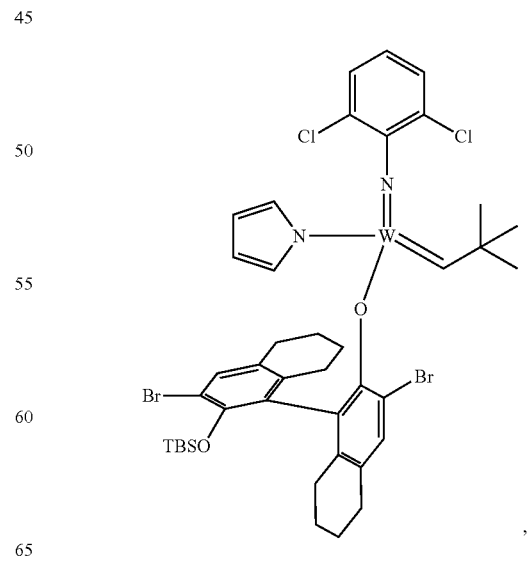

-continued
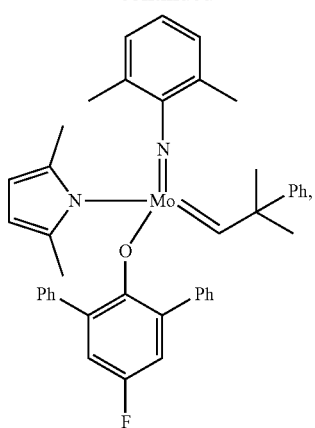
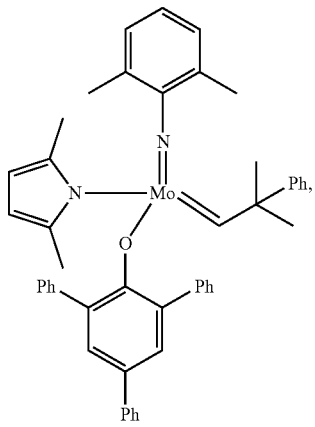
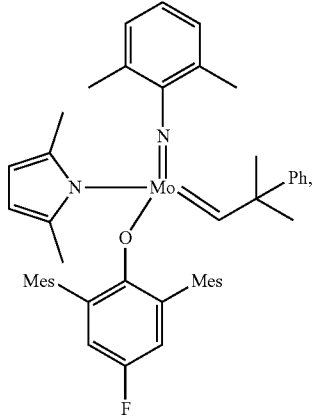
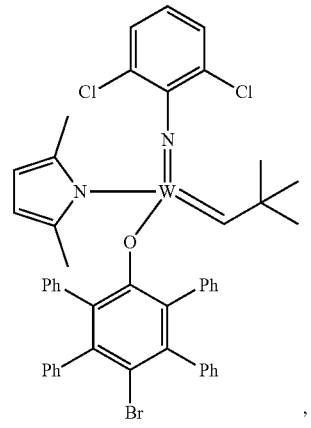
-continued
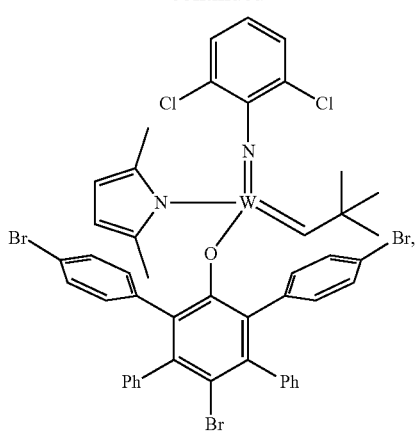
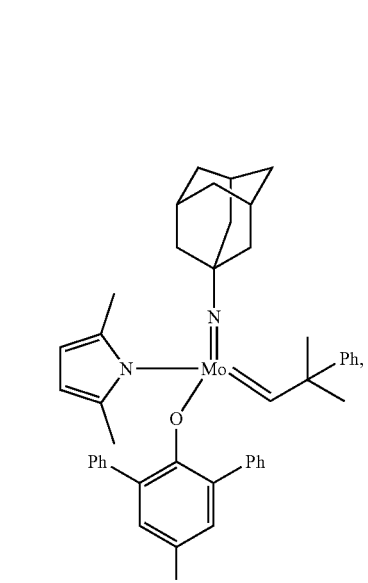
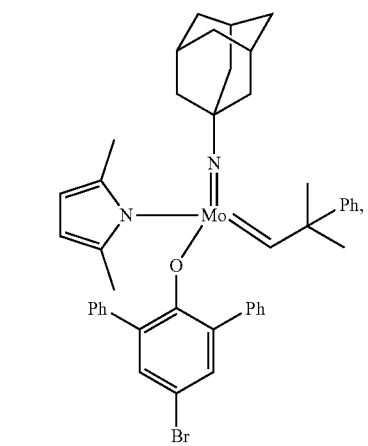

99
-continued
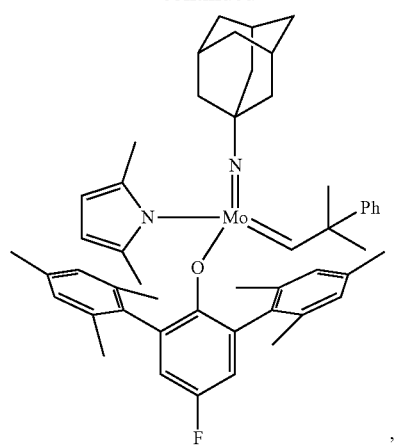
,
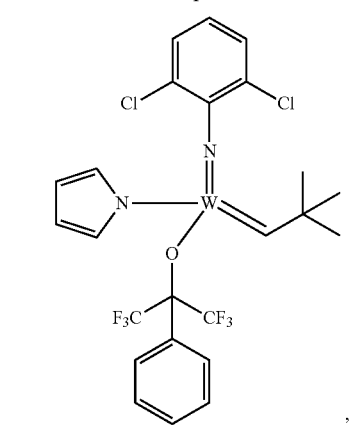
,
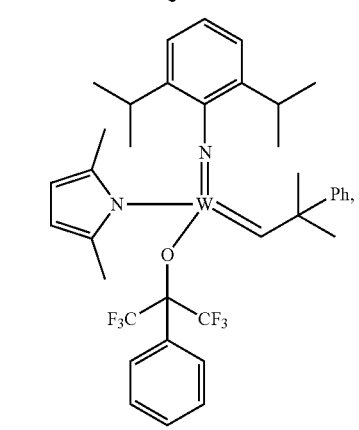
,
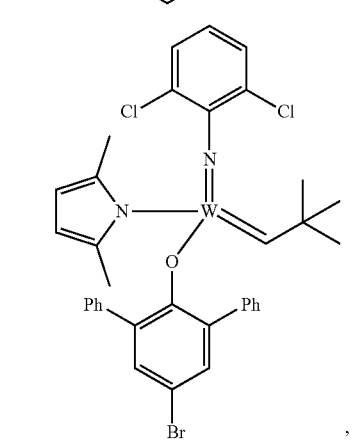
,
100
-continued
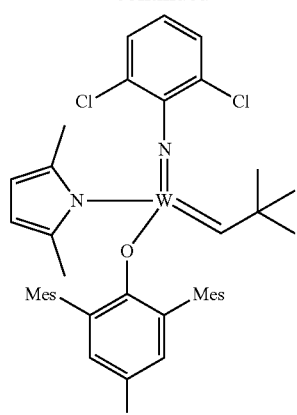
,
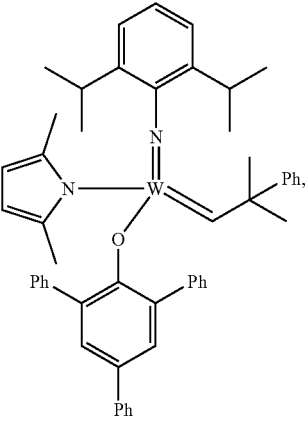
,
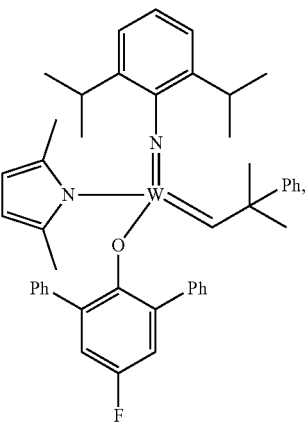
,
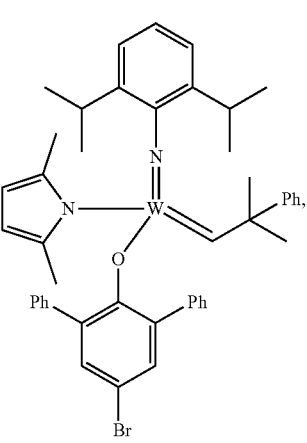
, -continued
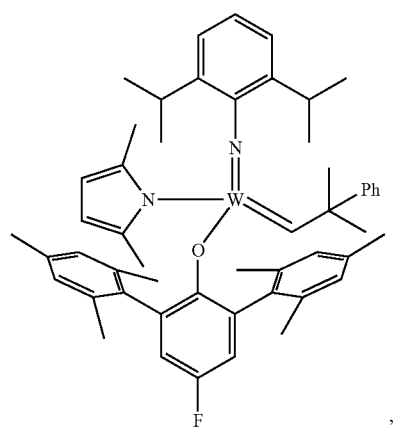
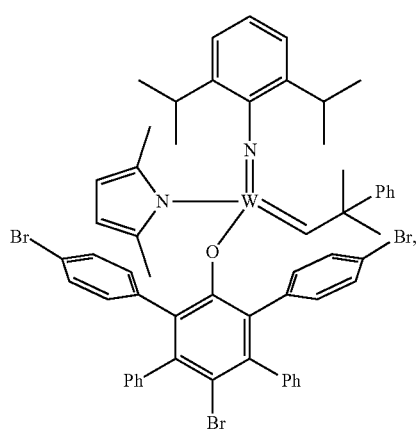
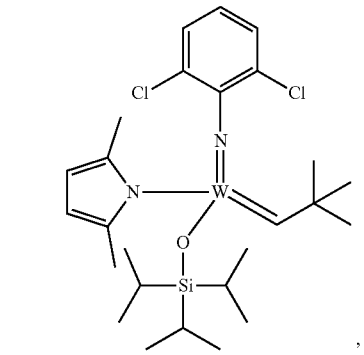
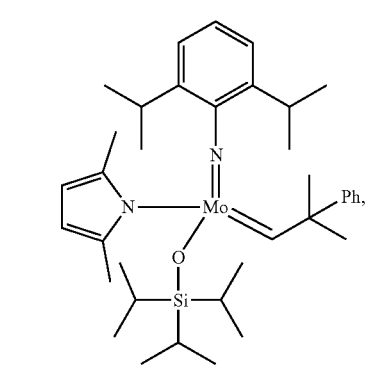
-continued
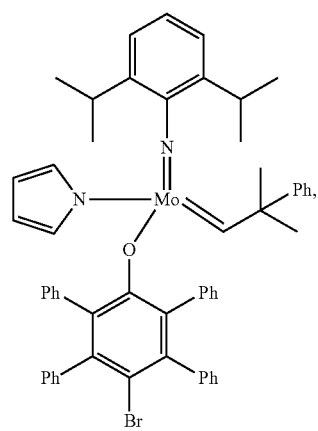
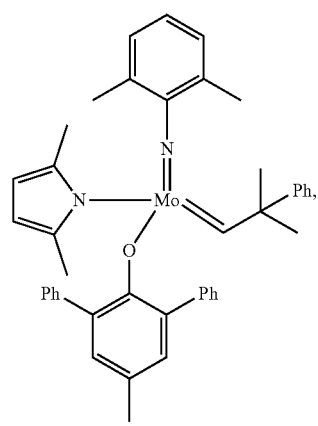
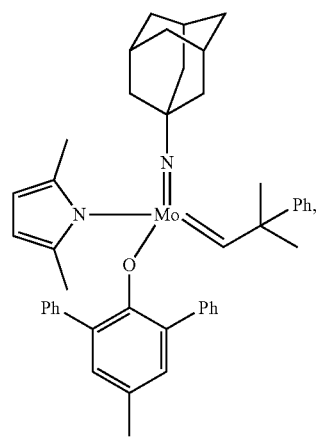
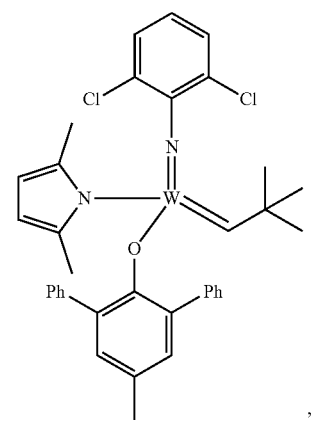

103
-continued
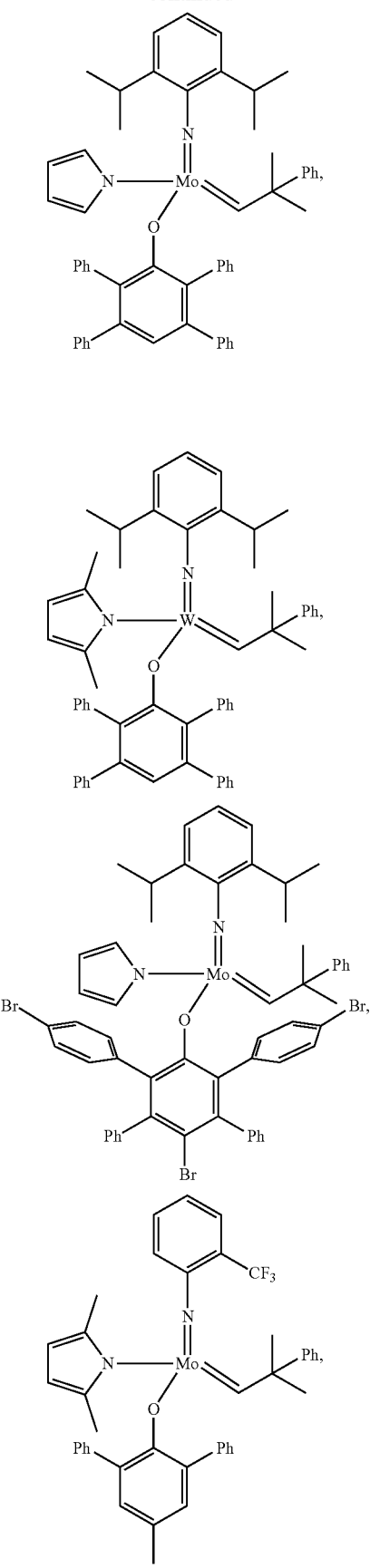
104
-continued
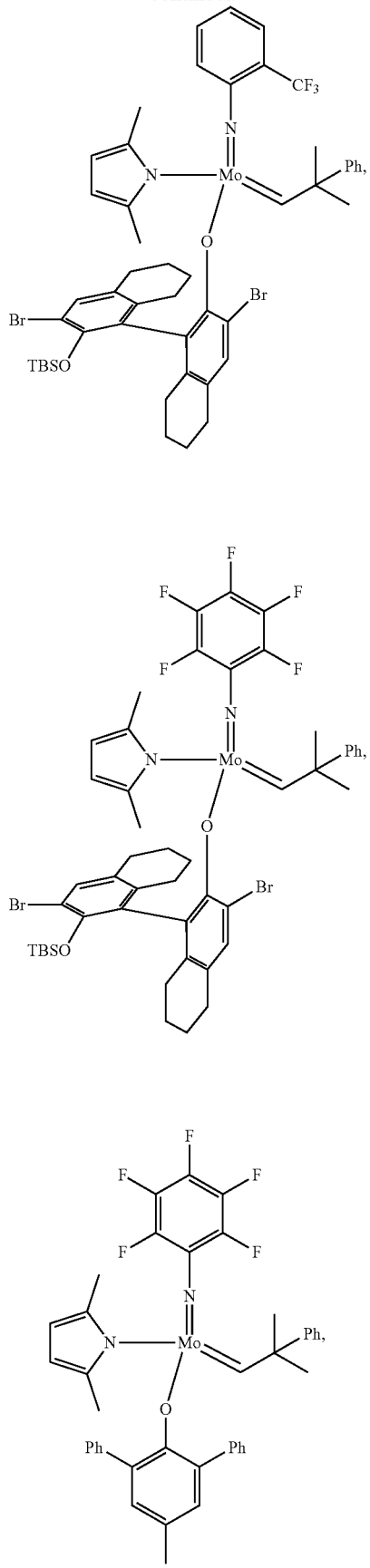

105
-continued
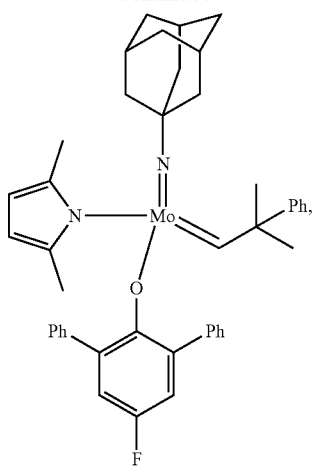
106
-continued
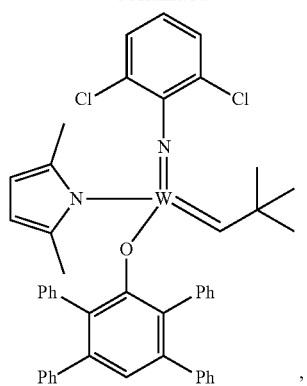
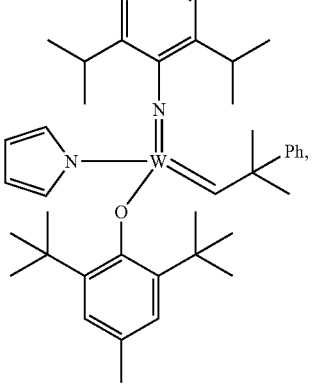
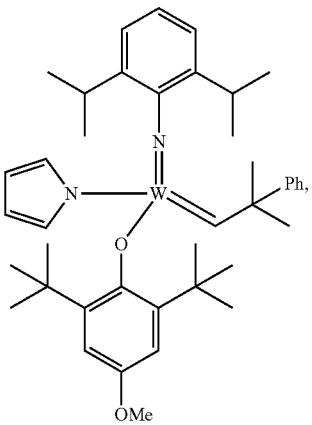
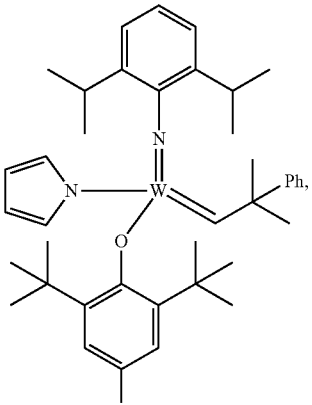

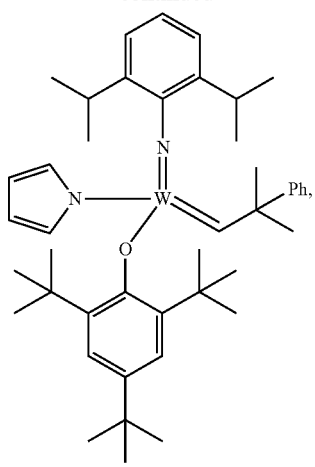
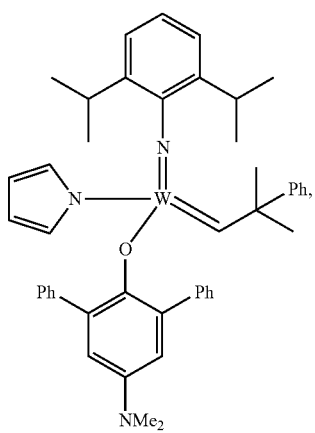
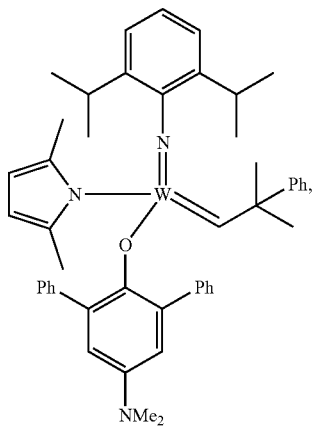
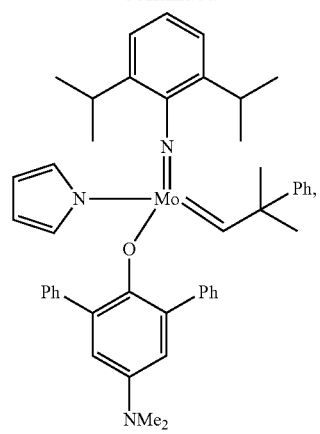
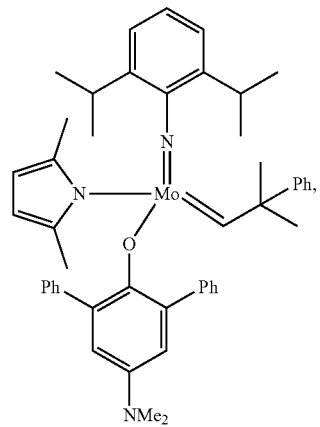
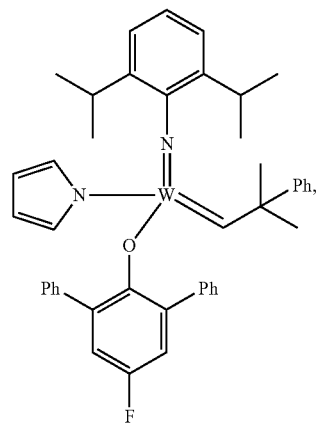
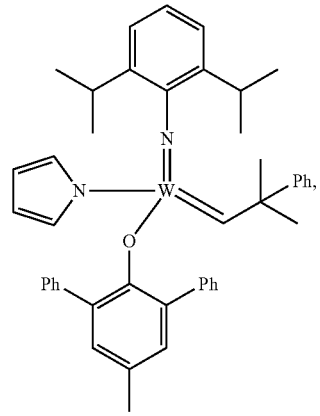

109
-continued
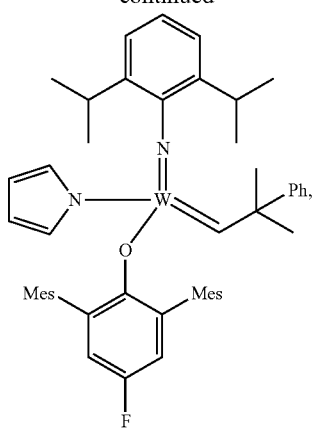
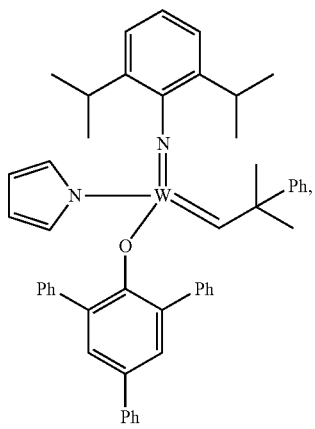
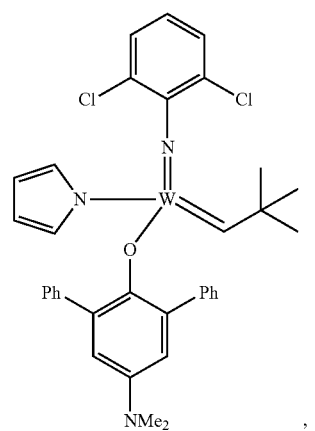
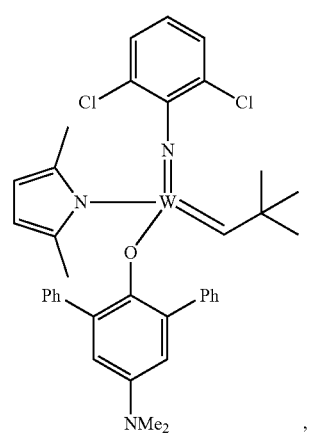,
110
-continued
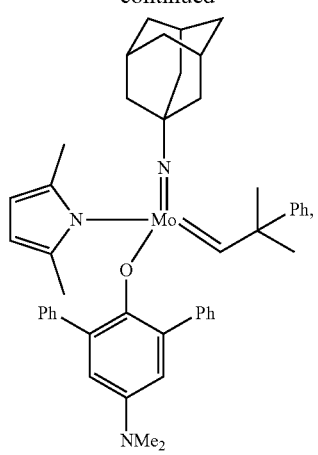
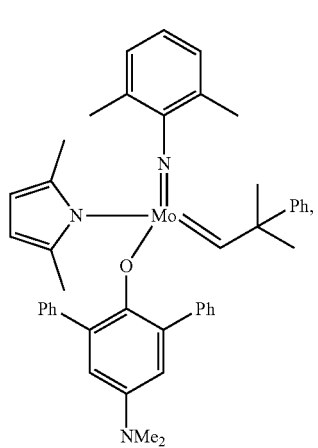
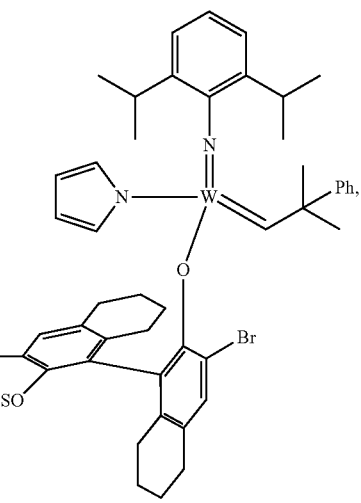

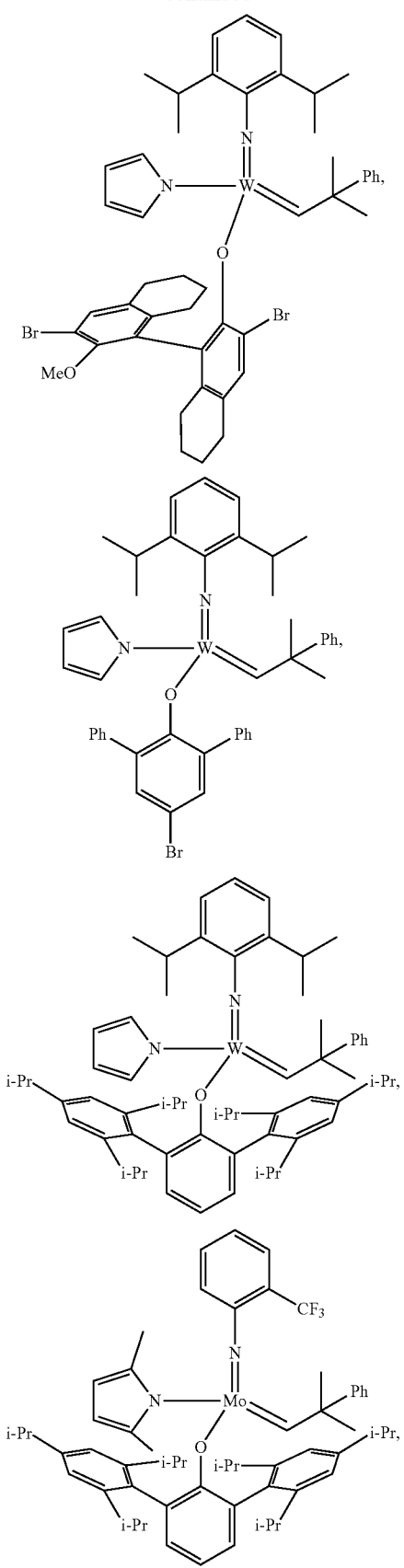
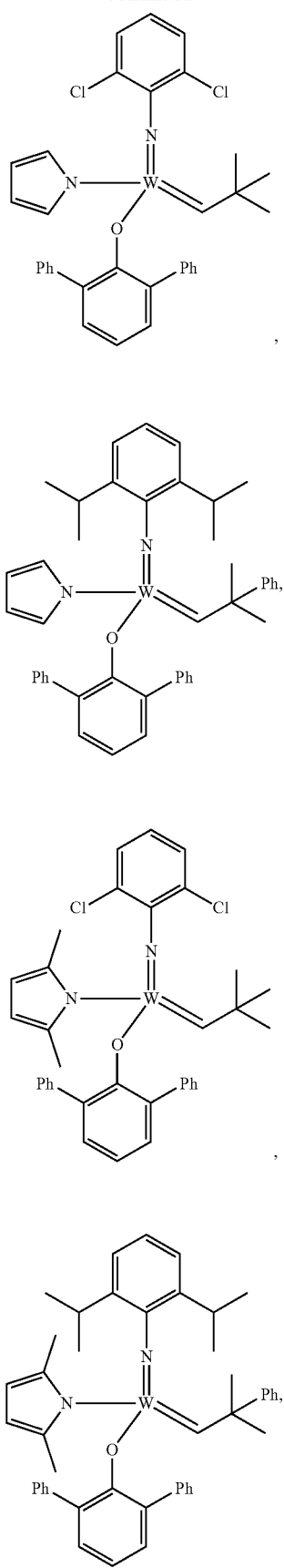

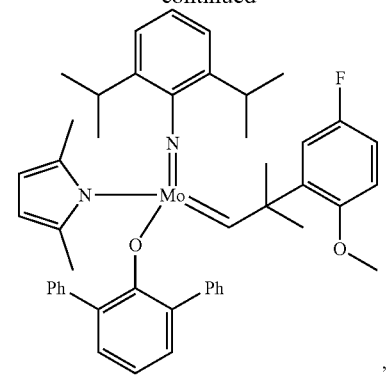
,
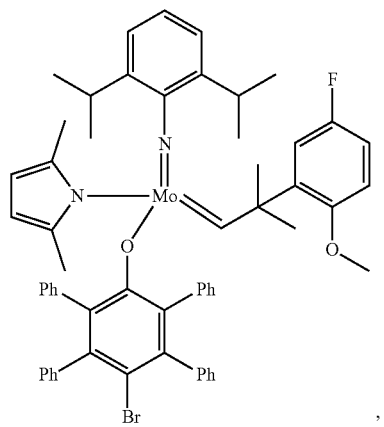
,
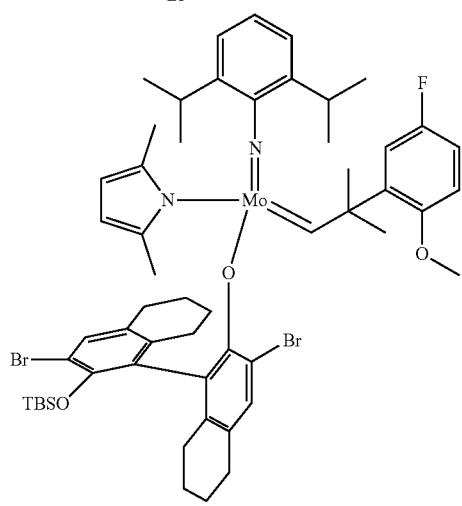
,
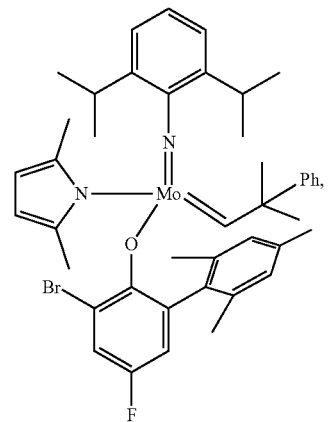
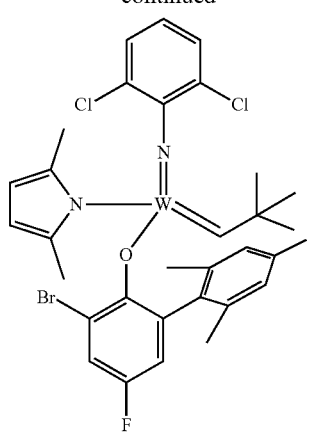
,
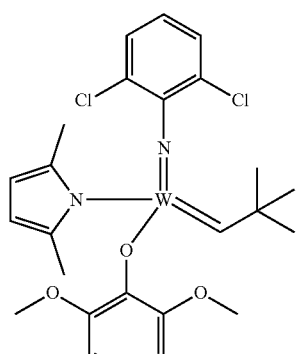
,
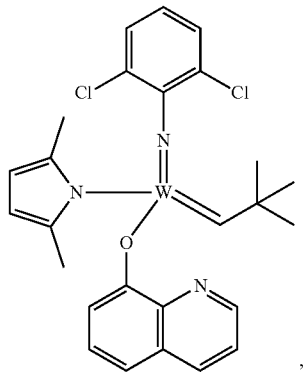
,
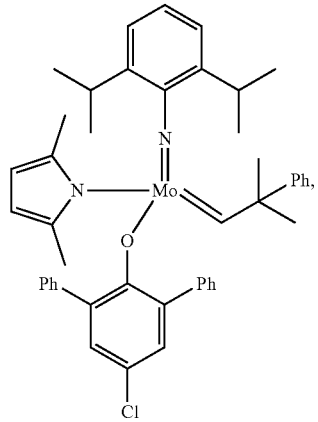

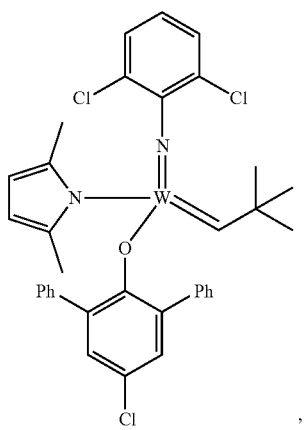
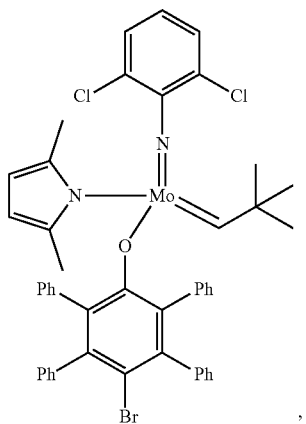
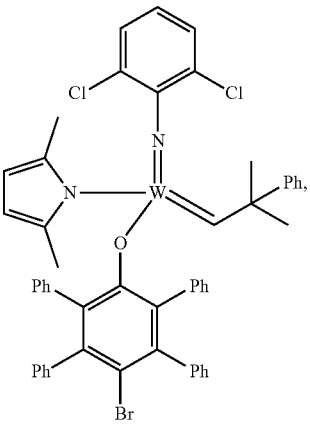
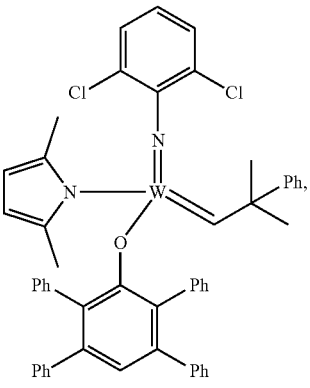
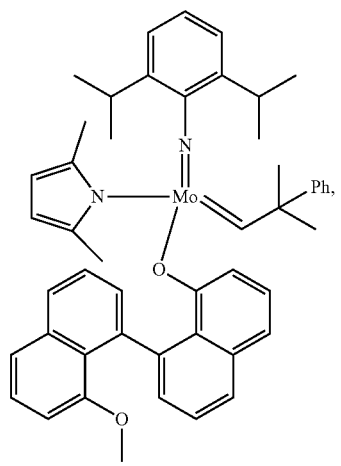
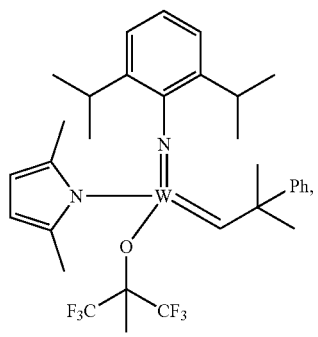
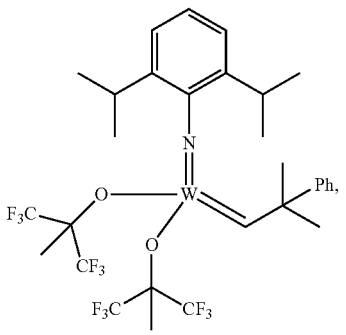
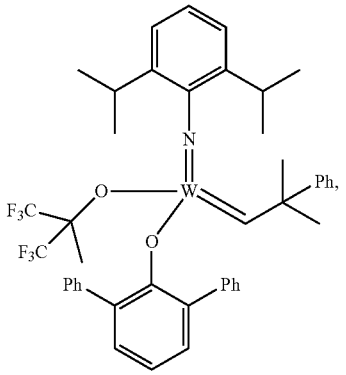

117
-continued
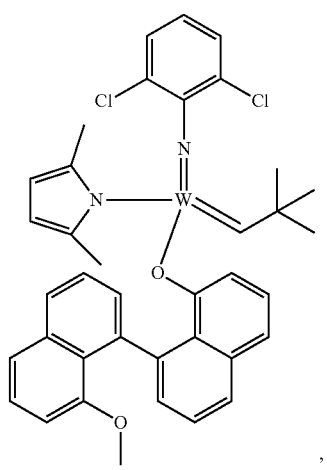
,
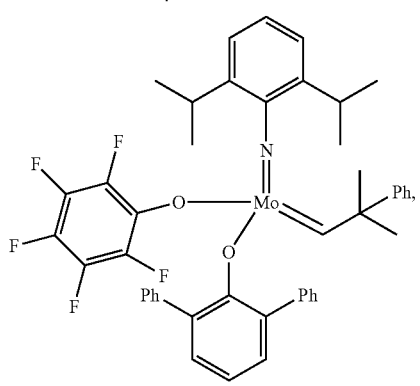
,
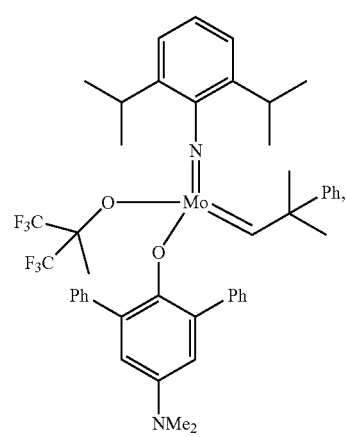
,
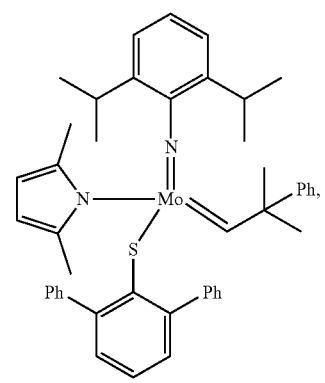
,
118
-continued
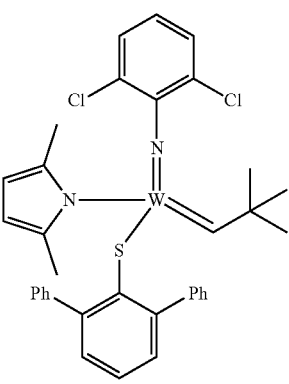
,
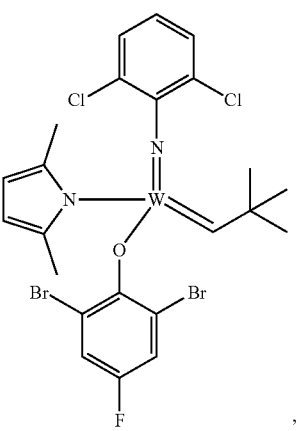
,
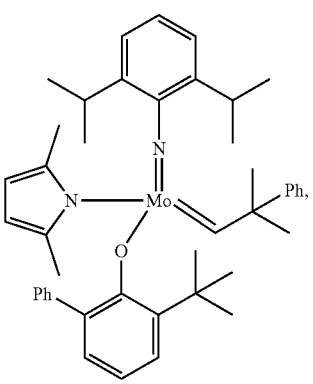
,
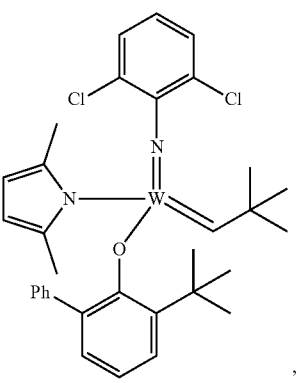
,

119
-continued
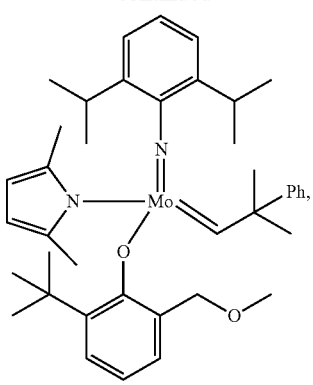
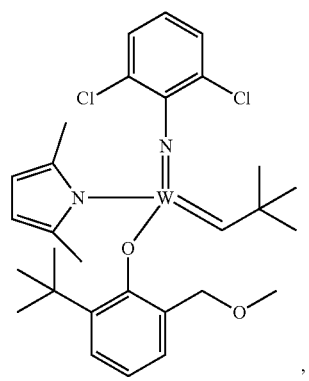
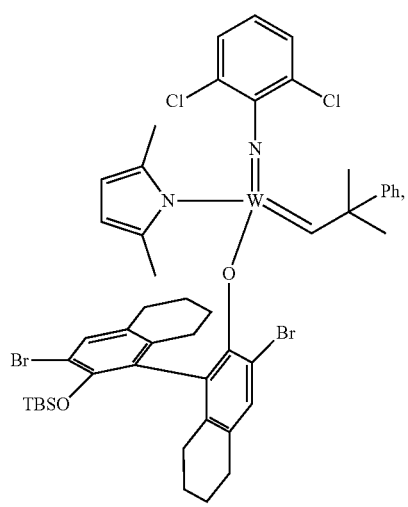
120
-continued
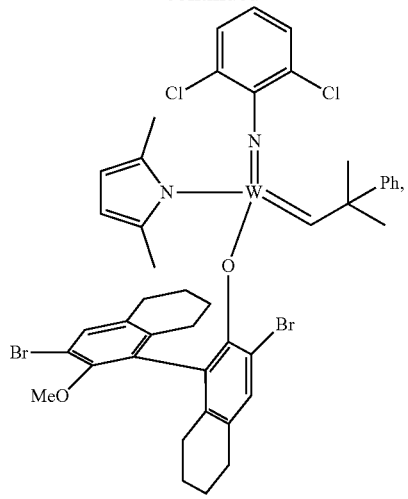
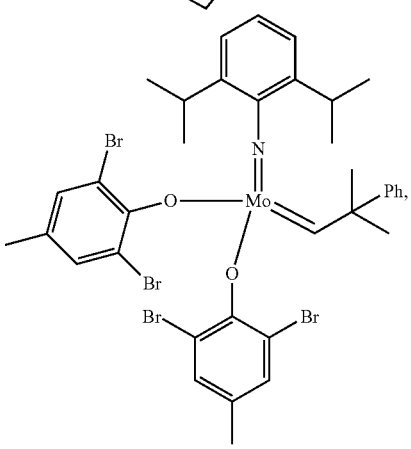
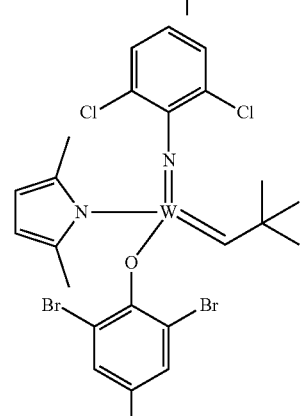
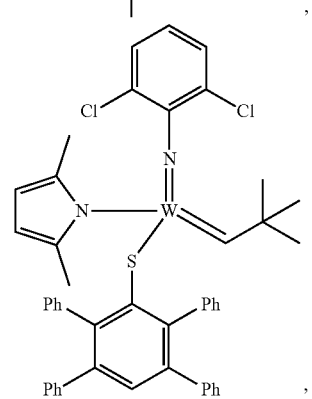

121
-continued
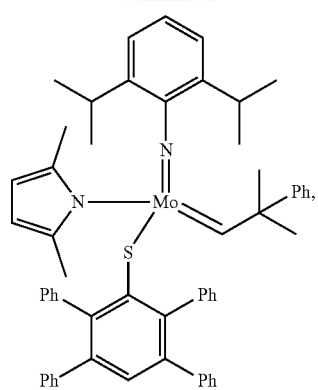
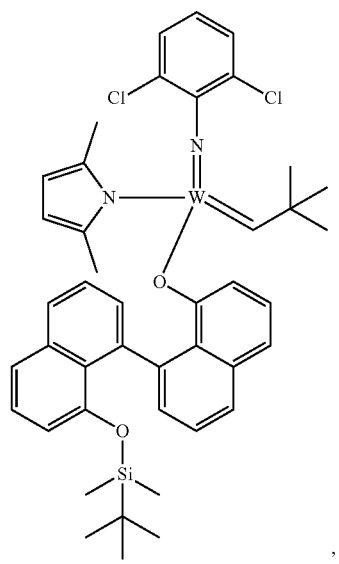
122
-continued
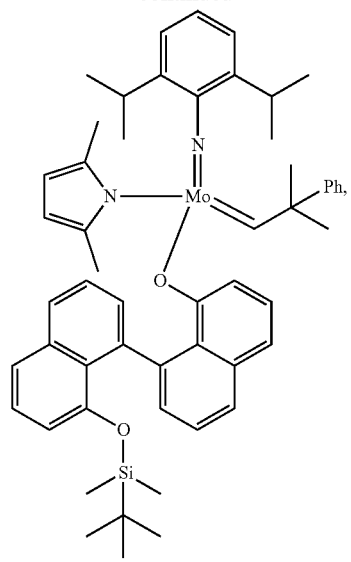
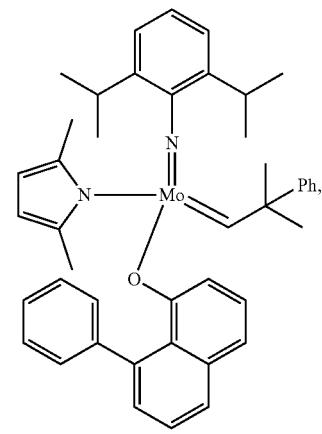
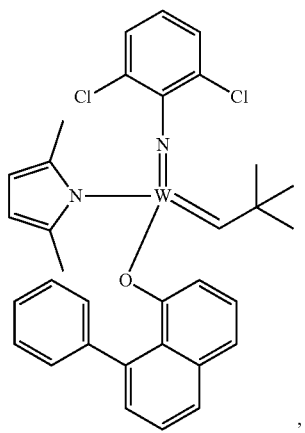
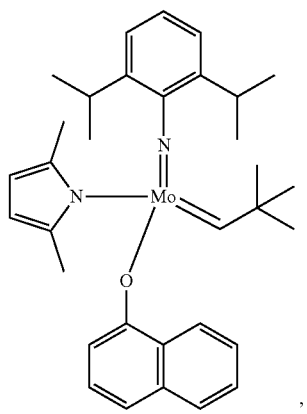

| 123 | 124 |
|---|---|
| -continued | -continued |
| 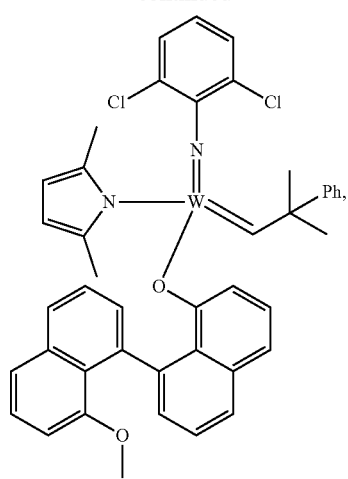 | 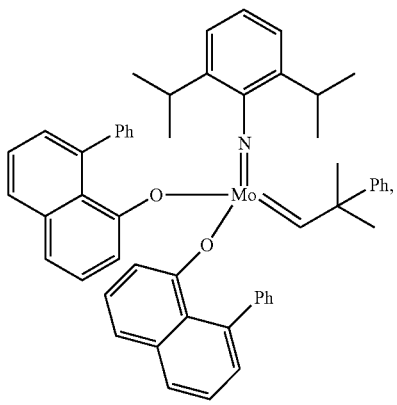 |
| 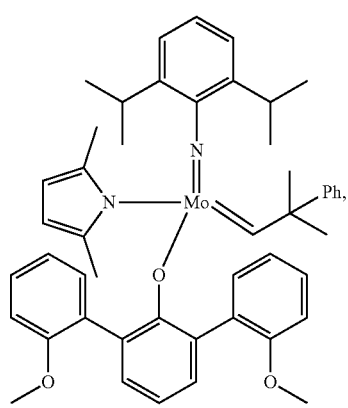 | 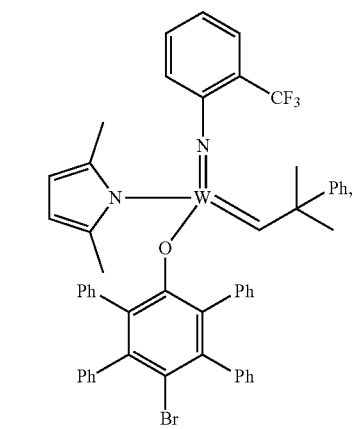 |
| 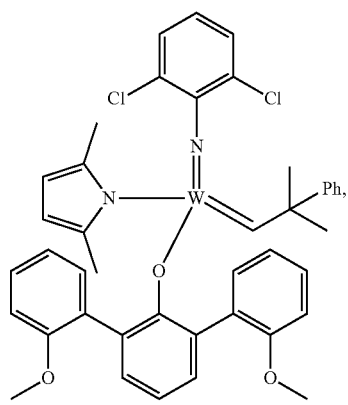 | |
| 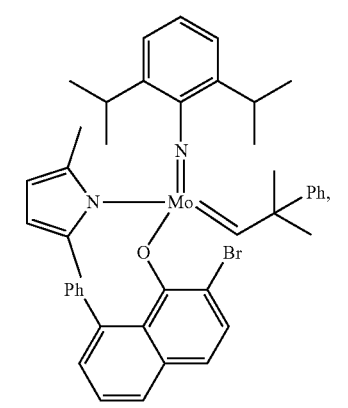 | 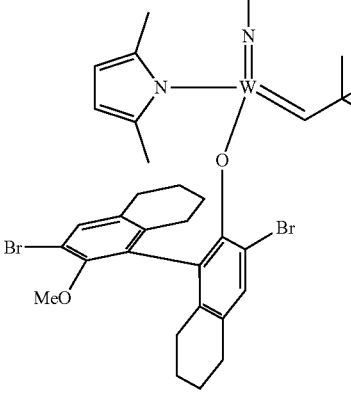 |

-continued
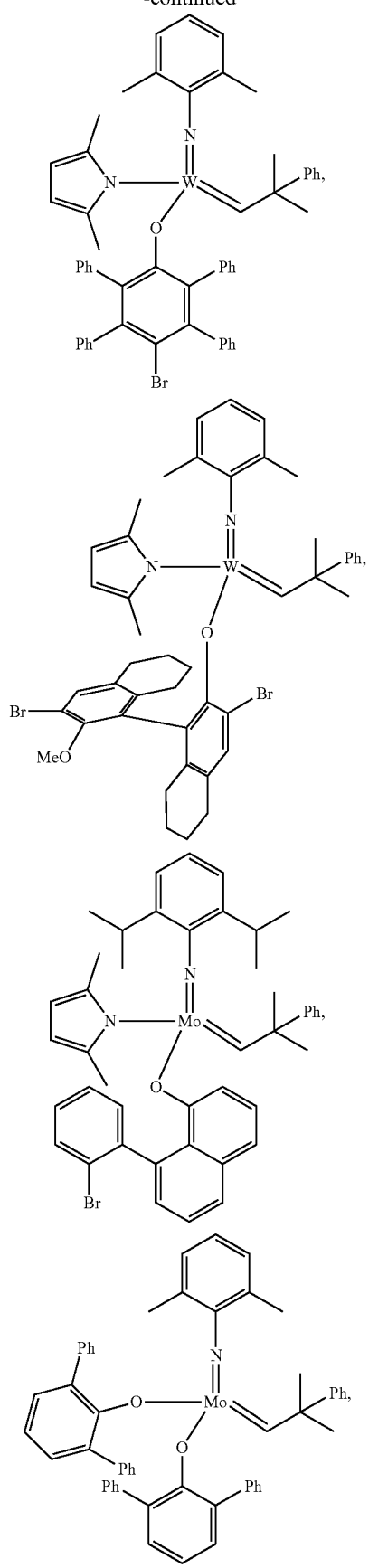
-continued
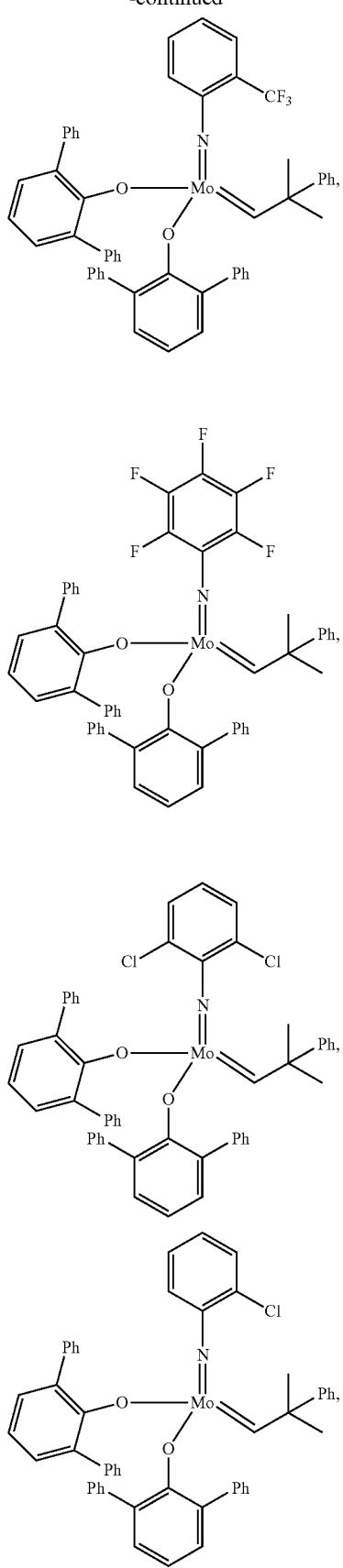

-continued
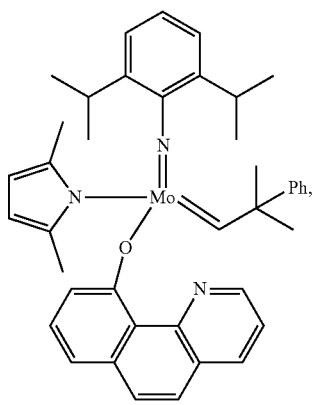
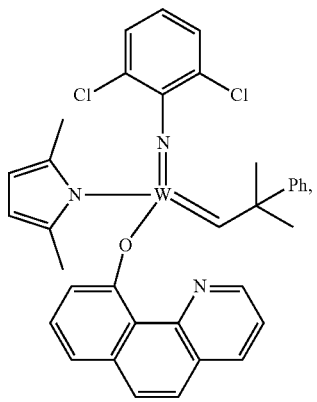
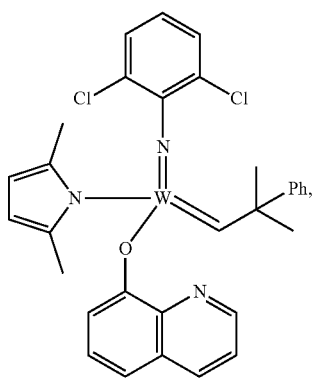
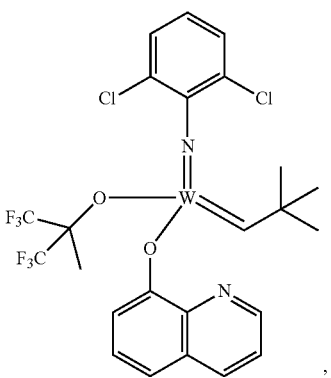
-continued
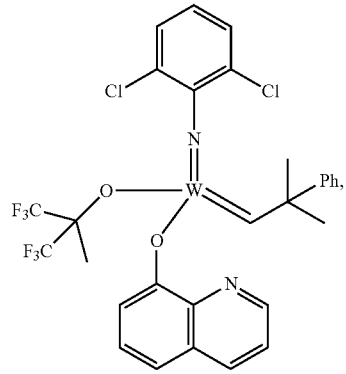
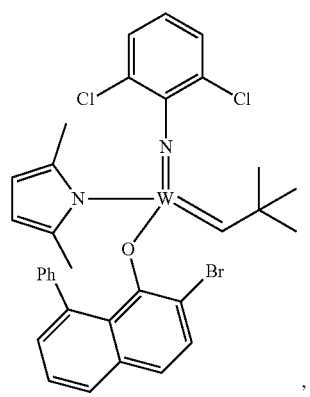
, and
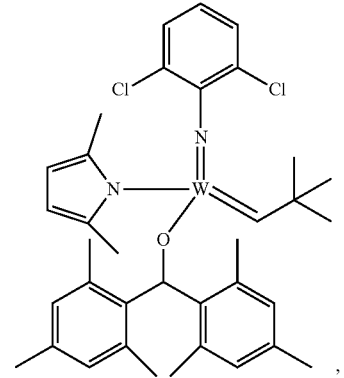
,
wherein "Me" is methyl, "Ph" is phenyl, "i-Pr" is isopropyl, "Mes" is mesityl (i.e., 2,4,6-trimethylphenyl), and "TBS" is tert-butyldimethylsilyl.

In some embodiments, the metathesis catalyst is

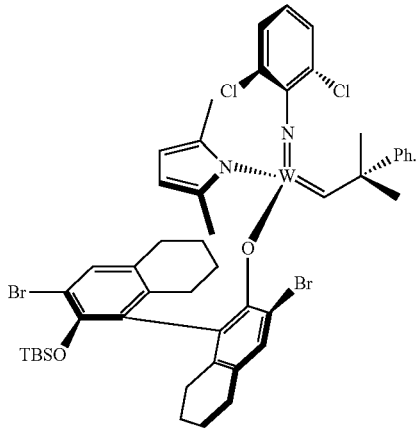

In some embodiments, the catalyst is a compound of Formula XLIII:

(XLIII)

wherein:
each of $R^{31}$ and $R^{32}$ is independently R, —OR, —SR, —N(R)$_2$, —OC(O)R, —SOR, —SO$_2$R, —SO$_2$N(R)$_2$, —C(O)N(R)$_2$, —NRC(O)R, or —NRSO$_2$R;
each of $R^{33}$ and $R^{34}$ is independently halogen, R, —N(R)$_2$, —NRC(O)R, —NRC(O)OR, —NRC(O)N(R)$_2$, —NRSO$_2$R, —NRSO$_2$N(R)$_2$, —NROR, NR$_3$, —OR, a phosphorus-containing ligand, or an optionally substituted group selected from:
a 5-6 membered monocyclic heteroaryl ring having at least one nitrogen and 0-3 additional heteroatoms independently selected from nitrogen, oxygen, or sulfur,
a 4-7 membered saturated or partially unsaturated heterocyclic ring having at least one nitrogen and 0-2 additional heteroatoms independently selected from nitrogen, oxygen, or sulfur,
a 7-10 membered bicyclic saturated or partially unsaturated heterocyclic ring having at least one nitrogen and 0-4 additional heteroatoms independently selected from nitrogen, oxygen, or sulfur, and
an 8-10 membered bicyclic heteroaryl ring having at least one nitrogen and 0-4 additional heteroatoms independently selected from nitrogen, oxygen, or sulfur;
each R is independently hydrogen or an optionally substituted group selected from:
phenyl,
ferrocene,
$C_{1-20}$ aliphatic, $C_{1-20}$ heteroaliphatic having 1-3 heteroatoms independently selected from nitrogen, oxygen, or sulfur,
a 3-7 membered saturated or partially unsaturated carbocyclic ring,
an 8-10 membered bicyclic saturated, partially unsaturated or aryl ring,
a 5-6 membered monocyclic heteroaryl ring having 1-4 heteroatoms independently selected from nitrogen, oxygen, or sulfur,
a 4-7 membered saturated or partially unsaturated heterocyclic ring having 1-3 heteroatoms independently selected from nitrogen, oxygen, or sulfur,
a 7-10 membered bicyclic saturated or partially unsaturated heterocyclic ring having 1-5 heteroatoms independently selected from nitrogen, oxygen, or sulfur; and
an 8-10 membered bicyclic heteroaryl ring having 1-5 heteroatoms independently selected from nitrogen, oxygen, or sulfur;
or two or three R groups on the same nitrogen atom are taken together with the nitrogen to form an optionally substituted 3-12 membered saturated, partially unsaturated, or aryl ring having 0-5 additional heteroatoms not including the same nitrogen atom independently selected from nitrogen, oxygen, or sulfur;
or two R groups on the same oxygen atom are taken together with the oxygen to form an optionally substituted 3-12 membered saturated, partially unsaturated, or aryl ring having 0-5 additional heteroatoms not including the same oxygen atom independently selected from nitrogen, oxygen, or sulfur;
n is 0, 1, or 2;
each $R^{35}$ is independently a monodentate ligand, or two $R^{35}$ are taken together with their intervening atoms to form an optionally substituted bidentate group; and
two or more of $R^{31}$, $R^{32}$, $R^{33}$, $R^{34}$ and $R^{35}$ may be taken together with their intervening atoms to form an optionally substituted polydentate ligand.

In some embodiments, the metathesis catalyst has a structure according to Formula XLIII and the metathesis product comprises a Z olefin.

In some embodiments, the catalyst is selected from:

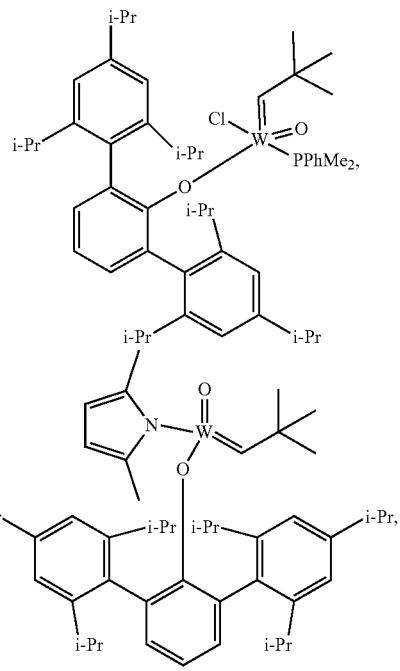

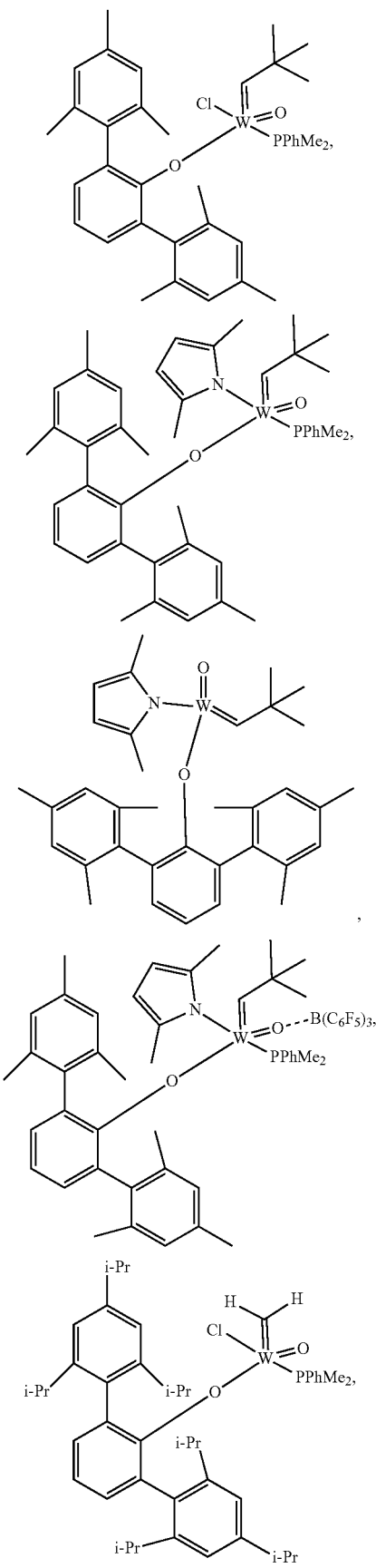

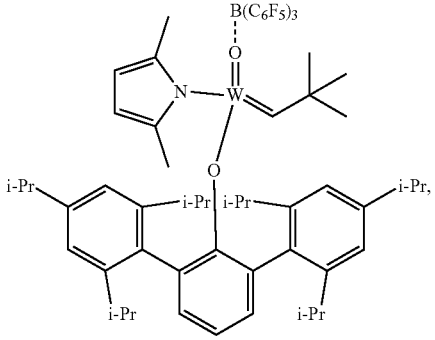

W(O)(CH-t-Bu)(Ph$_2$Pyr)(OHMT); W(O)(CH-t-Bu)(Ph$_2$Pyr)(OHIPT); W(O)(CH-t-Bu)[N(C$_6$F$_5$)$_2$](OHMT)(PPhMe$_2$); W(O)(CH-t-Bu)(PMe$_3$)$_2$Cl$_2$; W(O)(CH-t-Bu)(O-2,6-Ph$_2$C$_6$H$_3$)$_2$(PMe$_3$); W(O)(CH-t-Bu)(C$_1$)(OHIPT); W(O)(CH-t-Bu)(PMe$_3$); W(O)(CH-t-Bu)(PMe$_2$Ph)$_2$Cl$_2$; W(O)(CHCMe$_2$Ph)Cl$_2$(PMe$_2$Ph)$_2$; W[OB(C$_6$F$_5$)$_3$](CH-t-Bu)(Me$_2$Pyr)(OHMT); W(O)(CH-t-Bu)[N—(C$_6$F$_5$)$_2$](OHMT); W(O)(CH-t-Bu)(OHMT)$_2$; W(O)(CH-t-Bu)(OHIPT)$_2$; W(O)(CH-t-Bu)(Me$_2$Pyr)(DFTO)(PPhMe$_2$); W(O)(CH-t-Bu)(Me$_2$Pyr)(DFTO); W(O)(CHCMe$_2$Ph)(Me$_2$Pyr)(DFTO)(PPhMe$_2$); W(O)(CHCMe$_2$Ph)(Me$_2$Pyr)(DFTO); W(O)(CH-t-Bu)[N—(C$_6$F$_5$)$_2$](DFTO); and W(O)(CH-t-Bu)(DFTO)$_2$; wherein OHMT is O-2,6-dimesitylphenoxide; OHIPT is O-2,6-(2,4,6-triisopropylphenyl)$_2$C$_6$H$_3$; DFTO is 2,6-pentafluorophenylphenoxide; Ph$_2$Pyr is 2,5-diphenylpyrrol-1-yl; and Me$_2$Pyr is 2,5-dimethylpyrrol-1-yl.

In some embodiments, the catalyst is a compound of Formula XLIV:

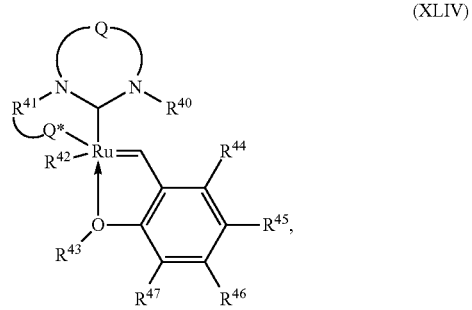

(XLIV)

wherein:
Q is selected from hydrocarbylene, substituted hydrocarbylene, heteroatom-containing hydrocarbylene, or substituted heteroatom-containing hydrocarbylene, wherein two or more substituents on adjacent atoms within Q may also be linked to form an additional cyclic structure;
Q* forms a carbon-ruthenium bond with the carbon from the R$^{41}$ group;
R$^{40}$ and R$^{41}$ are independently selected from hydrocarbyl, substituted hydrocarbyl, heteroatom-containing hydrocarbyl, or substituted heteroatom-containing hydrocarbyl;
R$^{42}$ is selected from halide, nitrate, alkyl, aryl, alkoxy, alkylcarboxylate, aryloxy, alkoxycarbonyl, aryloxycarbonyl, arylcarboxylate, acyl, acyloxy, alkylsulfonato, arylsulfonato, alkylsulfanyl, arylsulfanyl, alkylsulfinyl, and arylsulfinyl;

$R^{43}$ is selected from hydrogen, alkyl, and aryl, wherein alkyl and aryl are optionally substituted with one or more functional groups selected from the group consisting of alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and $R^{44}$, $R^{45}$, $R^{46}$, and $R^{47}$ are independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^{44}$, $R^{45}$, $R^{46}$, and $R^{47}$ is optionally linked to form one or more cyclic groups.

In some embodiments, Q in the catalyst according to Formula XLIV is hydrocarbylene, or alkyl substituted hydrocarbylene. In some embodiments, $R^{41}$ in the catalyst according to Formula XLIV is cycloalkyl or an alkyl substituted cycloalkyl group, and $R^{40}$ is an alkyl substituted aryl group. In some embodiments, $R^{43}$ in the catalyst according to Formula XLIV is alkyl. In some embodiments, $R^{44}$, $R^{45}$, $R^{46}$, and $R^{47}$ in the catalyst according to Formula XLIV are hydrogen. In some embodiments, $R^{42}$ in the catalyst according to Formula XLIV is nitrate or $C_1$-$C_{20}$ alkylcarboxylate. In some embodiments, the catalyst has the structure:

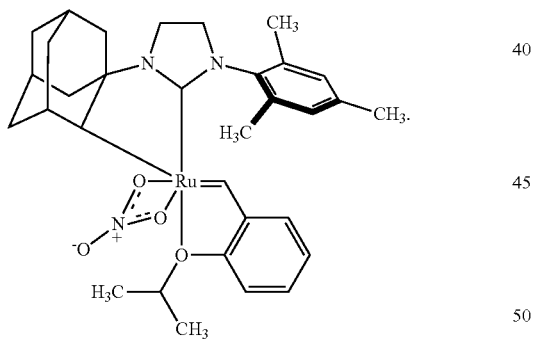

Other metathesis catalysts can be used in the methods of the invention. In general, any metathesis catalyst stable under the reaction conditions and nonreactive with the functional groups present on the reactants may be used with the present invention. Such catalysts are, for example, those described by Grubbs (Grubbs, R. H., "Synthesis of large and small molecules using olefin metathesis catalysts." *PMSE Prepr.*, 2012), herein incorporated by reference in its entirety. Depending on the desired isomer of the olefin, a cis-selective metathesis catalyst may be used, for example one of those described by Shahane et al. (Shahane, S., et al. *Chem Cat Chem*, 2013. 5(12): p. 3436-3459), herein incorporated by reference in its entirety. Specific catalysts 1-5 exhibiting cis-selectivity are shown below in Scheme 18 and have been described previously (Khan, R. K., et al. *J. Am. Chem. Soc.*, 2013. 135(28): p. 10258-61; Hartung, J. et al. *J. Am. Chem. Soc.*, 2013. 135(28): p. 10183-5.; Rosebrugh, L. E., et al. *J. Am. Chem. Soc.*, 2013. 135(4): p. 1276-9.; Marx, V. M., et al. *J. Am. Chem. Soc.*, 2013. 135(1): p. 94-7.; Herbert, M. B., et al. *Angew. Chem. Int. Ed. Engl.*, 2013. 52(1): p. 310-4; Keitz, B. K., et al. *J. Am. Chem. Soc.*, 2012. 134(4): p. 2040-3.; Keitz, B. K., et al. *J. Am. Chem. Soc.*, 2012. 134(1): p. 693-9.; Endo, K. et al. *J. Am. Chem. Soc.*, 2011. 133(22): p. 8525-7).

Scheme 18

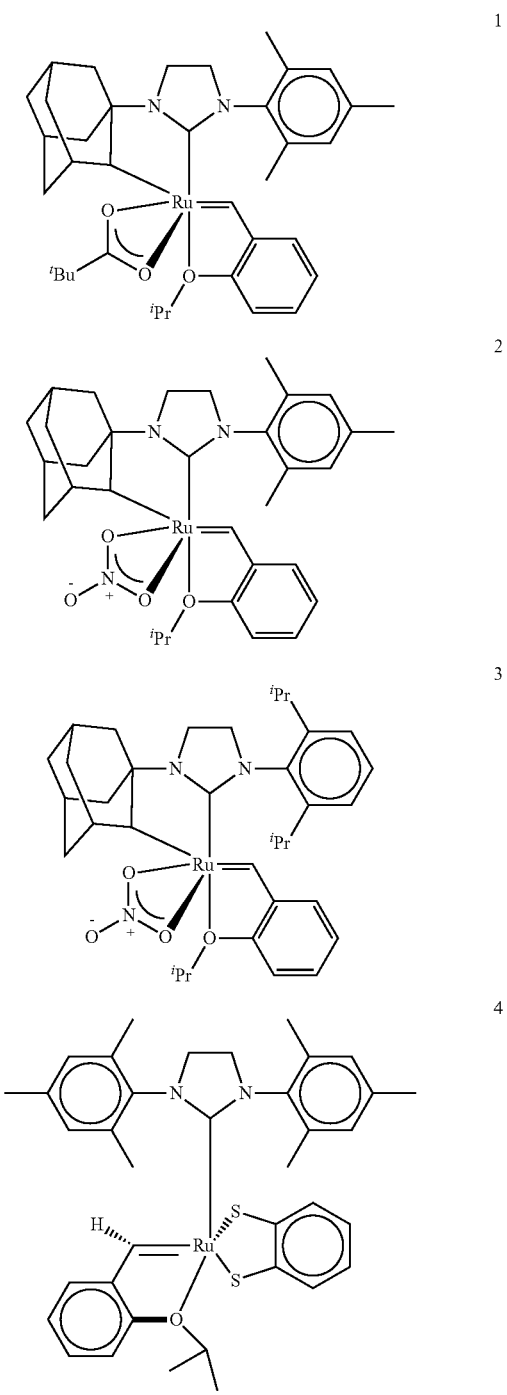

-continued

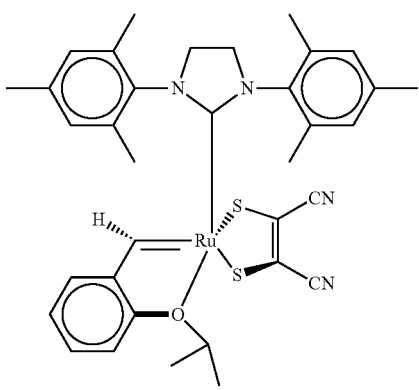

Additional Z-selective catalysts are described in (Cannon and Grubbs 2013; Bronner et al. 2014; Hartung et al. 2014; Pribisko et al. 2014; Quigley and Grubbs 2014) and are herein incorporated by reference in their entirety. Such metathesis catalysts include, but are not limited to, neutral ruthenium or osmium metal carbene complexes that possess metal centers that are formally in the +2 oxidation state, have an electron count of 16, are penta-coordinated, and are of the general formula LL'AA'M=CRbRc or LL'AA'M=(C=)nCRbRc (Pederson and Grubbs 2002); wherein M is ruthenium or osmium;

L and L' are each independently any neutral electron donor ligand and preferably selected from phosphine, sulfonated phosphine, phosphite, phosphinite, phosphonite, arsine, stibnite, ether, amine, amide, imine, sulfoxide, carboxyl, nitrosyl, pyridine, thioether, or heterocyclic carbenes; and A and A' are anionic ligands independently selected from halogen, hydrogen, $C_1$-$C_{20}$ alkyl, aryl, $C_1$-$C_{20}$ alkoxide, aryloxide, $C_2$-$C_{20}$ alkoxycarbonyl, arylcarboxylate, $C_1$-$C_{20}$ carboxylate, arylsulfonyl, $C_1$-$C_{20}$ alkylsulfonyl, $C_1$-$C_{20}$ alkylsulfinyl; each ligand optionally being substituted with $C_1$-$C_5$ alkyl, halogen, $C_1$-$C_5$ alkoxy; or with a phenyl group that is optionally substituted with halogen, $C_1$-$C_5$ alkyl, or $C_1$-$C_5$ alkoxy; and A and A' together may optionally comprise a bidentate ligand; and $R_b$ and $R_c$ are independently selected from hydrogen, $C_1$-$C_{20}$ alkyl, aryl, $C_1$-$C_{20}$ carboxylate, $C_1$-$C_{20}$ alkoxy, aryloxy, $C_1$-$C_{20}$ alkoxycarbonyl, $C_1$-$C_{20}$ alkylthio, $C_1$-$C_{20}$ alkylsulfonyl and $C_1$-$C_{20}$ alkylsulfinyl, each of $R_b$ and $R_c$ optionally substituted with $C_1$-$C_5$ alkyl, halogen, $C_1$-$C_5$ alkoxy or with a phenyl group that is optionally substituted with halogen, $C_1$-$C_5$ alkyl, or $C_1$-$C_5$ alkoxy.

Other metathesis catalysts such as "well defined catalysts" can also be used. Such catalysts include, but are not limited to, Schrock's molybdenum metathesis catalyst, 2,6-diisopropylphenylimido neophylidenemolybdenum (VI) bis (hexafluoro-t-butoxide), described by Grubbs et al. (*Tetrahedron* 1998, 54: 4413-4450) and Basset's tungsten metathesis catalyst described by Couturier, J. L. et al. (*Angew. Chem. Int. Ed. Engl.* 1992, 31: 628). Catalysts useful in the methods of the invention also include those described by Peryshkov, et al. *J. Am. Chem. Soc.* 2011, 133: 20754-20757; Wang, et al. *Angewandte Chemie*, 2013, 52: 1939-1943; Yu, et al. *J. Am. Chem. Soc.*, 2012, 134: 2788-2799; Halford. *Chem. Eng. News*, 2011, 89 (45): 11; Yu, et al. *Nature*, 2011, 479: 88-93; Lee. *Nature*, 2011, 471: 452-453; Meek, et al. *Nature,* 2011: 471, 461-466; Flook, et al. *J. Am. Chem. Soc.* 2011, 133: 1784-1786; Zhao, et al. *Org Lett.,* 2011, 13(4): 784-787; Ondi, et al. "High activity, stabilized formulations, efficient synthesis and industrial use of Mo- and W-based metathesis catalysts" *XiMo Technology Updates,* 2015: http://www.ximo-inc.com/files/ximo/uploads/download/Summary_3.11.15.pdf; Schrock, et al. *Macromolecules,* 2010: 43, 7515-7522; Peryshkov, et al. *Organometallics* 2013: 32, 5256-5259; Gerber, et al. *Organometallics* 2013: 32, 5573-5580; Marinescu, et al. *Organometallics* 2012: 31, 6336-6343; Wang, et al. *Angew. Chem. Int. Ed.* 2013: 52, 1939-1943; Wang, et al. *Chem. Eur. J.* 2013: 19, 2726-2740; Townsend et al. *J. Am. Chem. Soc.* 2012: 134, 11334-11337; Johns et al. *Org. Lett.* 2016: 18, 772-775; Torrente-Murciano, et al. *Front. Chem.* 2014: 2, Art. 37, 1-5; Wang, et al. *Angew. Chem. Int. Ed.* 2017: 56, 1614-1618; Gawin et al. *Angew. Chem. Int. Ed.* 2017: 56, 981-986; Engl et al. *Organometallics.* 2016: 35, 887-893; Shen et al. *Nature.* 2017: 541, 380-385; and Ahmed, et al. *J. Am. Chem. Soc.* 2017: 139, 1532-1537.

Catalysts useful in the methods of the invention also include those described in International Pub. No. WO 2014/155185; International Pub. No. WO 2014/172534; U.S. Pat. Appl. Pub. No. 2014/0330018; International Pub. No. WO 2015/003815; and International Pub. No. WO 2015/003814.

Catalysts useful in the methods of the invention also include those described in U.S. Pat. Nos. 7,276,616; 6,635,768; 7,632,772; International Pub. No. WO 2007/003135; International Pub. No. WO 2008/065187; International Pub. No. WO2008/135386; EP Pat. No. 1468004; U.S. Pat. Nos. 7,687,635; 7,205,424; 9,328,132; International Pub. No. WO 2014/016422; U.S. Pat. Nos. 8,933,242; 9,527,877; International Pub. No. WO 2014/001109; International Pub. No. WO 2004/035596; International Pub. No. WO 2013/127880; U.S. Pat. Nos. 9,403,860; and 9,371,345.

Catalysts useful in the methods of the invention also include those described in U.S. Pat. Nos. 4,231,947; 4,245,131; 4,427,595; 4,681,956; 4,727,215; International Pub. No. WO 1991/009825; U.S. Pat. Nos. 5,087,710; 5,142,073; 5,146,033; International Pub. No. WO 1992/019631; U.S. Pat. Nos. 6,121,473; 6,346,652; 8,987,531; U.S. Pat. Appl. Pub. No. 2008/0119678; International Pub. No. WO 2008/066754; International Pub. No. WO 2009/094201; U.S. Pat. Appl. Pub. No. 2011/0015430; U.S. Pat. Appl. Pub. No. 2011/0065915; U.S. Pat. Appl. Pub. No. 2011/0077421; International Pub. No. WO 2011/040963; International Pub. No. WO 2011/097642; U.S. Pat. Appl. Pub. No. 2011/0237815; U.S. Pat. Appl. Pub. No. 2012/0302710; International Pub. No. WO 2012/167171; U.S. Pat. Appl. Pub. No. 2012/0323000; U.S. Pat. Appl. Pub. No. 2013/0116434; International Pub. No. WO 2013/070725; U.S. Pat. Appl. Pub. No. 2013/0274482; U.S. Pat. Appl. Pub. No. 2013/0281706; International Pub. No. WO 2014/139679; International Pub. No. WO 2014/169014; U.S. Pat. Appl. Pub. No. 2014/0330018; and U.S. Pat. Appl. Pub. No. 2014/0378637.

Catalysts useful in the methods of the invention also include those described in International Pub. No. WO 2007/075427; U.S. Pat. Appl. Pub. No. 2007/0282148; International Pub. No. WO 2009/126831; International Pub. No. WO 2011/069134; U.S. Pat. Appl. Pub. No. 2012/0123133; U.S. Pat. Appl. Pub. No. 2013/0261312; U.S. Pat. Appl. Pub. No. 2013/0296511; International Pub. No. WO 2014/134333; and U.S. Pat. Appl. Pub. No. 2015/0018557.

Catalysts useful in the methods of the invention also include those set forth in the following table:

| Structure | Name |
|---|---|
| 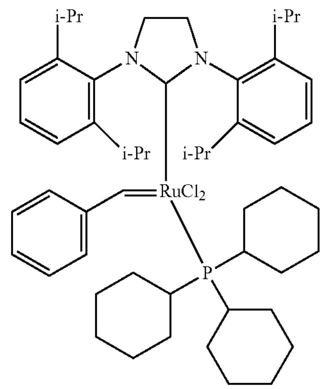 | dichloro[1,3-bis(2,6-isopropylphenyl)-2-imidazolidinylidene](benzylidene)(tricyclohexylphosphine)ruthenium(II) |
| 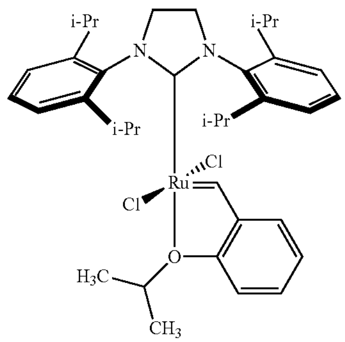 | dichloro[1,3-bis(2,6-isopropylphenyl)-2-imidazolidinylidene](2-isopropoxyphenylmethylene)ruthenium(II) |
| 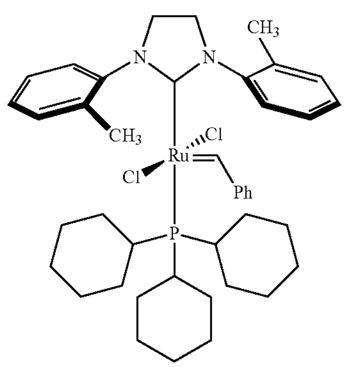 | dichloro[1,3-Bis(2-methylphenyl)-2-imidazolidinylidene](benzylidene)(tricyclohexylphosphine)ruthenium(II) |
| 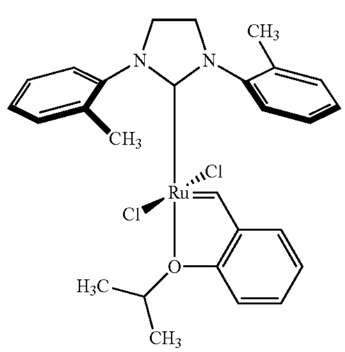 | dichloro[1,3-bis(2-methylphenyl)-2-imidazolidinylidene](2-isopropoxyphenylmethylene)ruthenium(II) |

-continued

| Structure | Name |
|---|---|
| 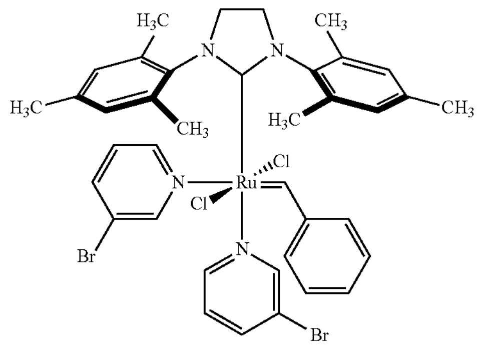 | dichloro[1,3-bis(2,4,6-trimethylphenyl)-2-imidazolidinylidene](benzylidene)bis(3-bromopyridine)ruthenium(II) |
| 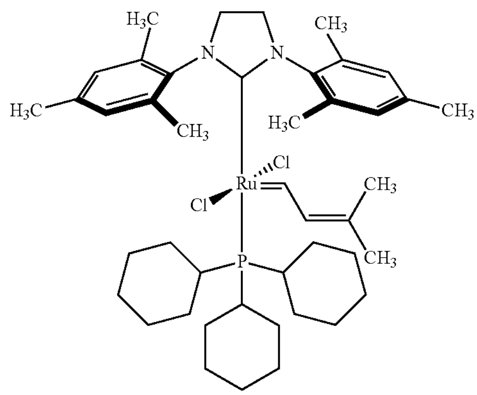 | dichloro[1,3-bis(2,4,6-trimethylphenyl)-2-imidazolidinylidene](3-methyl-2-butenylidene) (tricyclohexylphosphine) ruthenium(II) |
| 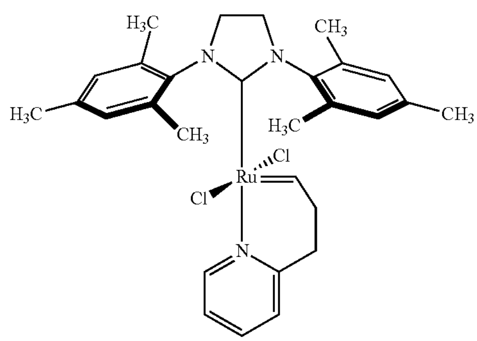 | dichloro[1,3-bis(2,4,6-trimethylphenyl)-2-imidazolidinylidene][3-(2-pyridinyl) propylidene]ruthenium(II) |
| 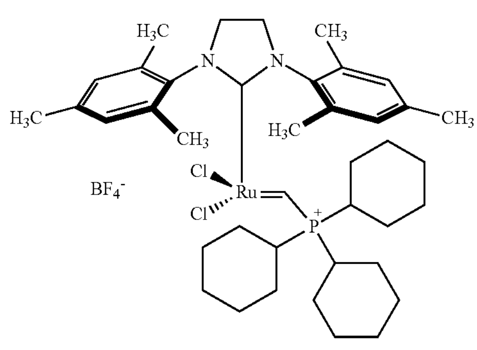 | dichloro[1,3-bis(2,4,6-trimethylphenyl)-2-imidazolidinylidene][(tricyclohexylphosphoranyl)methylidene]ruthenium(II) tetrafluoroborate |

-continued

| Structure | Name |
|---|---|
| 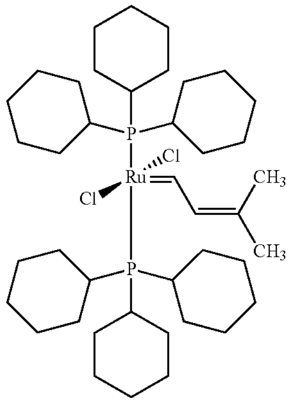 | dichloro(3-methyl-2-butenylidene)bis(tricyclohexylphosphine)ruthenium(II) |
| 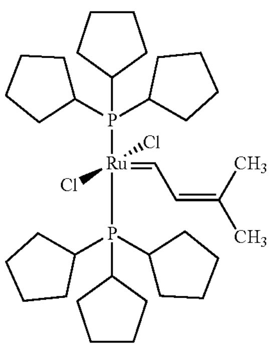 | dichloro(3-methyl-2-butenylidene)bis(tricyclopentylphosphine)ruthenium(II) |
| | dichloro(tricyclohexylphosphine)[(tricyclohexylphosphoranyl)methylidene]ruthenium(II) tetrafluoroborate |
| 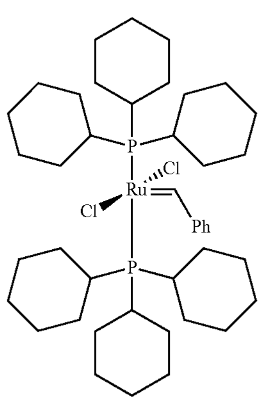 | bis(tricyclohexylphosphine) benzylidine ruthenium(IV) dichloride |

-continued

| Structure | Name |
|---|---|
| 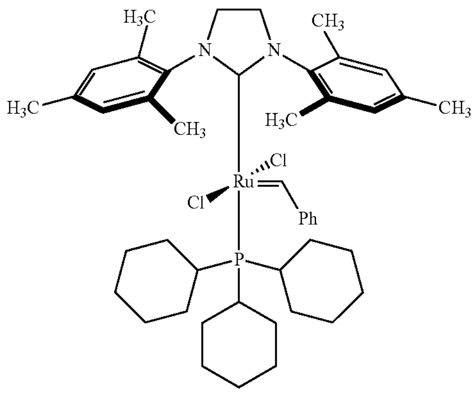 | [1,3-bis-(2,4,6-trimethylphenyl)-2-imidazolidinylidene]dichloro(phenylmethylene)(tricyclohexylphosphine)ruthenium |
| 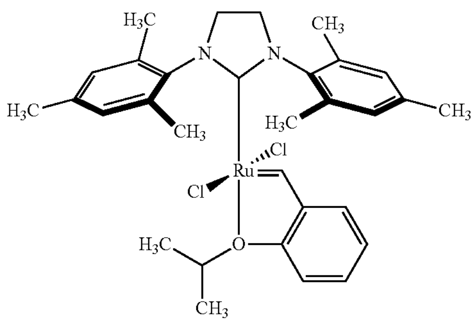 | (1,3-bis-(2,4,6-trimethylphenyl)-2-imidazolidinylidene)dichloro(o-isopropoxyphenylmethylene)ruthenium |
| 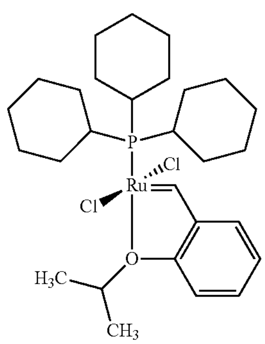 | dichloro(o-isopropoxyphenylmethylene)(tricyclohexylphosphine)ruthenium(II) |
| 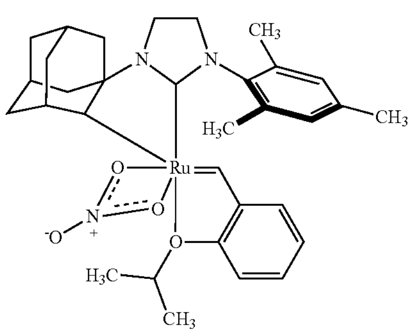 | [2-(1-methylethoxy-O)phenylmethyl-C](nitrato-O,O'){rel-(2R,5R,7R)-adamantane-2,1-diyl[3-(2,4,6-trimethylphenyl)-1-imidazolidinyl-2-ylidene]}ruthenium |

In some embodiments, the metathesis product comprises an E olefin (e.g., (E)-dec-5-en-1-ol, (E)-dec-5-en-1-yl acetate, (7E,9Z)-dodeca-7,9-dien-1-yl acetate, or (8E,10E)-dodeca-8,10-dien-1-ol) and the metathesis catalyst is selected from the group consisting of:
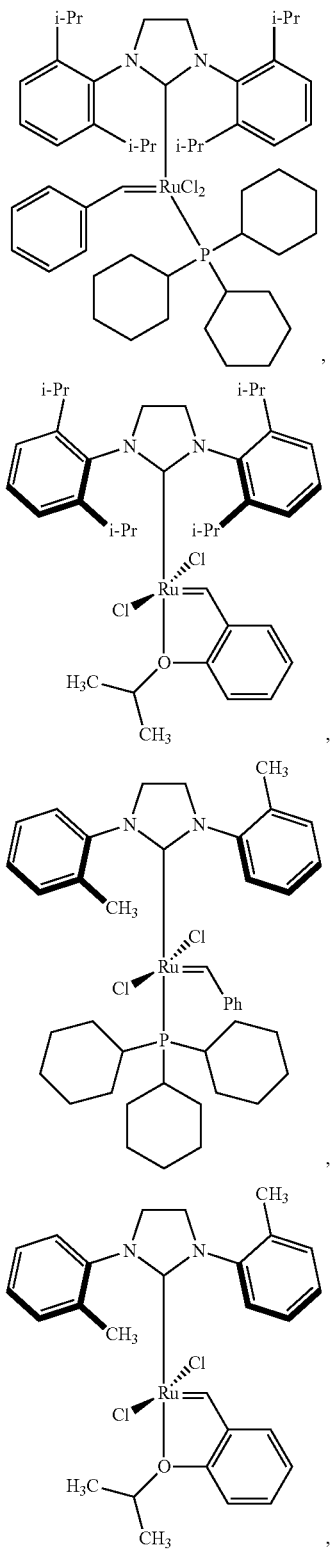
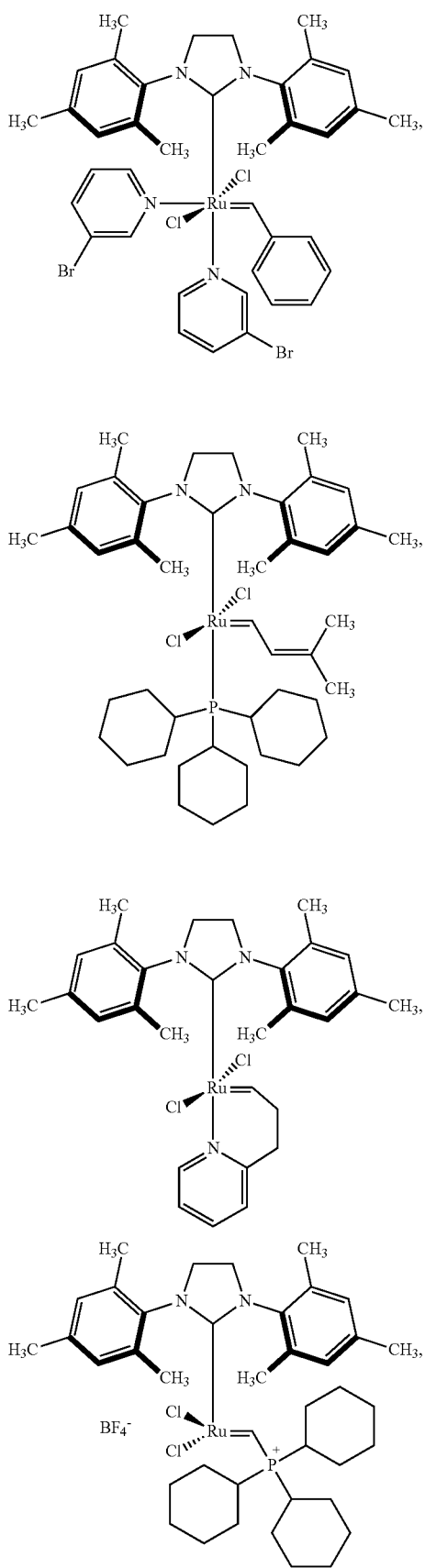

-continued
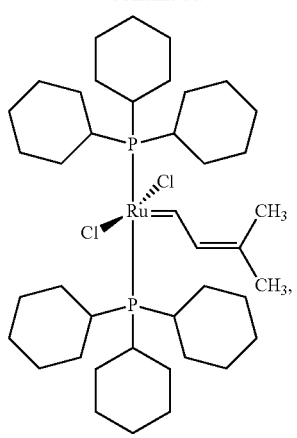
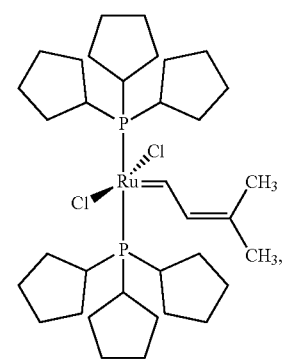
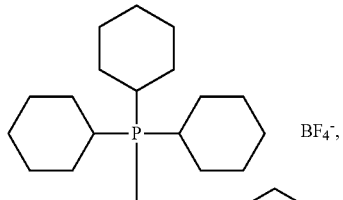
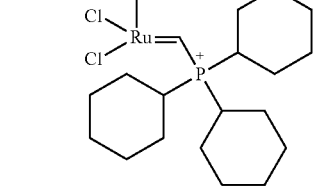
-continued
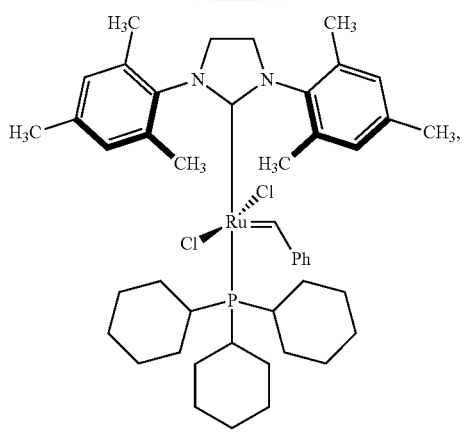
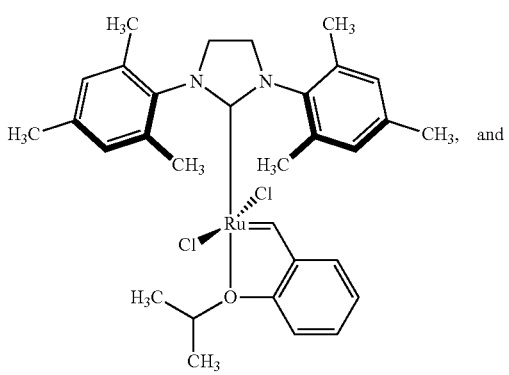
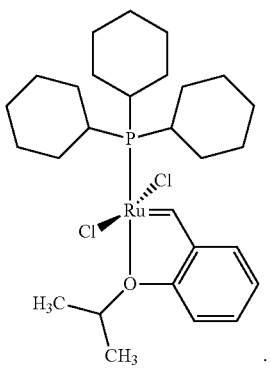
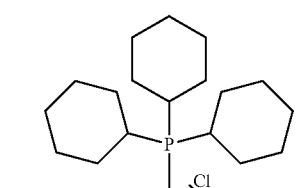
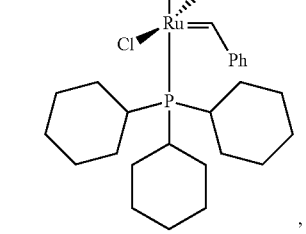
In some embodiments, the metathesis product comprises an E olefin (e.g., (E)-dec-5-en-1-ol, (E)-dec-5-en-1-yl acetate, (7E,9Z)-dodeca-7,9-dien-1-yl acetate, or (8E,10E)-dodeca-8,10-dien-1-ol) and the metathesis catalyst is selected from the group consisting of:

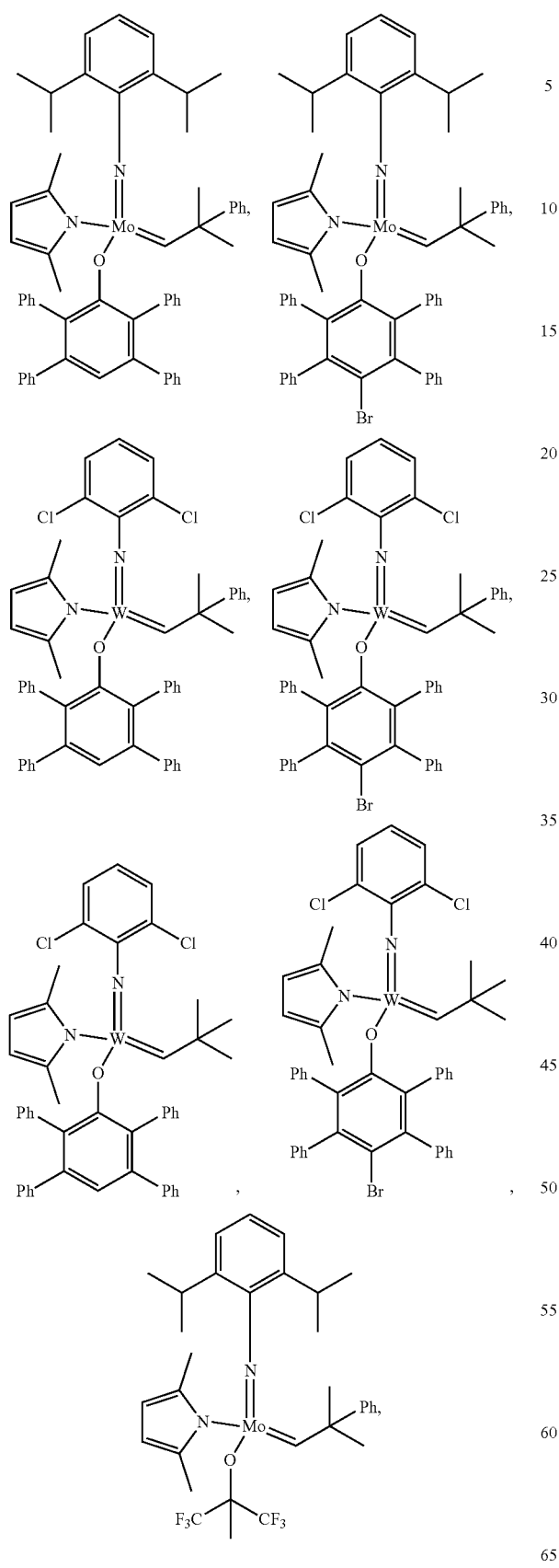
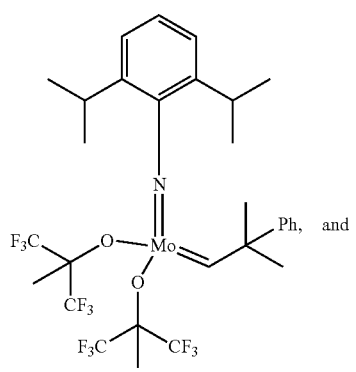
In some embodiments, the metathesis product comprises an E olefin (e.g., (E)-dec-5-en-1-ol, (E)-dec-5-en-1-yl acetate, (7E,9Z)-dodeca-7,9-dien-1-yl acetate, or (8E,10E)-dodeca-8,10-dien-1-ol) and the metathesis catalyst is selected from the group consisting of:
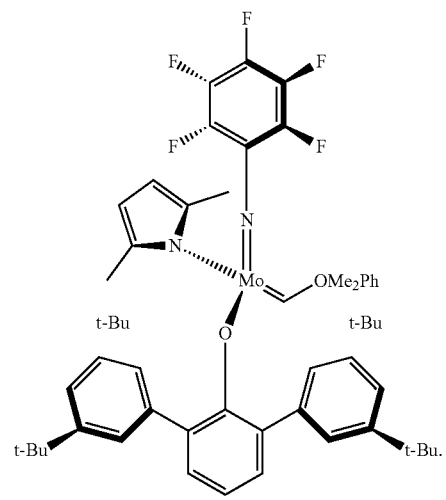
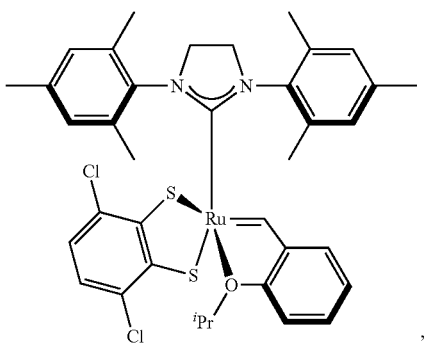

-continued

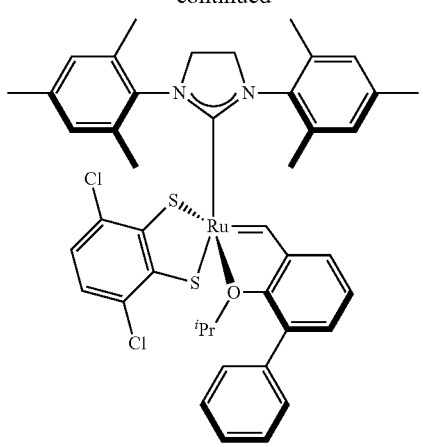

,

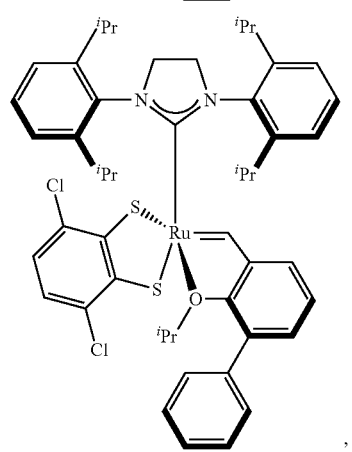

,

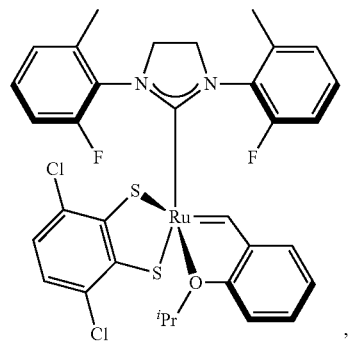

,

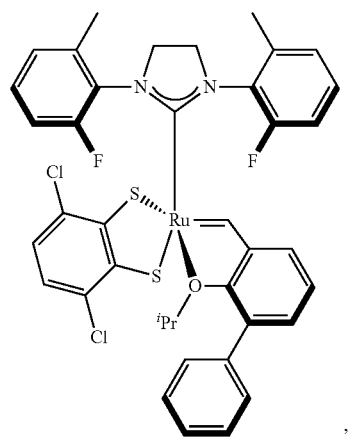

,

-continued

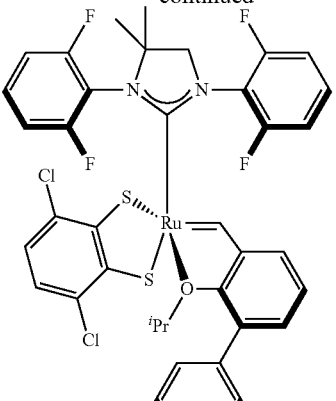

,

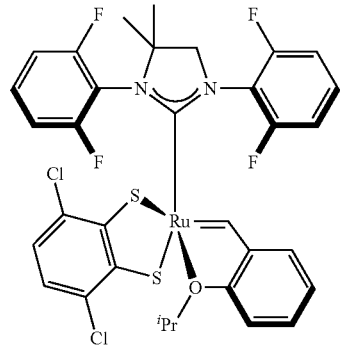

, and

Catalysts useful in the methods of the invention also include those described in U.S. Pat. Appl. Pub. No. 2008/0009598; U.S. Pat. Appl. Pub. No. 2008/0207911; U.S. Pat. Appl. Pub. No. 2008/0275247; U.S. Pat. Appl. Pub. No. 2011/0040099; U.S. Pat. Appl. Pub. No. 2011/0282068; and U.S. Pat. Appl. Pub. No. 2015/0038723.

Catalysts useful in the methods of the invention include those described in International Pub. No. WO 2007/140954; U.S. Pat. Appl. Pub. No. 2008/0221345; International Pub. No. WO 2010/037550; U.S. Pat. Appl. Pub. No. 2010/0087644; U.S. Pat. Appl. Pub. No. 2010/0113795; U.S. Pat. Appl. Pub. No. 2010/0174068; International Pub. No. WO 2011/091980; International Pub. No. WO 2012/168183; U.S. Pat. Appl. Pub. No. 2013/0079515; U.S. Pat. Appl. Pub. No. 2013/0144060; U.S. Pat. Appl. Pub. No. 2013/0211096; International Pub. No. WO 2013/135776; International Pub. No. WO 2014/001291; International Pub. No. WO 2014/067767; U.S. Pat. Appl. Pub. No. 2014/0171607; and U.S. Pat. Appl. Pub. No. 2015/0045558.

A number of intermediate catalysts are useful for forming the internal olefin according to Formula XXIIa-I described above. For example, the intermediate catalyst can be is a non-selective metathesis catalyst or a Z-selective catalyst (e.g., a Z-selective molybdenum catalyst or a Z-selective tungsten catalyst).

In some embodiments, the intermediate catalyst is a compound according to Formula XLII as described above. In some such embodiments, $R^{10a}$ is selected from the group consisting of pyrrol-1-yl; 2,5-dimethyl-pyrrol-1-yl; and $R^{11a}$ is phenyl which bears two substituents in the ortho positions with respect to O, or which bears at least three substituents, from which two substituents are in the ortho positions with respect to O and one substituent is in the para position with respect to O; or $R^{11a}$ is selected from the group consisting of optionally substituted 8-(naphthalene-1-yl)-naphthalene-1-yl and optionally substituted 8-phenylnaphthalene-1-yl.

In some embodiments, the intermediate catalyst is a compound according to Formula XLII as described, for example, in WO 2014/139679, which is incorporated herein by reference in its entirety. In some embodiments, the intermediate catalyst is:

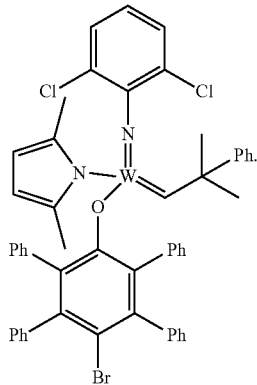

In some embodiments, the intermediate catalyst is a compound according to Formula XLV:

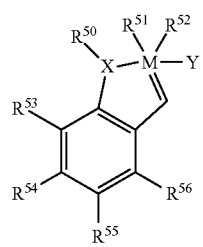

(XLV)

wherein:

M is a transition metal;

$R^{50}$ is an alkyl, alkenyl, alkynyl, aryl, alkoxy carbonyl, alkylsulfonyl, or alkylsulfinyl; each optionally substituted with an alkyl, alkoxy, aryl or heteroaryl moiety;

$R^{51}$ and $R^{52}$ each is or together are, an electron withdrawing anionic ligand;

$R^{53}$, $R^{54}$, $R^{55}$, and $R^{56}$ each are H, a halogen atom or an alkyl, alkenyl, alkynyl, aryl, alkoxy, alkenyloxy, alkynyloxy, aryloxy, alkoxycarbonyl, alkylamino, alkylthio, alkylsulfonyl, or alkylsulfinyl; each optionally substituted with an alkyl, halogen, aryl or heteroaryl moiety;

X is oxygen, sulfur, nitrogen or phosphorus; and

Y is an electron-donating heterocyclic carbene ligand.

In some embodiments, M is Ru. In some embodiments, X is O or S. In some embodiments, $R^{50}$ is a lower alkyl group (e.g., isopropyl). In some embodiments, $R^{51}$ and $R^{52}$ each is a halogen (e.g., Cl). In some embodiments, $R^{53}$, $R^{54}$, $R^{55}$, and $R^{56}$ each is H or a lower alkyl group.

In some embodiments, Y in the compound of XLV comprises a 4,5-dihydroimidazol-2-ylidene. In some embodiments, Y comprises a heterocyclic ring structure having the following formula:

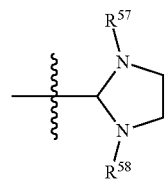

wherein $R^{57}$ and $R^{58}$ each comprises an aromatic ring moiety (e.g., 2,4,6-trimethylphenyl moieties).

In some embodiments, the intermediate catalyst is a compound according to Formula XLV as described, for example, in WO 02/14376, U.S. Pat. No. 7,723,255 and US 2016/168181, which are incorporated herein by reference in their entirety. In some embodiments, the intermediate catalyst is:

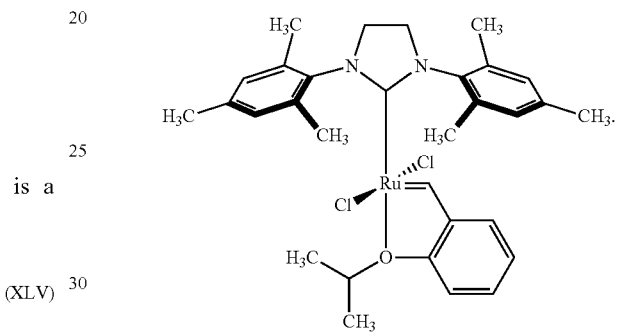

In some embodiments, the intermediate catalyst is present in an amount less than 0.01 mol % with respect to the compound according to Formula XXIIa-iii or to the reaction partner according to Formula XXIIa-ii.

D. Metathesis Reaction Conditions

The catalyst is typically provided in the reaction mixture in a sub-stoichiometric amount (e.g., a catalytic amount). In certain embodiments, that amount is in the range of about 0.001 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, less than about 0.1 mol %, less than about 0.015 mol %, less than about 0.01 mol %, less than about 0.0015 mol %, or less, relative to the limiting reagent. In some embodiments, the catalyst is present in the range of about 2.5 mol % to about 5 mol %, relative to the limiting reagent. In some embodiments, the reaction mixture contains about 0.5 mol % catalyst. In the case where the molecular formula of the catalyst complex includes more than one metal, the amount of the catalyst complex used in the reaction may be adjusted accordingly.

In some cases, the methods described herein can be performed in the absence of solvent (e.g., neat). In some cases, the methods can include the use of one or more solvents. Examples of solvents that may be suitable for use in the invention include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the method is performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the method is performed at a pressure of about less than 760 torr. In some embodiments, the method is performed at a pressure of about less than 700 torr. In some embodiments, the method is performed at a pressure of about less than 650 torr. In some embodiments, the method is performed at a pressure of about less than 600 torr. In some embodiments, the method is performed at a pressure of about less than 550 torr. In some embodiments, the method is performed at a pressure of about less than 500 torr. In some embodiments, the method is performed at a pressure of about less than 450 torr. In some embodiments, the method is performed at a pressure of about less than 400 torr. In some embodiments, the method is performed at a pressure of about less than 350 torr. In some embodiments, the method is performed at a pressure of about less than 300 torr. In some embodiments, the method is performed at a pressure of about less than 250 torr. In some embodiments, the method is performed at a pressure of about less than 200 torr. In some embodiments, the method is performed at a pressure of about less than 150 torr. In some embodiments, the method is performed at a pressure of about less than 100 torr. In some embodiments, the method is performed at a pressure of about less than 90 torr. In some embodiments, the method is performed at a pressure of about less than 80 torr. In some embodiments, the method is performed at a pressure of about less than 70 torr. In some embodiments, the method is performed at a pressure of about less than 60 torr. In some embodiments, the method is performed at a pressure of about less than 50 torr. In some embodiments, the method is performed at a pressure of about less than 40 torr. In some embodiments, the method is performed at a pressure of about less than 30 torr. In some embodiments, the method is performed at a pressure of about less than 20 torr. In some embodiments, the method is performed at a pressure of about 20 torr.

In some embodiments, the method is performed at a pressure of about 19 torr. In some embodiments, the method is performed at a pressure of about 18 torr. In some embodiments, the method is performed at a pressure of about 17 torr. In some embodiments, the method is performed at a pressure of about 16 torr. In some embodiments, the method is performed at a pressure of about 15 torr. In some embodiments, the method is performed at a pressure of about 14 torr. In some embodiments, the method is performed at a pressure of about 13 torr. In some embodiments, the method is performed at a pressure of about 12 torr. In some embodiments, the method is performed at a pressure of about 11 torr. In some embodiments, the method is performed at a pressure of about 10 torr. In some embodiments, the method is performed at a pressure of about 10 torr. In some embodiments, the method is performed at a pressure of about 9 torr. In some embodiments, the method is performed at a pressure of about 8 torr. In some embodiments, the method is performed at a pressure of about 7 torr. In some embodiments, the method is performed at a pressure of about 6 torr. In some embodiments, the method is performed at a pressure of about 5 torr. In some embodiments, the method is performed at a pressure of about 4 torr. In some embodiments, the method is performed at a pressure of about 3 torr. In some embodiments, the method is performed at a pressure of about 2 torr. In some embodiments, the method is performed at a pressure of about 1 torr. In some embodiments, the method is performed at a pressure of less than about 1 torr.

In some embodiments, the two metathesis reactants are present in equimolar amounts. In some embodiments, the two metathesis reactants are not present in equimolar amounts. In certain embodiments, the two reactants are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, or 1:2, 1:3, 1:4, 1:5, 1:6, 1:7, 1:0. In certain embodiments, 1:9, 1:10, 1:11, 1:12, 1:13, 1:14, the two reactants are present in a molar ratio of about 1:15, 1:16, 1:17, 1:18, 1:19, or 1:20. In certain embodiments, the two reactants are present in a molar ratio of about 10:1. In certain embodiments, the two reactants are present in a molar ratio of about 7:1. In certain embodiments, the two reactants are present in a molar ratio of about 5:1. In certain embodiments, the two reactants are present in a molar ratio of about 2:1. In certain embodiments, the two reactants are present in a molar ratio of about 1:10. In certain embodiments, the two reactants are present in a molar ratio of about 1:7. In certain embodiments, the two reactants are present in a molar ratio of about 1:5. In certain embodiments, the two reactants are present in a molar ratio of 1:2.

In some embodiments, one molar equivalent of the olefin is contacted with one molar equivalent of the metathesis reaction partner. In some embodiments, about 1.5, 2, 2.5, or 3 molar equivalents of the olefin is contacted with one molar equivalent of the metathesis reaction partner. In some embodiments, about 1.5 molar equivalents of the olefin is contacted with one molar equivalent of the metathesis reaction partner.

In general, the reactions with many of the metathesis catalysts disclosed herein provide yields better than 15%, e.g., better than 50%, or better than 75%, or better than 90%. In addition, the reactants and products are chosen to provide at least a 5° C. difference, e.g., a greater than 20° C. difference, or a greater than 40° C. difference in boiling points. Additionally, the use of metathesis catalysts allows for much faster product formation than byproduct, it is desirable to run these reactions as quickly as practical. In particular, the reactions are performed in less than about 24 hours, e.g., less than 12 hours, or less than 8 hours, or less than 4 hours. Advantageously, the methods of the invention provide metathesis products on a scale ranging from a few milligrams to hundreds of kilograms or more. For example, the methods can be conducted using around 1-10 grams of the olefin according to Formula I, Formula XI, Formula XXI, or Formula XXXI; or around 10-100 grams of the olefin according to Formula I, Formula XI, Formula XXI, or Formula XXXI; or around 100-500 grams of the olefin according to Formula I, Formula XI, Formula XXI, or Formula XXXI; or around 500-1000 grams of the olefin according to Formula I, Formula XI, Formula XXI, or Formula XXXI. The methods can be conducted using at least 1, 5, 10, 25, 50, 100, or 1,000 kilograms of starting material. The metathesis reactions can be conducted using a metathesis reactor as described, for example, in WO 2011/

046872, which reactor may be operated in conjunction with one or more downstream separation units for separating and/or recycling particular product or byproduct streams (e.g., an olefin stream, a $C_2$-$C_3$ compound stream, or a $C_3$-$C_5$ compound stream). The metathesis reactor and separation unit(s) can be operated in conjunction with one or more adsorbent beds to facilitate the separation of the metathesized products from the catalyst, as well as washing and drying units for purification of desired products. The metathesis, reduction, and acylation reactions can be conducted to provide products on the scale of metric tons.

One of skill in the art will appreciate that the time, temperature and solvent can depend on each other, and that changing one can require changing the others to prepare the metathesis products in the methods of the invention. The metathesis steps can proceed at a variety of temperatures and times. In general, reactions in the methods of the invention are conducted using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, reactions in the methods of the invention are conducted at a temperature of from about 0° C. to about 200° C. For example, reactions can be conducted at 15-100° C. In some embodiments, reaction can be conducted at 20-80° C. In some embodiments, reactions can be conducted at 100-150° C.

In certain instances, the efficacy of the metathesis catalyst can be improved (e.g., the turnover number can be increased or the overall catalyst loading may be decreased) through slow addition of the catalyst to a substrate. The overall catalyst loading can be decreased by at least 10%, at least 20%, or at least 30% when administered slowly to achieve the same turnover number as a single, full batch loading. The slow addition of overall catalyst loading can include adding fractional catalyst loadings to the reaction materials at an average rate of approximately 10 ppm by weight of catalyst per hour (ppmwt/hr), 5 ppmwt/hr, 1 ppmwt/hr, 0.5 ppmwt/hr, 0.1 ppmwt/hr, 0.05 ppmwt/hr, or 0.01 ppmwt/hr. In some embodiments, the catalyst is slowly added at a rate of between about 0.01-10 ppmwt/hr, 0.05-5 ppmwt/hr, or 0.1-1 ppmwt/hr. The slow addition of the catalyst can be conducted in batch loadings at frequencies of every 5 minutes, 15 minutes, 30 minutes, 1 hour, 2 hours, 4 hours, 12 hours, or 1 day. In other embodiments, the slow addition is conducted in a continuous addition process.

E. Conversion of Metathesis Products to Fatty Olefin Derivatives

The methods provided herein can include conversion of metathesis products to fatty olefin derivatives including pheromones. In some embodiments, converting the metathesis product to the fatty olefin derivative includes contacting a metathesis product according to Formula IIIb with a reducing agent under conditions sufficient to form an alkenol according to Formula IV:

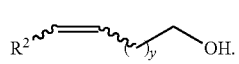
(IV)

In some embodiments, converting the metathesis product to the fatty olefin derivative includes contacting the metathesis product according to Formula XIII, wherein $R^4$ is —C(O)OR$^{4b}$, with a reducing agent under conditions sufficient to form an alkenol according to Formula XIV:

(XIV)

Any suitable conditions for reducing the metathesis products, e.g., those of Formula IIIb, to form the corresponding alkenols (e.g., alkenols according to Formula IV or Formula XIV) can be used in conjunction with the method of the invention. Homogenous or heterogenous conditions can be used. Examples of homogenous conditions include, but are not limited to: hydrogenolysis using ligated precious metal catalysts (Tan, et al. Org. Lett. 2015, 17 (3), 454; Spasyuk, D. et al. J. Am. Chem. Soc. 2015, 137, 3743; WO 2014/139030), metal hydride-catalyzed reduction using silane reagents (Mimoun, H. J. Org. Chem. 1999, 64, 2582.; U.S. Pat. No. 6,533,960); and reduction using aluminum reagents such as lithium aluminum hydride, sodium bis(2-methoxyethoxy)aluminumhydride (also known by the tradename RED-AL), or diisobutyl aluminum hydride (CN 103319704; Chandrasekhar, et al. Tetrahedron Lett. 1998, 39, 909). Unsaturated fatty alcohols can also be prepared via hydrogenolysis with heterogeneous catalysts, such as ZnO or CuO/ZnO supported on chromite, alumina, or other material. Typically, 1-2 molar equivalents of the reducing agent with respect to the fatty acid ester metathesis product will be used. In some embodiments, around 1.0, 1.1, 1.2, 1.3, 1.4, or 1.5 molar equivalents of the reducing agent with respect to the fatty acid ester is used to form the corresponding alkenol.

Any suitable solvent can be used for reducing the fatty acid ester metathesis product. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. The reduction reaction is typically conducted at temperatures ranging from around −78° C. to about 25° C. for a period of time sufficient to form the alkenol. The reaction can be conducted for a period of time ranging from a few minutes to several hours or longer, depending on the particular fatty acid ester and reducing agent used in the reaction. For example, the reduction of a methyl (Z)-tetradec-9-enoate with an aluminum reagent (e.g., sodium bis(2-methoxyethoxy)-aluminumhydride) can be conducted for 1-2 hours at a temperature ranging from around 0° C. to around 20° C.

In some embodiments, the fatty olefin derivative is an alkenol as described above. In some embodiments, an alkenol is converted to a desired fatty olefin derivative product via one or more chemical or biochemical transformations. In some such embodiments, the fatty olefin derivative is a pheromone.

In some embodiments, converting the metathesis product to the fatty olefin derivative further includes contacting the alkenol with an acylating agent under conditions sufficient to form an alkenol ester according to Formula V:

(V)

wherein $R^{4c}$ is selected from the group consisting of hydrogen, $C_{1-5}$ alkyl, and $C_{1-5}$ haloalkyl, and wherein the alkenol ester is the fatty olefin derivative.

In some embodiments, converting the metathesis product to the fatty olefin derivative further includes contacting an alkenol according to Formula XIV with an acylating agent under conditions sufficient to form an alkenol ester according to Formula XV:

(XV)

wherein $R^{4c}$ is selected from the group consisting of hydrogen, $C_{1-5}$ alkyl, and $C_{1-5}$ haloalkyl, and
wherein the alkenol ester is the fatty olefin derivative.

In some embodiments, converting the metathesis product to the fatty olefin derivative further includes contacting an alkenol according to Formula XXXIV with an acylating agent under conditions sufficient to form an alkenol ester according to Formula XXXV:

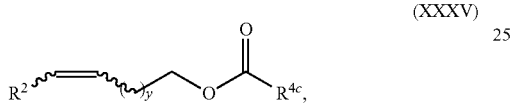

(XXXV)

wherein $R^{4c}$ is selected from the group consisting of hydrogen, $C_{1-5}$ alkyl, and $C_{1-5}$ haloalkyl, and wherein the alkenol ester is the fatty olefin derivative.

Any acylating agent suitable for forming the fatty olefin derivative of Formula V, Formula XV, or Formula XXXV can be used in the method of the invention. Examples of suitable acylating agents include acid anhydrides (e.g., acetic anhydride), acid chlorides (e.g., acetyl chloride), activated esters (e.g., pentafluorophenyl esters of carboxylic acids), and carboxylic acids used with coupling agents such as dicyclohexylcarbodiimide or carbonyl diimidazole. Typically, 1-10 molar equivalents of the acylating agent with respect to the alkenol will be used. For example, 1-5 molar equivalents of the acylating agent or 1-2 molar equivalents of the acylating agent can be used. In some embodiments, around 1.0, 1.1, 1.2, 1.3, 1.4, or 1.5 molar equivalents of the acylating agent (e.g., acetic anhydride) with respect to the alkenol is used to form the fatty olefin derivative of Formula V, Formula XV, or Formula XXXV.

A base can be used to promote acylation of the alkenol by the acylating agent. Examples of suitable bases include potassium carbonate, sodium carbonate, sodium acetate, Huenig's base (i.e., N,N-diisopropylethylamine), lutidines including 2,6-lutidine (i.e., 2,6-dimethylpyridine), triethylamine, tributylamine, pyridine, 2,6-di-tert-butylpyridine, 1,8-diazabicycloundec-7-ene (DBU), quinuclidine, and the collidines. Combinations of two or more bases can be used. Typically, less than one molar equivalent of base with respect to the alkenol will be employed in the methods of the invention. For example, 0.05-0.9 molar equivalents or 0.1-0.5 molar equivalents of the base can be used. In some embodiments, around 0.05, 0.1, 0.15, or 0.2 molar equivalents of the base (e.g., sodium acetate) with respect to the alkenol is used in conjunction with the acylating agent (e.g., acetic anhydride) to form the fatty olefin derivative of Formula V, Formula XV, or Formula XXXV.

Any suitable solvent can be used for acylating the alkenol. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. Alternatively, an alkenol can be combined with an acylating agent such as acetic anhydride and a base such as sodium acetate without an additional solvent. The acylation reaction is typically conducted at temperatures ranging from around 25° C. to about 100° C. for a period of time sufficient to form the fatty olefin derivative of Formula V, Formula XV, or Formula XXXV. The reaction can be conducted for a period of time ranging from a few minutes to several hours or longer, depending on the particular alkenol and acylating agent used in the reaction. For example, the reaction can be conducted for around 10 minutes, or around 30 minutes, or around 1 hour, or around 2 hours, or around 4 hours, or around 8 hours, or around 12 hours at around 40° C., or around 50° C., or around 60° C., or around 70° C., or around 80° C.

One of skill in the art will appreciate that acylation can occur at various points in the methods of the invention, including before olefin metathesis is conducted. Accordingly, some embodiments of the invention provide methods which comprise:

i) dehydrating a diol according to Formula VI:

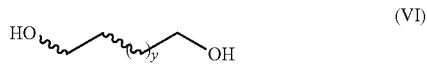

(VI)

to form an alkenol according to Formula X

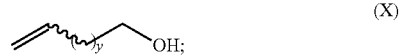

(X)

and
ii) acylating the alcohol to form an ester according to form the metathesis reaction partner according to Formula II, wherein $R^3$ is hydrogen, $R^4$ is —COC(O)$R^{4c}$, and $R^{4c}$ is $C_{1-8}$ alkyl.

In some embodiments, the methods of the invention comprise:

i) converting a diol according to Formula VI:

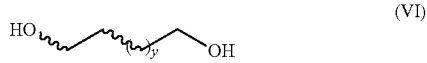

(VI)

to an alcohol according to Formula VIII:

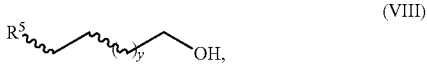

(VIII)

and
ii) eliminating leaving group $R^5$ to form to an alkenol according to Formula X

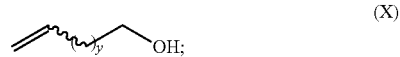

(X)

and iii) acylating the alkenyl to form the metathesis reaction partner according to Formula II, wherein $R^3$ is hydrogen and $R^4$ is —COC(O)$R^{4c}$.

In some embodiments, $R^4$ is halogen (e.g., chloride, bromide, iodide, etc.). In some such embodiments, converting the metathesis product to the fatty olefin derivative comprises contacting the metathesis product with a carboxylate salt under conditions sufficient to form an alkenol ester according to Formula XXXV:

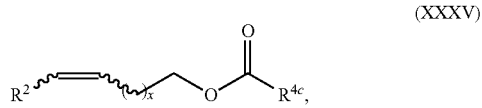

(XXXV)

wherein $R^{4c}$ is selected from the group consisting of hydrogen, $C_{1-5}$ alkyl, and $C_{1-5}$ haloalkyl, and wherein the alkenol ester is the fatty olefin derivative.

When $R^4$ is halogen, displacement with a suitable carboxylate salt (e.g., an acetate salt such as ammonium acetate, calcium acetate, lithium acetate, magnesium acetate, potassium acetate, or sodium acetate; a propionate salt; a butyrate salt; an isobutyrate salt; a valerate salt; and isovalerate salt; a formate salt; or the like) can provide convenient access to alkenol esters. Typically, 1-10 molar equivalents of the carboxylate salt with respect to the metathesis product will be used. For example, 1-5 molar equivalents of the carboxylate salt or 1-2 molar equivalents of the carboxylate salt can be used. In some embodiments, around 1.0, 1.1, 1.2, 1.3, 1.4, or 1.5 molar equivalents of the carboxylate salt (e.g., sodium acetate) with respect to the metathesis product is used to form the alkenol ester of Formula XXXV. Solvents and bases, as described above for acylation reactions, can be used for displacing the halogen $R^4$ with the carboxylate salt.

Many insect pheromones are fatty aldehydes or comprise a fatty aldehyde component. As such, synthesis of certain pheromones includes the conversion of alkenols prepared according to the methods of the invention to fatty aldehydes.

In some embodiments, converting the metathesis product to the fatty olefin derivative further includes contacting the alkenol with an oxidizing agent under conditions sufficient to form an alkenal according to Formula VI:

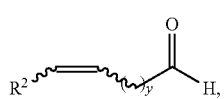

(VI)

wherein the alkenal is the fatty olefin derivative.

In some embodiments, converting the metathesis product to the fatty olefin derivative further includes contacting the alkenol according to Formula XIV with an oxidizing agent under conditions sufficient to form an alkenal according to Formula XVI:

(XVI)

wherein the alkenal is the fatty olefin derivative.

In some embodiments, converting the metathesis product to the fatty olefin derivative further includes contacting the alkenol according to Formula XXXIV with an oxidizing agent under conditions sufficient to form an alkenal according to Formula XXXVI:

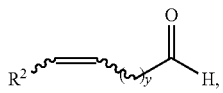

(XXXVI)

wherein the alkenal is the fatty olefin derivative.

Any oxidizing agent suitable for converting an alkenol of Formula IV, Formula XIV, or Formula XXXIV to the corresponding alkenal of Formula VI, Formula XVI, or Formula XXXVI can be used in the methods of the invention. Examples of suitable oxidizing agents include, but are not limited to, chromium-based reagents (e.g., chromic acid; Jones reagent-chromium trioxide in aqueous sulfuric acid; Collins reagent-chromium trioxide pyridine complex; pyridinium dichromate; pyridinium chlorochromate and the like); dimethyl sulfoxide (DMSO)-based reagents (e.g., DMSO/oxalyl chloride; DMSO/diycyclohexyl-carbodiimide; DMSO/acetic anhydride; DMSO/phosphorous pentoxide; DMSO/trifluoroacetic anhydride; and the like); hypervalent iodine compounds (e.g., Dess-Martin periodinane; o-iodoxybenzoic acid; and the like); ruthenium-based reagents (e.g., ruthenium tetroxide; tetra-n-propylammonium perruthenate; and the like); and nitroxyl-based reagents (e.g., TEMPO—2,2,6,6-tetramethylpiperidine 1-oxyl—employed with sodium hypochlorite, bromine, or the like).

Oxidation of fatty alcohols can be conducted using pyridinium chlorochromate (PCC), as shown in Scheme 19.

Scheme 19

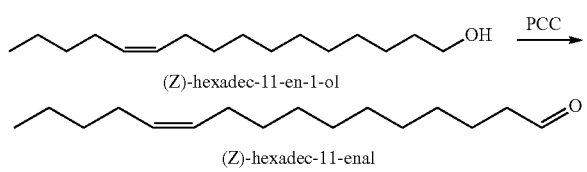

(Z)-hexadec-11-en-1-ol (Z)-hexadec-11-enal

Alternatively, TEMPO (TEMPO=2,2,6,6-tetramethylpiperidinyl-N-oxyl) and related catalyst systems can be used to selectively oxidize alcohols to aldehydes. These methods are described in Ryland and Stahl (2014), herein incorporated by reference in its entirety.

Fatty alcohol metathesis products can also be converted to fatty aldehydes using a long-chain or short-chain alcohol dehydrogenase (ADH), an alcohol oxidase (AOX), or a plant α-dioxygenase (α-DOX) as described, for example, in U.S. patent application Ser. No. 15/354,916 and International Pat. Appl. No. PCT/US2016/062595, which applications are incorporated herein by reference in their entirety.

In some embodiments, converting the metathesis product to the fatty olefin derivative comprises contacting the ester metathesis product according to Formula IIb with a reducing agent under conditions sufficient to form an alkenal according to Formula VI:

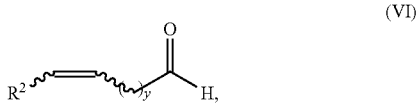

(VI)

wherein the alkenal is the fatty olefin derivative.

In some embodiments, converting the metathesis product to the fatty olefin derivative comprises contacting the ester metathesis product, wherein $R^4$ is —C(O)O$R^{4b}$, with a reducing agent under conditions sufficient to form an alkenal according to Formula XVI:

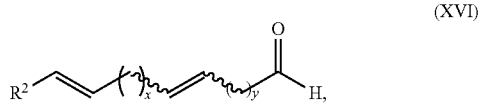

(XVI)

wherein the alkenal is the fatty olefin derivative.

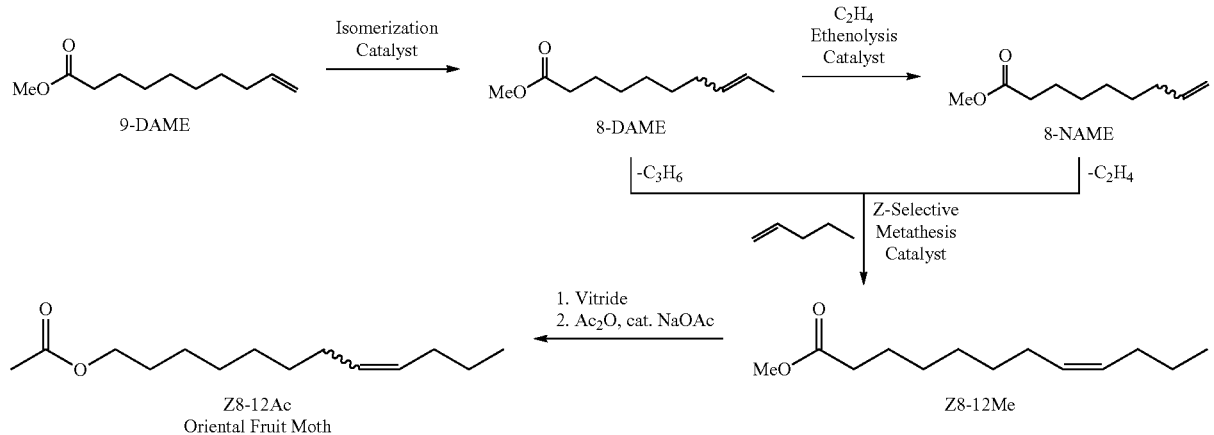

In some embodiments, converting the metathesis product to the fatty olefin derivative comprises contacting the ester metathesis product according to Formula XXXIIIb, $R^4$ is —C(O)O$R^{4b}$, with a reducing agent under conditions sufficient to form an alkenal according to Formula XXXVI:

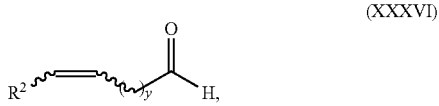

(XXXVI)

wherein the alkenal is the fatty olefin derivative.

In some embodiments, an ester metathesis product (e.g., an ester according to Formula IIb or an ester according to Formula XXXIIIb) is partially reduced to form the corresponding alkenal (e.g., an alkenal according to Formula VI, Formula XVI, or Formula XXXVI) with amine-modified sodium bis(2-methoxyethoxy)aluminumhydride. The amine-modified sodium bis(2-methoxyethoxy)aluminumhydride can be generated in situ via reaction of the sodium bis(2-methoxyethoxy)aluminumhydride with either a primary amine or secondary amine (as described, for example, by Shin, et al. *Bull. Korean Chem. Soc.* 2014, 35, 2169, which is incorporated herein by reference).

F. Pheromone Compositions and Uses Thereof

As described above, a number of the fatty olefin derivatives obtained via the methods of the invention can be used as insect pheromones or pheromone precursor materials. The precursor materials and pheromone products include the compounds listed in Tables 1-3 above for use as pheromones. Synthetic routes for the preparation of oriental fruit moth pheromone Z-dodec-8-enyl acetate, for example, are shown in Schemes 20-22. Synthetic routes for the preparation of corn earworm (*H. zea*) pheromone Z-hexadec-11-enyl acetate are shown in Schemes 23 and 24. Synthetic routes for the preparation of *Lobesia botrana* pheromone (7E,9Z)dodeca-7,9-dien-1-yl acetate and *Cydia pomonella* pheromone (8E,10E)-dodeca-8,10-dien-1-ol, for example, are described in Examples 13 and 14, respectively.

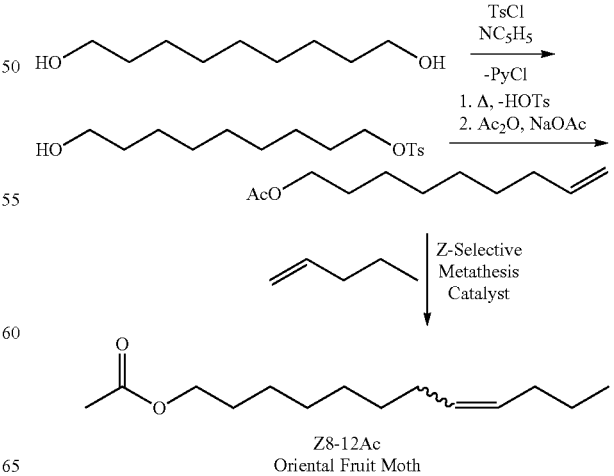

Scheme 22
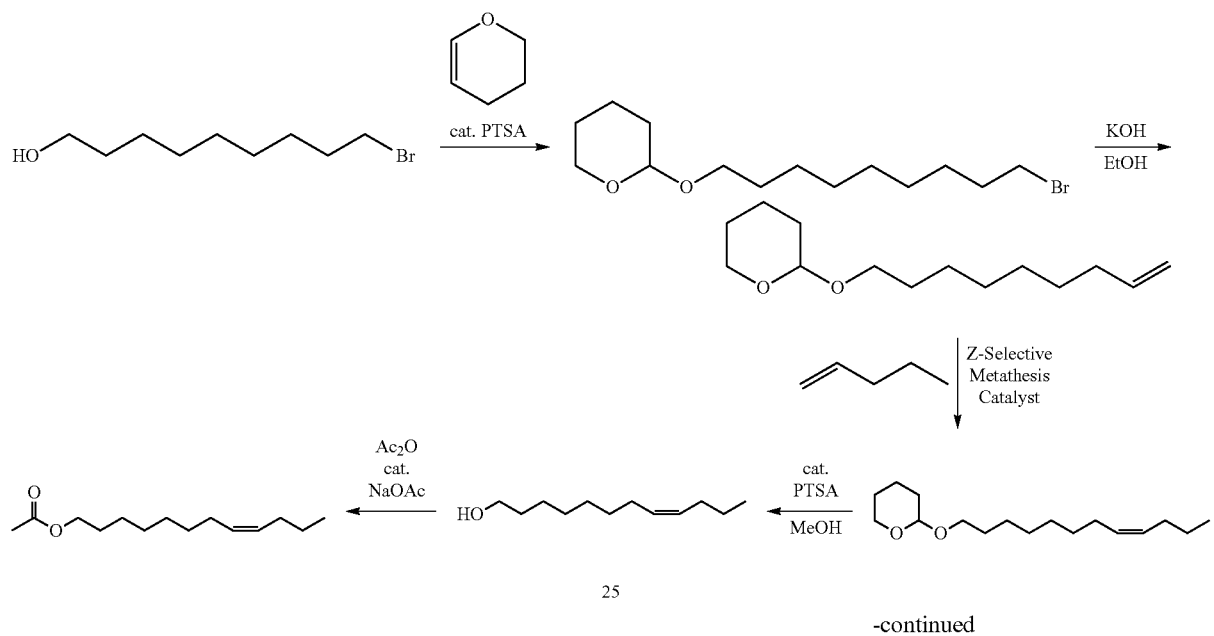
Scheme 23
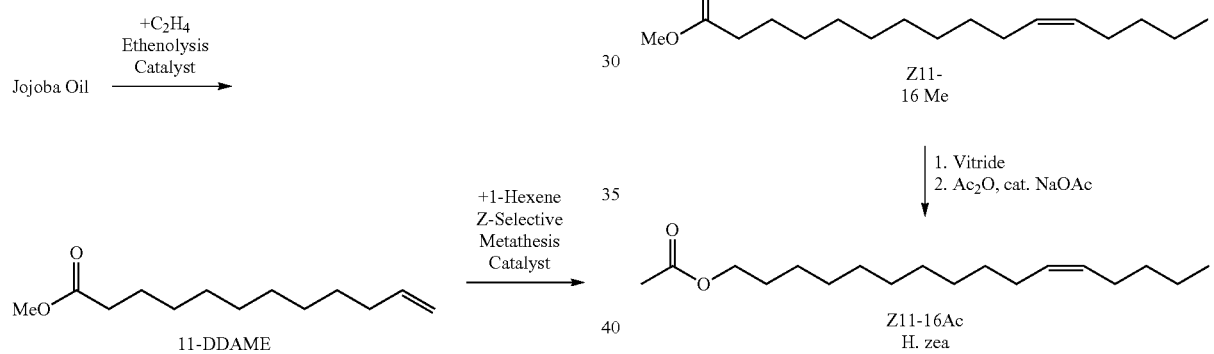
Scheme 24
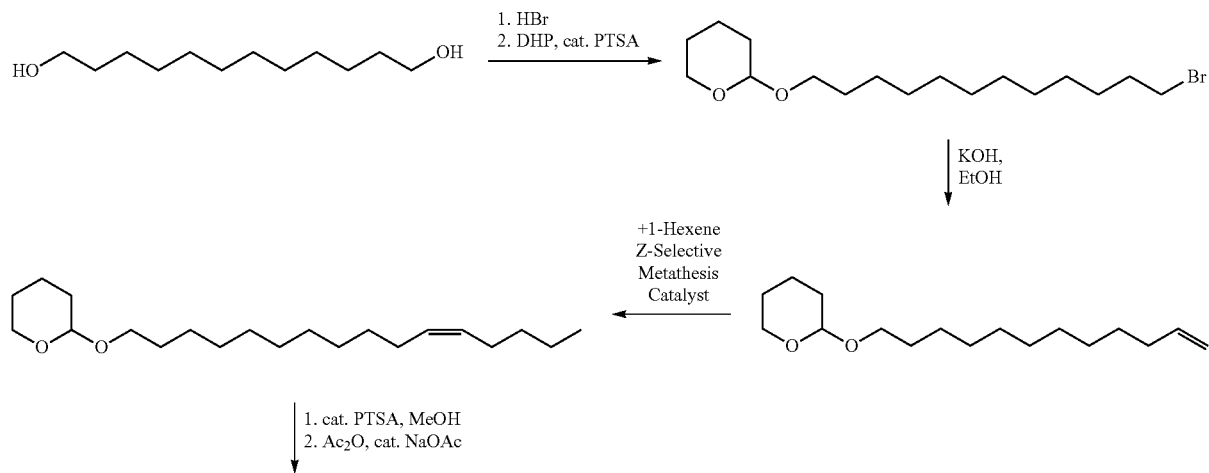

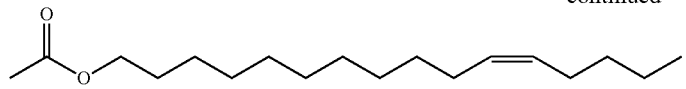

Pheromones prepared according to the methods of the invention can be formulated for use as insect control compositions. The pheromone compositions can include a carrier, and/or be contained in a dispenser. The carrier can be, but is not limited to, an inert liquid or solid.

Examples of solid carriers include but are not limited to fillers such as kaolin, bentonite, dolomite, calcium carbonate, talc, powdered magnesia, Fuller's earth, wax, gypsum, diatomaceous earth, rubber, plastic, silica and China clay. Examples of liquid carriers include, but are not limited to, water; alcohols, such as ethanol, butanol or glycol, as well as their ethers or esters, such as methylglycol acetate; ketones, such as acetone, cyclohexanone, methylethyl ketone, methylisobutylketone, or isophorone; alkanes such as hexane, pentane, or heptanes; aromatic hydrocarbons, such as xylenes or alkyl naphthalenes; mineral or vegetable oils; aliphatic chlorinated hydrocarbons, such as trichloroethane or methylene chloride; aromatic chlorinated hydrocarbons, such as chlorobenzenes; water-soluble or strongly polar solvents such as dimethylformamide, dimethyl sulfoxide, or N-methylpyrrolidone; liquefied gases; and mixtures thereof. Baits or feeding stimulants can also be added to the carrier.

Pheromone compositions can be formulated so as to provide slow release into the atmosphere, and/or so as to be protected from degradation following release. For example, the pheromone compositions can be included in carriers such as microcapsules, biodegradable flakes and paraffin wax-based matrices.

Pheromone compositions can contain other pheromones or attractants provided that the other compounds do not substantially interfere with the activity of the composition. The pheromone compositions can also include insecticides. Examples of suitable insecticides include, but are not limited to, buprofezin, pyriproxyfen, flonicamid, acetamiprid, dinotefuran, clothianidin, acephate, malathion, quinolphos, chloropyriphos, profenophos, bendiocarb, bifenthrin, chlorpyrifos, cyfluthrin, diazinon, pyrethrum, fenpropathrin, kinoprene, insecticidal soap or oil, and mixtures thereof.

Pheromone compositions can be used in conjunction with a dispenser for release of the composition in a particular environment. Any suitable dispenser known in the art can be used. Examples of such dispensers include but are not limited to bubble caps comprising a reservoir with a permeable barrier through which pheromones are slowly released, pads, beads, tubes rods, spirals or balls composed of rubber, plastic, leather, cotton, cotton wool, wood or wood products that are impregnated with the pheromone composition. For example, polyvinyl chloride laminates, pellets, granules, ropes or spirals from which the pheromone composition evaporates, or rubber septa. One of skill in the art will be able to select suitable carriers and/or dispensers for the desired mode of application, storage, transport or handling.

A variety of pheromones can be prepared according to the methods of the invention and formulated as described above. For example, the methods of the invention can be used to prepare peach twig borer (PTB) sex pheromone, which is a mixture of (E)-dec-5-en-1-ol (17%) and (E)-dec-5-en-1-yl acetate (83%), by metathesis of hex-5-en-1-ol and hex-1-ene, with or without acylation of the resulting (E)-dec-5-en-1-ol. The PTB sex pheromone can be used in conjunction with a sustained pheromone release device having a polymer container containing a mixture of the PTB sex pheromone and a fatty acid ester (such as a sebacate, laurate, palmitate, stearate or arachidate ester) or a fatty alcohol (such as undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol). The polymer container can be a tube, an ampule, or a bag made of a polyolefin or an olefin component-containing copolymer. Sex pheromones of other pest insects such the cotton bollworm (*Helicoverpa armigera*), fall army worm (*Spodoptera frugiperda*), oriental fruit moth (*Grapholita molesta*) and leaf roller (Tortricidae) can be used in this type of sustained pheromone release device. The sex pheromones typically include one or more aliphatic acetate compounds having from 10 to 16 carbon atoms (e.g., decyl acetate, decenyl acetate, decadienyl acetate, undecyl acetate, undecenyl acetate, dodecyl acetate, dodecenyl acetate, dodecadienyl acetate, tridecyl acetate, tridecenyl acetate, tridecadienyl acetate, tetradecyl acetate, tetradecenyl acetate, tetradecadienyl acetate, and the like) and/or one or more aliphatic aldehyde compounds having from 10 to 16 carbon atoms (e.g., 7-hexadecenal, 11-hexadecenal, 13-octadecenal, and the like).

Pheromones prepared according to the methods of the invention, as well as compositions containing the pheromones, can be used to control the behavior and/or growth of insects in various environments. The pheromones can be used, for example, to attract or repel male or female insects to or from a particular target area. The pheromones can be used to attract insects away from vulnerable crop areas. The pheromones can also be used example to attract insects as part of a strategy for insect monitoring, mass trapping, lure/attract-and-kill or mating disruption.

Mass trapping involves placing a high density of traps in a crop to be protected so that a high proportion of the insects are removed before the crop is damaged. Lure/attract-and-kill techniques are similar except once the insect is attracted to a lure, it is subjected to a killing agent. Where the killing agent is an insecticide, a dispenser can also contain a bait or feeding stimulant that will entice the insects to ingest an effective amount of the insecticide.

It will be appreciated by a person skilled in the art that a variety of different traps are possible. Suitable examples of such traps include water traps, sticky traps, and one-way traps. Sticky traps come in many varieties. One example of a sticky trap is of cardboard construction, triangular or wedge-shaped in cross-section, where the interior surfaces are coated with a non-drying sticky substance. The insects contact the sticky surface and are caught. Water traps include pans of water and detergent that are used to trap insects. The detergent destroys the surface tension of the water, causing insects that are attracted to the pan, to drown in the water. One-way traps allow an insect to enter the trap but prevent it from exiting. The traps of the invention can be colored brightly, to provide additional attraction for the insects.

The trap is positioned in an area infested (or potentially infested) with insects. Generally, the trap is placed on or close to a tree or large plant and the pheromone attracts the insects to the trap. The insects can then be caught, immobilized and/or killed within the trap, for example, by the killing agent present in the trap.

Pheromones prepared according to the methods of the invention can also be used to disrupt mating. Strategies of mating disruption include confusion, trail-masking and false-trail following. Constant exposure of insects to a high concentration of a pheromone can prevent male insects from responding to normal levels of the pheromone released by female insects. Trail-masking uses a pheromone to destroy the trail of pheromones released by females. False-trail following is carried out by laying numerous spots of a pheromone in high concentration to present the male with many false trails to follow. When released in sufficiently high quantities, the male insects are unable to find the natural source of the sex pheromones (the female insects) so that mating cannot occur.

Insect populations can be surveyed or monitored by counting the number of insects in a target area (e.g., the number of insects caught in a trap). Inspection by a horticulturist can provide information about the life stage of a population. Knowing where insects are, how many of them there are, and their life stage enables informed decisions to be made as to where and when insecticides or other treatments are warranted. For example, a discovery of a high insect population can necessitate the use of methods for removal of the insect. Early warning of an infestation in a new habitat can allow action to be taken before the population becomes unmanageable. Conversely, a discovery of a low insect population can lead to a decision that it is sufficient to continue monitoring the population. Insect populations can be monitored regularly so that the insects are only controlled when they reach a certain threshold. This provides cost-effective control of the insects and reduces the environmental impact of the use of insecticides.

As will be apparent to one of skill in the art, the amount of a pheromone or pheromone composition used for a particular application can vary depending on several factors such as the type and level of infestation; the type of composition used; the concentration of the active components; how the composition is provided, for example, the type of dispenser used; the type of location to be treated; the length of time the method is to be used for; and environmental factors such as temperature, wind speed and direction, rainfall and humidity. Those of skill in the art will be able to determine an effective amount of a pheromone or pheromone composition for use in a given application.

IV. EXAMPLES

Example 1. Screening of Triethylaluminum Pre-treatment Reagent Loading in the Z-Selective Cross-Metathesis of Fermentation-Derived (Z)-hexadec-11-en-1-yl acetate and but-1-ene In a nitrogen-filled glovebox, 2.35 g of approximately 65% pure (Z)-hexadec-11-en-1-yl acetate (Z11-16Ac), derived from the biocatalytic process described in WO 2017/214133, was transferred to a four identical 30 ml vials with septum caps and equipped with magnetic stir bars. The vials were cooled to −15° C. and either 0.125, 0.15, 0.175 or 0.2 mol % of triethylaluminum, relative to all feedstocks, was added to each vial through the septum cap as a solution in toluene. While maintaining the vials at −15° C., approximately 1.3 g of but-1-ene was condensed into each vial such that the molar ratio of (Z)-hexadec-11-en-1-yl acetate to but-1-ene is approximately 1:4. The mixtures were then warmed to ambient temperature and stirred by means of an external magnetic stirrer for 16 hours. The following morning the weights of each vial was recorded to ensure no loss of but-1-ene during the overnight storage. To the vials was then added 0.005 mol % of (T-4)-[(1R)-3,3'-Dibromo-2'-[[(1,1-dimethylethyl)dimethylsilyl]oxy]-5,5',6,6',7,7',8,8'-octahydro[1,1'-binaphthalen]-2-olato-κO][2,6-dichlorobenzenaminato(2-)-κN](2,5-dimethyl-TH-pyrrol-1-yl)[(2-methoxyphenyl)methylene]tungsten [CAS Reg. No. 1817807-15-0] as a solution in toluene through the septum cap. The reaction mixtures were then stirred at ambient temperature. After one hour had elapsed following the addition of catalyst, the vial was cooled to −10° C. and an aliquot taken for assay of 'Z11-16Ac Conversion (%)' (equation below) and the E/Z ratio of the 11-position of the desired product, (Z)-tetradec-11-en-1-yl acetate (Z11-14Ac), by GC-MS/FID using an Agilent DB-23 column. The vials were then warmed back to ambient temperature and stirring continued. This sampling process was repeated at two, four and 24 hours after the addition of catalyst and results for all four time points is presented in Tables 4 and 5.

$$Z11-16Ac \text{ Conversion } (\%) = 1 - \left(\frac{\text{Final mol } Z11-16Ac}{\text{Initial mol } Z11-16Ac}\right) \times 100$$

TABLE 4

| Added Triethylaluminum (mol %) | 1 Hour Reaction | | 2 Hour Reaction | |
|---|---|---|---|---|
| | Z11-16Ac Conversion (%) | Z11-14Ac E/Z Ratio | Z11-16Ac Conversion (%) | Z11-14Ac E/Z Ratio |
| 0.125 | 4 | 7/93 | 10 | 4/96 |
| 0.15 | 27 | 3/97 | 58 | 4/96 |
| 0.175 | 26 | 3/97 | 56 | 3/97 |
| 0.2 | 30 | 3/97 | 61 | 4/96 |

TABLE 5

| Added Triethylaluminum (mol %) | 4 Hour Reaction | | 24 Hour Reaction | |
|---|---|---|---|---|
| | Z11-16Ac Conversion (%) | Z11-14Ac E/Z Ratio | Z11-16Ac Conversion (%) | Z11-14Ac E/Z Ratio |
| 0.125 | 15 | 6/94 | 16 | 6/94 |
| 0.15 | 83 | 6/94 | 91 | 19/81 |
| 0.175 | 82 | 5/95 | 91 | 20/80 |
| 0.2 | 85 | 6/94 | 91 | 23/77 |

Example 2. Z-Selective Cross-Metathesis of Fermentation-Derived (Z)-hexadec-11-en-1-yl Acetate and but-1-ene In a nitrogen-filled glovebox, a 50 mL stainless steel pressure reactor was charged with magnetic stir bar and 15 g of 65% pure (Z)-hexadec-11-en-1-yl acetate (Z11-16Ac), derived from the biocatalytic process described in WO 2017/214133. The feedstock was agitated by means of an external magnetic stirrer and then 0.2 mol % of triethyl aluminum relative to the final amount of olefins to be used in the reaction was added as a solution in toluene. The vessel was sealed and stirred at ambient temperature for 16 hours.

The following morning the reactor was cooled to −10° C. and approximately 9 g of but-1-ene condensed through a valve on the head of the reactor. The reactor was then opened to a manifold consisting of a condenser cooled to −10° C., pressure-relief valve and pressure gauge. The vessel was warmed to ambient temperature, after which time the head pressure in the reactor was measured at 1.8 bar. To the feedstock was added 0.005 mol % of (T-4)-[(1R)-3,3'-Dibromo-2'-[[(1,1-dimethylethyl)dimethylsilyl]oxy]-5,5',6,6',7,7',8,8'-octahydro[1,1'-binaphthalen]-2-olato-κO][2,6-dichlorobenzenaminato(2-)-κN](2,5-dimethyl-1H-pyrrol-1-yl)[(2-methoxyphenyl)methylene]tungsten [CAS Reg. No. 1817807-15-0] as a solution in toluene through a valve on the reactor head. The pressure-relief valve on the reactor manifold was adjusted to vent the ethylene co-product/but-1-ene feedstock mixture in the reactor headspace such that a head pressure of 1.3-1.8 bar was maintained during the reaction. Samples were taken under pressure at both 90 and 120 minutes after the addition of catalyst. The samples were analyzed for 'Z11-16Ac Conversion (%)' (equation above) and the E/Z ratio of the 11-position of the desired product, (Z)-tetradec-11-en-1-yl acetate (Z11-14Ac), by GC-MS/FID using an Agilent DB-23 column. After 90 minutes of reaction time, the 'Z11-16Ac Conversion (%)' was found to be 77% and the Z11-14Ac E/Z Ratio 6/94. After 120 minutes of reaction time, the 'Z11-16Ac Conversion (%)' was found to be 83% and the Z11-14Ac E/Z Ratio 8/92.

Example 3. Z-Selective Cross-Metathesis of Fermentation-Derived (Z)-hexadec-11-en-1-yl Acetate and but-1-ene In a nitrogen-filled glovebox, a glass pressure vessel was charged with a magnetic stir bar and 10 g of 65% pure (Z)-hexadec-11-en-1-yl acetate (Z11-16Ac), derived from the biocatalytic process described in WO 2017/214133. To the feedstock was then added 0.1 mol % of [2-(1-Methylethoxy-O)phenylmethyl-C](nitrato-O,O'){rel-(2R,5R,7R)-adamantane-2,1-diyl[3-(2,4,6-trimethylphenyl)-1-imidazolidinyl-2-ylidene]}ruthenium [CAS Reg. No. 1352916-84-7] as a solution in dichloromethane. The vessel was sealed with a head equipped with a pressure gauge, pressure relief valve, a vent valve and a dip tube connected to a three-way ball valve. All valves were sealed and then the vessel removed from the glovebox. One outlet of the three-way ball valve was connected to a cylinder of but-1-ene via PTFE tubing. The other outlet of the three-way valve was connected to a needle valve to allow for in-process sampling. The vessel was cooled in a dry ice cooled isopropanol bath and but-1-ene condensed in through the three-way ball valve. The vessel was sealed and disconnected from the but-1-ene cylinder. The vessel was then weighed to determine that 7.8 g of but-1-ene had been charged. The reaction mixture was stirred by means of an external magnetic stirrer while being warmed to 40° C. in a water bath. After four hours had elapsed, a sample of the reaction mixture was retrieved through the dip tube. GC-FID analysis using an Agilent 6890 fitted with a HP-5 column showed the 'Z11-16Ac Conversion (%)' (equation above) to be 65%.

Example 4. Metathesis Catalyst Screening for the Z-Selective Cross-Metathesis of Natural Oil Derived (Z)-eicos-11-en-1-yl Acetate and Hex-1-ene (Z)-Eicos-11-en-1-yl acetate was prepared from jojoba oil through reduction of the fatty wax esters with 1.2 molar equivalents of sodium bis(2-methoxyethoxy)aluminum hydride, separation of the (Z)-eicos-11-en-1-ol fraction via vacuum distillation and esterification of (Z)-eicos-11-en-1-ol with 1.2 molar equivalents of acetic anhydride using 6 mol % of anhydrous sodium acetate as catalyst. In a nitrogen-filled glovebox, two 4 mL vials equipped with magnetic stir bars, 'Reaction A' and 'Reaction B', were charged with approximately 0.2 g of (Z)-eicos-11-en-1-yl acetate and 0.1 g hex-1-ene. To the vials was added 0.1 mol % of triethylaluminum, relative to all feedstocks, as a solution in toluene. The mixtures were then stirred at ambient temperature by means of an external magnetic stirrer for 16 hours. To 'Reaction A' was then added 0.01 mol % of (T-4)-[(1R)-3,3'-Dibromo-2'-[[(1,1-dimethylethyl)dimethylsilyl]oxy]-5,5',6,6',7,7',8,8'-octahydro[1,1'-binaphthalen]-2-olato-κO][2,6-dichlorobenzenaminato(2-)-κN](2,5-dimethyl-1H-pyrrol-1-yl)[(2-methoxyphenyl)methylene]tungsten [CAS Reg. No. 1817807-15-0] as a solution in toluene. To 'Reaction B' was then added 0.01 mol % of (T-4)-[2,6-Bis(1-methylethyl)benzenaminato(2-)](6'-bromo-4',5'-diphenyl[1,1':2',1''-terphenyl]-3'-olato-κO)(2,5-dimethyl-1H-pyrrol-1-yl)(2-methyl-2-phenylpropylidene)molybdenum [CAS Reg. No. 1445990-85-1] as a solution in toluene. The reaction mixtures were then stirred at ambient temperature. After 12 hours had elapsed following the addition of catalyst, an aliquot of each reaction taken for composition analysis and determination the E/Z ratio of the desired product, (Z)-hexadec-11-en-1-yl acetate, by GC-MS/FID using an Agilent DB-23 column. The composition of 'Reaction A' was found to be 12 area % dec-5-ene self-metathesis co-product, 19 area % tetradec-5-ene cross-metathesis co-product, 2 area % dodec-11-en-1-yl acetate cross-metathesis co-product, 7 area % octadecene self-metathesis co-product, 24 area % of the desired hexadec-11-en-1-yl acetate cross-metathesis product and 35 area % eicos-11-en-1-yl acetate. The E/Z ratio of the 'Reaction A' hexadec-11-en-1-yl acetate product was 3/97. The composition of 'Reaction B' was found to be 23 area % dec-5-ene self-metathesis co-product, 16 area % tetradec-5-ene cross-metathesis co-product, 10 area % dodec-11-en-1-yl acetate cross-metathesis co-product, 4 area % octadecene self-metathesis co-product, 20 area % of the desired hexadec-11-en-1-yl acetate cross-metathesis product and 28 area % eicos-11-en-1-yl acetate. The E/Z ratio of the 'Reaction A' hexadec-11-en-1-yl acetate product was 85/15.

Example 5. Metathesis Catalyst Screening for the Cross-Metathesis of Oct-7-en-1-yl Acetate and (Z)-hexa-1,3-diene In a nitrogen-filled glovebox, a glass vial was charged a with a magnetic stir bar and 0.5 g of a 1:2 on a molar basis of oct-7-en-1-yl acetate and (Z)-hexa-1,3-diene previously treated with triethylaluminum to reduce impurities according to the method described of U.S. Pat. No. 9,388,097. To the olefin mixture was added 0.01 mol % of a tungsten metathesis catalyst (Tables 6/7) as a toluene solution. The vial was then closed with a perforated cap and the reaction mixtures stirred by means of an external magnetic stirrer at ambient temperature. An aliquot of the reaction mixture was taken four and 24 hours after the addition of catalyst. This aliquot was analyzed to determine 'Oct-7-en-1-yl Acetate Conversion (%)' (equation below) and the E/Z ratio of the 14-(acetyloxy)tetradec-7-en-1-yl acetate self-metathesis co-product by GC-MS/FID (Tables 6/7). GC chromatograms were recorded using a Shimadzu GC2010 Plus instrument equipped with an Agilent DB-23 capillary column. The results of the GC analyses are presented in Table 6.

$$Oct\text{-}7\text{-}en\text{-}1\text{-}yl \text{ Acetate Conversion } (\%) =$$

$$1 - \left(\frac{\text{Final } mol \ Oct\text{-}7\text{-}en\text{-}1\text{-}yl \text{ acetate}}{\text{Initial } mol \ Oct\text{-}7\text{-}en\text{-}1\text{-}yl \text{ acetate}}\right) \times 100$$

TABLE 6

| Catalyst | 4 Hour Reaction Length | | 24 Hour Reaction Length | |
|---|---|---|---|---|
| | Oct-7-en-1-yl Acetate Conversion (%) | E/Z Ratio of 14-(acetyloxy) tetradec-7-en-1-yl acetate | Oct-7-en-1-yl Acetate Conversion (%) | E/Z Ratio of 14-(acetyloxy) tetradec-7-en-1-yl acetate |
| 1 | 29 | 67/33 | 58 | 68/32 |
| 2 | 18 | 71/29 | 29 | 72/28 |
| 3 | 33 | 74/26 | 42 | 74/26 |
| 4 | 28 | 60/40 | 31 | 60/40 |
| 5 | 44 | 2/98 | 53 | 2/98 |
| 6 | 11 | 2/98 | 42 | 2/98 |

TABLE 7

| Catalyst | Drawing | CAS Reg. No. |
|---|---|---|
| 1 | | 1628041-62-2 |
| 2 | | 1628041-63-3 |
| 3 | | 1817807-72-9 |

TABLE 7-continued

| Catalyst | Drawing | CAS Reg. No. |
|---|---|---|
| 4 | | 1628041-83-7 |
| 5 | | 1817807-15-0 |
| 6 | | 1817807-66-1 |

Example 6. Cross-Metathesis of Oct-7-en-1-yl Acetate and (Z)-hexa-1,3-diene

In a nitrogen-filled glovebox, a 250-mL round-bottomed flask with a magnetic stirrer bar and reflux condenser was charged 40.6 g of oct-7-en-1-yl acetate and 40.2 g of (Z)-hexa-1,3-diene. The mixture was stirred by means of an external magnetic stirrer mixture. To mixture was added 0.25 mol % of triethylaluminum as a solution in toluene at ambient temperature and agitation continued overnight. Starting the following day, 0.08 mol % of (T-4)-(6'-bromo-4',5'-diphenyl[1,1':2',1'-terphenyl]-3'-olato)[2,6-dichlorobenzenaminato (2-)-κN](2,5-dimethyl-1H-pyrrol-1-yl)(2-methyl-2-phenylpropylidene)tungsten [CAS Reg. No. 1628041-62-2; Tables 6/7, Catalyst 1] was added portion wise as a solution in toluene to the reaction mixture over the next 40 hours. After that time had elapsed, all volatile reaction components were separated by vacuum distillation at 10 mbar and ambient temperature. 10 mL of methanol was added to reaction mixture and the yellow-orange residue filtered through a filter bed consisting of alumina (depth=3 cm, height=3 cm) atop diatomaceous earth (depth=3 cm, height=3 cm). The filter bed was washed with dichloromethane. The combined extracts were concentrated on a rotary evaporator and the resultant yellow liquid transferred to a pot still with a Vigreux column 10 cm in length. Following distillation, all fractions containing >97% dodeca-7,9-dien-1-yl acetate isomers, as determined by GC-MS/FID analysis using an Agilent DB-23 column, were combined to yield 7.76 g of mixed isomers. The sample was found to be an approx. 2:1 mixture of (E,Z)-dodeca-7,9-dien-1-yl acetate and (Z,Z)-dodeca-7,9-dien-1-yl acetate $^1$H NMR analysis.

Example 7. Cross-Metathesis of Oct-7-en-1-yl Acetate and 4-Bromobut-1-ene Using a Molybdenum Catalyst In a nitrogen-filled glovebox, a round-bottomed flask equipped with a magnetic stirrer bar and reflux condenser was charged with 83 g of oct-7-en-1-yl acetate and 66 g of 4-bromobut-1-ene. Both feedstocks were treated with activated, basic alumina prior to the metathesis reaction to reduce catalyst deactivating impurities to an acceptable level. At ambient temperature, 0.1 mol % of (T-4)-(6'-bromo-4',5'-diphenyl[1,1':2',1"-terphenyl]-3'-olato)[2,6-dichlorobenzenaminato (2-)-κN](2,5-dimethyl-1H-pyrrol-1-yl)(2-methyl-2-phenylpropylidene) tungsten [CAS Reg. No. 1628041-62-2; Tables 6/7, Catalyst 1] as a solution in toluene was added to the reaction mixture. The mixture was stirred by means of external magnetic stirrer for 12 hours. After that time had elapsed, an aliquot of the reaction mixture was analyzed by GC-MS/FID. The composition of the mixture was found to be 12.8% 1,6-dibromohex-3-ene, 15.6 area % oct-7-en-1-yl acetate, 25 area % 14-(acetyloxy)tetradec-7-en-1-yl acetate self-metathesis co-product and 46.5 area % 10-bromodec-7-en-1-yl acetate. The crude product mixture was then separated by fractional vacuum distillation. Fractions containing >99% (E/Z)-10-bromodec-7-en-1-yl acetate were found to distill at 117° C./0.9-1.3 mbar. Those cuts were combined to yield 41.2 g.

Example 8. Synthesis of (E/Z)-deca-7,9-dien-1-yl Acetate from (E/Z)-10-Bromodec-7-En-1-yl Acetate In a nitrogen-filled glovebox, a round-bottomed flask equipped with a magnetic stirrer bar and reflux condenser was charged with 41.2 g of (E/Z)-10-bromodec-7-en-1-yl acetate, 60 mL of low-moisture content benzene and 30.5 g of 1,8-diazabicyclo[5.4.0]undec-7-ene. The mixture was stirred by means of the external magnetic stirrer for 16 hours. The precipitated 1,8-diazabicyclo[5.4.0]undec-7-ene hydrobromide was removed by filtration through a bed of silica gel and the bed was washed with excess benzene. The benzene solvent was evaporated at 30° C. yielding a yellow, biphasic liquid mixture. The upper phase was vacuum distilled (85° C./1 mbar) yielding 18.26 g of a colorless oil. GC-MS/FID analysis on an Agilent DB23 column showed the distillate to be 85 area % (E/Z)-deca-7,9-dien-1-yl acetate and 15 area % unreacted 1,8-diazabicyclo[5.4.0]undec-7-ene.

Example 9. Preparation of *Lobesia botrana* Sex Pheromone Precursor Via Cross-Metathesis of Oct-7-en-1-yl Acetate and but-3-en-1-yl Mesylate Using a Tungsten Catalyst In a nitrogen-filled glovebox, a glass vial was charged a with a magnetic stir bar and 5 g of an equimolar mixture of oct-7-en-1-yl acetate and but-3-en-1-yl mesylate. The combined feedstocks were then treated with 0.125 mol % of triethylaluminum and the resultant mixture stirred for 16 hours. The following day, 0.005 mol % of (T-4)-(6'-bromo-4'5'-diphenyl[1,15':2',1'-terphenyl]-3'-olato)[2,6-dichlorobenzenaminato(2-)-κN](2,5-dimethyl-1H-pyrrol-1-yl)(2-methyl-2-phenyl propylidene)tungsten [CAS Reg. No. 1628041-62-2; Tables 6/7, Catalyst 1] was added a solution in toluene. After six hours, an aliquot was taken and analyzed by GC-MS/FID. The composition of the mixture was found to be 8 area % unreacted but-3-en-1-yl mesylate, 10 area % unreacted oct-7-en-1-yl acetate, 12 area % (E/Z)-6-(methanesulfonyloxy)hex-3-en-1-yl mesylate self-metathesis co-product, 30 area % (E/Z)-14-(acetyloxy)tetradec-7-en-1-yl acetate self-metathesis co-product and 41 area % (E/Z)-10-(methanesulfonyloxy)dec-7-en-1-yl acetate.

Example 10. Preparation of *Lobesia botrana* Sex Pheromone Precursor Via Cross-Metathesis of oct-7-en-1-yl Acetate and but-3-en-1-yl Mesylate Using a Ruthenium Catalyst Under an inert atmosphere, a five liter round bottom flask equipped with an overhead stirrer and addition funnel was charged with 891 g of oct-7-en-1-yl acetate and 863 g of but-3-en-1-yl mesylate. To the mixture was then added 48 g of triisobutylaluminum dropwise with stirring at ambient temperature. After one hour, the flask was equipped with a thermowell and then warmed to 40° C. via a heating mantle. A solution of 0.689 g of [1,3-bis-(2,4,6-trimethylphenyl)-2-imidazolidinylidene]dichloro(o-isopropoxyphenyl methylene)ruthenium [CAS Reg. No. 301224-40-8] in 40 mL of toluene was added dropwise to the stirring feedstock and then the resultant mixture stirred for an additional three hours.

The reaction was quenched by the addition of 60 mL of a 1.0 M solution of tris(hydroxymethyl)phosphine to the reaction mixture, followed by stirring at 60° C. for three hours. 1.5 L of both a saturated aqueous sodium chloride solution and toluene were added to the flask and the mixture stirred for five minutes. Agitation was ceased and the phases allowed to separate for one hour. The bottom, aqueous phase was discarded and the top, organic phase washed again with one liter of deionized water as described above. The organic phase was then dried over anhydrous sodium sulfate, filtered, and concentrated using a rotary evaporator (40° C./20-40 torr) yielding 1.65 kg of an orange liquid. Approximately 250 g of unreacted oct-7-en-1-yl acetate and but-3-en-1-yl mesylate were recovered together from the crude mixture by short distillation (35-56° C./0.1-0.2 Torr) as a clear liquid. The composition of the remaining 1.388 kg of crude material was found to be 1.6 area % but-3-en-1-yl mesylate, 14 area % 1,6-bis(methanesulfonyloxy)hex-3-en-1-yl, 30 area % 14-(acetyloxy)tetradec-7-en-1-yl acetate and 47 area % 10-(methanesulfonyloxy)dec-7-en-1-yl acetate by GC-FID using an Agilent 6890 GC equipped with a HP-5 column.

Example 11. Preparation of *Lobesia botrana* Sex Pheromone Precursor deca-7,9-dien-1-yl Acetate A 12 liter round bottom flask equipped with a thermowell and an overhead stirrer was charged with the 1.388 kg of crude material prepared in Example 10. Six liters of anhydrous toluene was transferred in to the flask and the resultant mixture sparged with nitrogen while stirring for one hour. The feedstock solution was cooled to 0-5° C. by means of an ice bath. Then 446.6 g of potassium tert-butoxide was added slowly as a solid to reaction mixture at a rate such that the temperature of the reaction did not exceed 40° C. After the addition of potassium tert-butoxide was complete, the reaction mixture was agitated for an additional hour. The reaction mixture was then cooled to ambient temperature and quenched by the addition of four liters of deionized water. The resultant mixture was stirred for five minutes and then allowed to settle for 16 hours during which time two layers had formed. The bottom, aqueous layer was removed and an additional two liters of deionized water added to the flask. The mixture was agitated for five minutes and then allowed to settle for one hour. The bottom aqueous layer was separated and this wash procedure repeated once more with an additional two liters of deionized water. The remaining organic phase was dried over anhydrous sodium sulfate, filtered and then concentrated using a rotary evaporator (40° C./20-40 Torr) to yield 746 g of a dark red liquid. 320 g of a clear liquid was collected by short-path distillation (97-140° C./0.1-0.3 Torr). This distillate was determined to contain >93 area % of deca-7,9-dien-1-yl acetate by GC-FID using an Agilent 6890 GC equipped with a HP-5 column.

Example 12. Preparation of *Lobesia botrana* Sex Pheromone Via Z-Selective Cross-Metathesis of (E/Z)-deca-7,9-dien-1-yl Acetate and but-1-ene In a nitrogen-filled glovebox, two 30 mL glass vials with septum caps, 'Reaction A' and 'Reaction B', were charged a with a magnetic stir bar and cooled to −15° C. Approximately 1.3 g of but-1-ene was condensed into the through the septum and then the vials weighed. Based on that exact mass exactly 0.25 molar equivalents of (E/Z)-deca-7,9-dien-1-yl acetate (E/Z≈85/15), precooled to −15° C., was added through the septum. The substrate mixture was warmed to room temperature and then 0.01 mol %, relative to the total substrate content, of (T-4)-[(1R)-3,3'-Dibromo-2'-[[(1,1-dimethylethyl)dimethylsilyl]oxy]-5,5',6,6',7,7',8,8'-octahydro[1,1'-binaphthalen]-2-olato-κO][2,6-dichlorobenzenaminato (2-)-κN](2,5-dimethyl-1H-pyrrol-1-yl)[(2-methoxyphenyl)methylene]tungsten [CAS Reg. No. 1817807-15-0; Tables 6/7, Catalyst 5] was added as a solution in toluene to both reaction mixtures. The vials were cooled to −15° C. every 30 minutes after the addition of catalyst and opened to release the ethylene co-product. 'Reaction A' was quenched 60 minutes after the addition of catalyst an aliquot taken for composition analysis by GC-MS/FID using an Agilent DB-23 column. The composition of 'Reaction A' was found to be 2 area % oct-7-en-1-yl acetate, 2 area % dec-7-en-1-yl acetate isomers, 62 area % deca-7,9-dien-1-yl acetate isomers and 34 area % dodeca-7,9-dien-1-yl acetate isomers. 'Reaction B' was quenched after 150 minutes had elapsed following catalyst addition. The composition of 'Reaction B' was found to be 3 area % oct-7-en-1-yl acetate, 3 area % dec-7-en-1-yl acetate isomers, 52 area % deca-7,9-dien-1-yl acetate isomers and 42 area % dodeca-7,9-dien-1-yl acetate isomers by GC-MS/FID.

Both samples were purified through Kugelrohr short-path distillation at 130° C./3 mbar. 'Reaction A' yielded 0.320 g of a material found to be 10 area % deca-7,9-dien-1-yl acetate isomers and 90 area % dodeca-7,9-dien-1-yl acetate isomers. The major component was found to be a 77/23 mixture of (E,Z)-dodeca-7,9-dien-1-yl acetate and (E,E)-dodeca-7,9-dien-1-yl acetate by $^1$H NMR. 'Reaction B' yielded 0.301 g of a material found to be 10 area % deca-7,9-dien-1-yl acetate isomers and 90 area % dodeca-7,9-dien-1-yl acetate isomers. The major component was found to be a 75/25 mixture of (E,Z)-dodeca-7,9-dien-1-yl acetate and (E,E)-dodeca-7,9-dien-1-yl acetate by $^1$H NMR.

Example 13. Preparation of *Lobesia botrana* Pheromone (7E,9Z) dodeca-7,9-dien-1-yl Acetate (7E,9Z)dodeca-7,9-dien-1-yl acetate (E7Z9-12Ac) is synthesized via metathesis of functionalized olefins derived from diol starting materials as outlined Scheme 25. Octane-1,8-diol is dehydrated to form oct-7-en-1-ol, which is acylated to provide oct-7-en-1-yl acetate. Butane-1,4-diol is dehydrated to form but-3-en-1-ol, which is sulfonylated to provide but-3-en-1-yl tosylate. Oct-7-en-1-yl acetate and but-3-en-1-yl tosylate are reacted in the presence of a metathesis catalyst (e.g., catalyst 7, 8, 9, or 10, as shown below) to form 10-(tosyloxy)dec-7-en-1-yl acetate. 1-Butene and the 10-(tosyloxy)dec-7-en-1-yl acetate are reacted in the presence of a Z-selective metathesis catalyst (e.g., 11 or 12, as shown below) to provide the desired E7Z9-12Ac product.

| | Catalyst Name | Catalyst Structure |
|---|---|---|
| 7 | [1,3-Bis-(2,6-diisopropylphenyl)-2-imidazolidinylidene]dichloro(2-isopropoxyphenylmethylene) ruthenium | |
| 8 | [1,3-Bis(2,6-diisopropylphenyl)-2-imidazolidinylidene]dichloro[(2-isopropoxy)(5-trifluoroacetamido)benzylidene] ruthenium | |

-continued

| | Catalyst Name | Catalyst Structure |
|---|---|---|
| 9 | 1-((6'-Bromo-4',5'-diphenyl-[1,1':2',1''-terphenyl]-3'-yl)oxy)-N-(2,6-diisopropylphenyl)-1-(2,5-dimethyl-1H-pyrrol-1-yl)-1-(2-methyl-2-phenylpropylidene)molybdenumimine | |
| 10 | 1-((6'-Bromo-4',5'-diphenyl-[1,1':2',1''-terphenyl]-3'-yl)oxy)-N-(2,6-dichlorophenyl)-1-(2,5-dimethyl-1H-pyrrol-1-yl)-1-(2-methyl-2-phenylpropylidene)tungstenimine | |
| 11 | [2-(1-Methylethoxy-O)phenylmethyl-C](nitrato-O,O'){rel-(2R,5R,7R)-adamantane-2,1-diyl[3-(2,4,6-trimethylphenyl)-1-imidazolidinyl-2-ylidene]}ruthenium | |
| 12 | (R)-1-((3,3'-Dibromo-2'-((tert-butyldimethylsilyl)oxy)-5,5',6,6',7,7',8,8'-octahydro-[1,1'-binaphthalen]-2-yl)oxy)-N-(2,6-dichlorophenyl)-1-(2,5-dimethyl-1H-pyrrol-1yl)-1-(2-methoxybenzylidene)tungstenimine | |

Scheme 25

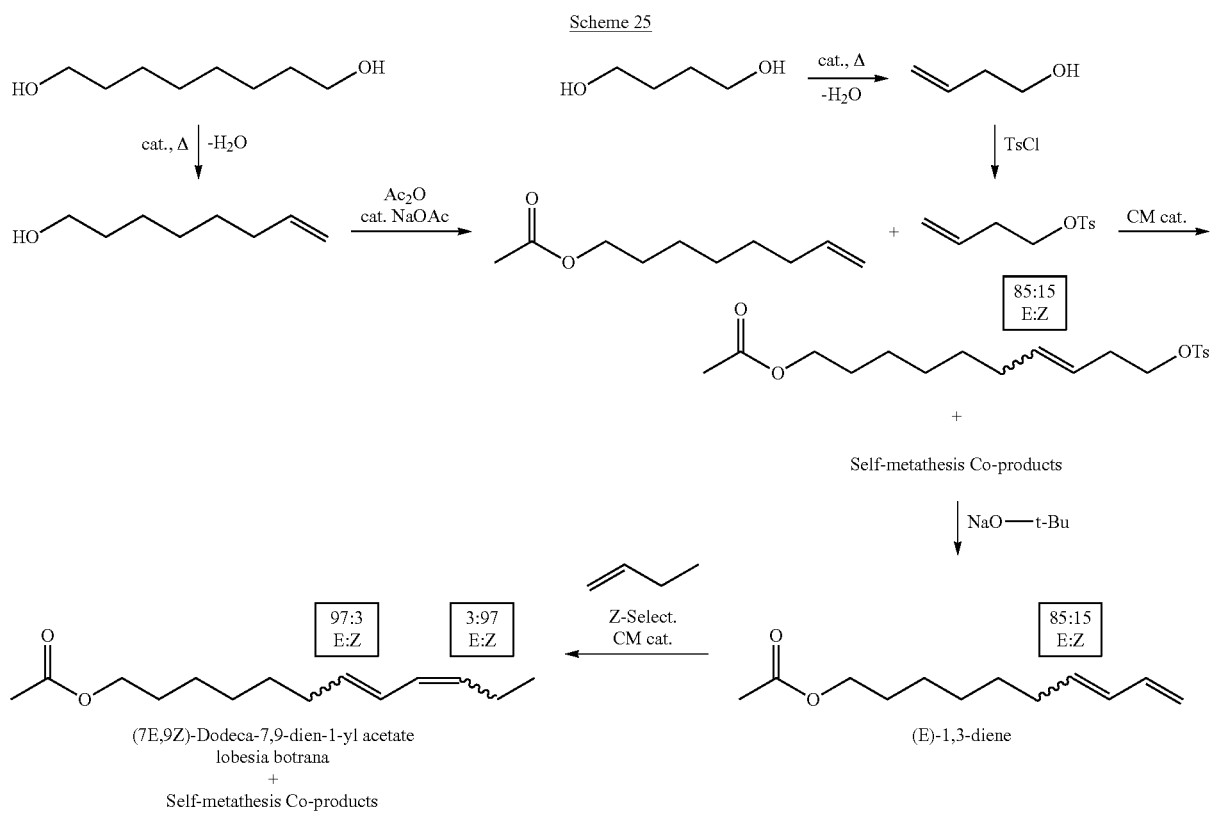

Example 14. Preparation of *Cydia pomonella* Pheromone (8E,10E)-dodeca-8,10-dien-1-ol (8E,10E)dodeca-8,10-dien-1-ol (E8E10-12OH) is synthesized beginning with nonane-1,9-diol as outlined Scheme 26. The diol is dehydrated to form non-8-en-1-ol, which is reacted with penta-1,3-diene in the presence of a metathesis catalyst (e.g., catalyst 7, 8, 9, or 10) to form the desired E8E10-12OH product. Alternatively, the non-8-en-1-ol is acylated prior to metathesis with the penta-1,3-diene; the resulting (8E,10E)dodeca-8,10-dien-1-yl acetate is then hydrolyzed with potassium carbonate to afford the desired E8E10-12OH product.

Scheme 26

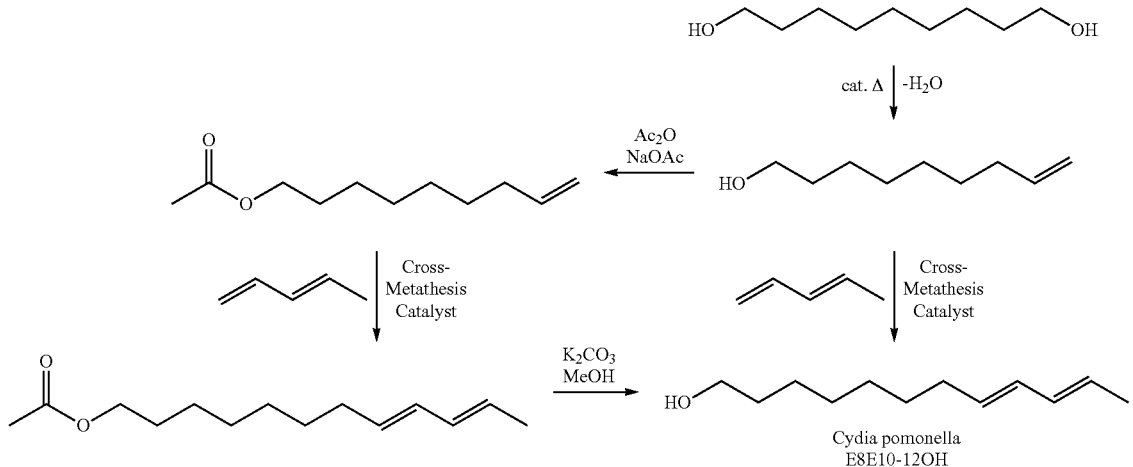

Example 15. Tosylation of Leaf Alcohol

A 6 L four-necked flask equipped with an overhead stirrer, addition funnel, gas outlet and cooling bath was charged with 200 g (1.997 mol, 1 eq.) (Z)-hex-3-ene-1-ol (leaf alcohol), 2 L (2.66 kg) dichloromethane and 399.72 g (2.096 mol, 1.05 eq.) p-toluenesulfonyl chloride. The stirred reaction mixture was cooled to 0° C. and 896.2 g (15.974 mol, 8 eq.) KOH in 1344 mL (1344 g) water was added dropwise. The reaction mixture was allowed warm to RT, then it was stirred vigorously overnight. Additional water was added slowly to the reaction mixture which was then stirred for 30 min. The resultant biphasic mixture was separated to yield a clear aqueous phase and an emulsion. As the emulsion did not get clear upon standing an additional 1500 ml (1500 g) water and 500 mL (665 g) dichloromethane were added. Phase separation was not observed. The pH of the medium was then adjusted to 1-2 using 200 mL (206 g) 2 M aq. HCl which yield two clear phases which were then separated. The aqueous phase was extracted with 2×400 mL (1064 g) dichloromethane. The combined organic phase was dried over $Na_2SO_4$, filtered and evaporated under reduced pressure to yield 433.51 g (85% yield) of (Z)-hex-3-en-1-ol tosylate (CAS No. 34019-85-7). The purity of the product, as determined by gas chromatography (GC), was 98.54 area %. GC data were collected with Varian 3900 instrument equipped with a FID detector using a RTX-1301 column 30 m in length, and internal diameter 0.32 mm and a film thickness of 0.5 µm. The injector temperature was set to 200° C. and the detector temperature to 250° C. The oven was first maintained at 60° C. for two minutes, raised to 120° C. at a rate of 10° C./min, further raised to 250° C. at a rate of 20° C./min and finally held at 250° C. for eight minutes. The product was found to elute with a retention time of approximately 5.1 minutes under these conditions.

Example 16. Synthesis of (Z)-hexa-1,4-diene

An argon-flushed 6 L four-necked flask equipped with an overhead stirrer, addition funnel, gas inlet and cooling bath flask was charged with 433.4 g (1.704 mol, 1 eq.) (Z)-hex-3-en-1-ol tosylate prepared above and 2.6 L (2.25 kg) of toluene. The solution was cooled to 0-5° C., then 245.6 g (2.556 mol, 1.5 eq.) sodium tert-butoxide was added portion wise over the course of 20 minutes to maintain the reaction temperature between 0-5° C. After stirring for an additional 20 minutes between 0-5° C., the reaction mixture was warmed to 40° C. and stirred until the reaction reached completion (~20 h) as determined by GC analysis using the instrument and parameters described above. The suspension was cooled to 15° C., then 2.5 L (2.5 kg) water was added slowly. The phases were separated and the organic phase was washed with 6×300 mL (1.8 kg) water to aid in the removal of the tert-butanol co-product. The organic phase was dried over $MgSO_4$, filtered and then separated by fractional distillation using a Raschig-packed column and a reflux controller. A forecut containing mostly water was removed first and then three fractions of mass 16.4, 14.4 and 13.5 g each were collected containing (Z)-hexa-1,4-diene with a small amount of tert-butanol contaminant. A 51.7 g fraction was collected, which contained low levels of tert-butanol and toluene, as determined via GC analysis. A 65.0 g fraction was collected that contained a higher amount of toluene as well as a final fraction which contained no (Z)-hexa-1,4-diene. The middle four cuts that were most rich in (Z)-hexa-1,4-diene were combined to yield 96 g (66%) of (Z)-hexa-1,4-diene (CAS No. 14596-92-0). The product was found to elute with a retention time of approximately 3.1 minutes using the GC conditions defined above. The purity of the product, as determined by GC, was 97.88 area % and the Z-isomer content 99.60 area %. GC analysis also showed the presence of 0.25 area % tert-butanol and 0.89 area % toluene. $^1H$ and $^{13}C$ NMR were collected in $CDCl_3$ solution using a Bruker Avance 500 spectrometer and were found to be consistent with the expected structure.

V. EXEMPLARY EMBODIMENTS

Exemplary embodiments provided in accordance with the presently disclosed subject matter include, but are not limited to, the claims and the following embodiments:
1. A method for synthesizing a fatty olefin derivative, the method comprising:
a) contacting an olefin according to Formula I

with a metathesis reaction partner according to Formula II

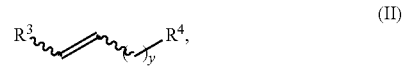

in the presence of a metathesis catalyst under conditions sufficient to form a metathesis product according to Formula III:

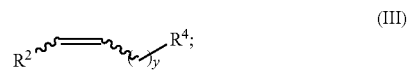

and
b) converting the metathesis product to the fatty olefin derivative;
wherein:
$R^1$ is selected from the group consisting of hydrogen and $C_{1-18}$ alkyl;
$R^2$ is $C_{1-18}$ alkyl;
$R^3$ is selected from the group consisting of $C_{1-18}$ alkyl and hydrogen;
$R^4$ is selected from the group consisting of —$CH_2OR^{4a}$ and —$C(O)OR^{4b}$;
$R^{4a}$ is selected from the group consisting of —$C(O)R^{4c}$, an alcohol protecting group, and hydrogen;
$R^{4b}$ is selected from the group consisting of hydrogen and $C_{1-8}$ alkyl;
$R^{4c}$ is $C_{1-5}$ alkyl; and
subscript y is 9 or 6.
2. The method of embodiment 1, wherein $R^4$ is —$CH_2OR^{4a}$ in the metathesis reaction partner of Formula II.
3. The method of embodiment 2, wherein $R^{4a}$ is —$C(O)R^{4c}$.
4. The method of embodiment 3, wherein the fatty olefin derivative is obtained without converting step b as metathesis product according to the formula:

5. The method of embodiment 2, wherein $R^{4a}$ is an alcohol protecting group and converting the metathesis product to the fatty olefin derivative comprises deprotecting the metathesis product to form an alkenol according to Formula IV:

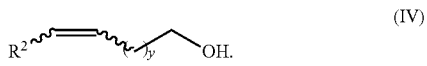

(IV)

6. The method of embodiment 5, wherein converting the metathesis product to the fatty olefin derivative further comprises contacting the alkenol with an acylating agent under conditions sufficient to form an alkenol ester according to Formula V:

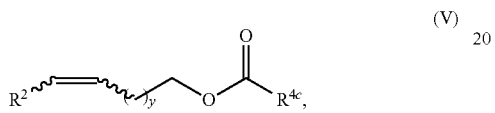

(V)

wherein $R^{4c}$ is selected from the group consisting of hydrogen, $C_{1-5}$ alkyl, and $C_{1-5}$ haloalkyl, and
wherein the alkenol ester is the fatty olefin derivative.
7. The method of any one of embodiments 1-6, wherein subscript y is 9.
8. The method of embodiment 7, wherein the metathesis reaction partner according to Formula II is hexadec-11-en-1-ol or an ester thereof.
9. The method of embodiment 7, wherein the metathesis reaction partner according to Formula II is a Δ11-unsaturated fatty acid alkyl ester, a protected Δ11-unsaturated fatty alcohol, or a Δ11-unsaturated fatty alcohol.
10. The method of embodiment 9, wherein the Δ11-unsaturated fatty acid alkyl ester, protected Δ11-unsaturated fatty alcohol, or Δ11-unsaturated fatty alcohol is derived from a natural oil.
11. The method of any one of embodiments 7-10, wherein the olefin according to Formula I is selected from the group consisting of but-1-ene, hex-1-ene, hept-1-ene, oct-1-ene, and dec-1-ene.
12. The method of embodiment 11, wherein the fatty olefin derivative is selected from the group consisting of (Z)-11-tetradecen-1-ol, (Z)-11-hexadecen-1-ol, (Z)-11-octadecen-1-ol, and (Z)-11-eicosen-1-ol.
13. The method of embodiment 11, wherein the fatty olefin derivative is selected from the group consisting of (Z)-11-tridecenyl acetate, (Z)-11-tetradecenyl acetate, (Z)-11-hexadecenyl acetate, (Z)-11-hexadecenyl formate, (Z)-11-hexadecenyl trifluoroacetate, (Z)-11-heptadecenyl acetate, (Z)-11-octadecenyl acetate, and (Z)-11-eicosenyl acetate.
14. The method of embodiment 11, wherein the fatty olefin derivative is selected from the group consisting of (Z)-11-tetradecenal, (Z)-11-hexadecenal, (Z)-11-octadecenal, and (Z)-11-eicosenal.
15. The method of any one of embodiments 1-6, wherein subscript y is 6.
16. The method of embodiment 15, wherein the olefin is selected from the group consisting of but-1-ene, pent-1-ene, hex-1-ene, hept-1-ene, oct-1-ene, and 7-methyl-1-nonene.

17. The method of embodiment 16, wherein the fatty olefin derivative is selected from the group consisting of (E)-8-dodecen-1-ol, (Z)-8-dodecen-1-ol, (Z)-8-tetradecen-1-ol, (E)-14-methyl-8-hexadecen-1-ol, and (Z)-14-methyl-8-hexadecen-1-ol.
18. The method of embodiment 16, wherein the fatty olefin derivative is selected from the group consisting of (E)-8-undecenyl acetate, (Z)-8-undecenyl acetate, (E)-8-dodecenyl acetate, (Z)-8-dodecenyl acetate, (E)-8-tridecenyl acetate, (Z)-8-tridecenyl acetate, (E)-8-tetradecenyl acetate, (E)-8-tetradecenyl formate, (Z)-8-tetradecenyl acetate, (Z)-8-tetradecenyl formate, and (Z)-8-pentadecenyl acetate.
19. A method for synthesizing a fatty polyene derivative, the method comprising:
a) contacting an olefin according to Formula XI

(XI)

with a metathesis reaction partner according to Formula XII

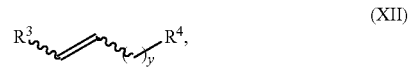

(XII)

in the presence of a metathesis catalyst under conditions sufficient to form a metathesis product according to Formula XIII:

(XIII)

and
b) optionally converting the metathesis product to the fatty olefin derivative; wherein:
$R^1$ and $R^3$ are independently selected from the group consisting of hydrogen, $C_{1-18}$ alkyl, and $C_{2-18}$ alkenyl;
$R^2$ is selected from the group consisting of $C_{1-18}$ alkyl and $C_{2-18}$ alkenyl;
$R^4$ is selected from the group consisting of $—CH_2X$, $—CH_2OR^{4a}$, $—C(O)OR^{4b}$, and $—COC(O)R^{4c}$;
X is halogen;
$R^{4a}$ is selected from the group consisting of an alcohol protecting group and hydrogen;
$R^{4b}$ is selected from the group consisting of hydrogen and $C_{1-8}$ alkyl;
$R^{4c}$ is selected from the group consisting of hydrogen, $C_{1-5}$ alkyl, and $C_{1-5}$ haloalkyl;
subscript x is 0 or 1; and
subscript y is an integer ranging from 0 to 15.
20. The method of embodiment 19, further comprising converting an alcohol according to Formula XVII:

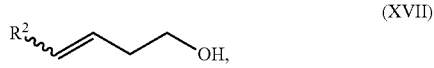

(XVII)

to a compound according to Formula XVIII:

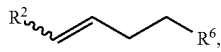
(XVIII)

wherein $R^6$ is a leaving group; and eliminating the leaving group to form an olefin according to Formula XIa:

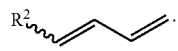
(XIa)

21. The method of embodiment 20, wherein the olefin according to Formula XIa is (Z)-hexa-1,3-diene.
22. The method of any one of embodiments 19-21, wherein the metathesis reaction partner is an ester according to Formula XIIc

(XIIc)

and wherein the fatty olefin derivative is obtained as metathesis product according to Formula XV:

(XV)

without converting step (b).

23. The method of any one of embodiments 19-21, wherein the metathesis reaction is partner is a compound according to Formula XIId

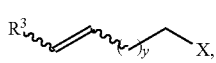
(XIId)

the metathesis product is a halide according to Formula XIIId

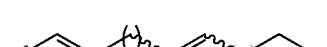
(XIIId)

and converting the metathesis product to the fatty olefin derivative comprises contacting the halide according to Formula XIIId with a $C_{1-8}$ alkanoate under conditions sufficient to form an alkenol ester according to Formula XV:

(XV)

wherein the alkenol ester is the fatty olefin derivative.

24. The method of any one of embodiments 19-21, wherein $R^4$ is —$CH_2OR^{4a}$ in the metathesis reaction partner of Formula XII.
25. The method of embodiment 24, wherein converting the metathesis product to the fatty olefin derivative comprises deprotecting the metathesis product to form an alkenol according to Formula XIV:

(XIV)

26. The method of embodiment 25, wherein converting the metathesis product to the fatty olefin derivative further comprises contacting the alkenol with an acylating agent under conditions sufficient to form an alkenol ester according to Formula XV:

(XV)

wherein $R^{4c}$ is selected from the group consisting of hydrogen, $C_{1-5}$ alkyl, and $C_{1-5}$ haloalkyl, and wherein the alkenol ester is the fatty olefin derivative.

27. The method of embodiment 19, wherein $R^4$ is —C(O)OR^{4b}$ in the metathesis reaction partner according to Formula XII.
28. The method of embodiment 27, wherein converting the metathesis product to the fatty olefin derivative comprises contacting the metathesis product with a reducing agent under conditions sufficient to form an alkenol according to Formula XIV:

(XIV)

29. The method of embodiment 28, wherein converting the metathesis product to the fatty olefin derivative further comprises contacting the alkenol with an acylating agent under conditions sufficient to form an alkenol ester according to Formula XV:

(XV)

wherein $R^{4c}$ is selected from the group consisting of hydrogen, $C_{1-5}$ alkyl, and $C_{1-5}$ haloalkyl, and wherein the alkenol ester is the fatty olefin derivative.

30. The method of any one of embodiments 19-29, wherein the olefin according to Formula XI is selected from the group consisting of (E)-pent-1,3-diene, (Z)-pent-1,3-diene, (E)-hepta-1,3-diene, (Z)-hepta-1,3-diene, (E)-octa-1,3-diene, and (Z)-octa-1,3-diene.
31. The method of any one of embodiments 19-30, wherein the fatty polyene derivative is selected from the group consisting of (E,E)-8,10-dodecadien-1-ol, (E,Z)-8,10-dodecadien-1-ol, (Z,E)-8,10-dodecadien-1-ol, (Z,Z)-8,10-dodecadien-1-ol, and (E,E)-8,10-tetradecadien-1-ol.
32. The method of any one of embodiments 19-30, wherein the fatty polyene derivative is selected from the group consisting of (E,E)-8,10-dodecadienyl acetate, (E,Z)-8,10-dodecadienyl acetate, (Z,E)-8,10-dodecadienyl acetate, (Z,Z)-8,10-dodecadienyl acetate, (E,E)-8,10-tetradecadienyl acetate, (E,E)-8,10-pentadecadienyl acetate, (E,Z)-8,10-pentadecadienyl acetate, (Z,E)-8,10-pentadecadienyl acetate, and (Z,Z)-8,10-pentadecadienyl acetate.
33. The method of any one of embodiments 19-30, wherein the fatty polyene derivative is selected from the group consisting of (E,E)-8,10-dodecadienal, (E,Z)-8,10-dodecadienal, (Z,E)-8,10-dodecadienal, (E,E)-8,10-tetradecadienal, and (E,Z)-8,10-tetradecadienal.
34. A method for synthesizing a fatty olefin derivative, the method comprising:
a) contacting an olefin according to Formula XXI

(XXI)

with a polyene reaction partner according to Formula XXII

(XXII)

in the presence of a metathesis catalyst under conditions sufficient to form a metathesis product according to Formula XXIII

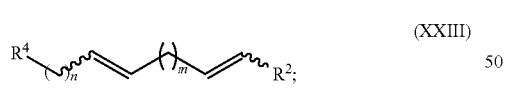
(XXIII)

and
b) optionally converting the metathesis product to the fatty olefin derivative;
wherein:
$R^1$ and $R^3$ are independently selected from the group consisting of hydrogen, $C_{1-18}$ alkyl, and $C_{2-18}$ alkenyl;
$R^2$ is selected from the group consisting of $C_{1-18}$ alkyl and $C_{2-18}$ alkenyl;
$R^4$ is selected from the group consisting of —COC(O)$R^{4a}$, —CH$_2$OR$^{4b}$, —C(O)OR$^{4C}$, and —CH$_2$X;
$R^{4a}$ is selected from the group consisting of hydrogen, $C_{1-5}$ alkyl, and $C_{1-5}$ haloalkyl;
$R^{4b}$ is an alcohol protecting group;
$R^{4c}$ is selected from the group consisting of hydrogen and $C_{1-8}$ alkyl;

X is halogen;
subscript m is 0 or 1; and
subscript n is an integer ranging from 0 to 15.
35. The method of embodiment 34, wherein the polyene reaction partner is an ester according to Formula XXIIa

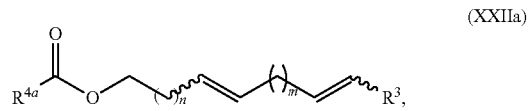
(XXIIa)

and
wherein the fatty olefin derivative is obtained as a metathesis product according to Formula XXIIIa

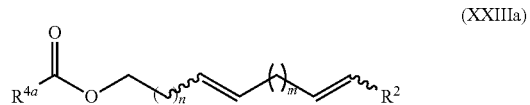
(XXIIIa)

without converting step (b).
36. The method of embodiment 35, wherein the ester according to Formula XXIIa is obtained by a process comprising:
converting an internal olefin according to Formula XXIIa-i

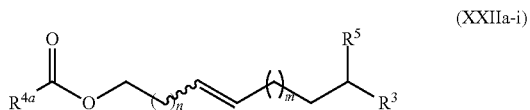
(XXIIa-i)

to the ester according to Formula XXIIa,
wherein $R^5$ is a leaving group.
37. The method of embodiment 36, wherein the leaving group is selected from the group consisting of a sulfonate and a halide.
38. The method of embodiment 36, wherein the internal olefin according to Formula XXIIa-i is obtained by a process comprising
contacting a compound according to Formula XXIIa-iii

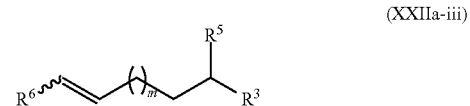
(XXIIa-iii)

with a reaction partner according to formula XXIIa-ii

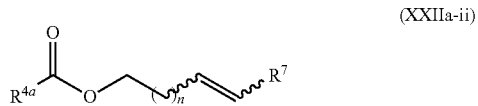
(XXIIa-ii)

in the presence of an intermediate catalyst under conditions sufficient to form the internal olefin according to Formula XXIIa-i;
wherein $R^6$ and $R^7$ are independently selected from the group consisting of hydrogen, $C_{1-18}$ alkyl, and $C_{2-18}$ alkenyl.

39. The method of any one of embodiments 36-38, wherein $R^5$ is mesylate or tosylate.
40. The method of any one of embodiments 34-39, wherein the olefin is selected from the group consisting of but-1-ene, pent-1-ene, hex-1-ene, hept-1-ene, oct-1-ene, and 7-methyl-1-nonene.
41. The method of any one of embodiments 34-40, wherein the fatty olefin derivative is selected from the group consisting of (7E,9Z) dodeca-7,9-dien-1-yl acetate and (8E,10E)-dodeca-8,10-dien-1-ol.
42. A method for synthesizing a fatty olefin derivative, the method comprising:
a) contacting an olefin according to Formula XXXI

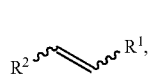

(XXXI)

with a metathesis reaction partner according to Formula XXXII

(XXXII)

in the presence of a metathesis catalyst under conditions sufficient to form a metathesis product according to Formula XXXIII:

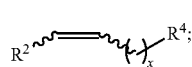

(XXXIII)

and
b) optionally converting the metathesis product to the fatty olefin derivative; wherein:
$R^1$ and $R^3$ are independently selected from the group consisting of hydrogen and $C_{1-18}$ alkyl;
$R^2$ is selected from the group consisting of $C_{1-18}$ alkyl and $C_{2-18}$ alkenyl;
$R^4$ is selected from the group consisting of $—CH_2OR^{4a}$, $—C(O)OR^{4b}$, $—CH_2OC(O)R^{4c}$, and halogen;
$R^{4a}$ is selected from the group consisting of hydrogen and an alcohol protecting group;
$R^{4b}$ is selected from the group consisting of hydrogen and $C_{1-8}$ alkyl;
$R^{4c}$ is selected from the group consisting of hydrogen, $C_{1-8}$ alkyl, and $C_{1-8}$ haloalkyl; and
subscript x is an integer ranging from 3 to 15.
43. The method of embodiment 42, further comprising:
i) dehydrating a diol according to Formula XXXVII:

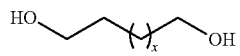

(XXXVII)

to form the an alkenol according to Formula XXXIId:

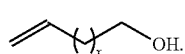

(XXXIId)

44. The method of embodiment 43, further comprising protecting the alkenol to form the metathesis reaction partner according to Formula XXXIIa

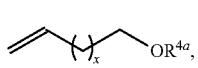

(XXXIIa)

wherein $R^{4a}$ is an alcohol protecting group.
45. The method of embodiment 43, further comprising acylating the alkenol to form the metathesis reaction partner according to Formula XXXIIc:

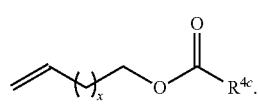

(XXXIIc)

46. The method of embodiment 42, further comprising:
i) converting a diol according to Formula XXXVII:

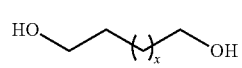

(XXXVII)

to an alcohol according to Formula XXXVIII:

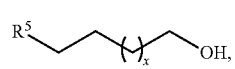

(XXXVIII)

wherein $R^5$ is a leaving group;
ii) acylating the alcohol to form an ester according to Formula XXXIXb

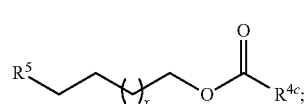

(XXXIXc)

and
iii) eliminating leaving group $R^5$ to form the metathesis reaction partner according to Formula IIc:

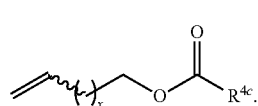

(XXXIIc)

47. The method of embodiment 42 or embodiment 44, wherein $R^{4a}$ in the metathesis reaction product is an alcohol protecting group, and wherein converting the metathesis product to the fatty olefin derivative comprises deprotecting the metathesis product to form an alkenol according to Formula XXXIV:

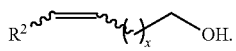
(XXXIV)

48. The method of embodiment 47, wherein converting the metathesis product to the fatty olefin derivative comprises contacting the alkenol according to Formula XXXIV with an acylating agent under conditions sufficient to form an alkenol ester according to Formula XXXV:

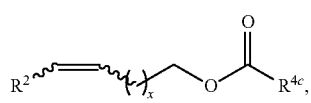
(XXXV)

wherein $R^{4c}$ is selected from the group consisting of hydrogen, $C_{1-5}$ alkyl, and $C_{1-5}$ haloalkyl, and
wherein the alkenol ester is the fatty olefin derivative.

49. The method of embodiment 42, wherein $R^4$ is halogen and converting the metathesis product to the fatty olefin derivative comprises contacting the metathesis product with a carboxylate salt under conditions sufficient to form an alkenol ester according to Formula XXXV:

(XXXV)

wherein $R^{4c}$ is selected from the group consisting of hydrogen, $C_{1-5}$ alkyl, and $C_{1-5}$ haloalkyl, and
wherein the alkenol ester is the fatty olefin derivative.

50. The method of embodiment 47, wherein converting the metathesis product to the fatty olefin derivative comprises contacting the alkenol according to Formula XXXIV with an oxidizing agent under conditions sufficient to form an alkenal according to Formula XXXVI:

(XXXVI)

wherein the alkenal is the fatty olefin derivative.

51. The method of any one of embodiments 42-50, wherein the olefin is selected from the group consisting of but-1-ene, pent-1-ene, hex-1-ene, hept-1-ene, oct-1-ene, 7-methyl-1-nonene, and trans-1,3-pentadiene.

52. The method of embodiment 51, wherein the fatty olefin derivative is selected from the group consisting of (E)-dec-5-en-1-ol and (8E,10E)-dodeca-8,10-dien-1-ol.

53. The method of embodiment 51, wherein the fatty olefin derivative is selected from the group consisting of (E)-dec-5-en-1-yl acetate, (Z)-dodec-7-en-1-yl acetate; (Z)-dodec-8-en-1-yl acetate; (Z)-dodec-9-en-1-yl acetate; (Z)-tetradec-9-en-1-yl acetate; (Z)-tetradec-11-en-1-yl acetate; (Z)-hexadec-11-en-1-yl acetate; and (7E,9Z) dodeca-7,9-dien-1-yl acetate.

54. The method of embodiment 51, wherein the fatty olefin derivative is selected from the group consisting of (Z)-hexadec-9-enal, (Z)-hexadec-11-enal, and (Z)-octadec-13-enal.

55. The method of any one of embodiments 1-54, wherein the metathesis product comprises a Z olefin.

56. The method of embodiment 55, wherein at least about 80% of the olefin is a Z olefin.

57. The method of embodiment 55, wherein at least about 90% of the olefin is a Z olefin.

58. The method of any one of embodiments 55-57, wherein the metathesis catalyst is a Z-selective molybdenum catalyst, a Z-selective tungsten catalyst, or a Z-selective ruthenium catalyst.

59. The method of embodiment 58, wherein the metathesis catalyst has a structure according to Formula XLII:

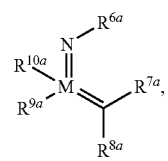
(XLII)

wherein:
M is Mo or W;
$R^{6a}$ is selected from the group consisting of aryl, heteroaryl, alkyl, heteroalkyl, cycloalkyl, and heterocycloalkyl, each of which is optionally substituted;
$R^{7a}$ and $R^{8a}$ are independently selected from the group consisting of hydrogen, optionally substituted alkyl, optionally substituted alkenyl, optionally substituted heteroalkyl, optionally substituted heteroalkenyl, optionally substituted aryl, and optionally substituted heteroaryl;
$R^{10a}$ is selected from the group consisting of alkyl, alkoxy, heteroalkyl, aryl, aryloxy, heteroaryl, silylalkyl, and silyloxy, each of which is optionally substituted; and
$R^{9a}$ is $R^{11a}$—X—, wherein
X is O or S and $R^{11a}$ is optionally substituted aryl; or
X is O and $R^{11a}$ is $SiR^{12a}R^{13a}R^{14a}$ or $CR^{15a}R^{16a}R^{17a}$, wherein $R^{12a}$, $R^{13a}$, $R^{14a}$, $R^{15a}$, $R^{16a}$ and $R^{17a}$ are independently selected from the group consisting of optionally substituted alkyl and optionally substituted phenyl; or
$R^{9a}$ and $R^{10a}$ are linked together and are bonded to M via oxygen.

60. The method of embodiment 59, wherein:
$R^{10a}$ is selected from the group consisting of alkyl, alkoxy, heteroalkyl, aryl, aryloxy, and heteroaryl, each of which is optionally substituted; and
X is O or S and $R^{11a}$ is optionally substituted aryl; or
X is O and $R^{11a}$ is $CR^{15a}R^{16a}R^{17a}$ 61. The method of embodiment 59, wherein
$R^{6a}$ is selected from the group consisting of 2,6-dimethylphenyl; 2,6-diisopropylphenyl; 2,6-dichlorophenyl; and adamant-1-yl;
$R^{7a}$ is selected from the group consisting of —C(CH$_3$)$_2$C$_6$H$_5$ and —C(CH$_3$)$_3$;
$R^{8a}$ is H;
$R^{10a}$ is selected from the group consisting of pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenyl-phenoxy; and t-butyloxy; and $R^{9a}$ is $R^{11a}$—X—, wherein X=O and $R^{11a}$ is phenyl which bears two substituents in the ortho positions with respect to O, or which bears at least three substituents, from which two substituents are in the ortho positions with respect to O and one substituent is in the para position with respect to 0; or $R^{11a}$ is selected from the group consisting of optionally substituted 8-(naphthalene-1-yl)-naphthalene-1-yl; optionally substituted 8-phenylnaphthalene-1-yl; optionally substituted quinoline-8-yl; triphenylsilyl; triisopropylsilyl; triphenylmethyl; tri(4-methylphenyl)methyl; 9-phenyl-fluorene-9-yl; 2-phenyl-1,1,1,3,3,3-hexafluoro-prop-2-yl; 2-methyl-1,1,1,3,3,3-hexafluoro-prop-2-yl; and t-butyl.

62. The method of embodiment 61, wherein:

$R^{10a}$ is selected from the group consisting of pyrrol-1-yl; 2,5-dimethyl-pyrrol-1-yl; and $R^{11a}$ is phenyl which bears two substituents in the ortho positions with respect to O, or which bears at least three substituents, from which two substituents are in the ortho positions with respect to 0 and one substituent is in the para position with respect to O; or $R^{11a}$ is selected from the group consisting of optionally substituted 8-(naphthalene-1-yl)-naphthalene-1-yl and optionally substituted 8-phenylnaphthalene-1-yl.

63. The method of embodiment 59, wherein the metathesis catalyst has a structure according to Formula XLIIa:

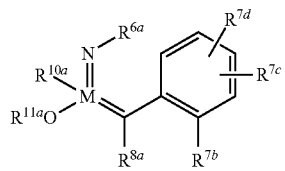

(XLIIa)

$R^{6a}$ is aryl, heteroaryl, alkyl, or cycloalkyl, each of which is optionally substituted; $R^{10a}$ is pyrrolyl, imidazolyl, indolyl, pyrazolyl, azaindolyl, or indazolyl, each of which is optionally substituted;

$R^{11a}$ is optionally substituted aryl;

$R^{8a}$ is a hydrogen atom, alkyl, or alkoxy;

$R^{7b}$ is a hydrogen atom, —O—($C_{1-6}$ alkyl), —$CH_2$—O—($C_{1-6}$ alkyl), heteroalkoxy, or —N($C_{1-6}$ alkyl)$_2$;

$R^{7c}$ and $R^{7d}$ are independently a hydrogen atom, $C_{1-6}$ alkyl, $C_{1-6}$ alkoxy, a halogen atom, —$NO_2$, an amide, or a sulfonamide.

64. The method of embodiment 63, wherein:

$R^{10a}$ is pyrrolyl, imidazolyl, pyrazolyl, azaindolyl, or indazolyl, each of which is optionally substituted; and $R^{8a}$ is a hydrogen atom.

65. The method of embodiment 63, wherein $R^{6a}$ is phenyl, 2,6-dichlorophenyl, 2,6-dimethylphenyl, 2,6-diisopropylphenyl, 2-trifluoromethylphenyl, pentafluorophenyl, tert-butyl, or 1-adamantyl.

66. The method of embodiment 63 or embodiment 65, wherein $R^{6a}$ is

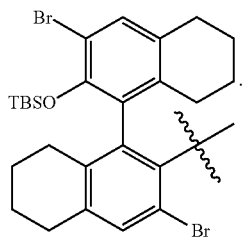

67. The method of embodiment 63, wherein $R^{7b}$ is methoxy, $R^{7c}$ is hydrogen, and $R^{7d}$ is hydrogen.

68. The method of embodiment 58, wherein the metathesis catalyst is selected from the group consisting of

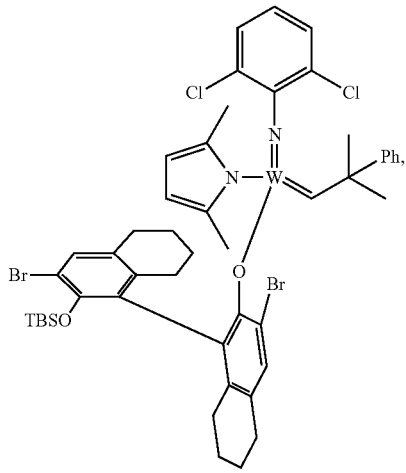

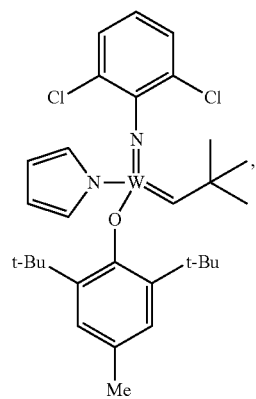

-continued

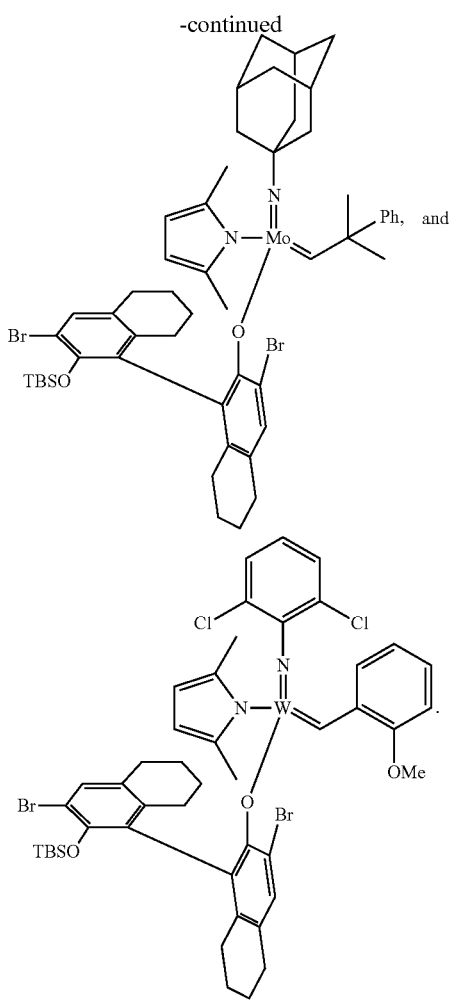

69. The method of embodiment 58, wherein the metathesis catalyst has a structure according to Formula XLIV:

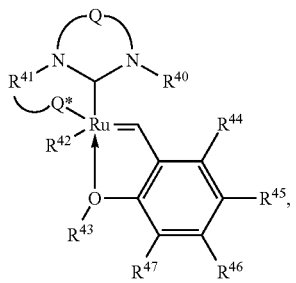

(XLIV)

wherein:

Q is selected from hydrocarbylene, substituted hydrocarbylene, heteroatom-containing hydrocarbylene, or substituted heteroatom-containing hydrocarbylene, wherein two or more substituents on adjacent atoms within Q may also be linked to form an additional cyclic structure;

Q* forms a carbon-ruthenium bond with the carbon from the $R^{41}$ group;

$R^{40}$ and $R^{41}$ are independently selected from hydrocarbyl, substituted hydrocarbyl, heteroatom-containing hydrocarbyl, or substituted heteroatom-containing hydrocarbyl;

$R^{42}$ is selected from halide, nitrate, alkyl, aryl, alkoxy, alkylcarboxylate, aryloxy, alkoxycarbonyl, aryloxycarbonyl, arylcarboxylate, acyl, acyloxy, alkylsulfonato, arylsulfonato, alkylsulfanyl, arylsulfanyl, alkylsulfinyl, and arylsulfinyl;

$R^{43}$ is selected from hydrogen, alkyl, and aryl, wherein alkyl and aryl are optionally substituted with one or more functional groups selected from the group consisting of alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and $R^{44}$, $R^{45}$, $R^{46}$, and $R^{47}$ are independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^{44}$, $R^{45}$, $R^{46}$, and $R^{47}$ is optionally linked to form one or more cyclic groups.

70. The method of any one of embodiments 1-69, wherein the metathesis catalyst is present in an amount less than 0.01 mol % with respect to the olefin or to the metathesis reaction partner.

71. The method of any one of embodiments 1-54, wherein the metathesis product comprises an E olefin.

72. The method of embodiment 71, wherein greater than about 85% of the olefin is an E olefin.

73. The method of embodiment 71, wherein at least about 90% of the olefin is an E olefin.

74. The method of embodiment 71, wherein the metathesis catalyst is an E-selective ruthenium catalyst.

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

What is claimed is:

1. A method for synthesizing a compound according to Formula III, the method comprising:
  a) contacting an alkyl ester of 9-decenoate with a ruthenium isomerization catalyst or an iridium isomerization catalyst to form an alkyl ester of 8-decenoate; and
  b) contacting an olefin according to Formula I

(I)

with the alkyl ester of dec-8-enoate
in the presence of a metathesis catalyst to form the compound according to Formula III:

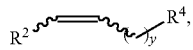

(III)

wherein the metathesis catalyst is a molybdenum catalyst, a tungsten catalyst, or a ruthenium catalyst; and
wherein:
$R^1$ is selected from the group consisting of hydrogen and $C_{1-18}$ alkyl;
$R^2$ is $C_{1-18}$ alkyl;
$R^4$ is —C(O)O$R^{4b}$;
$R^{4b}$ is $C_{1-8}$ alkyl; and
subscript y is 6.

2. The method of claim 1, further comprising reducing the compound according to Formula III to form an alkenol according to Formula IV:

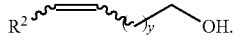

(IV)

3. The method of claim 2, further comprising contacting the alkenol according to Formula IV with an acylating agent to form an alkenol ester according to Formula V:

(V)

wherein $R^{4c}$ is selected from the group consisting of hydrogen, $C_{1-5}$ alkyl, and $C_{1-5}$ haloalkyl.

4. The method of claim 1, wherein the compound of Formula III is a Z olefin.

5. The method of claim 4, wherein the metathesis catalyst has a structure according to Formula XLII:

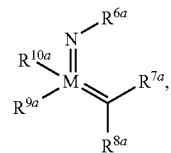

(XLII)

wherein:
M is Mo or W;
$R^{6a}$ is selected from the group consisting of aryl, heteroaryl, alkyl, heteroalkyl, cycloalkyl, and heterocycloalkyl, each of which is optionally substituted;
$R^{7a}$ and $R^{8a}$ are independently selected from the group consisting of hydrogen, optionally substituted alkyl, optionally substituted alkenyl, optionally substituted heteroalkyl, optionally substituted heteroalkenyl, optionally substituted aryl, and optionally substituted heteroaryl;
$R^{10a}$ is selected from the group consisting of alkyl, alkoxy, heteroalkyl, aryl, aryloxy, heteroaryl, silylalkyl, and silyloxy, each of which is optionally substituted; and $R^{9a}$ is $R^{11a}$—X—, wherein
X is O or S and $R^{11a}$ is optionally substituted aryl; or
X is O and $R^{11a}$ is $SiR^{12a}R^{13a}R^{14a}$ or $CR^{15a}R^{16a}R^{17a}$, wherein $R^{12a}$, $R^{13a}$, $R^{14a}$, $R^{15a}$, $R^{16a}$, and $R^{17a}$ are independently selected from the group consisting of optionally substituted alkyl and optionally substituted phenyl; or
$R^{9a}$ and $R^{10a}$ are linked together and are bonded to M via oxygen.

6. The method of claim 5, wherein the metathesis catalyst has a structure according to Formula XLIIa:

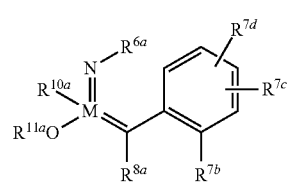

(XLIIa)

$R^{6a}$ is aryl, heteroaryl, alkyl, or cycloalkyl, each of which is optionally substituted;
$R^{10a}$ is pyrrolyl, imidazolyl, indolyl, pyrazolyl, azaindolyl, or indazolyl, each of which is optionally substituted;
$R^{11a}$ is optionally substituted aryl;
$R^{8a}$ is a hydrogen atom, alkyl, or alkoxy;
$R^{7b}$ is a hydrogen atom, —O—($C_{1-6}$ alkyl), —CH$_2$—O—($C_{1-6}$ alkyl), heteroalkoxy, or —N($C_{1-6}$ alkyl)$_2$;
$R^{7c}$ and $R^{7d}$ are independently a hydrogen atom, $C_{1-6}$ alkyl, $C_{1-6}$ alkoxy, a halogen atom, —NO$_2$, an amide, or a sulfonamide.

7. The method of claim 6, wherein $R^{6a}$ is

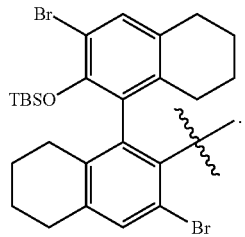 [SMILES: *c1c(Br)cc2c(c1-c1c3c(cc(Br)c1O[Si](C)(C)C(C)(C)C)CCCC3)CCCC2]

8. The method of claim 6, wherein the metathesis catalyst is selected from the group consisting of

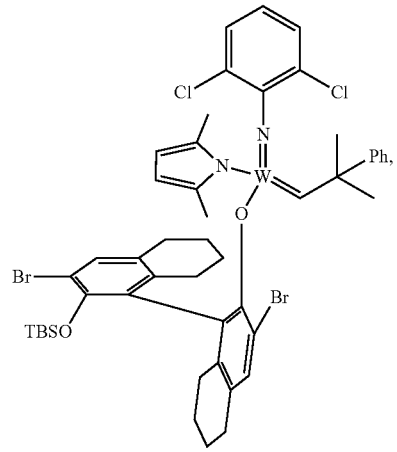

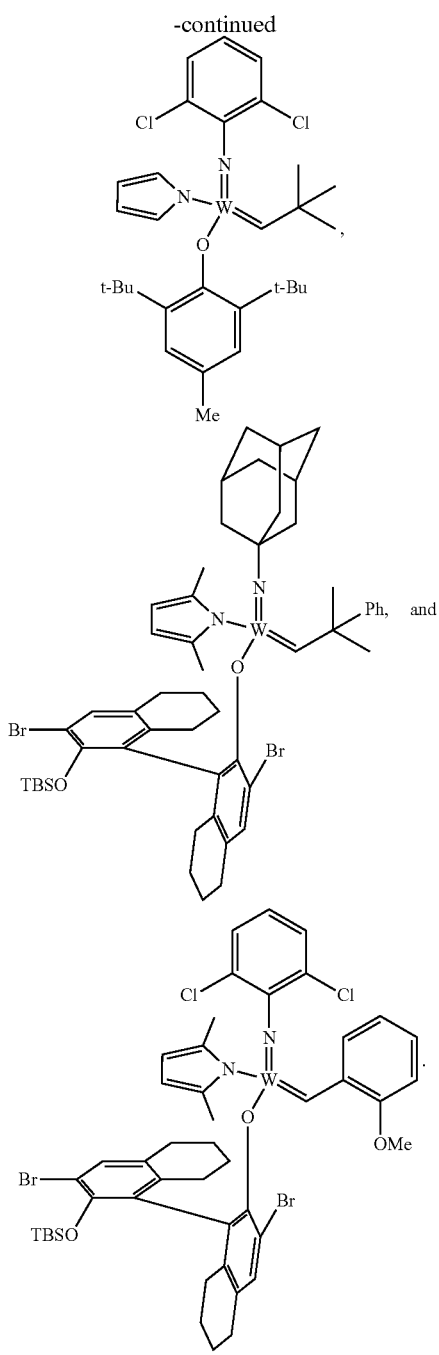

9. The method of claim 4, wherein the metathesis catalyst has a structure according to Formula XLIV:

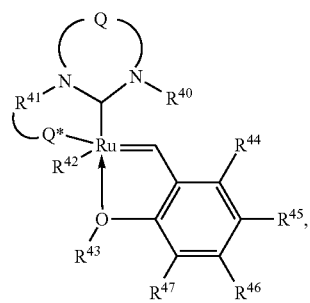

(XLIV)

wherein:
Q is selected from hydrocarbylene, substituted hydrocarbylene, heteroatom-containing hydrocarbylene, or substituted heteroatom-containing hydrocarbylene, wherein two or more substituents on adjacent atoms within Q may also be linked to form an additional cyclic structure;

Q* forms a carbon-ruthenium bond with the carbon from the $R^{41}$ group;

$R^{40}$ and $R^{41}$ are independently selected from hydrocarbyl, substituted hydrocarbyl, heteroatom-containing hydrocarbyl, or substituted heteroatom-containing hydrocarbyl;

$R^{42}$ is selected from halide, nitrate, alkyl, aryl, alkoxy, alkylcarboxylate, aryloxy, alkoxycarbonyl, aryloxycarbonyl, arylcarboxylate, acyl, acyloxy, alkylsulfonato, arylsulfonato, alkylsulfanyl, arylsulfanyl, alkylsulfinyl, and arylsulfinyl;

$R^{43}$ is selected from hydrogen, alkyl, and aryl, wherein alkyl and aryl are optionally substituted with one or more functional groups selected from the group consisting of alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and $R^{44}$, $R^{45}$, $R^{46}$ and $R^{47}$ are independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkyl sulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^{44}$, $R^{45}$, $R^{46}$, and $R^{47}$ is optionally linked to form one or more cyclic groups.

10. The method of claim 1, wherein the metathesis catalyst is present in an amount less than 0.01 mol % with respect to the olefin or to the alkyl ester of dec-8-enoate.

11. The method of claim 1, wherein the compound of Formula III is an E olefin.

12. The method of claim 11, wherein the metathesis catalyst is selected from the group consisting of:

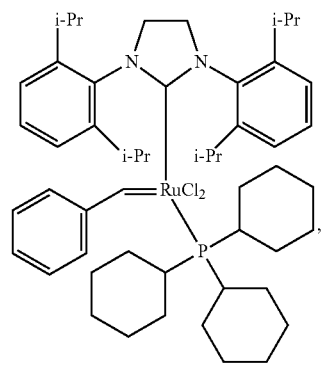

205
-continued

206
-continued

207
-continued
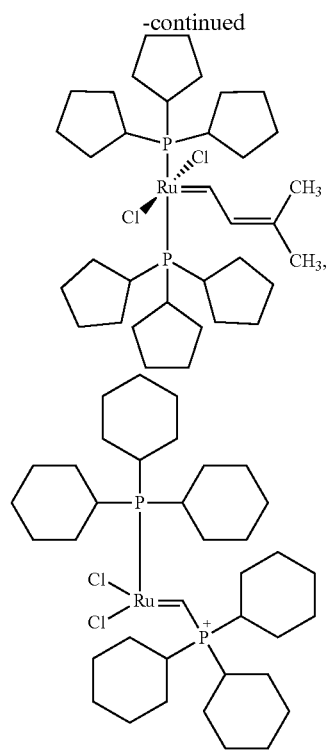
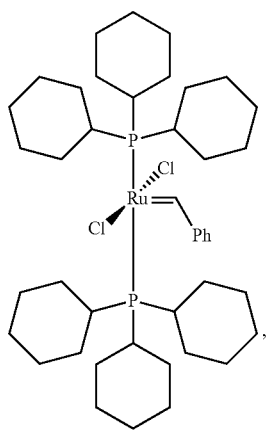
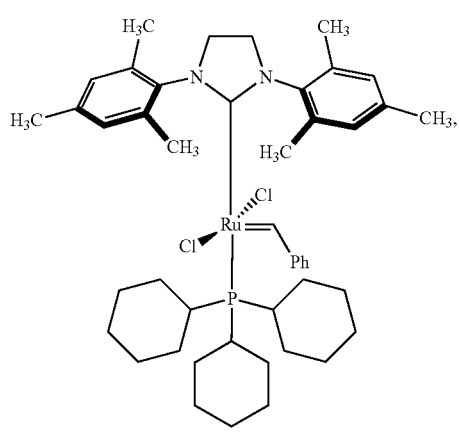
208
-continued
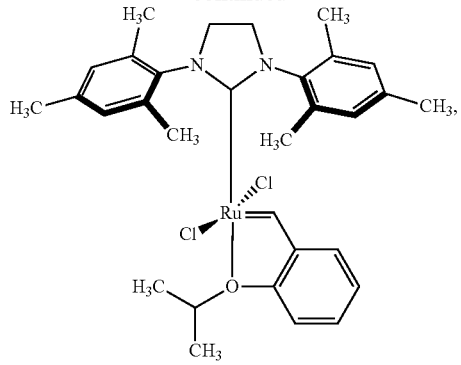
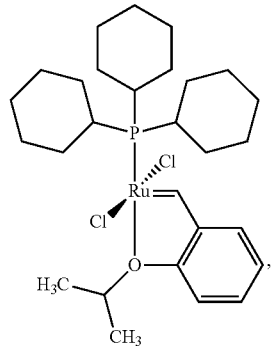
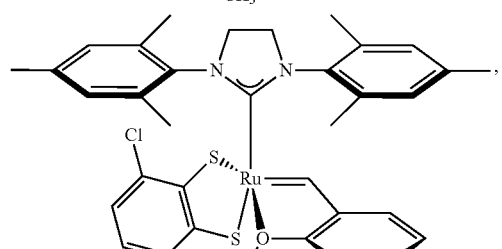
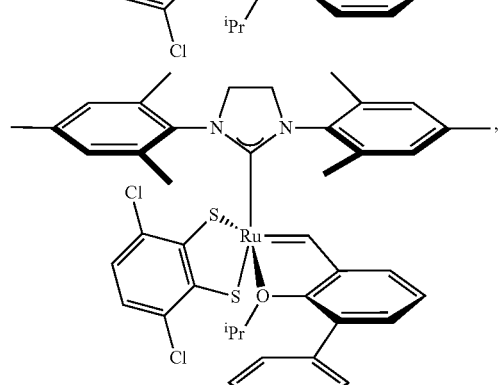
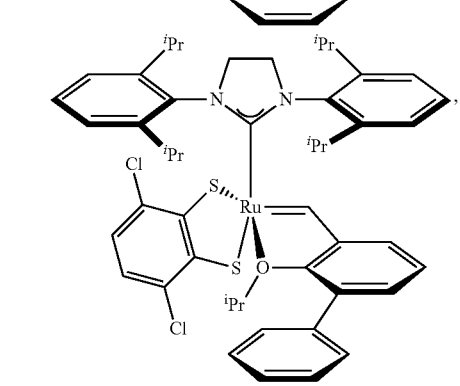

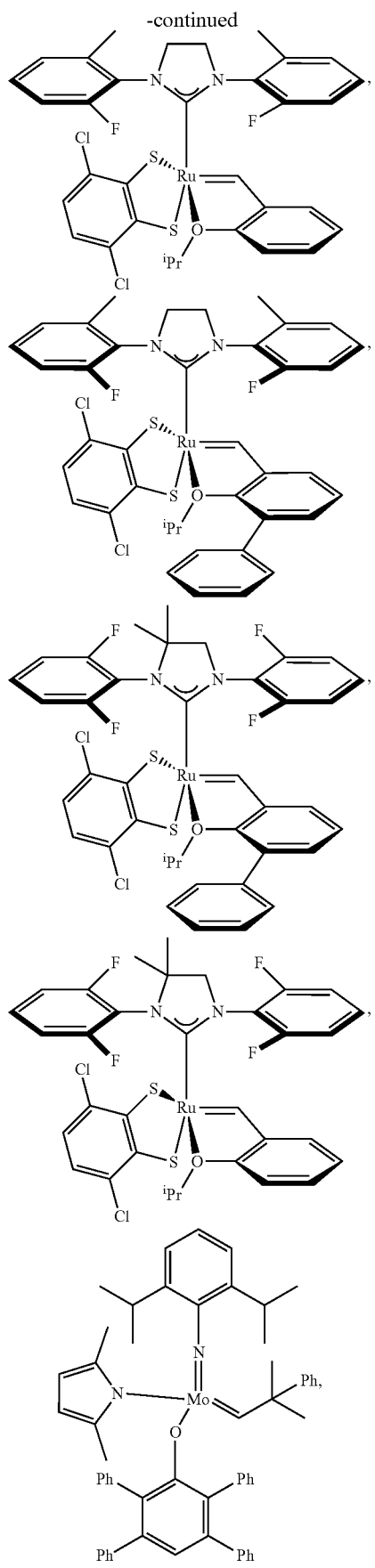
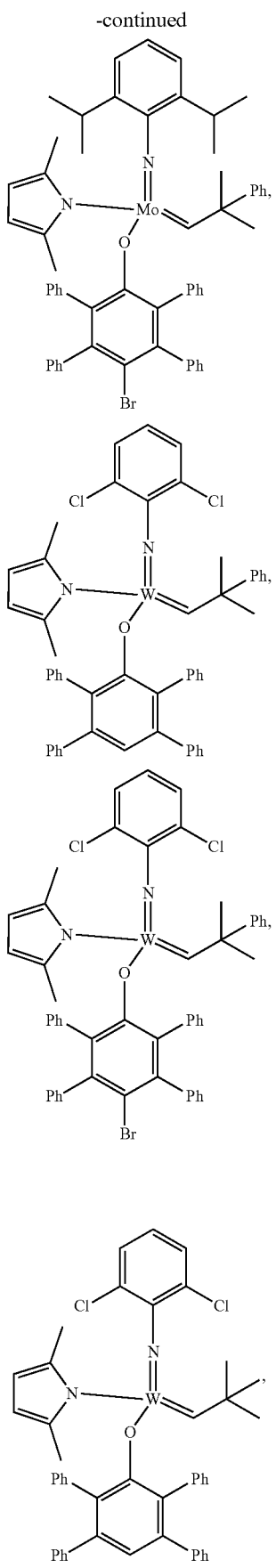

-continued

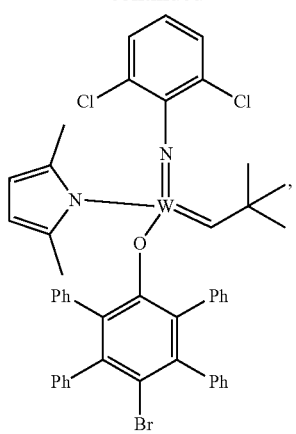

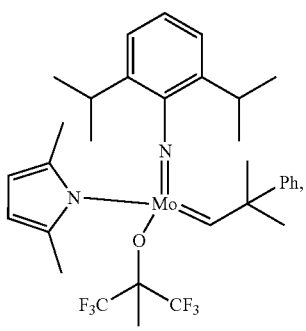

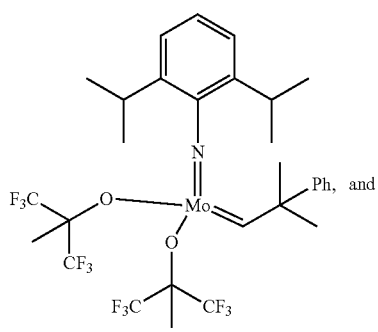

-continued

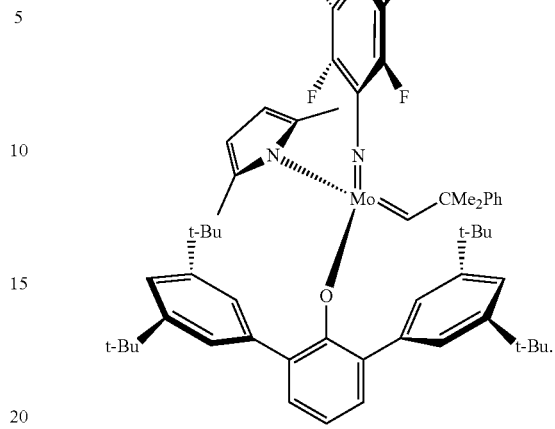

13. The method of claim 1, wherein the ruthenium isomerization catalyst is Ru(H)Cl(PPh₃)₃.

14. The method of claim 1, wherein the iridium isomerization catalyst is:

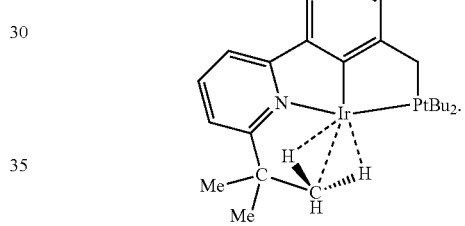

15. The method of claim 2, wherein the alkenol according to Formula IV is selected from the group consisting of (E)-8-dodecen-1-ol, (Z)-8-dodecen-1-ol, (Z)-8-tetradecen-1-ol, (E)-8-dodecen-1-ol, (Z)-8-dodecen-1-ol, and (Z)-8-tetradecen-1-ol.

16. The method of claim 2, wherein the alkenol is non-8-en-1-ol and the method further comprises reacting the non-8-en-1-ol in the presence of a molybdenum catalyst, a tungsten catalyst, or a ruthenium catalyst to form (8E,10E)-dodeca-8,10-dien-1-ol.

17. The method of claim 3, wherein the alkenol ester according to Formula V is selected from the group consisting of (E)-8-undecenyl acetate, (Z)-8-undecenyl acetate, (E)-8-dodecenyl acetate, (Z)-8-dodecenyl acetate, (E)-8-tridecenyl acetate, (Z)-8-tridecenyl acetate, (E)-8-tetradecenyl acetate, (Z)-8-tetradecenyl acetate, (Z)-8-pentadecenyl acetate, (E)-8-undecenyl acetate, (Z)-8-undecenyl acetate, (E)-8-dodecenyl acetate, (Z)-8-dodecenyl acetate, (E)-8-tridecenyl acetate, (Z)-8-tridecenyl acetate, (E)-8-tetradecenyl acetate, (Z)-8-tetradecenyl acetate, and (Z)-8-pentadecenyl acetate.

* * * * *